(12) United States Patent
Mulder et al.

(10) Patent No.: US 11,446,336 B2
(45) Date of Patent: Sep. 20, 2022

(54) COMPOSITIONS COMPRISING BACTERIAL STRAINS

(71) Applicant: 4D Pharma Research Limited, Aberdeen (GB)

(72) Inventors: Imke Elisabeth Mulder, Aberdeen (GB); Anna Ettorre, Aberdeen (GB); Suaad Ahmed, Aberdeen (GB); Parthena Fotiadou, Aberdeen (GB)

(73) Assignee: 4D Pharma Research Limited, Aberdeen (GB)

(*) Notice: Subject to any disclaimer, the term of this patent is extended or adjusted under 35 U.S.C. 154(b) by 0 days.

(21) Appl. No.: 17/325,502

(22) Filed: May 20, 2021

(65) Prior Publication Data

US 2021/0283194 A1 Sep. 16, 2021

Related U.S. Application Data

(63) Continuation of application No. PCT/EP2019/084994, filed on Dec. 12, 2019, which is a continuation of application No. PCT/EP2019/080131, filed on Nov. 4, 2019.

(30) Foreign Application Priority Data

Dec. 12, 2018 (EP) .................................... 18212087
Nov. 4, 2019 (GB) .................................... 1916001

(51) Int. Cl.
*A61K 35/74* (2015.01)

(52) U.S. Cl.
CPC .................................... *A61K 35/74* (2013.01)

(58) Field of Classification Search
None
See application file for complete search history.

(56) References Cited

U.S. PATENT DOCUMENTS 5,595,756 A * 1/1997 Bally .................. A61K 9/1272
264/4.1
2018/0169153 A1 6/2018 Berry et al.

FOREIGN PATENT DOCUMENTS

| WO | WO-03046580 A1 | 6/2003 |
| WO | WO-2007071978 A1 | 6/2007 |
| WO | WO-2013008039 A2 | 1/2013 |
| WO | WO-2013050792 A1 | 4/2013 |
| WO | WO-2014167338 A1 | 10/2014 |
| WO | WO-2016149449 A1 | 9/2016 |
| WO | WO-2016203220 A1 | 12/2016 |
| WO | WO-2017160711 A1 | 9/2017 |
| WO | WO-2018094190 A2 | 5/2018 |
| WO | WO-2018112363 A1 | 6/2018 |
| WO | WO-2018112365 A2 | 6/2018 |
| WO | WO-2018117263 A1 | 6/2018 |
| WO | WO-2019010255 A1 | 1/2019 |

OTHER PUBLICATIONS

Sporn et al, "Chemoprevention of Cancer," Carcinogenesis, vol. 21 (2000), 525-530.*
Auerbach et al (Cancer and Metastasis Reviews, 2000, 19: 167-172).*
Gura T (Science, 1997, 278(5340): 1041-1042.*
Jain RK (Scientific American, Jul. 1994,58-65).*
Abel, Alex M et al., Natural Killer Cells: Development, Maturation, and Clinical Utilization, Frontiers inimmunology vol. 9 1869. Aug. 13, 2018, doi:10.3389/fimmu.2018.01869.
Ascierto, Paolo A et al., The role of BRAF V600 mutation in melanoma, 2012, Journal of Translational Medicine, 10,85, 9 pages.
Azad, M.B. et al., Probiotic supplementation during pregnancy or infancy for the prevention of asthma and wheeze: systematic review and meta-analysis BMJ 2013; 347 :f6471, Dec. 4, 2013.
Berraondo, P., Sanmamed, M.F., Ochoa, M.C. et al., Cytokines in clinical cancer immunotherapy, British Journal of Cancer120, 6-15 (2019). https://doi.org/10.1038/s41416-018-0328-y.
Bronte, Vincenzo, and Mikael J Pittet, The spleen in local and systemic regulation of immunity, Immunity vol. 39,5 (2013): 806-18.doi:10.1016/j.immuni.2013.10.010.
Dankner M, et al., Classifying BRAF alterations in cancer: new rational therapeutic strategies for actionable mutations, Oncogene, Jun. 2018;37(24):3183-3199. doi: 10.1038/s41388-018-0171-x. Epub Mar. 15, 2018. PMID: 29540830.
Eckburg, PB. et al., Diversity of the human intestinal microbial flora. Science. Jun. 10, 2005;308(5728):1635-8. Epub Apr. 14, 2005.
Fabbi, Marina et al., Dual Roles ofIL-27 in Cancer Biology and Immunotherapy, 2017, Mediators of Inflammation, 1-14.10.1155/2017/3958069.
Frank, D. et al., Molecular-phylogenetic characterization of microbial community imbalances in human inflammatory bowel diseases. 2007. PNAS. 104(34):13780-5.online Aug. 15, 2007.
Goldin, B. R. and Gorbach, S. L., Clinical Indications for Probiotics: An Overview, Clin Infect Dis., 2008, vol. 46, No. 2, pp. 96-100.
Jones, Jeremy C. et al., Non-V600BRAF Mutations Define a Clinically Distinct Molecular Subtype of Metastatic Colorectal Cancer, 2017, J Clin Oncol. Aug. 10, 2017;35(23): 2624-2630.
Kailasapathy, K. Microencapsulation of Probiotic Bacteria:Technology and Potential Applications. Curr. Issues Intest. Microbiol. (2002) 3: 39-48.
Kang, S. et al. (2010), Dysbiosis of fecal microbiota inCrohn's disease patients as revealed by a custom phylogenetic microarray,Inflammatory BowelDiseases. Dec. 2010;16(12):2034-2042. doi:10.1002/ibd.21319.
Koh, Gar Yee et al., Parabacteroides distasonis attenuate toll-like receptor 4 signaling and Akt activation and blocks colon tumor formulation in high-fat-diet-fed azoxymethane-treated mice, International Journal of Cancer,2018, 143, 1797-1805. Accepted Article, doi:10.1002/ijc.31559,Apr. 26, 2018.

(Continued)

*Primary Examiner* — Brian Gangle
(74) *Attorney, Agent, or Firm* — Wilson Sonsini Goodrich & Rosati

(57) ABSTRACT

The invention provides a composition comprising a bacterial strain of the genus *Parabacteroides*, for use in a method of treating or preventing cancer in a subject; wherein the cancer comprises oncogenic ERK signalling.

20 Claims, 46 Drawing Sheets

Specification includes a Sequence Listing.

(56) References Cited

OTHER PUBLICATIONS

Kubica, Agnieszka W, and Jerry D Brewer, Melanoma in immunosuppressed patients, Mayo Clinic proceedings vol. 87,10 (2012): 991-1003.doi:10.1016/j.mayocp.2012.04.018.
Leslie, et al., Trehalose and sucrose protect both membranes and proteins in intact bacteria during drying. (1995) Appl. Environ. Microbiol. 61, 3592-3597.
Liu, Feifei et al., Targeting ERK, an Achilles' Heel of the MAPK pathway, in cancer therapy, 2018, Acta Pharmaceutica Sinica B; 8, 4; 552-562.
Livak KJ, Schmittgen TD., Analysis of relative gene expression data using real-time quantitative PCR and the 2(-Delta Delta C(T)) Method. Methods. Dec. 2001;25(4):402-8. doi:10.1006/meth.2001. 1262. PMID: 11846609.
Machiels, K., A decrease of the butyrate-producing species Roseburia hominis and Faecalibacterium prausnitzii defines dysbiosis in patients with ulcerative colitis. Gut. Aug. 2014;63(8):1275-83. doi: 10.1136/gutjnl-2013-304833. Epub Sep. 10, 2013.
Macpherson, AJ. et al., IgA responses in the intestinal mucosa against pathogenic and non-pathogenic microorganisms. Oct. 2001. 3(12). 1021-1035.
Macpherson, AJ., et al., The functions of mucosal T cells in containing the indigenous commensal flora of the intestine. Cell Mol Life Sci. Dec. 2002;59(12):2088-96.
Masco, L., et al., Identification of Bifidobacterium Species Using rep-PCR Fingerprinting. Systematic and Applied Microbiology 26(4):557-63 • Nov. 2003.
Mazmanian, SK., An immunomodulatory molecule of symbiotic bacteria directs maturation of the host immune system. Cell. Jul. 15, 2005;122(1):107-18.
McCarter, MD, Martin D. et al., Immunosuppressive Dendritic and Regulatory T Cells are Upregulated in Melanoma Patients,2007, Annals of Surgical Oncology 14(10):2854-2860, DOI:10.1245/s10434-007-9488-3.
Mitropoulou, G. et al. Immobilization Technologies in Probiotic Food Production. (2013) Journal Nutr Metab. (2013) 716861.
Miyamoto-Shinohara et al. Survival of freeze-dried bacteria. J Gen Appl Microbiol 54(1):9-24 (2008).
Morvan MG, Lanier LL, NK cells and cancer: you can teach innate cells new tricks, Nat Rev Cancer, Jan. 2016;16(1):7-19. doi: 10.1038/nrc.2015.5.PMID: 26694935.
Ni, Ling, and Jian Lu, Interferon gamma in cancer immunotherapy, 2018, Cancer medicine vol. 7,9: 4509-4516.doi:10.1002/cam4. 1700.
Qin, Meng-Bin et al, Inhibition of SPHK1 Suppresses Phorbol 12-Myristate 13-Acetate-Induced Metastatic Phenotype in Colorectal Cancer HT-29 Cells, Oncology Research Featuring Preclinical and Clinical Cancer Therapeutics, 2011, vol. 19, No. 12, pp. 573-582(10).
Sakamoto, Mitsuo et al. "Reclassification of Bacteroides distasonis, *Bacteroides goldsteinii* and *Bacteroides merdae* as *Parabacteroides distasonis* gen. nov., comb, nov., *Parabacteroides goldsteinii* comb. nov. and *Parabacteroides merdae* comb. nov.", Journal of Systematic and Evolutionary Microbiology, 2006, vol. 56, No. 7, 1599-1605, Jul. 2006.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Shi, Hubing et al., Acquired resistance and clonal evolution in melanoma during BRAF inhibitor therapy, Cancer discovery vol. 4,1 (2014): 80-93.doi:10.1158/2159-8290.CD-13-0642.
Smith and Waterman, "Comparison of biosequences", Advances in Applied Mathematics, vol. 2, Issue 4, Dec. 1981, pp. 482-489.
Soltani, Mohammad H et al, Microtubule-Associated Protein 2, a Marker of Neuronal Differentiation, Induces Mitotic Defects, Inhibits Growth of Melanoma Cells, and Predicts Metastatic Potential of Cutaneous Melanoma, 2005, Am J Pathol;166:1841-50.

Spor, A. et al., Unravelling the effects of the environment and host genotype on the gut microbiome. Nat Rev Microbiol. Apr. 2011;9(4):279-90. doi: 10.1038/nrmicro2540.
Srutkova, D. et al., Efficiency of PCR-based methods in discriminating *Bifidobacterium longum* ssp. longum and *Bifidobacterium longum* ssp. infantis strains of human origin.J Microbiol Methods. Oct. 2011;87(1):10-6. doi: 10.1016/j.mimet.2011.06.014. Epub Jul. 2, 2011.
Strobel, H.J. Basic laboratory culture methods for anaerobic bacteria. Methods Mol Biol. 2009;581:247-61. doi: 10.1007/978-1-60761-214-8_16.
Thangaraju, Muthusamy et al., GPR109A is a G-protein-Coupled Receptor for the Bacterial Fermentation Product Butyrate and Functions as a Tumor Suppressor in Colon (2009). Cancer Res. 67, 9: 2826-2832, Published Online First Mar. 10, 2009; DOI:10.1158/0008-5472.CAN-08-4466.
UniProtKB—P15056 (BRAF_HUMAN), https://www.uniprot.org/uniprot/P15056,accessed Dec. 18, 2020.
Viguier M, et al., Foxp3 expressing CD4+CD25(high) regulatory T cells are overrepresented in human metastatic melanoma lymph nodes and inhibit the function of infiltrating T cells. J Immunol. Jul. 15, 2004;173(2):1444-53. doi: 10.4049/jimmunol.173.2.1444. PMID: 15240741.
Wu, Tsung-Ru et al., Gut commensal Parabacteroides goldsteinii plays a predominant role in the anti-obesity effects of polysaccharides isolated from Hirsutella sinensis, 2019, Gut;68:248-262. doi:10.1136/gutjnl-2017-315458.
Xie, Songbo et al., Microtubule-Binding Proteins as Promising Biomarkers of Paclitaxel Sensitivity in Cancer Chemotherapy, 2016; Med Res Rev; 36,2: 300-312.
Yan, Wan-Lun et al., Recent progress in GM-CSF-based cancer immunotherapy, 2017, Immunotherapy 9(4), 347-360.10.2217/imt-2016-0141.
Celgene Ltd, Vidaza 25 mg/ml powder for suspension for injection, Last updated on emc: Nov. 26, 2020.
Lal, Neeraj et al., KRAS Mutation and Consensus Molecular Subtypes 2 and 3 are Independently Associated with Reduced Immune Infiltration and Reactivity in Colorectal Cancer, 2018, Clinical Cancer Research; 24(1), 224-234.
Roche Products Limited, Zelboraf 240mg Film-coated Tablets, Last updated on emc:May 21, 2021.
Ruan, Jhen-Wei et al., Dual-specificity phosphatase 6 deficiency regulates gut microbiome and transcriptome response against diet-induced obesity in mice, 2016, Nature Microbiology, vol. 2, article16220, pp. 1-12.
Akache, B. et al. "Sulfated archaeol glycolipids: Comparison with other immunological adjuvants in mice," PLos One, Dec. 4, 2018, 13(12): e0208067.
Ali, S. et al. "Chemokines: novel targets for breast cancer metastasis," Cancer Metastasis Rev, Aug. 2007,26(3-4), pp. 1-31.
Al-Lahham, S. et al. "Propionic acid affects immune status and metabolism in adipose tissue from overweight subjects," European Journal of Clinical Investigation, 2012, vol. 42, No. 4, pp. 357-364.
Anacker, C. et al., "The glucocorticoid receptor: Pivot of depression and of antidepressant treatment?", Psychoneuroendocrinology, 2011, 36(3), pp. 1-19.
Andreakos, E. et al. "Activation of NF-kB by the intracellular expression of NF-kB-inducing kinase acts as a powerful vaccine adjuvant," PNAS, Sep. 26, 2006, vol. 103, No. 93, pp. 14459-14464.
Andresen, L. et al. "Propionic Acid Secreted from Propionibacteria Induces NKG2D Ligand Expression on Human-Activated T Lymphocytes and Cancer Cells," J. Immunol., 2009, vol. 183, pp. 897-906.
Antunes, K.H. et al. "Microbiota-derived acetate projects against respiratory syncytial virus infection through a GPR43-type 1 interferon response," Nature Communication, 2019, Article No. 3273, pp. 897-906.
Aoshi, T. et al. "Modes of Action for Mucosal Vaccine Adjuvants" Viral Immunology, 2017, vol. 30, No. 6, pp. 463-470.
Bastola, R. et al., "Vaccine adjuvants: smart components to boost the immune system", Arch. Pharm. Res., 2017, vol. 40, pp. 1238-1248.

(56) References Cited

OTHER PUBLICATIONS

Bektas, Arsun et al. "Human T cell immunosenescence and inflammation in aging." Journal of leukocyte biology vol. 102,4 (2017): 977-988. doi:10.1189/jlb.3RI0716-335R.
Bent, R. et al., "Interleukin-1 Beta—A Friend or Foe in Malignancies?", International Journal of Molecular Sciences, 2018, 19(8): 2155, pp. 1-34.
Berstad A K H et al., "Inactivated meningococci and pertussis bacteria are immunogenic and act as mucosal adjuvants for a nasal inactivated influenza virus vaccine", Vaccine, 2000, vol. 18, No. 18, pp. 1910-1919.
Bhat, A. et al., "Tight Junction Proteins and Signaling Pathways in Cancer and Inflammation: A Functional Crosstalk", frontiers in Physiology, Jan. 2019, vol. 9, Article 1942, pp. 1-19.
Bonapace, L. et al., "Cessation of CCL2 inhibition accelerates breast cancer metastasis by promoting angiogenesis", Nature, Nov. 6, 2014, vol. 515, pp. 1-17.
Castle, J. et al., Immunomic, genomic and transcriptomic characterization of CT26 colorectal carcinoma, BMC Genomics, 2014, 15:190, pp. 1-11.
Cervenka, I. et al. "Kynurenines: Tryptophan's metabolites in exercise, inflammation, and mental health," Science, Jul. 28, 2017, 357(6349), pp. 1-10.
Cochran, D. et al., "The role of oxytocin in psychiatric disorders: A review of biological and therapeutic research findings", Harv Rev Psychiatry, 2013, 21(5), pp. 1-34.
Connors, J. et al. "The Role of Succinate in the Regulation of Intestinal Inflammation," Nutrients, 2019, 11(1), 25, pp. 1-12.
Cremolini, C. et al., "Early tumor shrinkage and depth of response predict long-term outcome in metastatic colorectal cancer patients treated with first-line chemotherapy plus bevacizumab: results from phase III TRIBE trial by Gruppo Oncologico del Nord Ovest", Annals of Oncology, 2015, 26(6), pp. 1188-1194.
De Kloet, E.R. et al., "Stress and Depression: a Crucial Role of the Mineralcorticoid Receptor", Journal of Neuroendocrinology, 2016, vol. 28, pp. 1-12.
Deshmane, S. et al. "Monocyte Chemoattractant Protein-1 (MCP-1): An Overview," Journal of Interferon & Cytokine Research, 2009, vol. 29, No. 6, pp. 313-326.
Engin, E. et al., α2-containing GABAa receptors: A target for the development of novel treatment strategies for CNS disorders, Pharmacol. Ther., Nov. 2012, 136(2), pp. 1-24.
Fülöp T, Dupuis G, Witkowski JM, Larbi A. The Role of Immunosenescence in the Development of Age-Related Diseases. Rev Invest Clin. Mar.-Apr. 2016;68(2):84-91. PMID: 27103044.
Fulop, Tamas et al., "Immunosenescence and Cancer" (2013) Critical Reviews in Oncogenesis 2013;18(6):489-513.
Fulop, Tamas et al. "Immunosenescence and Inflamm-Aging as Two Sides of the Same Coin: Friends or Foes?." Frontiers in immunology vol. 8 1960. Jan. 10, 2018, doi:10.3389/fimmu.2017.01960.
Furukawa, S. et al., "MCP-1 Promotes Invasion and Adhesion of Human Ovarian Cancer Cells", Anticancer Research, 2013, vol. 33, No. 11, pp. 4785-4790.
Ghose, S. et al., "The GABAB receptor as a target for antidepressant drug action", British Journal of Pharmacology, 2011, vol. 16, pp. 1-17.
Glenn, Justin D and Whartenby, Katharine, Mesenchymal stem cells: Emerging mechanisms of immunomodulation and therapy, World J Stem Cells Nov. 26, 2014; 6(5): 526-539, ISSN 1948-0210.
Gray, A. et al., "Sex differences in glutamate receptor gene expression in major depression and suicide", Molecular Psychiatry, 2015, vol. 20, pp. 1057-1068.
Heng, Boon Chin et al., Strategies for directing the differentiation of stem cells into the cardiomyogenic lineage in vitro (2004) Cardiovasc Res. Apr. 1, 2004;62(1):34-42.
Hommes, DW et al., Mitogen activated protein (MAP) kinase signal transduction pathways and novel anti-inflammatory targets, Gut, 2003, vol. 52, pp. 144-151.
Huang, L. et al. "Metabolic control of tumor progression and anti-tumor immunity," Curr Opin Oncol., Jan. 2014, vol. 26, No. 1, pp. 92-99.
Issler, O. et al., Increased anxiety in corticotropin-releasing factor type 2 receptor-null mice requires recent acute stress exposure and is associated with dysregulated serotonergic activity in limbic brain areas, Biology of Mood and Anxiety Disorders, 2014, vol. 4, No. 1, pp. 1-20.
Ito, S. et al., "IL-4 blockade alters the tumor microenvironment and augments the response to cancer immunotherapy in a mouse model", Cancer Immunol Immunother, 2017, vol. 66, No. 11, pp. 1485-1496.
Iwakiri, M. et al., "Changes in hippocampal GABAbRI subunit expression in Alzheimer's patients: association with Braak staging", Acta Neuropathologica, 2005, vol. 109, pp. 467-474.
Johnson, D. et al., "Targeting the IL-6/JAK/STAT3 signalling axis in cancer", Nat Rev Clin Oncol, 2018, vol. 15, No. 4, pp. 1-35.
Kadmiel, K. et al., "Glucocorticoid receptor signaling in health and disease", Trends Pharmacol Sci, 2013, vol. 34, No. 9, pp. 1-25.
Kayamuro, H. et al., "The use of a mutant TNF-α as a vaccine adjuvant for the induction of mucosal immune responses", Biomaterials, 2009, vol. 30, pp. 5896-5876.
Kumari, N. et al., "Role of interleukin-6 in cancer progression and therapeutic resistance", Tumor Biol., 2016, vol. 37, pp. 11553-11572.
Kverka, M. et al., "Oral administration of Parabacteroides distasonis antigens attenuates experimental murine colitis through modulation of immunity and microbiota composition", Clinical and Experimental Immunology, Feb. 19, 2011, vol. 163, No. 2, pp. 250-259.
Lapteva, N. et al., "CCL5 as an adjuvant for cancer immunotherapy", Expert Opinion on Biological Therapy, 2010, vol. 10, No. 5, pp. 725-733.
Li, X. et al. "Succinate Modulates Intestinal Barrier Function and Inflammation Response in Pigs," Biomolecules, 2019, vol. 9, No. 486, pp. 1-14.
Li, Y. et al. "HDACs and HDAC Inhibitors in Cancer Development and Therapy," Cold Spring Harb Perspect Med, 2016, 6(10), pp. 1-34.
Locy, H. et al. "Immunomodulation of the Tumor Microenvironment: Turn Foe Into Friend," frontiers in Immunology, Dec. 11, 2018, vol. 9, Article 2909, pp. 1-18.
Magudia, K. et al., "K-Ras and B-Raf oncogenes inhibit colon epithelial polarity establishment through up-regulation of c-myc", J. Cell Biol., 2012, vol. 198 No. 2, pp. 185-194.
Martin, T. et al. "Loss of tight junction barrier function and its role in cancer metastasis," Biochimica et Biophysica Acta 1788, 2009, pp. 872-891.
Mills, E.. et al. "Succinate: a metabolic signal in inflammation," Trends in Cell Biology, May 2014, vol. 24, No. 5, pp. 313-320.
Mohan, Teena et al., Applications of chemokines as adjuvants for vaccine immunotherapy, Immunobiology vol. 223,6-7 (2018): 477-485.doi:10.1016/j.imbio.2017.12.001.
Ngiow, S. et al. "A balance of interleukin-12 and -23 in cancer," Trends in Immunology, Nov. 2013, vol. 34, No. 11, pp. 548-555.
Nguyen-Hoai, T. et al. "CCL4 as an adjuvant for DNA vaccination in a Her2/neu mouse tumor model," Cancer Gene Therapy, 2016, vol. 23, No. 6, pp. 162-167.
No Author, "451LuViable Cells (1×10≠cells)", retrieved from internet https://rockland-inc.com/Product.aspx?id=51606Sep. 30, 2021, pp. 1-2.
No Author, "ATCC Human Cell Products: HTB-38", retrieved from internet https://www.atcc.org/products/htb-38?geo_country=gb#characteristicsSep. 30, 2021, pp. 1-9.
No Author, "Cell Lines by Gene Mutation", retrieved from internet https://www.atcc.org/-/media/resources/brochures/cell-lines-by-gene-mutation.pdf?rev=c12284cdfe784c04b17fb046ce2743d6, Oct. 5, 2021, pp. 1-40.
No Author, "Paclitaxel 6 mg/ml Concentrate for Solution for Infusion", retrieved from internet https://www.medicines.org.uk/emc/product/6076/smpc, Oct. 15, 2021, pp. 1-16.
No Author, "SampleCOSS688054", retrieved from internet https://cancer.sanger.ac.uk/cosmic/sample/overview?id=688054retrieved online Sep. 30, 2021, pp. 1-3.

(56) References Cited

OTHER PUBLICATIONS

Nocito, A. et al., Serotonin Regulates Macrophage-Mediated Angiogenesis in a Mouse Model of Colon Cancer Allografts, 2008, Cancer Res., vol. 68, No. 13, pp. 5152-5158.
Nowak, E. et al. "Tryptophan hyroxylase-1 regulates immune tolerance and inflammation," J. Exp. Med., 2012, vol. 209, No. 11, pp. 2127-2135.
Okemoto, Kazuo et al., A Potent Adjuvant Monophosphoryl Lipid A Triggers Various Immune Responses, but Not Secretion of IL-1β or Activation of Caspase-1, J Immunol Jan. 15, 2006, 176 (2) 1203-1208; DOI: https://doi.Org/10.4049/jimmunol.176.2.1203.
Park, M. et al. "Roles of NF-kB in Cancer and Inflammatory Diseases and Their Therapeutic Approaches," Cells, 2016, vol. 59, No. 15, pp. 1-13.
Peters, T., "Immunosenescence; Current status and molecular mechanisms", Immunoseneszenz, Bestandsaufnahme und molekulare Grundlagen, Der Hautarzt; Zeitschrift fur Dermatologie, Venerologie und Verwandte Gebiete, Springer, Berlin, DE, vol. 62, No. 8, Jul. 6, 2011, pp. 598-606.
Pham, T. et al., "An update on Immunotherapy for Solid Tumors: A Review", Ann Surg Oncol, 2018, vol. 25, pp. 3404-3412.
Qian, B. et al. "CCL2 recruits inflammatory monocytes to facilitate breast tumor metastasis," Nature, 2011, 475(7355), pp. 1-14.
Qiu, J. et al. "Acetate Promotes T Cell Effector Function during Glucose Restriction," Cell Rep., May 14, 2019, 27(7), pp. 1-31.
Rashidi, Armin et al. "Pretransplant Gut Colonization with Intrinsically Vancomycin-Resistant Enterococci (E. gallinarum and E. casseliflavus) and Outcomes of Allogeneic Hematopoietic Cell Transplantation." Biology of blood and marrow transplantation : journal of the American Society for Blood and Marrow Transplantation vol. 24,6 (2018): 1260-1263. doi:10.1016/j.bbmt.2018.01.025.
Ruffell, B. et al. "Macrophage IL-10 blocks CD8+ T cell-dependent responses to chemotherapy by suppressing IL-12 expression in intratumoral dendritic cells," Cancer Cell, Nov. 10, 2014, 26(5), pp. 1-28.
Ryan, D. et al. "Coupling Krebs cycle metabolites to signalling in immunity and cancer," Nat Metab, Jan. 2019, vol. 1, pp. 1-40.
Seubert, Anja et al., The Adjuvants Aluminum Hydroxide and MF59 Induce Monocyte and Granulocyte Chemoattractants and Enhance Monocyte Differentiation toward Dendritic Cells, J Immunol Apr. 15, 2008, 180(8) 5402-5412; DOI: https://doi.org/10.4049/jimmunol.180.8.5402.
Shen, Y. et al., "Effectors of Epidermal Growth Factor Receptor Pathway: The Genetic Profiling of KRAS, BRAF, PIK3CA, NRAS Mutations in Colorectal Cancer Characteristics and Personalized Medicine", PLoS One, Dec. 2013, vol. 8, No. 1, e81628, pp. 1-8.
Smyth, M. et al., "Combination cancer immunotherapies tailored to the tumour microenvironment", Nature Reviews Clinical Oncology, Mar. 2016, vol. 13, pp. 143-158.
Su, Baowei et al., The effects of IL-6 and TNF-alpha as molecular adjuvants on immune responses to FMDV and maturation of dendritic cells by DNA vaccination. (2008)Vaccine. 26. 5111-22. 10.1016/j.vaccine.2008.03.089.
Taghavi, M. et al. "Zymosan attenuates melanoma growth progression, increases splenocyte proliferation and induces TLR-2/4 and TNF-a expression in mice," Journal of Inflammation 2018, vol. 15, No. 5, pp. 1-10.
Tap, W. et al., "Pharmacodynamic Characterization of the Efficacy Signals Due to Selective BRAF Inhibition with PLX4032 in Malignant Melanoma", Neoplasia, Aug. 2010, vol. 12, No. 8, pp. 637-649.
Thaker, A. et al. "IDO1 Metabolites Activate B-cantenin Signaling to Promote Cancer Cell Proliferation and Colon Tumorigenesis in Mice," Gasteroenterology, 2013, vol. 145, No. 2, pp. 1-18.
Tung, C. et al., Activation of dendritic cell function by soypeptide lunasin as a novel vaccine adjuvant, Vaccine, 2014, vol. 320, pp. 5411-5419.
Wasserman, D. et al., "The CRHR1 gene: a marker for suicidality in depressed males exposed to low stress", Genes, Brain and Behavior, 2008, vol. 7, pp. 14-19.
Wilkins, A. et al. "AS03-and MF59-Adjuvanted Influenza Vaccines in Children," frontiers in Immunology, Dec. 13, 2017, vol. 8, Article 1760, pp. 1-17.
Yoshino, S. et al., "Bacterial lipopolysaccharide acts as an adjuvant to induce autoimmune arthritis in mice", Immunology, 2000, vol. 99, pp. 607-614.
Young, E. et al., Mineralocorticoid Receptor Function in Major Depression, Arch Gen Psychiatry, Jan. 2003, vol. 60, No. 1, pp. 24-28.
Zhang, X.D.. et al. "Tight Junction Protein 1 Modulates Proteasome Capacity and Proteasome Inhibitor Sensitivity in Multiple Myeloma via EGFR/JAK1/STAT3 Signaling," Cancer Cell, May 9, 2016, vol. 29, No. 5, pp. 1-32.
Zhang, Y. et al., "Extended access oxycodone self-administration and neurotransmitter receptor gene expression in the dorsal striatum of adult C57BL/6J mice", Psychopharmacology (Berl), Apr. 2014, vol. 231, No. 7, pp. 1-21.
Ahmed, D. et al., "Epigenetic and genetic features of 24 colon cancer cell lines", Oncogenes, 2013, vol. 2, e71; doi:10.1038/oncsis.2013.35, pp. 1-8.
Ashraf, S. et al., "*Paenibacillus xanthanilyticus* sp. nov., a xanthan-degrading bacterium isolated from soil", Int J Syst Evol Microbiol, 2018;68:76-80.
Derry, M. et al., "Grape Seed Extract Efficacy against Azoxymethane-induced Colon Tumorigenesis in A/J Mice; Interlinking miRNA with Cytokine Signaling and Inflammation", Cancer Prev Res, Jul. 2013, 6(7), pp. 625-633.
Hu, Y. et al., "Detection of K-ras mutations in azoxymethane-induced aberrant crypt foci in mice using LNA-mediated real-time PCR clamping and mutant-specific probes", Mutation Research, 2009, pp. 27-32.
Leung, S.J. et al., "In vivo molecular mapping of the tumor microenvironment in an azoxymethane-treated mouse model of colon carcinogenesis", Lasers Surg Med., Jan. 2015, 47(1): pp. 40-49.
Panka, D. et al., "An inexpensive, specific and highly sensitive protocol to detect the Brafv600E mutation in melanoma tumor biopsies and blood", Melanoma Res., Oct. 2010, 20(5): 401-407.
Zdanov, S. et al., "Mutant KRAS Conversion of Conventional T Cells into Regulatory T Cells", Cancer Immunol Res; Apr. 2016, 4(4), pp. 354-365.
Zhang, B. et al., "Targeting Transforming Growth Factor-B signaling in liver", Cancer Lett., May 2009, 277(1), pp. 114-120.

\* cited by examiner

FIG. 1 SKMEL2 cell line – MAP2 gene expression
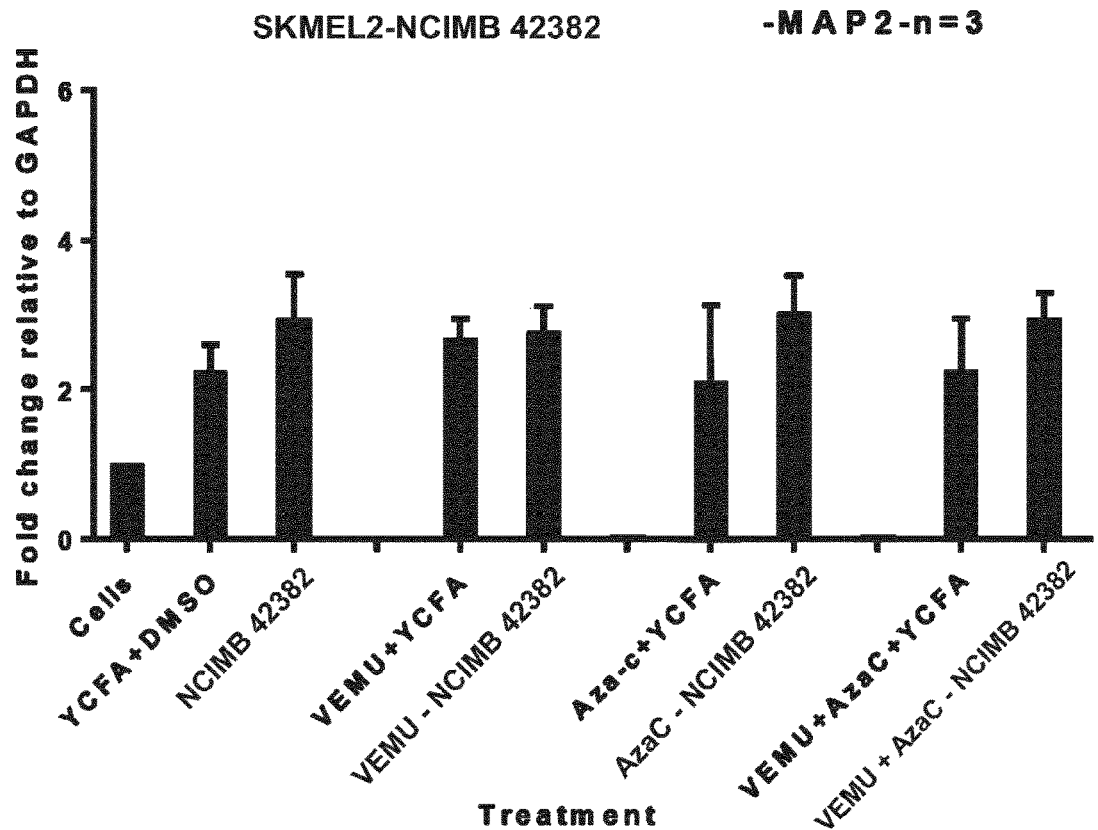
FIG. 2 SKMEL2 cell line – clonogenic survival
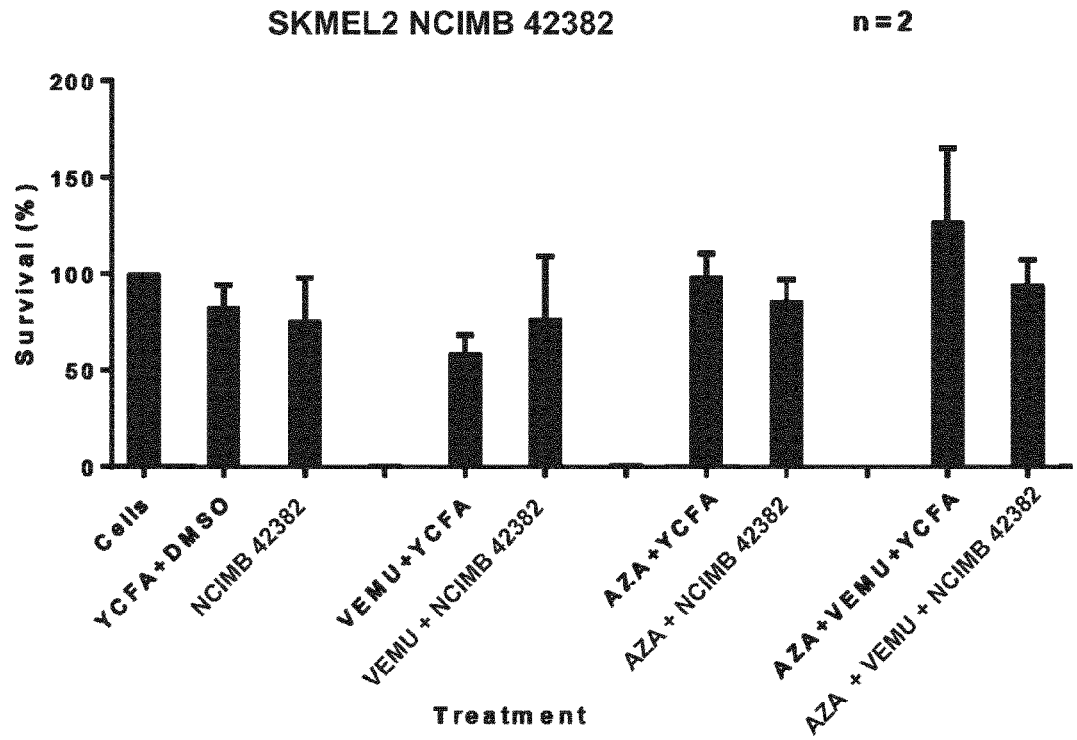

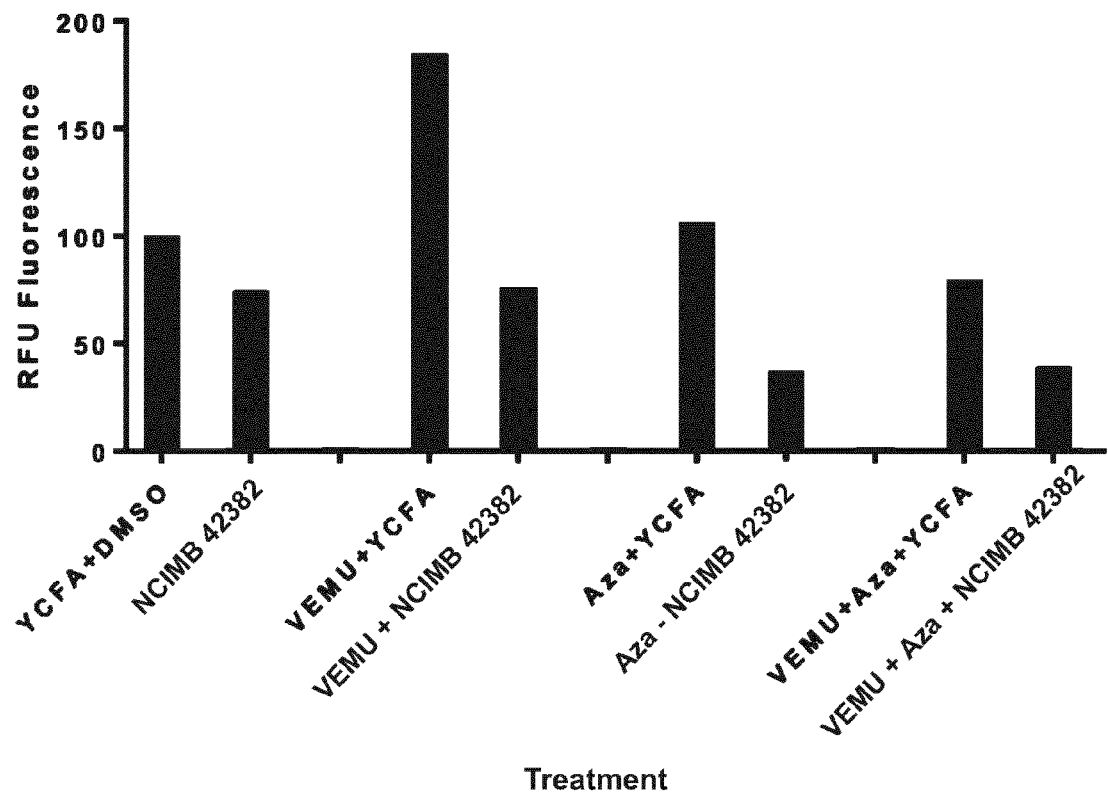
FIG. 3 SKMEL2 cell line – soft agar growth

FIG. 4
SKMEL2 cell line – ERK signalling
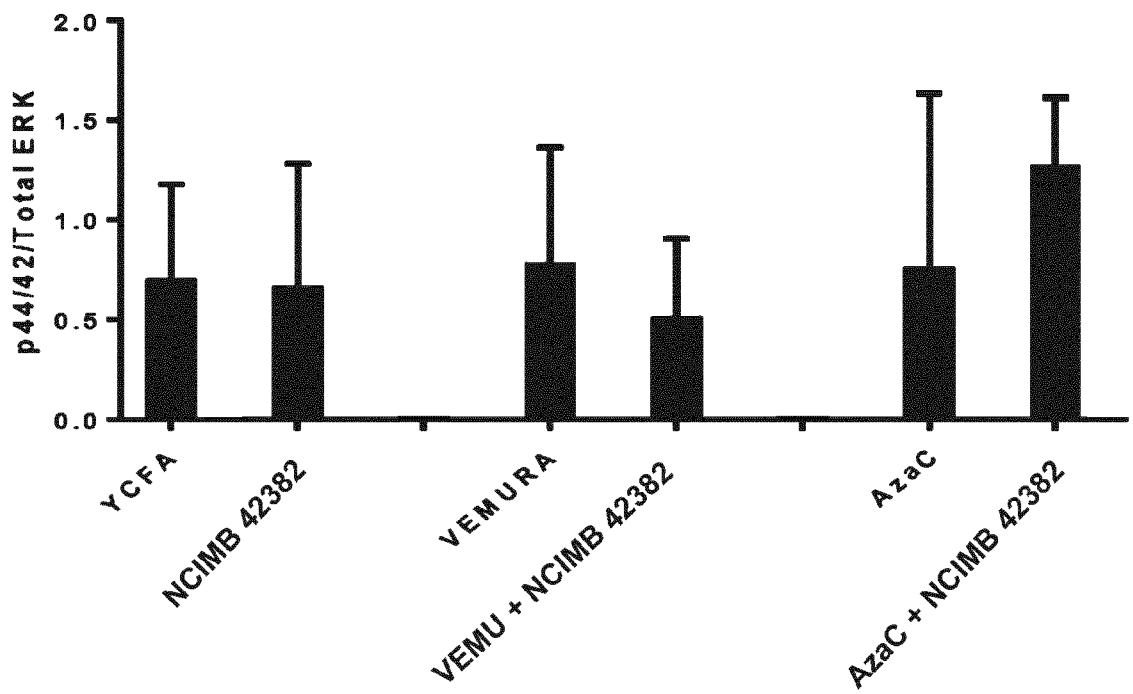
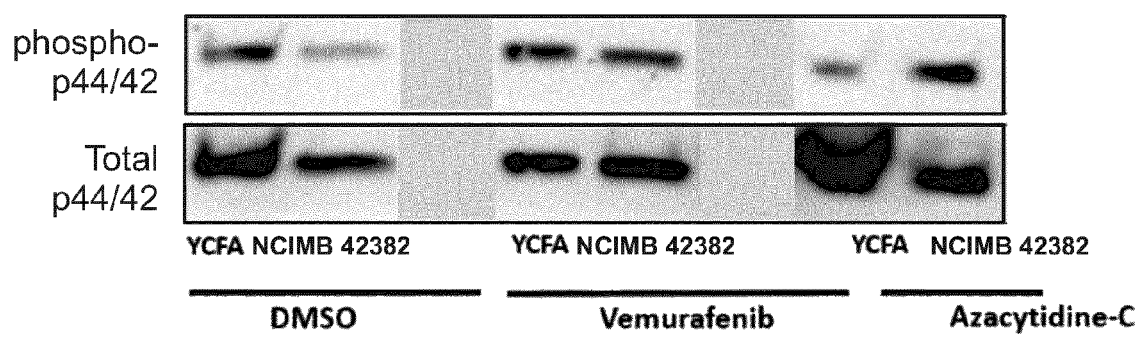

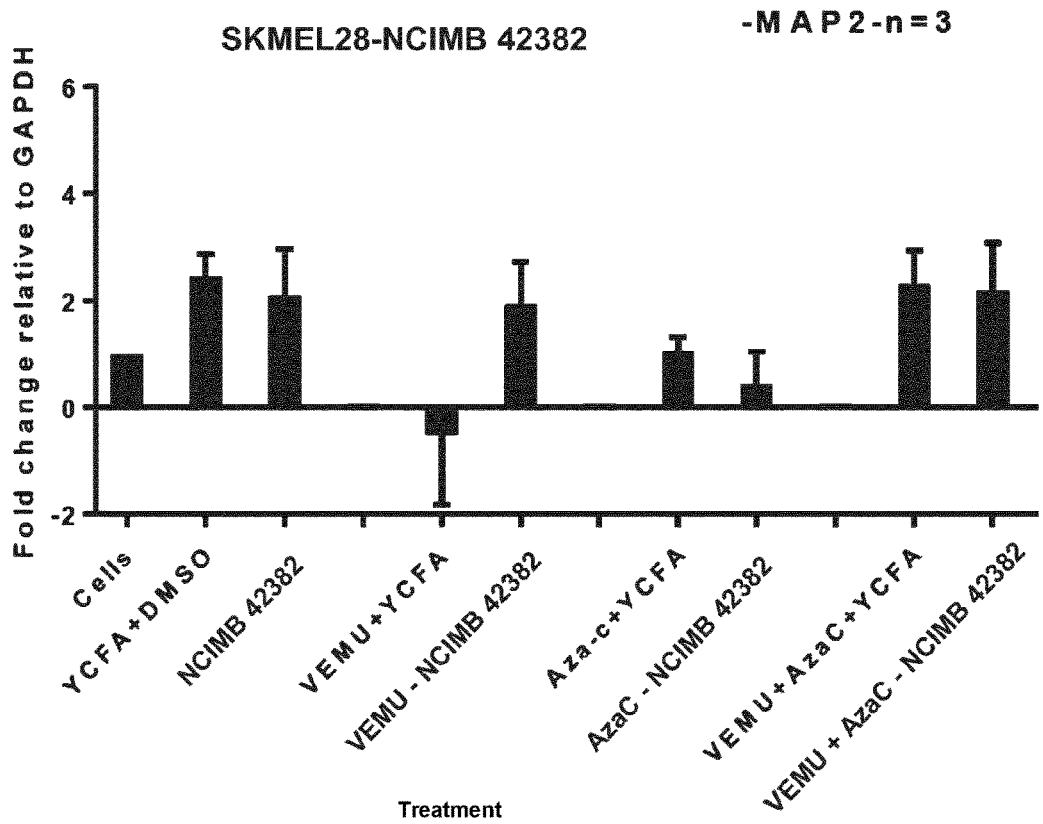
FIG. 5 SKMEL28 cell line – MAP2 gene expression
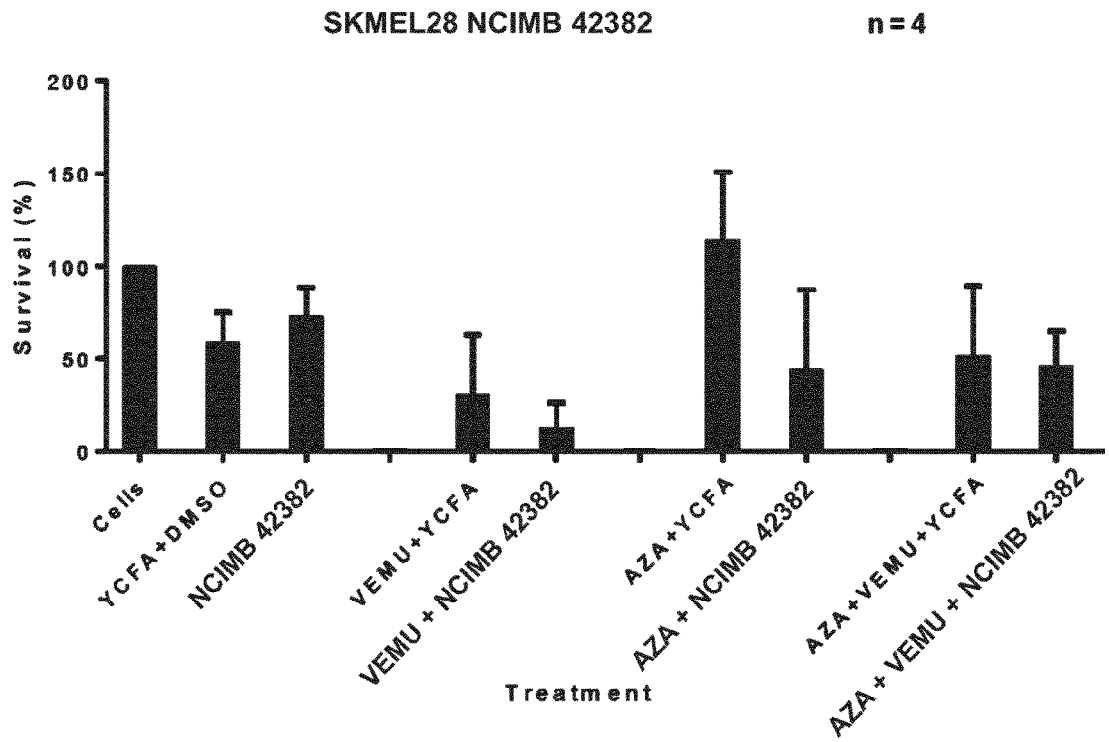
FIG. 6 SKMEL28 cell line – clonogenic survival

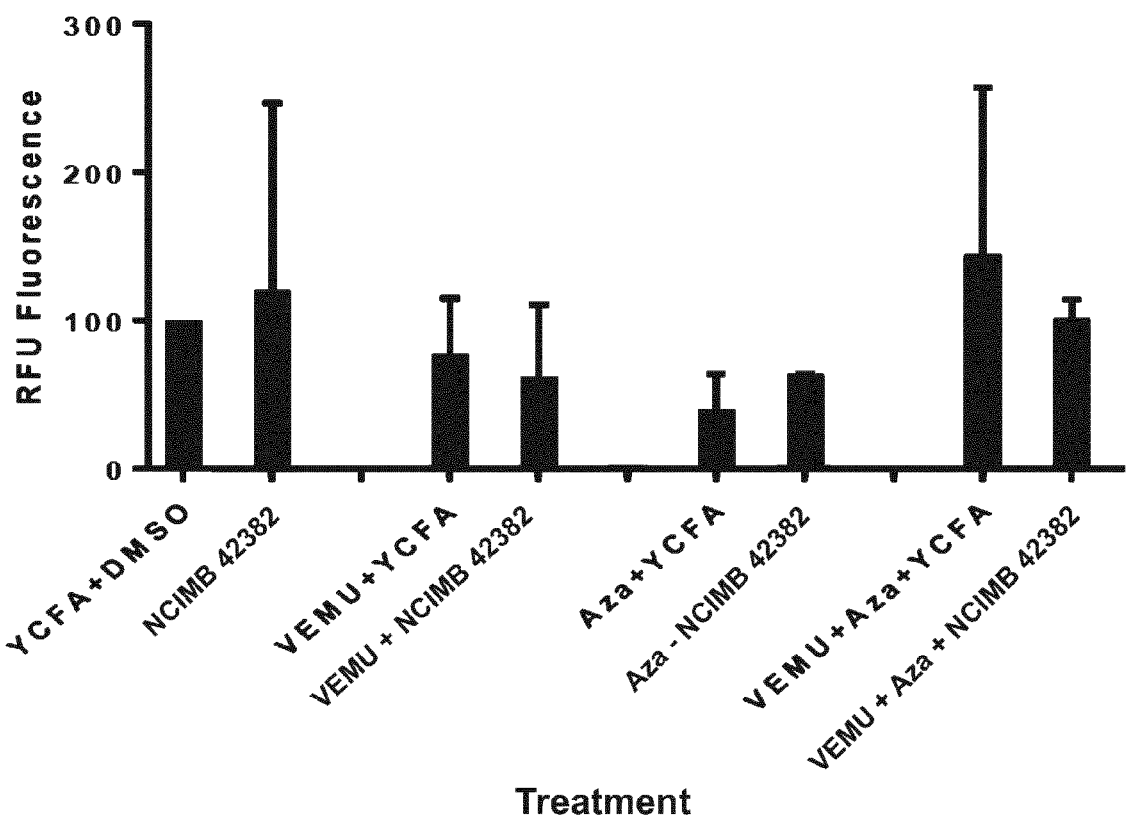
FIG. 7 SKMEL28 cell line – soft agar growth

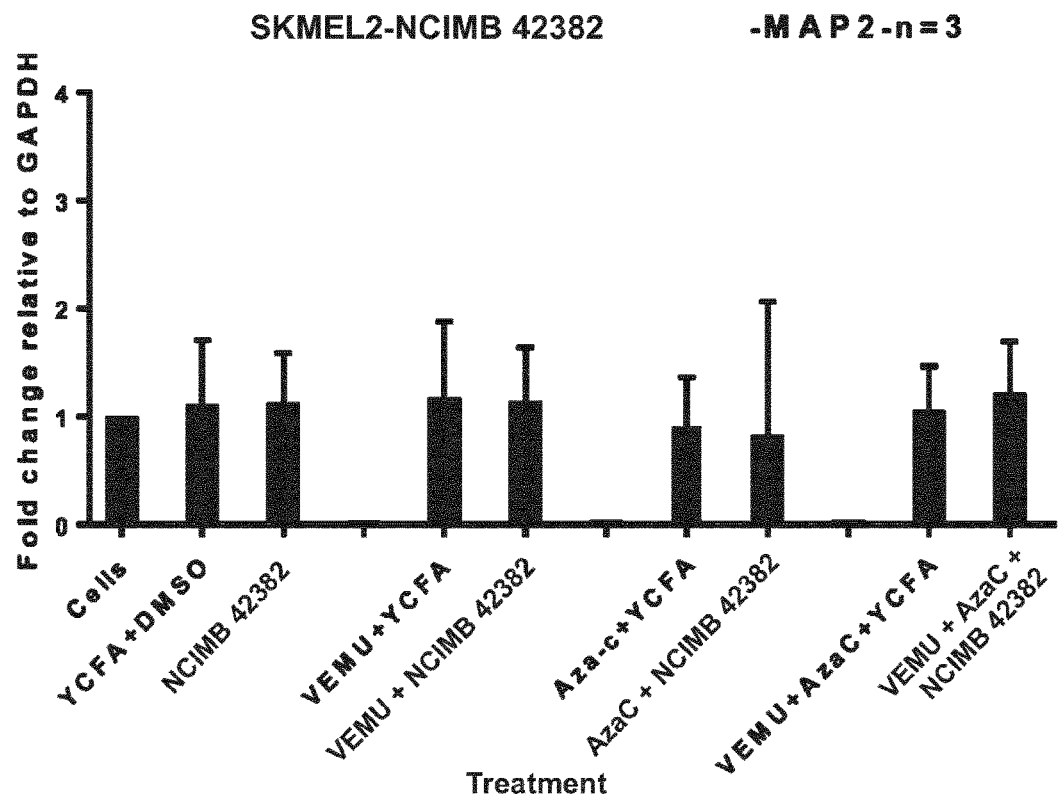
FIG. 9 SKMEL31 cell line – MAP2 gene expression
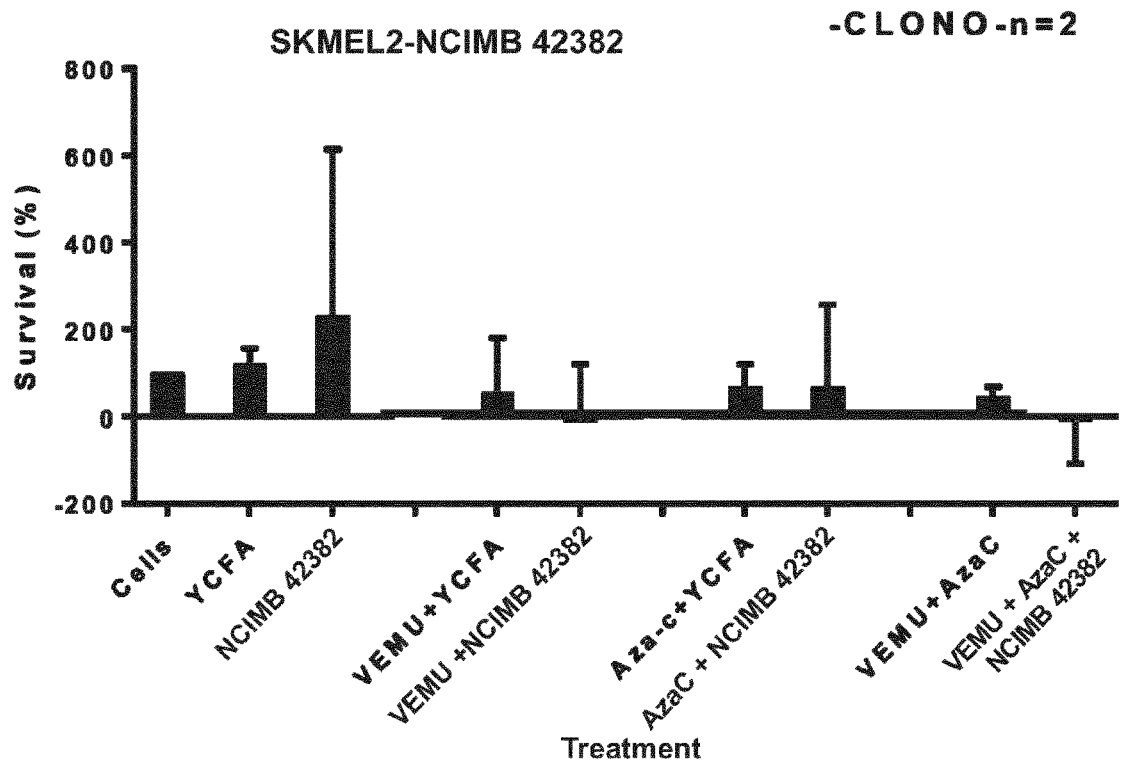
FIG. 10 SKMEL31 cell line – clonogenic survival SKMEL31 cell line – soft agar growth

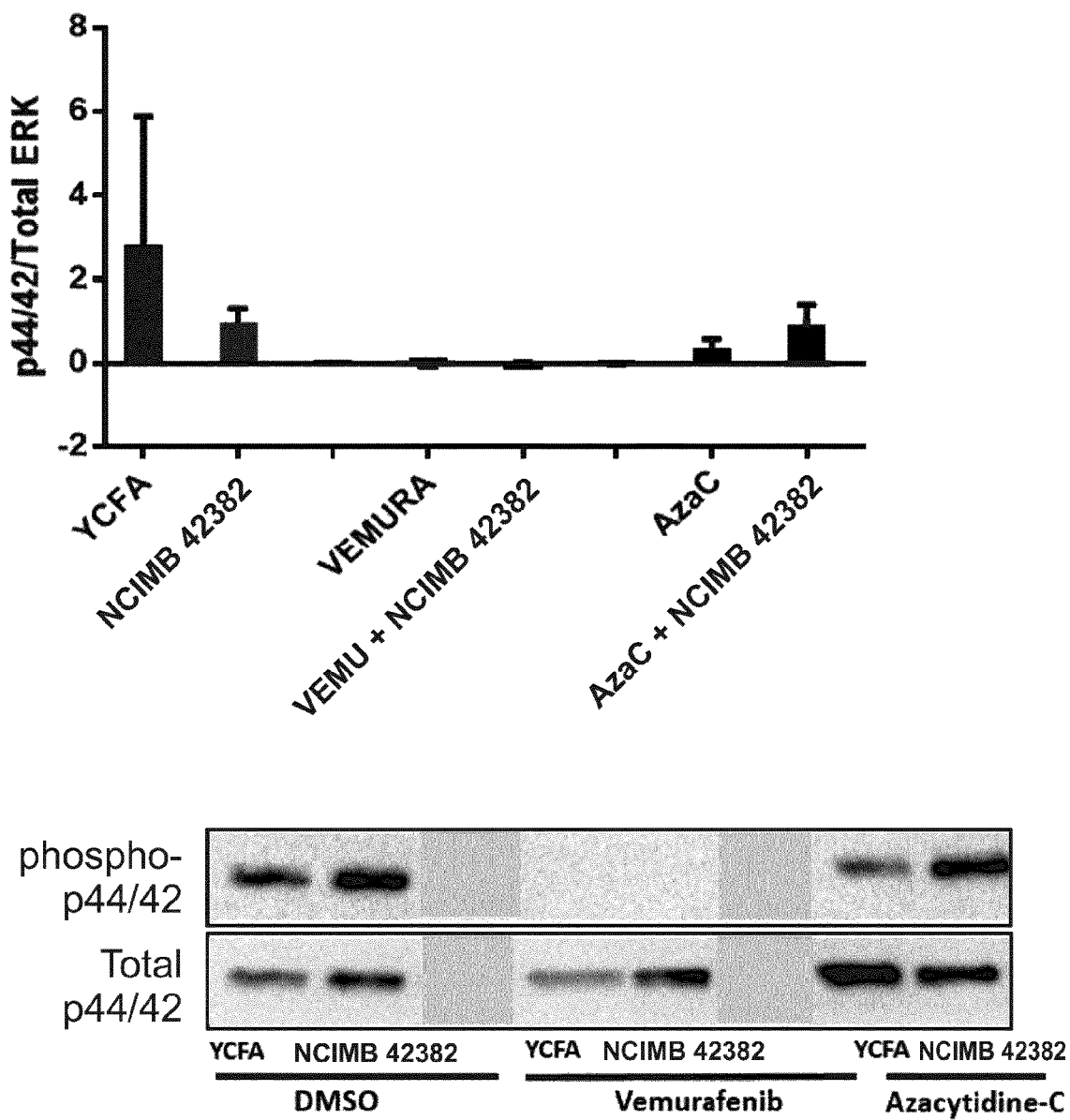

FIG. 13 451Lu cell line – MAP2 gene expression
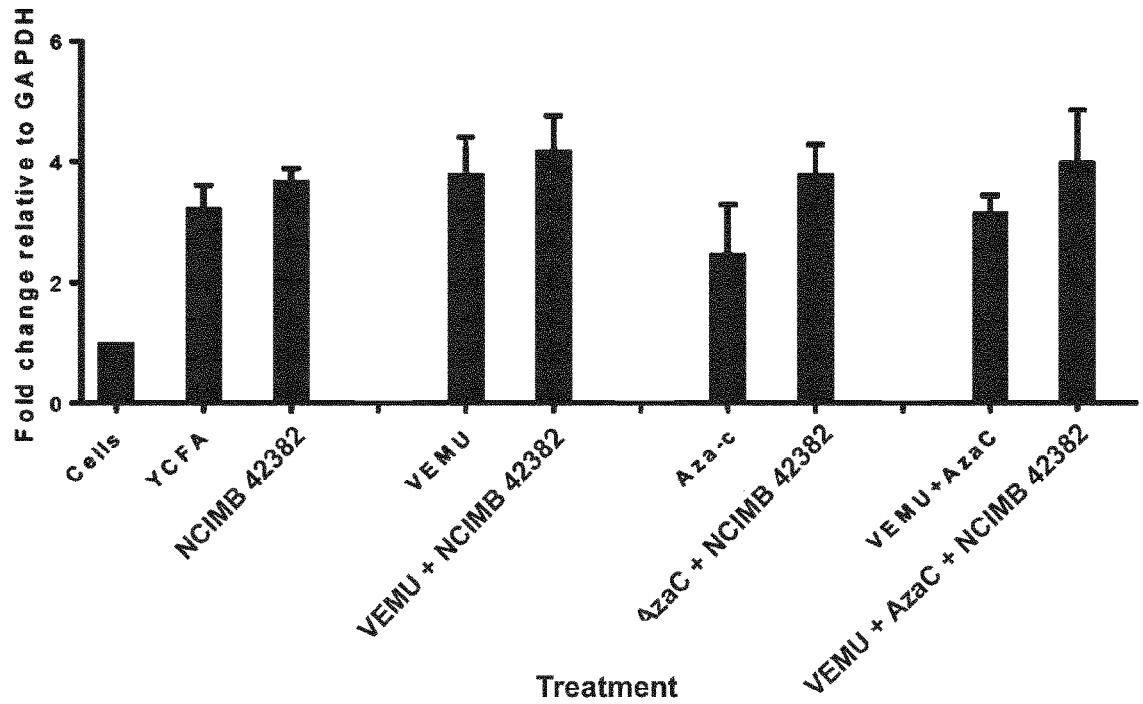
FIG. 14 451Lu cell line – clonogenic survival
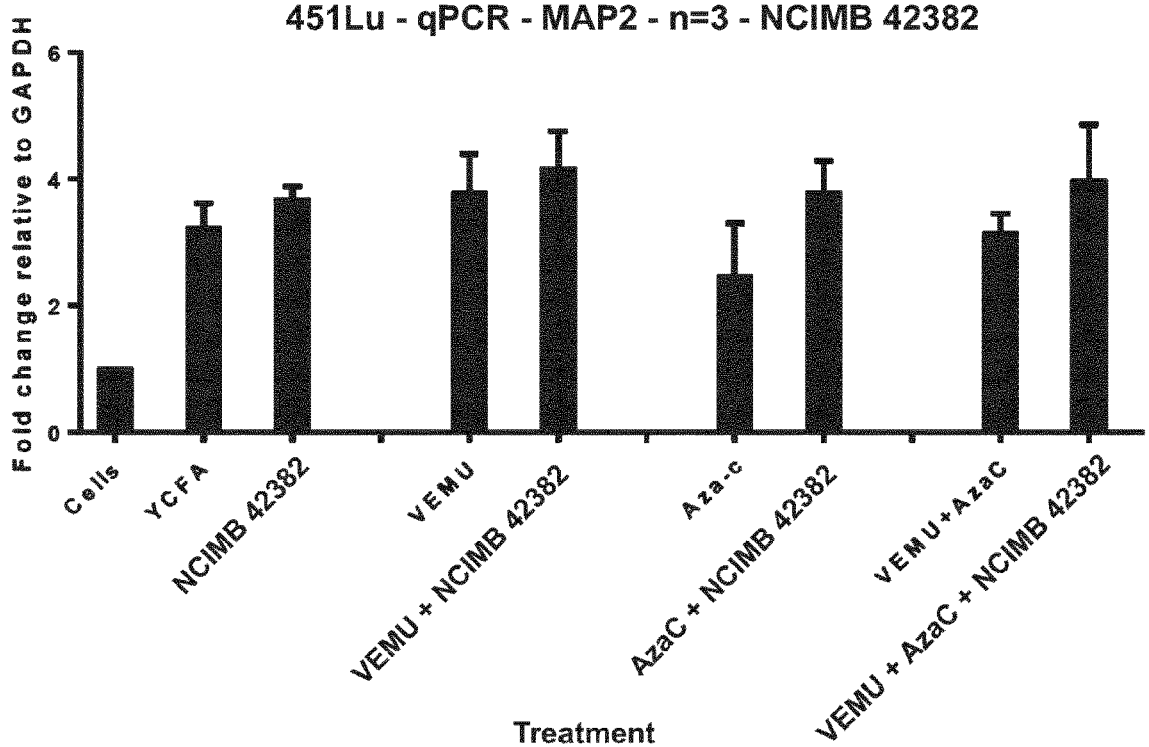

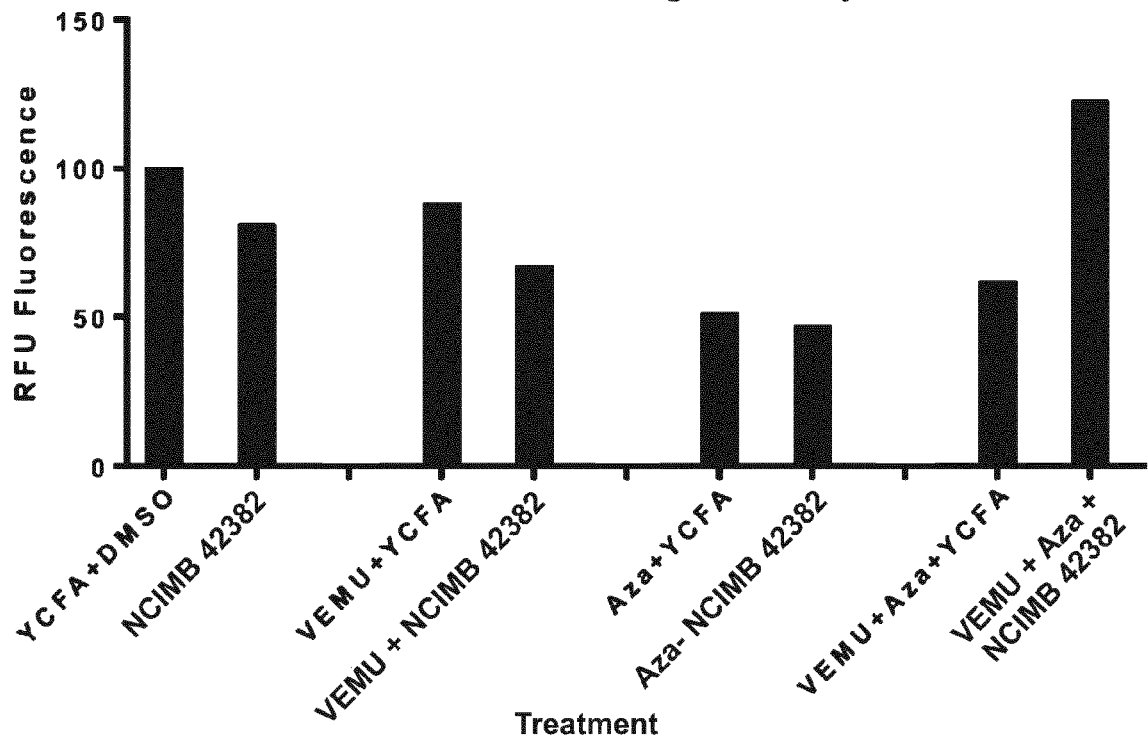
FIG. 15 451Lu cell line – soft agar growth

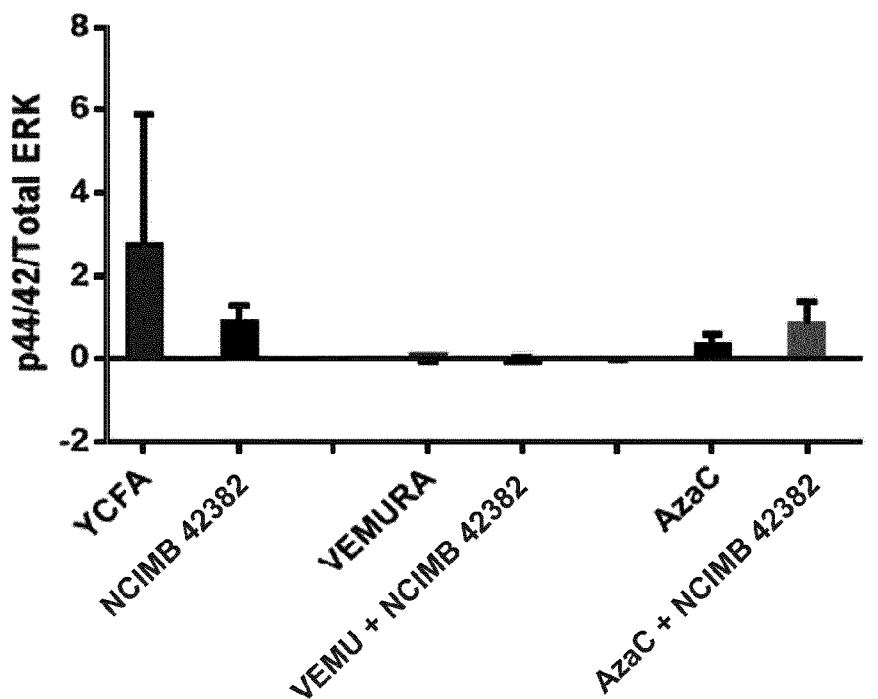
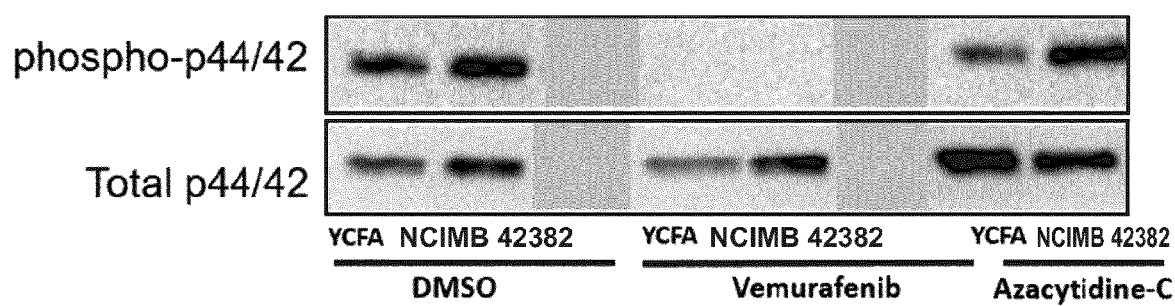
FIG. 16 451Lu cell line – ERK signalling

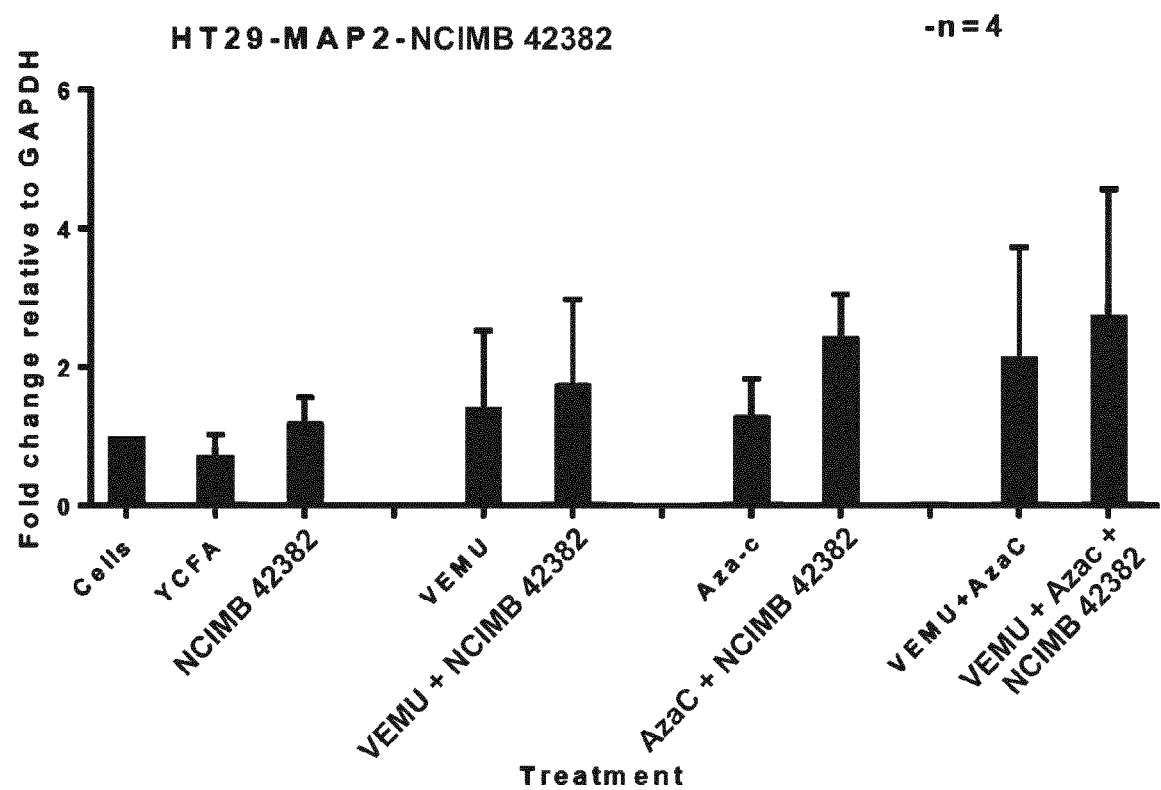

FIG. 18 HT-29 cell line – clonogenic survival
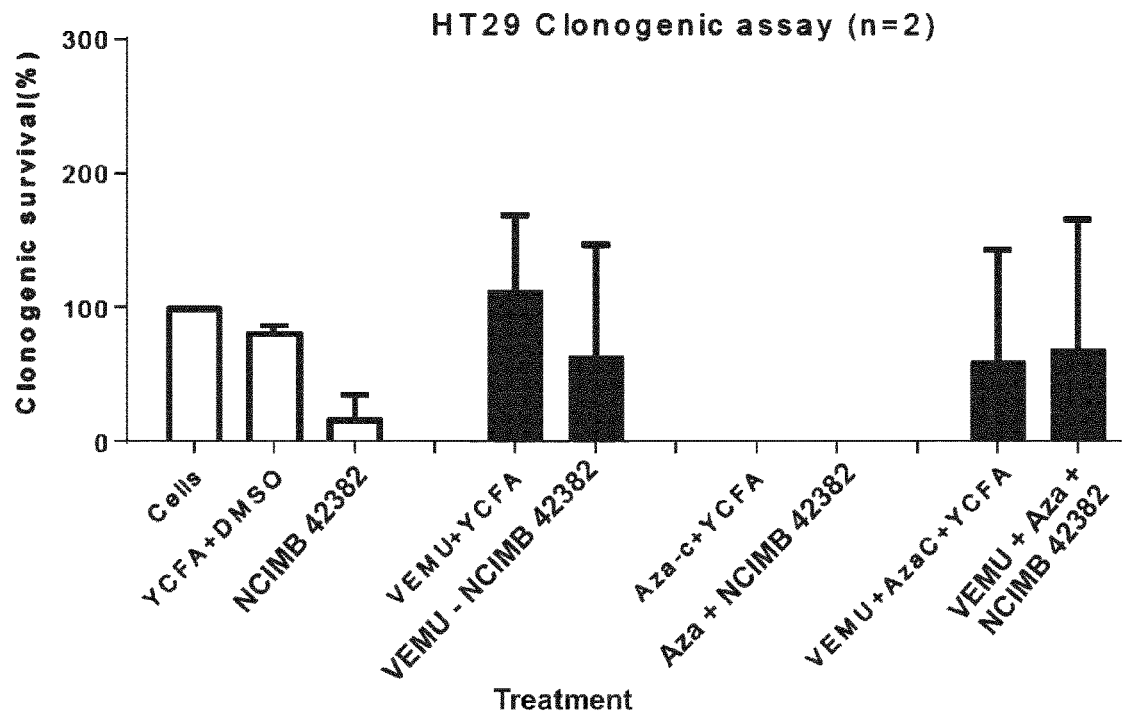
FIG. 19A HT-29 cell line - soft agar growth
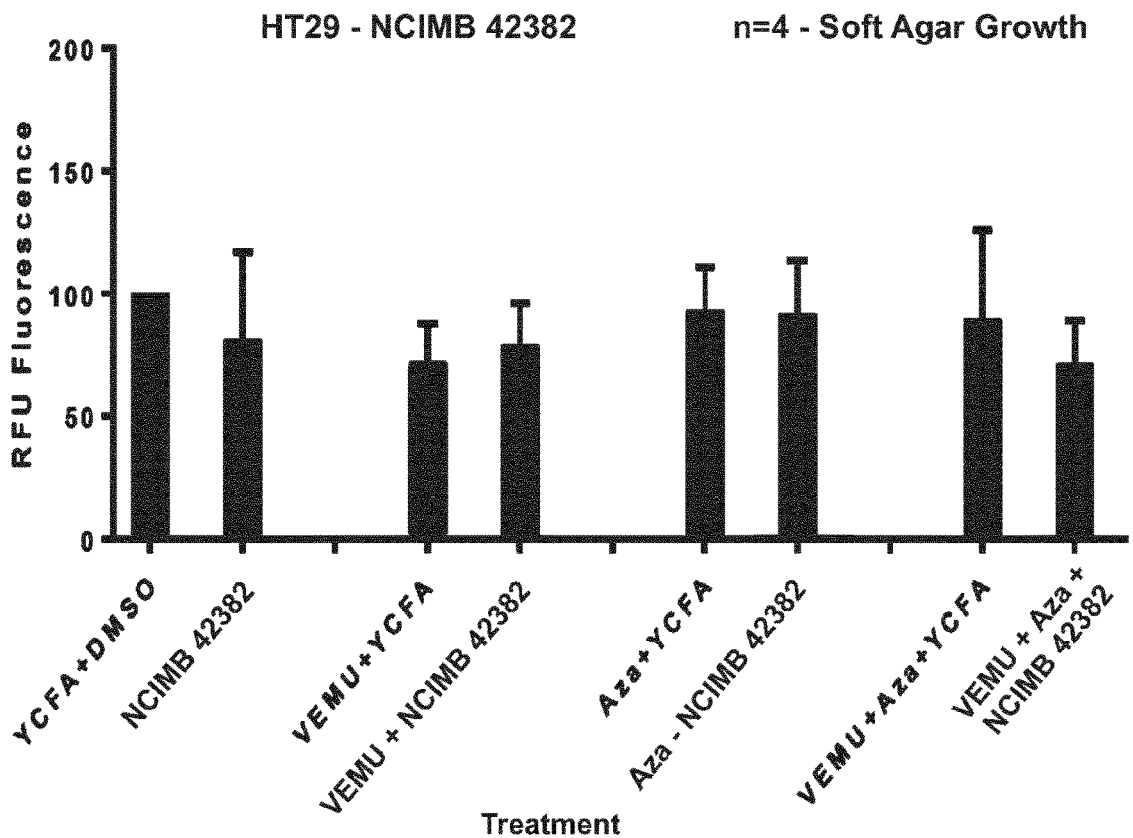

HT-29 cell line – soft agar growth (colonies after treatments)

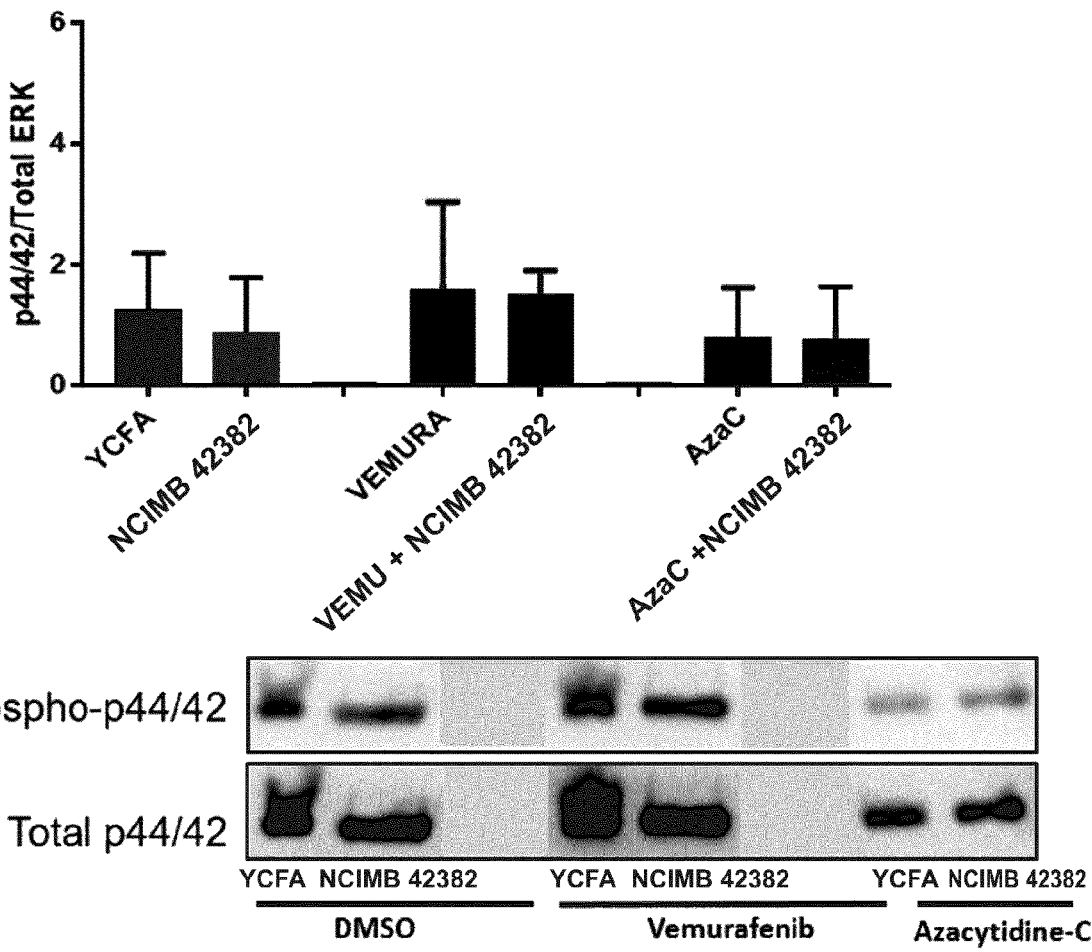

HT-29 cell line – GPR109a expression

TNF-a secretion from HT29 N=2

TNF-a secretion from HT29 N=2

Fermentation profile of NCIMB 42382

Splenocyte proliferation following treatment with *Parabacteroides* strains

Cytokine secretion from splenocytes following treatment with *Parabacteroides* strains

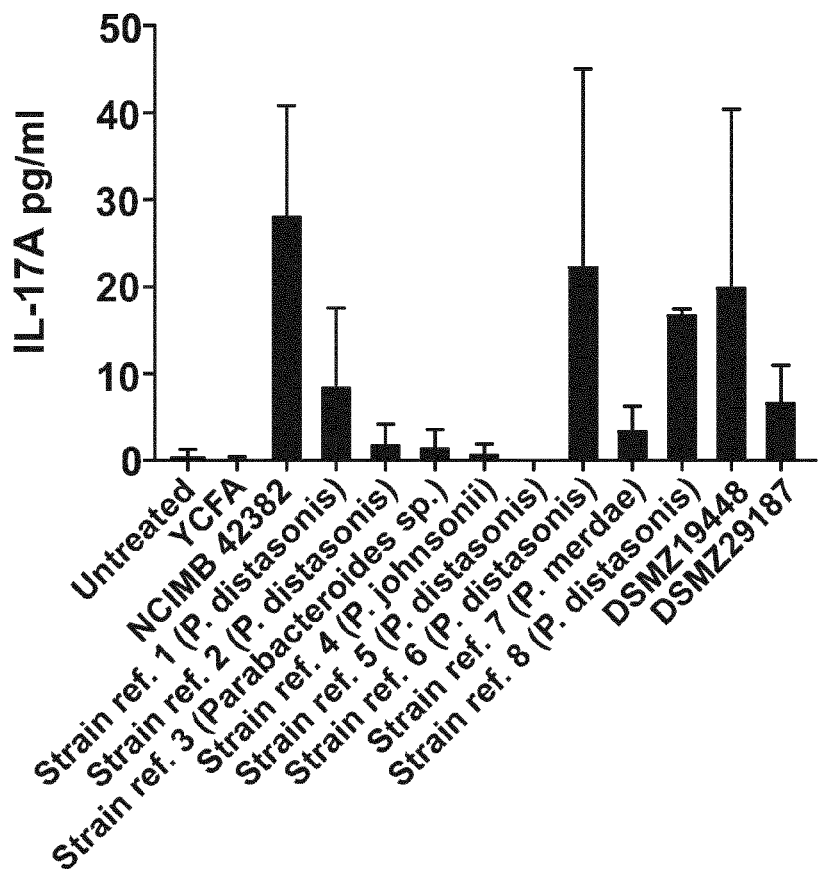

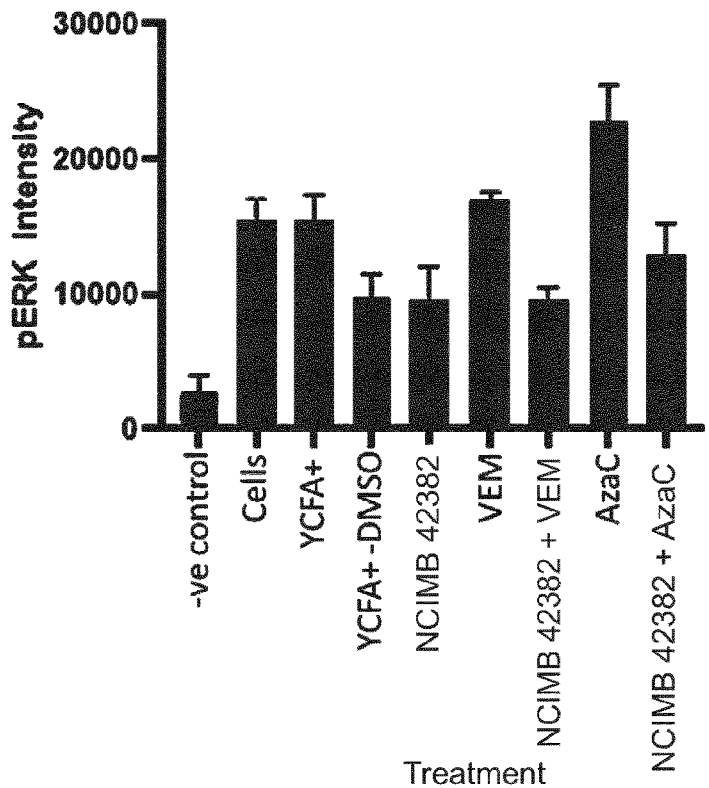
FIG. 27 SKMEL2-pERK
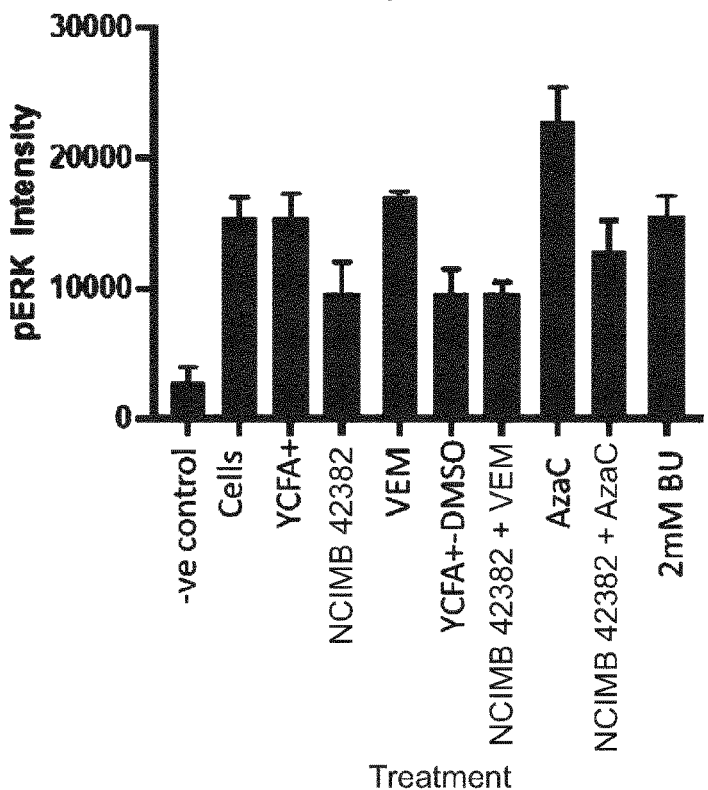
FIG. 28 SKMEL28-pERK n=123-both HT29-pERK

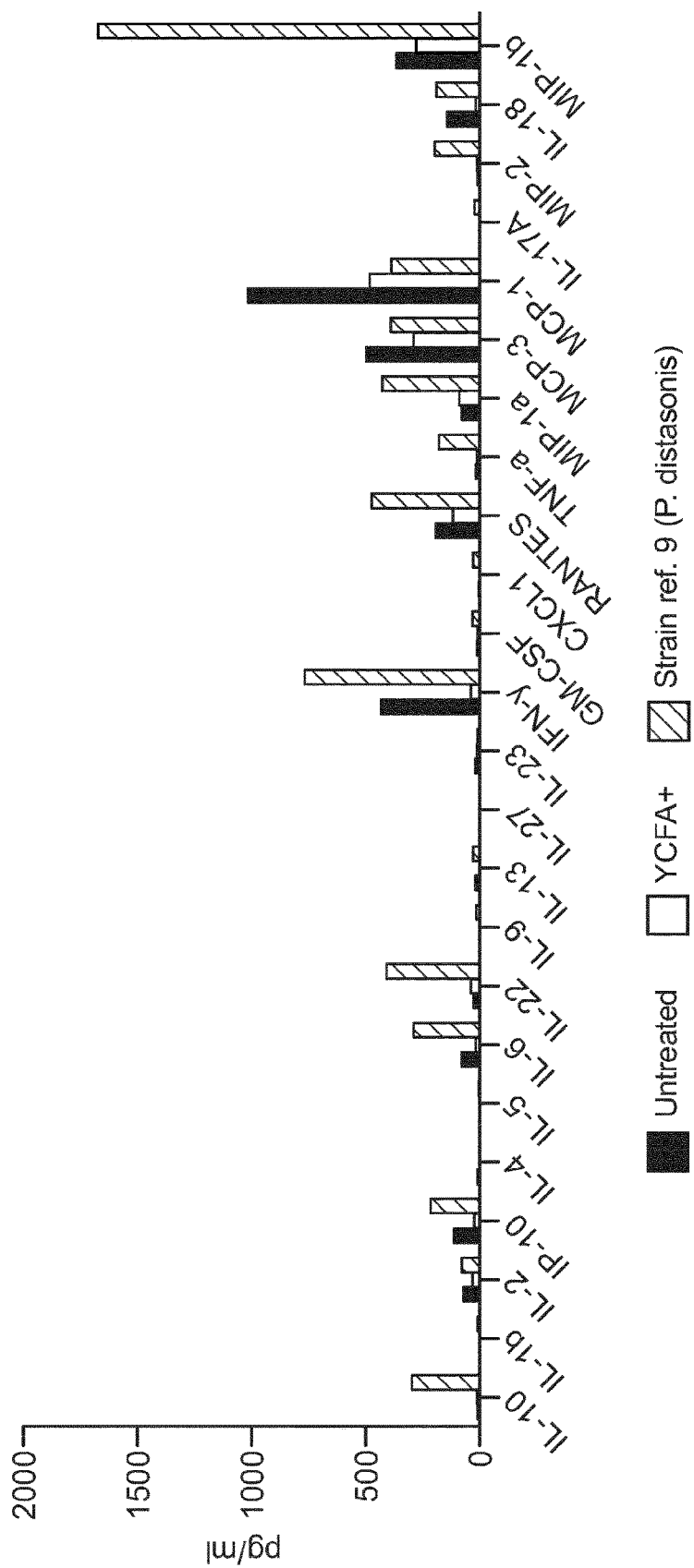

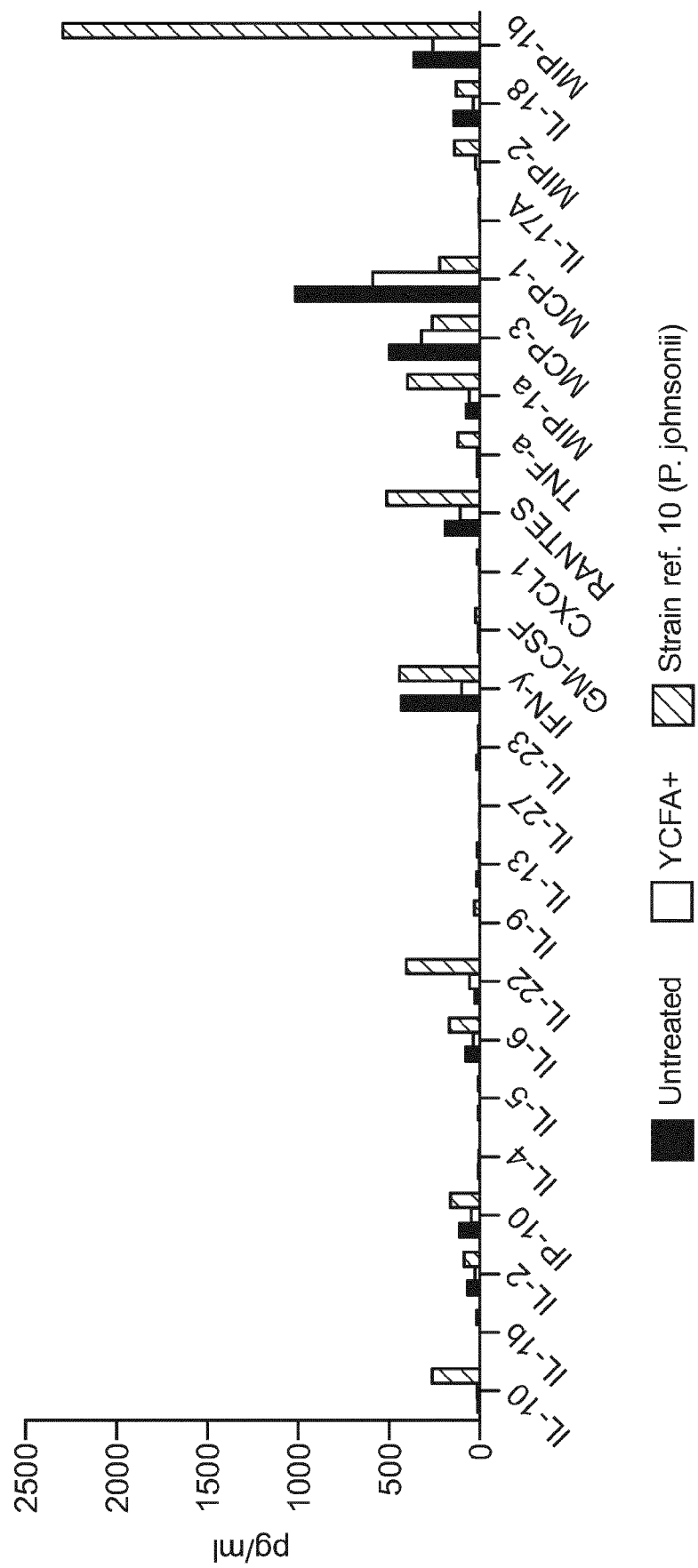

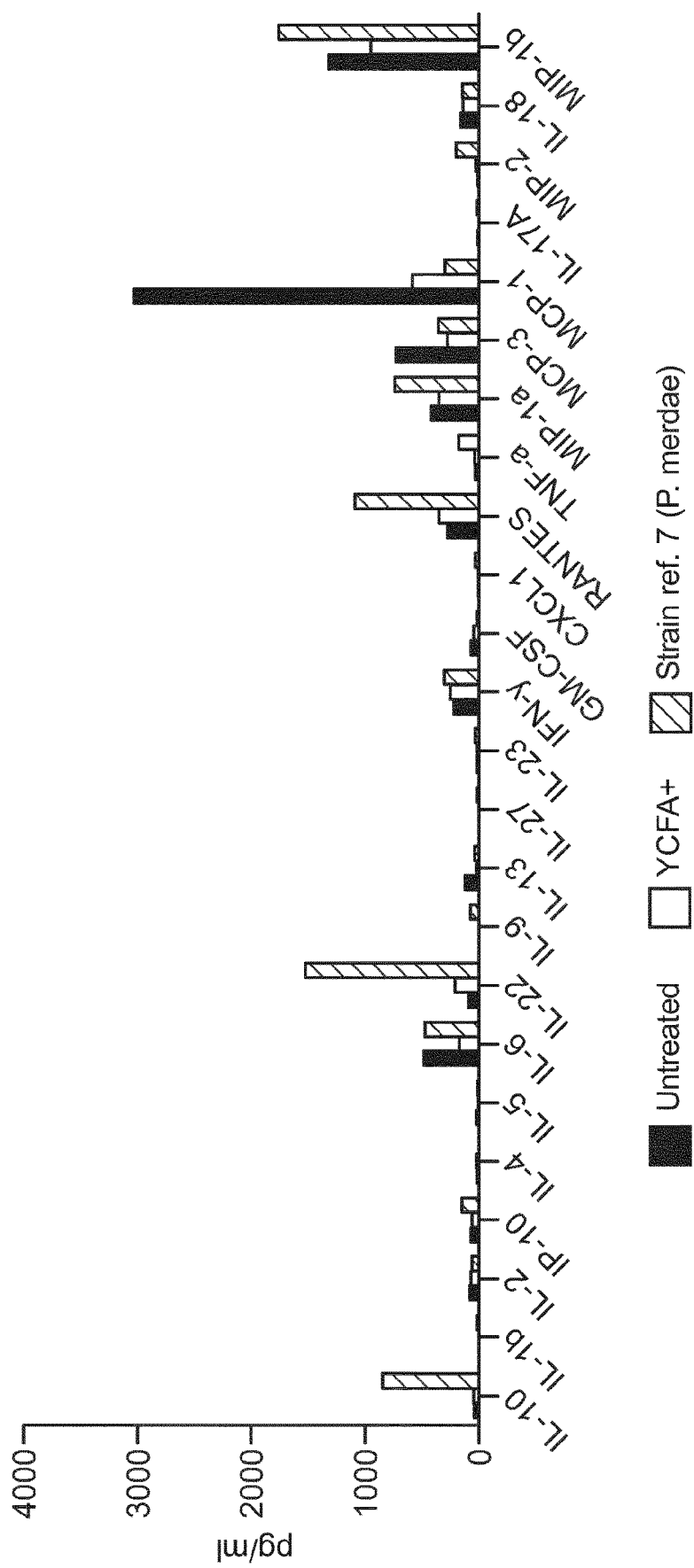

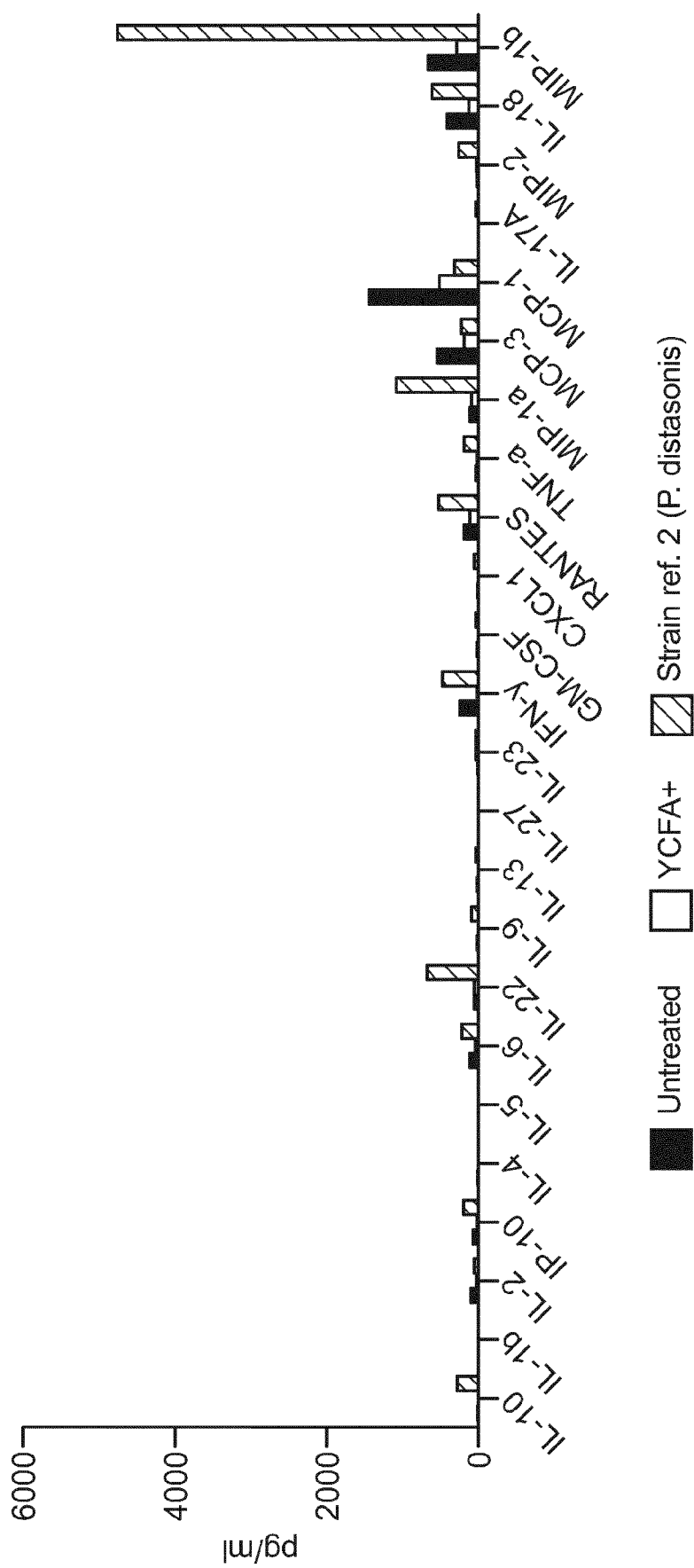

Cytokines secretion from mouse splenocytes N=1

Cytokines secretion from mouse splenocytes N=1

US 11,446,336 B2

COMPOSITIONS COMPRISING BACTERIAL STRAINS

CROSS-REFERENCE

This application is a continuation of International Application No. PCT/EP2019/084994, filed Dec. 12, 2019, which claims the benefit of European Application No. 18212087.3, filed Dec. 12, 2018, Great Britain Application No. 1916001.9, filed Nov. 4, 2019, and International Application No. PCT/EP2019/080131, filed Nov. 4, 2019, all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Apr. 27, 2021, is named 56708_753_301_SL.txt and is 53,123 bytes in size.

TECHNICAL FIELD

This invention is in the field of compositions comprising bacterial strains isolated from the mammalian digestive tract and the use of such compositions in the treatment of disease.

BACKGROUND TO THE INVENTION

The human intestine is thought to be sterile in utero, but it is exposed to a large variety of maternal and environmental microbes immediately after birth. Thereafter, a dynamic period of microbial colonization and succession occurs, which is influenced by factors such as delivery mode, environment, diet and host genotype, all of which impact upon the composition of the gut microbiota, particularly during early life. Subsequently, the microbiota stabilizes and becomes adult-like [1]. The human gut microbiota contains more than 500-1000 different phylotypes belonging essentially to two major bacterial divisions, the Bacteroidetes and the Firmicutes [2]. The successful symbiotic relationships arising from bacterial colonization of the human gut have yielded a wide variety of metabolic, structural, protective and other beneficial functions. The enhanced metabolic activities of the colonized gut ensure that otherwise indigestible dietary components are degraded with release of by-products providing an important nutrient source for the host. Similarly, the immunological importance of the gut microbiota is well-recognized and is exemplified in germfree animals which have an impaired immune system that is functionally reconstituted following the introduction of commensal bacteria [3-5].

Dramatic changes in microbiota composition have been documented in gastrointestinal disorders such as inflammatory bowel disease (IBD). For example, the levels of *Clostridium* cluster XIVa bacteria are reduced in IBD patients whilst numbers of *E. coli* are increased, suggesting a shift in the balance of symbionts and pathobionts within the gut [6-9].

In recognition of the potential positive effect that certain bacterial strains may have on the animal gut, various strains have been proposed for use in the treatment of various diseases (see, for example, [10-13]). Also, certain strains, including mostly *Lactobacillus* and *Bifidobacterium* strains, have been proposed for use in treating various inflammatory and autoimmune diseases that are not directly linked to the intestines (see [14] and [15] for reviews). However, the relationship between different diseases and different bacterial strains, and the precise effects of particular bacterial strains on the gut and at a systemic level and on any particular types of diseases are poorly characterised.

Recently, various Parabacteroides species have been investigated for their anti-inflammatory properties and therapeutic properties. For instance, *Parabacteroides distasonis* was demonstrated as having a broad anti-inflammatory effect in a number of disease models, such as severe asthma, rheumatoid arthritis and multiple sclerosis [16]. *Parabacteroides distasonis* has also been tested in an animal model of colorectal cancer, and on such cell lines in vitro as a membrane fraction [17]. Furthermore, *Parabacteroides distasonis* has been suggested as a prophylactic for colorectal cancer [18]. Anti-inflammatory effects of other Parabacteroides species such as *Parabacteroides goldsteinii* have been observed [19]. Furthermore, *Parabacteroides goldsteinii* has also been tested in in vivo cancer models [20], [21]. In addition, abundances of different Parabacteroides strains have been suggested to have both pro- and anti-tumourigenic associations, in pooled datasets from mice bearing different cancer types [22]. Accordingly, the mechanism by which Parabacteroides strains have an effect has not been fully characterised. Furthermore, specific cancer subtypes against which *Parabacteroides* strains are effective remain to be identified.

There is a requirement in the art for new cancer therapies, and for the potential effects of gut bacteria to be characterised so that new therapies using such bacteria can be developed.

SUMMARY OF THE INVENTION

The inventors have developed new therapies for treating and preventing cancer using gut bacteria.

The inventors have identified that bacterial strains from the genus *Parabacteroides* may be effective for treating or preventing cancer comprising oncogenic extracellular signal-related kinase (ERK) signalling. As described in the examples, administration of compositions comprising *Parabacteroides* strains can inhibit ERK signalling in cancer cell lines; that is, reduce cellular levels of phosphorylated ERK relative to total ERK protein. The inventors have also identified that treatment with *Parabacteroides* strains can reduce the clonogenic survival of cancer cell lines comprising oncogenic ERK signalling, in particular in melanoma and colorectal cancer cell lines. The inventors have also identified that treatment with *Parabacteroides* strains can induce gene expression of microtubule-associated protein 2 (MAP2), indicating particular utility in treating metastatic cancers. Furthermore, the inventors have identified that treatment with *Parabacteroides* strains can stimulate the immune system, by enhancing splenocyte proliferation and enhancing the secretion of immunostimulatory cytokines from splenocytes. Therefore, *Parabacteroides* strains may have particular utility in immunocompromised or immunosuppressed subjects.

In a first aspect, the invention provides a composition comprising a bacterial strain of the genus *Parabacteroides*, for use in a method of treating or preventing cancer, wherein the cancer comprises oncogenic ERK signalling.

Any cancer comprising oncogenic ERK signalling may be treated or prevented by a composition comprising a bacterial strain of the genus *Parabacteroides*, and preferably colorectal cancer, melanoma, small bowel cancer such as small bowel adenocarcinoma, prostate cancer, lung adenocarcinoma such as non-small cell lung adenocarcinoma, pancreatic cancer, bladder cancer, leukaemia such as hairy cell leukaemia or acute myeloid leukaemia, glioma, pilocytic astrocytoma, ovarian cancer, papillary or follicular thyroid cancer, seminoma, liver cancer, myelodysplastic syndrome, kidney cancer or Hodgkin's disease.

In preferred embodiments, the invention provides a composition comprising a bacterial strain of the genus *Parabacteroides*, for use in a method of treating or preventing cancer comprising an oncogenic mutation in BRAF, optionally wherein the cancer further comprises overexpression of BRAF. The inventors have identified that treatment with *Parabacteroides* strains can inhibit the clonogenic survival, inhibit ERK signalling and upregulate MAP2 gene expression in cancer cell lines comprising oncogenic BRAF mutations, in particular the oncogenic BRAF V600E mutation in colorectal cancer and melanoma cell lines. Therefore, in preferred embodiments, the invention also provides a composition comprising a bacterial strain of the genus *Parabacteroides*, for use in a method of treating or preventing cancer comprising an oncogenic mutation at position 600 of BRAF, preferably BRAF V600E. In especially preferred embodiments, the cancer is colorectal cancer or melanoma.

In addition to, or instead of, an oncogenic mutation at position 600 of BRAF (such as V600E), the cancer may comprise an oncogenic mutation selected from BRAF K601E, G469A, G469V, L597R, K601N, G464V, N581S, L597Q, A598V, G464R, G466A or G469E; optionally wherein the cancer is colorectal cancer. In another embodiment, in addition to, or instead of, the V600E mutation, the cancer may comprise an oncogenic mutation selected from BRAF V600K, V600R or V600D; optionally wherein the cancer is melanoma.

In preferred embodiments of the invention, the bacterial strain in the composition is of *Parabacteroides distasonis* or *Parabacteroides goldsteinii*, in particular *Parabacteroides distasonis*. Closely related strains may also be used, such as bacterial strains that have a 16S rRNA gene sequence that is (in increasing preference) at least 90%, 91%, 92%, 93%, 94%, 95%, 96%, 97%, 98%, 99%, 99.5% or 99.9% identical to the 16S rRNA gene sequence of a bacterial strain of *Parabacteroides distasonis*. The bacterial strain may have a 16S rRNA gene sequence that is (in increasing preference) at least 90%, 91%, 92%, 93% or 94% identical to SEQ ID NO:1, 2, 3, 4, 5, 6, 7, 8, 9, 10, 17, 18, 19, 20, 21, 22, 23, 24, 25, 26, 27, 28, 29, 30, 31 or 32. Preferably, the bacterial strain has a 16S rRNA gene sequence that is (in increasing preference) at least 95%, 96%, 97%, 98%, 99%, 99.5% or 99.9% identical to SEQ ID NO:1, 2, 3, 4, 5, 6, 7, 8, 9, 10, 17, 18, 19, 20, 21, 22, 23, 24, 25, 26, 27, 28, 29, 30, 31 or 32. Preferably, the sequence identity is to SEQ ID NO:9. Preferably, the bacterial strain for use in the invention has the 16S rRNA gene sequence represented by SEQ ID NO:9. Most preferably, the bacterial strain for use in the invention is of the *Parabacteroides distasonis* strain deposited under accession number NCIMB 42382.

In a further aspect, the invention also provides a composition comprising a bacterial strain of the species *Parabacteroides distasonis*, for use in a method of treating colorectal cancer, such as metastatic colorectal cancer. As shown in the examples, the inventors have found that *Parabacteroides distasonis* strains can inhibit clonogenic survival and ERK signalling in colorectal cancer cell lines.

In a further aspect, the invention also provides a composition comprising a bacterial strain of the species *Parabacteroides distasonis*, for use in a method of treating melanoma, such as metastatic melanoma. As shown in the examples, the inventors have found that *Parabacteroides distasonis* strains can inhibit clonogenic survival and ERK signalling in melanoma cell lines. Furthermore, the ability of *Parabacteroides distasonis* strains to induce MAP2 gene expression in melanoma cell lines indicates particular efficacy against metastatic melanoma.

In preferred embodiments, a BRAF inhibitor is administered simultaneously, separately or sequentially, relative to administration of the composition comprising a bacterial strain of the genus *Parabacteroides*. Preferably, the BRAF inhibitor is a selective inhibitor of $BRAF^{V600E}$, preferably selected from Vemurafenib, Dabrafinib or Encorafenib. More preferably, the BRAF inhibitor is Vemurafenib.

In a further aspect, the invention also provides a composition comprising a bacterial strain of the genus *Parabacteroides* and a BRAF inhibitor, preferably those defined above, for simultaneous, separate or sequential use in the treatment or prevention of cancer.

In other preferred embodiments, a cytidine analogue is administered simultaneously, separately or sequentially, relative to administration of the composition comprising a bacterial strain of the genus *Parabacteroides*. Preferably, the cytidine analogue is selected from Azacytidine-c, Decitabine, or Zebularine. More preferably, the cytidine analogue is Azacytidine-c.

In a further aspect, the invention also provides a composition comprising a bacterial strain of the genus *Parabacteroides* and a cytidine analogue, preferably those defined above, for simultaneous, separate or sequential use in the treatment or prevention of cancer.

In other preferred embodiments, a tubulin polymerisation inhibitor or tubulin depolymerisation inhibitor is administered simultaneously, separately or sequentially, relative to administration of the composition comprising a bacterial strain of the genus Parabacteroides. Preferably, the tubulin polymerisation inhibitor or tubulin depolymerisation inhibitor is selected from Paclitaxel, ABRAXANE® (Paclitaxel), Docetaxel, Epothilone, (+)-Discodermolide, Colchicine, Combretastatin, 2-Methoxyestradiol, E7010, Vincristine, Vinblastine, Vinorelbine or Vinflunine; more preferably Paclitaxel.

In a further aspect, the invention also provides a composition comprising a bacterial strain of the genus *Parabacteroides* and a tubulin polymerisation inhibitor or tubulin depolymerisation inhibitor, preferably those defined above, for simultaneous, separate or sequential use in the treatment or prevention of cancer. In a further aspect, the invention also provides a composition comprising a bacterial strain of the genus *Parabacteroides*, for use in cancer therapy by increasing the susceptibility of the cancer to a tubulin polymerisation or depolymerisation inhibitor, preferably those defined above.

In certain embodiments, the composition of the invention comprises one or more pharmaceutically acceptable excipients or carriers.

In certain embodiments, the composition of the invention comprises a bacterial strain that has been lyophilised. Lyophilisation is an effective and convenient technique for preparing stable compositions that allow delivery of bacteria.

In certain embodiments, the invention provides a food product comprising the composition as described above.

In certain embodiments, the invention provides a vaccine composition comprising the composition as described above.

In a further aspect, the invention also provides a composition comprising a bacterial strain of the genus *Parabacte-*

*roides*, for use in a method of inhibiting ERK1 and/or ERK2 signalling in the treatment or prevention of cancer.

In a further aspect, the invention also provides a composition comprising a bacterial strain of the genus *Parabacteroides*, for use in a method of inhibiting ERK1 and/or ERK2 phosphorylation in the treatment or prevention of cancer.

In a further aspect, the invention also provides a composition comprising a bacterial strain of the genus *Parabacteroides*, for use in a method of inducing MAP2 gene expression in the treatment or prevention of cancer.

In a further aspect, the invention also provides a composition comprising a bacterial strain of the genus *Parabacteroides* for use in a method of inducing GPR109a gene expression in the treatment or prevention of cancer.

In a further aspect, the invention provides a composition comprising a bacterial strain of the genus *Parabacteroides* for use in a method of inducing TNF-α cytokine production in the treatment or prevention of cancer.

In a further aspect, the invention provides a composition comprising a bacterial strain of the genus *Parabacteroides* for use in a method of inducing IL-1B cytokine production in the treatment or prevention of cancer.

In a further aspect, the invention provides a composition comprising a bacterial strain of the genus *Parabacteroides* for use in a method of inducing IL-2 cytokine production in the treatment or prevention of cancer.

In a further aspect, the invention provides a composition comprising a bacterial strain of the genus *Parabacteroides* for use in a method of inducing GM-CSF cytokine production in the treatment or prevention of cancer.

In a further aspect, the invention provides a composition comprising a bacterial strain of the genus *Parabacteroides* for use in a method of inducing IFN-γ cytokine production in the treatment or prevention of cancer.

In a further aspect, the invention provides a composition comprising a bacterial strain of the genus *Parabacteroides* for use in a method of inducing IL-27 cytokine production in the treatment or prevention of cancer.

In a further aspect, the invention provides a composition comprising a bacterial strain of the genus *Parabacteroides* for use in a method of inducing IP-10 cytokine production in the treatment or prevention of cancer.

In a further aspect, the invention provides a composition comprising a bacterial strain of the genus *Parabacteroides* for use in a method of inducing RANTES cytokine production in the treatment or prevention of cancer.

In a further aspect, the invention provides a composition comprising a bacterial strain of the genus *Parabacteroides* for use in a method of inducing MIP-1α cytokine production in the treatment or prevention of cancer.

In a further aspect, the invention provides a composition comprising a bacterial strain of the genus *Parabacteroides* for use in a method of inducing MIP-1ß cytokine production in the treatment or prevention of cancer.

In a further aspect, the invention provides a composition comprising a bacterial strain of the genus *Parabacteroides* for use in a method of inducing MIP-2 cytokine production in the treatment or prevention of cancer.

In a further aspect, the invention provides a composition comprising a bacterial strain of the genus *Parabacteroides* for use in a method of inducing IL-10 cytokine production in the treatment or prevention of cancer.

In a further aspect, the invention provides a composition comprising a bacterial strain of the genus *Parabacteroides* for use in a method of inducing IL-22 cytokine production in the treatment or prevention of cancer.

In a further aspect, the invention provides a composition comprising a bacterial strain of the genus *Parabacteroides* for use in a method of inducing IL-5 cytokine production in the treatment or prevention of cancer.

In a further aspect, the invention provides a composition comprising a bacterial strain of the genus *Parabacteroides* for use in a method of inducing IL-18 cytokine production in the treatment or prevention of cancer.

In a further aspect, the invention provides a composition comprising a bacterial strain of the genus *Parabacteroides* for use in a method of inducing IL-23 cytokine production in the treatment or prevention of cancer.

In a further aspect, the invention provides a composition comprising a bacterial strain of the genus *Parabacteroides* for use in a method of inducing CXCL1 cytokine production in the treatment or prevention of cancer.

In a further aspect, the invention provides a composition comprising a bacterial strain of the genus *Parabacteroides* for use in a method of inducing IL-6 cytokine production in the treatment or prevention of cancer.

In a further aspect, the invention provides a composition comprising a bacterial strain of the genus *Parabacteroides*, for use in the treatment or prevention of cancer in an immunocompromised or immunosuppressed subject.

In further aspects, the invention also provides various bacterial strains of the genus *Parabacteroides* (as set out below in the Bacterial strains section); preferably wherein the bacterial strains are for use in therapy.

Additionally, the invention provides a method of treating or preventing cancer, wherein the cancer comprises oncogenic ERK signalling, comprising administering a composition comprising a bacterial strain of the genus *Parabacteroides*.

All microorganism deposits were made under the terms of the Budapest Treaty and thus viability of the deposit is assured. Maintenance of a viable culture is assured for 30 years from the date of deposit. During the pendency of the application, access to the deposit will be afforded to one determined by the Commissioner of the United States Patent and Trademark Office to be entitled thereto. All restrictions on the availability to the public of the deposited microorganisms will be irrevocably removed upon the granting of a patent for this application. The deposit will be maintained for a term of at least thirty (30) years from the date of the deposit or for the enforceable life of the patent or for a period of at least five (5) years after the most recent request for the furnishing of a sample of the deposited material, whichever is longest. The deposit will be re-placed should it become necessary due to inviability, contamination or loss of capability to function in the manner described in the specification.

In certain embodiments, the invention provides:
1. A composition comprising a bacterial strain of the genus *Parabacteroides*, for use in a method of treating or preventing cancer in a subject; wherein the cancer comprises oncogenic ERK signalling.
2. A composition for use according to embodiment 1, wherein the cancer comprises an oncogenic mutation in, or overexpression of, BRAF, NRAS, ARAF, CRAF, EGFR, GRB2, SOS, HRAS, KRAS, such as KRAS4A or KRAS4B, MEK1, MEK2, ERK1 or ERK2.
3. A composition for use according to any preceding embodiment, wherein the cancer comprises an oncogenic mutation in, or downregulated expression of, RSK, DUSP1, DUSP5, DUSP6 or SPRY.
4. A composition for use according to embodiment 2, wherein the cancer comprises an oncogenic mutation in, or overexpression of, BRAF, KRAS, ARAF, CRAF, EGFR, GRB2, SOS, HRAS, MEK1, MEK2, ERK1 or ERK2.
5. A composition for use according to embodiment 2, wherein the cancer comprises an oncogenic mutation in BRAF, NRAS, KRAS, ARAF, CRAF, EGFR, GRB2, SOS, HRAS, MEK1, MEK2, ERK1 or ERK2.
6. The composition for use according to any preceding embodiment, wherein the cancer comprises an oncogenic mutation in BRAF or NRAS, optionally wherein the cancer further comprises overexpression of BRAF or NRAS.
7. The composition for use according to embodiment 6, wherein the cancer comprises an oncogenic mutation in BRAF, optionally wherein the cancer further comprises overexpression of BRAF.
8. The composition for use according to embodiment 7, wherein the cancer comprises an oncogenic mutation at position 600 of BRAF.
9. The composition for use according to any of embodiments 6-8, wherein the cancer comprises an oncogenic mutation selected from BRAF V600E, K601E, G469A, G469V, L597R, K601N, G464V, N581S, L597Q, A598V, G464R, G466A or G469E; optionally wherein the cancer is colorectal cancer.
10. The composition for use according to any of embodiments 6-8, wherein the cancer comprises an oncogenic mutation selected from BRAF V600E, V600K, V600R or V600D; optionally wherein the cancer is melanoma.
11. The composition for use according to any of embodiments 6-10, wherein the cancer comprises the mutation BRAF V600E.
12. The composition for use according to any of embodiments 6-11, wherein the cancer comprises the oncogenic mutation NRAS Q61R, optionally wherein the cancer is melanoma.
13. The composition for use according to any of claims 1-5, wherein the cancer comprises an oncogenic mutation in KRAS, preferably in position 13 of KRAS, more preferably wherein the oncogenic mutation is KRAS G13D.
14. The composition for use according to any preceding embodiment, wherein the cancer is selected from colorectal cancer, melanoma, small bowel cancer such as small bowel adenocarcinoma, prostate cancer, lung adenocarcinoma such as non-small cell lung adenocarcinoma, pancreatic cancer, bladder cancer, leukaemia such as hairy cell leukaemia or acute myeloid leukaemia, glioma, pilocytic astrocytoma, ovarian cancer, papillary or follicular thyroid cancer, seminoma, liver cancer, myelodysplastic syndrome, kidney cancer or Hodgkin's disease.
15. The composition for use according to any preceding embodiment, wherein the cancer is colorectal cancer.
16. The composition for use according to any of embodiments 1-14, wherein the cancer is melanoma.
17. The composition for use according to any preceding embodiment, wherein the bacterial strain is of the species *Parabacteroides* distasonis, *Parabacteroides goldsteinii* or *Parabacteroides merdae*.
18. The composition for use according to embodiment 17, wherein the bacterial strain is of the species *Parabacteroides distasonis* or *Parabacteroides goldsteinii*.
19. The composition for use according to embodiment 18, wherein the bacterial strain is of the species *Parabacteroides distasonis*.
20. The composition for use according to embodiment 18, wherein the bacterial strain is of the species *Parabacteroides goldsteinii*.
21. A composition comprising a bacterial strain of the species *Parabacteroides distasonis*, for use in a method of treating colorectal cancer.
22. A composition comprising a bacterial strain of the species *Parabacteroides distasonis*, for use in a method of treating melanoma.
23. The composition for use according to any preceding embodiment, wherein the cancer is metastatic.
24. The composition for use according to any preceding embodiment, wherein the bacterial strain has a 16s rRNA gene sequence that is at least 90%, 91%, 92%, 93%, 94%, 95%, 96%, 97%, 98%, 99%, 99.5% or 99.9% identical to SEQ ID NO:1, 2, 3, 4, 5, 6, 7, 8, 9, 10, 17, 18, 19, 20, 21, 22, 23, 24, 25, 26, 27, 28, 29, 30, 31 or 32.
25. The composition for use according to embodiment 24, wherein the bacterial strain has a 16s rRNA gene sequence that is at least 90%, 91%, 92%, 93%, or 94%, preferably 95%, 96%, 97%, 98%, 99%, 99.5% or 99.9% identical to SEQ ID NO:9, more preferably wherein the bacterial strain has the 16s rRNA gene sequence represented by SEQ ID NO:9.
26. The composition for use according to embodiment 25, wherein the bacterial strain is of the *Parabacteroides distasonis* strain deposited under accession number NCIMB 42382.
27. The composition of any of embodiments 1-19 or 21-24, wherein the bacterial strain has a 16s rRNA gene sequence that is at least 98%, 99%, 99.5% or 99.9% identical to SEQ ID NO: 9, 19, 20, 23, 24, 26 or 27, or wherein the bacterial strain has a 16s rRNA gene sequence represented by SEQ ID NO: 9, 19, 20, 23, 24, or 27.
28. The composition of any of embodiments 1-18, 20, 23 or 24, wherein the bacterial strain has a 16s rRNA gene sequence that is at least 98%, 99%, 99.5% or 99.9% identical to SEQ ID NO: 17 or 18, or wherein the bacterial strain has a 16s rRNA gene sequence represented by SEQ ID NO: 17 or 18.
29. The composition of embodiment 28, wherein the bacterial strain is the strain deposited under either accession number DSMZ19448 or DSMZ29187.
30. The composition of any of embodiments 1-17, 23 or 24, wherein the bacterial strain has a 16s rRNA gene sequence that is at least 98%, 99%, 99.5% or 99.9% identical to SEQ ID NO: 25 or wherein the bacterial strain has a 16s rRNA gene sequence represented by SEQ ID NO: 25.
31. The composition of any of embodiments 1-6 or 21-23, wherein the bacterial strain has a 16s rRNA gene sequence that is at least 98%, 99%, 99.5% or 99.9% identical to SEQ ID NO: 22 or 28, or wherein the bacterial strain has a 16s rRNA gene sequence represented by SEQ ID NO: 22 or 28.
32. The composition for use according to any preceding embodiment, in a method of inhibiting ERK1 and/or ERK2 signalling in the treatment or prevention of the cancer.
33. The composition for use according to any preceding embodiment, in a method of inhibiting ERK1 and/or ERK2 phosphorylation in the treatment or prevention of the cancer.
34. The composition for use according to any preceding embodiment, in a method of inducing MAP2 gene expression in the treatment or prevention of the cancer.
35. The composition for use according to any preceding embodiment, in a method of inducing GPR109a gene expression in the treatment or prevention of the cancer.

36. The composition for use according to any preceding embodiment, in a method of inducing TNF-α cytokine production in the treatment or prevention of the cancer.
37. The composition for use according to any preceding embodiment, in a method of inducing IL-1B cytokine production, in the treatment or prevention of the cancer.
38. The composition for use according to any preceding embodiment, in a method of inducing IL-2 cytokine production in the treatment or prevention of the cancer.
39. The composition for use according to any preceding embodiment, in a method of inducing GM-CSF cytokine production in the treatment or prevention of the cancer.
40. The composition for use according to any preceding embodiment, in a method of inducing IFN-γ cytokine production in the treatment or prevention of the cancer.
41. The composition for use according to any preceding embodiment, in a method of inducing IL-27 cytokine production in the treatment or prevention of the cancer.
42. The composition for use according to any preceding embodiment, in a method of inducing IP-10 cytokine production in the treatment or prevention of the cancer.
43. The composition for use according to any preceding embodiment, in a method of inducing RANTES cytokine production in the treatment or prevention of the cancer.
44. The composition for use according to any preceding embodiment, in a method of inducing MIP-la cytokine production in the treatment or prevention of the cancer.
45. The composition for use according to any preceding embodiment, in a method of inducing MIP-1B cytokine production in the treatment or prevention of the cancer.
46. The composition for use according to any preceding embodiment, in a method of inducing MIP-2 cytokine production in the treatment or prevention of the cancer.
47. The composition for use according to any preceding embodiment, in a method of inducing IL-10 cytokine production in the treatment or prevention of the cancer.
48. The composition for use according to any preceding embodiment, in a method of inducing IL-22 cytokine production in the treatment or prevention of the cancer.
49. The composition for use according to any preceding embodiment, in a method of inducing IL-5 cytokine production in the treatment or prevention of the cancer.
50. The composition for use according to any preceding embodiment, in a method of inducing IL-18 cytokine production in the treatment or prevention of the cancer.
51. The composition for use according to any preceding embodiment, in a method of inducing IL-23 cytokine production in the treatment or prevention of the cancer.
52. The composition for use according to any preceding embodiment, in a method of inducing CXCL1 cytokine production in the treatment or prevention of the cancer.
53. The composition for use according to any preceding embodiment, in a method of inducing IL-6 cytokine production in the treatment or prevention of the cancer.
54. The composition for use according to any preceding embodiment, in a method of reducing tumour size, tumour growth, preventing or inhibiting metastasis, or preventing angiogenesis in the treatment or prevention of the cancer.
55. The composition for use according to any preceding embodiment, in a method of inhibiting metastasis in the treatment of the cancer.
56. The composition for use according to any preceding embodiment, wherein the method comprises simultaneous, separate or sequential administration of a BRAF inhibitor, relative to administration of the composition.
57. The composition for use according to embodiment 56, wherein the BRAF selectively inhibits BRAF$^{V600E}$, preferably wherein the BRAF inhibitor is selected from Vemurafenib, Dabrafinib or Encorafenib.
58. The composition for use according to embodiment 57, wherein the BRAF inhibitor is Vemurafenib.
59. The composition for use according to any preceding embodiment, wherein the method comprises simultaneous, separate or sequential administration of a cytidine analogue, relative to administration of the composition.
60. The composition for use according to embodiment 59, wherein the cytidine analogue is selected from Azacytidine-c, Decitabine, or Zebularine.
61. The composition for use according to embodiment 60, wherein the cytidine analogue is Azacytidine-c.
62. The composition for use according to any preceding embodiment, wherein the method comprises simultaneous, separate or sequential administration of a tubulin polymerisation inhibitor or tubulin depolymerisation inhibitor, relative to administration of the composition.
63. The composition for use according to embodiment 62, wherein the tubulin polymerisation inhibitor or tubulin depolymerisation inhibitor is selected from Paclitaxel, Abraxane, Docetaxel, Epothilone, (+)-Discodermolide, Colchicine, Combretastatin, 2-Methoxyestradiol, E7010, Vincristine, Vinblastine, Vinorelbine or Vinflunine.
64. The composition for use according to any preceding embodiment, wherein the composition is for oral administration, optionally wherein the composition is administered orally.
65. The composition for use according to embodiments 1-63, wherein the composition is for intratumoural administration, optionally wherein the composition is administered intratumourally.
66. The composition for use according to any preceding embodiment, wherein the composition comprises one or more pharmaceutically acceptable excipients or carriers.
67. The composition for use according to any preceding embodiment, wherein the bacterial strain is lyophilised.
68. The composition for use according to any preceding embodiment, wherein the mutation status of the cancer has been determined prior to administration of the composition, preferably wherein the cancer has been determined as comprising an oncogenic mutation as recited in any of embodiments 2-13 prior to administration of the composition.
69. The composition for use according to any preceding embodiment, wherein the subject is immunocompromised.
70. The composition for use according to any preceding embodiment, wherein the subject is immunosuppressed.
71. The composition for use according to embodiment 69 or 70, wherein the subject has an elevated number of regulatory T cells (Tregs) within a lymph node, such as a metastatic lymph node, compared to a lymph node of a subject free of cancer.
72. The composition for use according to any of embodiments 63-71, wherein the subject has an elevated number of Tregs within a volume of peripheral blood mononuclear cells (PBMCs), compared to the same volume of PBMCs from a subject free of cancer.
73. The composition for use according to any of embodiments 63-72, wherein the subject has an elevated number of myeloid dendritic cells (mDCs) within a volume of PBMCs, compared to the same volume of PBMCs from a subject free of cancer.
74. The composition for use according to any of embodiments 63-73, wherein the subject has an elevated number of plasmacytoid dendritic cells (pDCs) within a volume of PBMCs, compared to the same volume of PBMCs from a subject free of cancer.

75. A food product comprising the composition of any preceding embodiment, for the use of any preceding embodiment.
76. A vaccine composition comprising the composition of any preceding embodiment, for the use of any preceding embodiment.
77. The composition for use according to any preceding embodiment, wherein the bacterial strain is live when administered to the subject.
78. A composition for use according to any preceding embodiment, wherein the bacterial strain is administered to a human subject.
79. A composition for use according to any preceding embodiment, wherein the composition does not contain any other bacterial strains or species or wherein the composition comprises only de minimis or biologically irrelevant amounts of other bacterial strains or species.

BRIEF DESCRIPTION OF DRAWINGS

FIG. 1: Gene expression of MAP2 in the SKMEL2 cell line following various treatments, relative to GAPDH ("YCFA"=YCFA+).

FIG. 2: Clonogenic survival of the SKMEL2 cell line following various treatments ("YCFA"=YCFA+).

FIG. 3: Soft agar growth of the SKMEL2 cell line following various treatments ("YCFA"=YCFA+).

FIG. 4: ERK signalling (phosphorylated ERK1 and 2 (p44 and p42)/total ERK) in the SKMEL2 cell line following various treatments ("YCFA"=YCFA+).

FIG. 5: Gene expression of MAP2 in the SKMEL28 cell line following various treatments, relative to GAPDH ("YCFA"=YCFA+).

FIG. 6: Clonogenic survival of the SKMEL28 cell line following various treatments ("YCFA"=YCFA+).

FIG. 7: Soft agar growth of the SKMEL28 cell line following various treatments ("YCFA"=YCFA+).

FIG. 9: Gene expression of MAP2 in the SKMEL31 cell line following various treatments, relative to GAPDH ("YCFA"=YCFA+).

FIG. 10: Clonogenic survival of the SKMEL31 cell line following various treatments ("YCFA"=YCFA+).

FIG. 12: ERK signalling (phosphorylated ERK1 and 2 (p44 and p42)/total ERK) in the SKMEL31 cell line following various treatments ("YCFA"=YCFA+).

FIG. 13: Gene expression of MAP2 in the 451Lu cell line following various treatments, relative to GAPDH ("YCFA"=YCFA+).

FIG. 14: Clonogenic survival of the 451Lu cell line following various treatments ("YCFA"=YCFA+).

FIG. 15: Soft agar growth of the 451Lu cell line following various treatments ("YCFA"=YCFA+).

FIG. 16: ERK signalling (phosphorylated ERK1 and 2 (p44 and p42)/total ERK) in the 451Lu cell line following various treatments ("YCFA"=YCFA+).

FIG. 17: Gene expression of MAP2 in the HT-29 cell line following various treatments, relative to GAPDH ("YCFA"=YCFA+).

FIG. 18: Clonogenic survival of the HT-29 cell line following various treatments ("YCFA"=YCFA+).

FIG. 19A: Soft agar growth of the HT-29 cell line following various treatments ("YCFA"=YCFA+).

FIG. 20: ERK signalling (phosphorylated ERK1 and 2 (p44 and p42)/total ERK) in the HT29 cell line following various treatments ("YCFA"=YCFA+).

FIG. 27: Phospho-ERK (pERK) staining intensity in the SKMEL2 melanoma cell line, following various treatments ("VEM"=Vemurafenib, "AzaC"=Azacytidine C).

FIG. 28: Phospho-ERK (pERK) staining intensity in the SKMEL28 melanoma cell line, following various treatments ("VEM"=Vemurafenib, "AzaC"=Azacytidine C, BU=2 mM sodium butyrate).

FIGS. 33A-33I: Cytokine secretion from splenocytes following treatment with various *Parabacteroides* strains— (FIG. 33A) strain ref 9 (*P. distasonis*), (FIG. 33B) strain ref 10 (*P. johnsonii*), (FIG. 33C) strain ref 7 (*P. merdae*), (FIG. 33D) strain ref 11 (*Parabacteroides* sp.), (FIG. 33E) strain ref 2 (*P. distasonis*), (FIG. 33F) strain ref 12 (*Parabacteroides* sp.), (FIG. 33G) strain ref 13 (*Parabacteroides* sp.), (FIG. 33H) strain ref 14 (*Parabacteroides* sp.) and (FIG. 33I) strain ref 15 (*Parabacteroides* sp.).

DISCLOSURE OF THE INVENTION

Bacterial Strains

Figure 8:
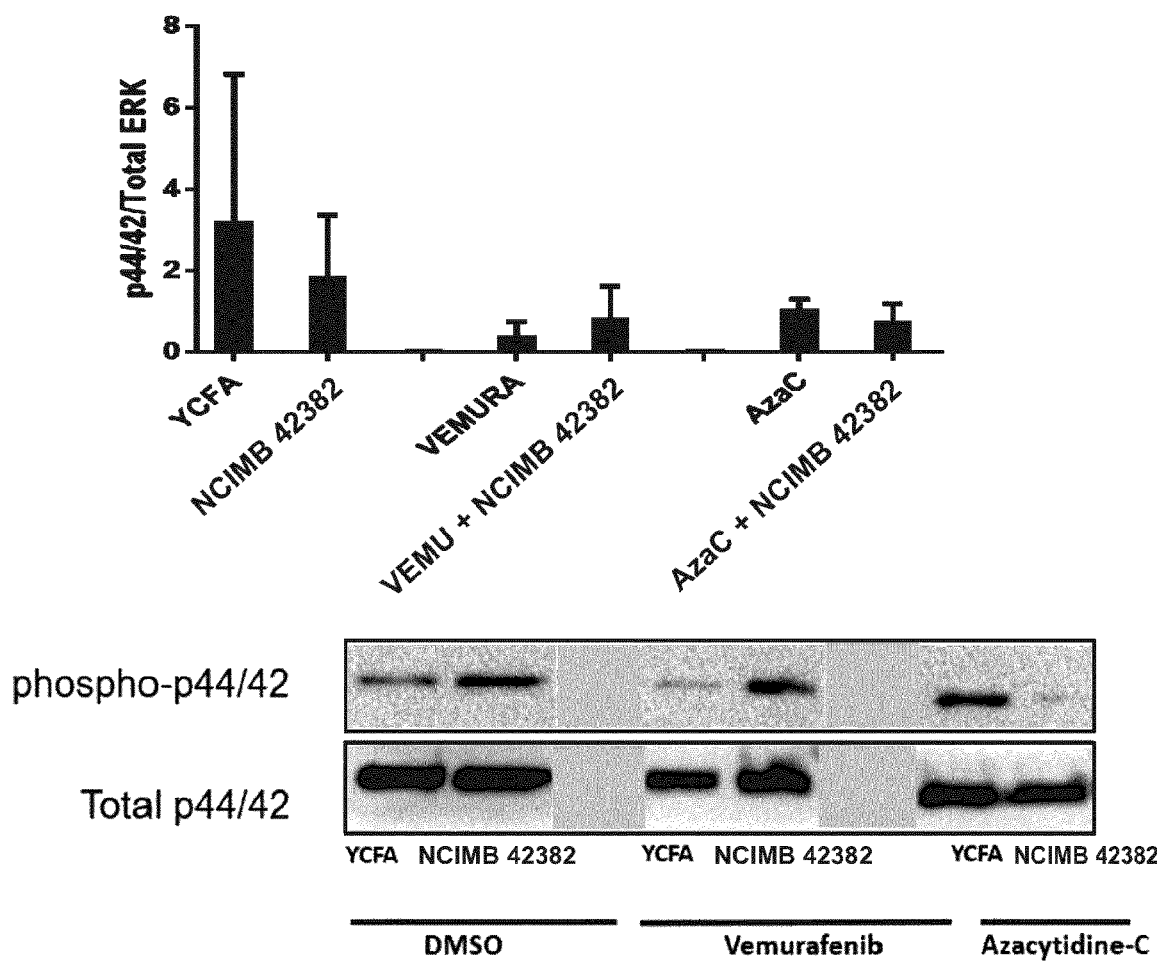
FIG. 8: ERK signalling (phosphorylated ERK1 and 2 (p44 and p42)/total ERK) in the SKMEL28 cell line following various treatments ("YCFA"=YCFA+).

The compositions of the invention comprise a bacterial strain of the genus *Parabacteroides*. The examples indicate that bacteria of this genus are useful for treating or preventing treating or preventing cancer, wherein the cancer comprises oncogenic ERK signalling.

Examples of *Parabacteroides* species for use in the invention include *Parabacteroides* distasonis, *Parabacteroides goldsteinii, Parabacteroides merdae* and *Parabacteroides johnsonii. Parabacteroides gordonii* is a further exemplary species for use in the invention. The preferred bacterial strains are of the species *Parabacteroides* distasonis, *Parabacteroides goldsteinii* and *Parabacteroides merdae*, with *Parabacteroides distasonis* being especially preferred.

The *Parabacteroides* resemble the *Bacteroides* and are Gram-negative, obligately anaerobic, non-spore-forming, non-motile and rod-shaped, and 0.8-1.6×1.2-12m in size. *Parabacteroides distasonis* is one of the most common species in human faeces. The type strain of *P. distasonis* is JCM 5825$^T$ (=CCUG 4941$^T$=DSM 20701$^T$=ATCC 8503$^T$) The GenBank/EMBL/DDBJ accession numbers for the 16S rRNA gene sequences of *P. distasonis* strains JCM 5825T, JCM 13400, JCM 13401, JCM 13402, JCM 13403 and JCM 13404 and *P. merdae* strains JCM 9497T and JCM 13405 are AB238922-AB238929, respectively (disclosed herein as SEQ ID NOs:1-8). The type strain of *P. goldsteinii* is JCM13446$^T$/WAL 12034 (=CCUG 48944$^T$). The GenBank/EMBL/DDBJ accession number for the 16s rRNA partial gene sequence of *P. goldsteinii* strain JCM13446 is AY974070 (disclosed herein as SEQ ID NO: 10). Exemplary strains are also described in [23]. The type strain of *Parabacteroides gordonii* is MS-1$^T$ (=JCM 15724$^T$=CCUG 57478$^T$). The GenBank/EMBL/DDBJ accession number for the 16S rRNA gene sequence of strain MS-1$^T$ is AB470343 (disclosed herein as SEQ ID NO: 33).

The *Parabacteroides distasonis* bacterium deposited under accession number NCIMB 42382 was tested in the Examples and is also referred to herein as strain 755. A 16S rRNA gene sequence for the 755 strain that was tested is provided in SEQ ID NO:9. Strain 755 was deposited with the international depositary authority NCIMB, Ltd. (Ferguson Building, Aberdeen, AB21 9YA, Scotland) by GT Biologics Ltd. (Life Sciences Innovation Building, Aberdeen, AB25 2ZS, Scotland) on 12 Mar. 2015 as "*Parabacteroides* sp 755" and was assigned accession number NCIMB 42382. GT Biologics Ltd. Subsequently changed its name to 4D Pharma Research Limited.

WO 2016/203220 describes administration of strain 755 to mice and shows that it can affect disease processes outside of the gut (such as asthma and arthritis). A genome sequence for strain 755 is provided in SEQ ID NO:10 of WO 2016/203220. This sequence was generated using the PacBio RS II platform.

The *Parabacteroides goldsteinii* strains deposited under accession numbers DSMZ19448 and DSMZ29187 were tested in the Examples. A 16s rRNA gene sequence for strain DSMZ19448 is provided in SEQ ID NO: 17. A 16s rRNA gene sequence for strain DSMZ19448 is provided in SEQ ID NO: 18. The strains were deposited with the DSMZ— German Collection of Microorganisms and Cell Cultures GmbH (Inhoffenstr. 7B 38124 Braunschweig, Germany) and are publically available.

The following *Parabacteroides* strains tested also tested in the Examples: strain ref 1 (*Parabacteroides distasonis*), strain ref 2 (*Parabacteroides distasonis*), strain ref. 3 (*Parabacteroides* sp.), strain ref 4 (*Parabacteroides johnsonii*), strain ref 5 (*Parabacteroides distasonis*), strain ref 6 (*Parabacteroides distasonis*), strain ref 7 (*Parabacteroides merdae*), strain ref 8 (*Parabacteroides distasonis*), strain ref 9 (*Parabacteroides distasonis*), strain ref 10 (*Parabacteroides johnsonii*), strain ref. 11 (*Parabacteroides* sp.), strain ref 12 (*Parabacteroides* sp.), strain ref 13 (*Parabacteroides* sp.), strain ref 14 (*Parabacteroides* sp.), strain ref 15 (*Parabacteroides* sp.). A 16s rRNA gene sequence for strain ref 1 (*Parabacteroides distasonis*) is provided in SEQ ID NO: 19. A 16s rRNA gene sequence for strain ref 2 (*Parabacteroides distasonis*) is provided in SEQ ID NO: 20. A 16s rRNA gene sequence for strain ref 3 (*Parabacteroides* sp.) is provided in SEQ ID NO: 21. A 16s rRNA gene sequence for strain ref 4 (*Parabacteroides johnsonii*) is provided in SEQ ID NO: 22. A 16s rRNA gene sequence for strain ref 5 (*Parabacteroides distasonis*) is provided in SEQ ID NO: 23. A 16s rRNA gene sequence for strain ref 6 (*Parabacteroides distasonis*) is provided in SEQ ID NO: 24. A 16s rRNA gene sequence for strain ref 7 (*Parabacteroides merdae*) is provided in SEQ ID NO: 25. A 16s rRNA gene sequence for strain ref 8 (*Parabacteroides distasonis*) is provided in SEQ ID NO: 26. A 16s rRNA gene sequence for strain ref 9 (*Parabacteroides distasonis*) is provided in SEQ ID NO: 27. A 16s rRNA gene sequence for strain ref 10 (*Parabacteroides johnsonii*) is provided in SEQ ID NO: 28. A 16s rRNA gene sequence for strain ref 11 (*Parabacteroides* sp) is provided in SEQ ID NO: 29. A 16s rRNA gene sequence for strain ref 12 (*Parabacteroides* sp) is provided in SEQ ID NO: 30. A 16s rRNA gene sequence for strain ref 14 (*Parabacteroides* sp) is provided in SEQ ID NO: 31. A 16s rRNA gene sequence for strain ref 15 (*Parabacteroides* sp) is provided in SEQ ID NO: 32.

The invention also provides a bacterial strain of the species *Parabacteroides distasonis*, wherein the bacterial strain has a 16s rRNA gene sequence that is (in increasing preference) at least 98%, 99% or 99.5% identical to SEQ ID NO: 19, preferably wherein the bacterial strain has the 16s rRNA gene sequence represented by SEQ ID NO: 19. Preferably, said bacterial strain is for use in therapy.

The invention also provides a bacterial strain of the species *Parabacteroides distasonis*, wherein the bacterial strain has a 16s rRNA gene sequence that is (in increasing preference) at least 98%, 99% or 99.5% identical to SEQ ID NO: 20, preferably wherein the bacterial strain has the 16s rRNA gene sequence represented by SEQ ID NO: 20. Preferably, said bacterial strain is for use in therapy.

The invention also provides a bacterial strain of the genus *Parabacteroides*, wherein the bacterial strain has a 16s rRNA gene sequence that is (in increasing preference) at least 98%, 99% or 99.5% identical to SEQ ID NO: 21, preferably wherein the bacterial strain has the 16s rRNA gene sequence represented by SEQ ID NO: 21. Preferably, said bacterial strain is for use in therapy.

The invention also provides a bacterial strain of the species *Parabacteroides johnsonii*, wherein the bacterial strain has a 16s rRNA gene sequence that is (in increasing preference) at least 98%, 99% or 99.5% identical to SEQ ID NO: 22, preferably wherein the bacterial strain has the 16s rRNA gene sequence represented by SEQ ID NO: 22. Preferably, said bacterial strain is for use in therapy.

The invention also provides a bacterial strain of the species *Parabacteroides distasonis*, wherein the bacterial strain has a 16s rRNA gene sequence that is (in increasing preference) at least 98%, 99% or 99.5% identical to SEQ ID NO: 23, preferably wherein the bacterial strain has the 16s rRNA gene sequence represented by SEQ ID NO: 23. Preferably, said bacterial strain is for use in therapy.

The invention also provides a bacterial strain of the species *Parabacteroides distasonis*, wherein the bacterial strain has a 16s rRNA gene sequence that is (in increasing preference) at least 98%, 99% or 99.5% identical to SEQ ID NO: 24, preferably wherein the bacterial strain has the 16s rRNA gene sequence represented by SEQ ID NO: 24. Preferably, said bacterial strain is for use in therapy.

The invention also provides a bacterial strain of the species *Parabacteroides merdae*, wherein the bacterial strain has a 16s rRNA gene sequence that is (in increasing preference) at least 98%, 99% or 99.5% identical to SEQ ID NO: 25, preferably wherein the bacterial strain has the 16s rRNA gene sequence represented by SEQ ID NO: 25. Preferably, said bacterial strain is for use in therapy.

The invention also provides a bacterial strain of the species *Parabacteroides distasonis*, wherein the bacterial strain has a 16s rRNA gene sequence that is (in increasing preference) at least 98%, 99% or 99.5% identical to SEQ ID NO: 26, preferably wherein the bacterial strain has the 16s rRNA gene sequence represented by SEQ ID NO: 26. Preferably, said bacterial strain is for use in therapy.

The invention also provides a bacterial strain of the species *Parabacteroides distasonis*, wherein the bacterial strain has a 16s rRNA gene sequence that is (in increasing preference) at least 98%, 99% or 99.5% identical to SEQ ID NO: 27, preferably wherein the bacterial strain has the 16s rRNA gene sequence represented by SEQ ID NO: 27. Preferably, said bacterial strain is for use in therapy.

The invention also provides a bacterial strain of the species *Parabacteroides johnsonii*, wherein the bacterial strain has a 16s rRNA gene sequence that is (in increasing preference) at least 98%, 99% or 99.5% identical to SEQ ID NO: 28, preferably wherein the bacterial strain has the 16s rRNA gene sequence represented by SEQ ID NO: 28. Preferably, said bacterial strain is for use in therapy.

The invention also provides a bacterial strain of the genus *Parabacteroides*, wherein the bacterial strain has a 16s rRNA gene sequence that is (in increasing preference) at least 98%, 99% or 99.5% identical to SEQ ID NO: 29, preferably wherein the bacterial strain has the 16s rRNA gene sequence represented by SEQ ID NO: 29. Preferably, said bacterial strain is for use in therapy.

The invention also provides a bacterial strain of the genus *Parabacteroides*, wherein the bacterial strain has a 16s rRNA gene sequence that is (in increasing preference) at least 98%, 99% or 99.5% identical to SEQ ID NO: 30, preferably wherein the bacterial strain has the 16s rRNA gene sequence represented by SEQ ID NO: 30. Preferably, said bacterial strain is for use in therapy.

The invention also provides a bacterial strain of the genus *Parabacteroides*, wherein the bacterial strain has a 16s rRNA gene sequence that is (in increasing preference) at least 98%, 99% or 99.5% identical to SEQ ID NO: 31, preferably wherein the bacterial strain has the 16s rRNA gene sequence represented by SEQ ID NO: 31. Preferably, said bacterial strain is for use in therapy.

The invention also provides a bacterial strain of the genus *Parabacteroides*, wherein the bacterial strain has a 16s rRNA gene sequence that is (in increasing preference) at least 98%, 99% or 99.5% identical to SEQ ID NO: 32, preferably wherein the bacterial strain has the 16s rRNA gene sequence represented by SEQ ID NO: 32. Preferably, said bacterial strain is for use in therapy.

Bacterial strains closely related to the strain tested in the examples are also expected to be effective for treating or preventing cancer comprising oncogenic ERK signalling. In certain embodiments, the bacterial strain for use in the invention has a 16s rRNA gene sequence that is (in increasing preference) at least 90%, 91%, 92%, 93%, 94%, 95%, 96%, 97%, 98%, 99%, 99.5% or 99.9% identical to the 16s rRNA gene sequence of a bacterial strain of *Parabacteroides distasonis*. The bacterial strain for use in the invention may have a 16s rRNA gene sequence that is (in increasing preference) at least 90%, 91%, 92%, 93% or 94% identical to SEQ ID NO:1, 2, 3, 4, 5, 6, 7, 8, 9, 10, 17, 18, 19, 20, 21, 22, 23, 24, 25, 26, 27, 28, 29, 30, 31 or 32, preferably to SEQ ID NO: 9. Preferably, the bacterial strain for use in the invention has a 16s rRNA gene sequence that is (in increasing preference) at least 95%, 96%, 97%, 98%, 99%, 99.5% or 99.9% identical to SEQ ID NO:1, 2, 3, 4, 5, 6, 7, 8, 9, 10, 17, 18, 19, 20, 21, 22, 23, 24, 25, 26, 27, 28, 29, 30, 31 or 32. Preferably, the sequence identity is to SEQ ID NO:9. Preferably, the bacterial strain for use in the invention has the 16s rRNA gene sequence represented by SEQ ID NO:9. Most preferably, the bacterial strain for use in the invention is of the *Parabacteroides distasonis* strain deposited under accession number NCIMB 42382.

In embodiments where the bacterial strain used in compositions of the invention is of the species *Parabacteroides distasonis*, preferred strains have a 16s rRNA gene sequence that is (in increasing preference) at least 98%, 99%, 99.5% or 99.9% identical to SEQ ID NO: 9, 19, 20, 23, 24, 26 or 27, preferably to SEQ ID NO: 9. More preferably, such preferred strains have the 16s rRNA gene sequence represented by SEQ ID NO: 9, 19, 20, 23, 24, 26 or 27, in particular SEQ ID NO: 9. Most preferably, the bacterial strain is the strain of *Parabacteroides distasonis* deposited under accession number NCIMB 43382.

In embodiments where the bacterial strain used in compositions of the invention is of the species *Parabacteroides goldsteinii*, preferred strains have a 16s rRNA gene sequence that is (in increasing preference) at least 98%, 99%, 99.5% or 99.9% identical to SEQ ID NO: 17 or 18, or more preferably have the 16s rRNA gene sequence represented by SEQ ID NO: 17 or 18, or most preferably are either of the *Parabacteroides goldsteinii* strains deposited under accession numbers DSMZ19448 and DSMZ29187.

In embodiments where the bacterial strain used in compositions of the invention is of the species *Parabacteroides merdae*, preferred strains have a 16s rRNA gene sequence that is (in increasing preference) at least 98%, 99%, 99.5% or 99.9% identical to SEQ ID NO: 25 or more preferably have the 16s rRNA gene sequence represented by SEQ ID NO: 25.

In embodiments where the bacterial strain used in compositions of the invention is of the species *Parabacteroides johnsonii*, preferred strains have a 16s rRNA gene sequence that is (in increasing preference) at least 98%, 99%, 99.5% or 99.9% identical to SEQ ID NO: 22 or 28, or more preferably have the 16s rRNA gene sequence represented by SEQ ID NO: 22 or 28.

In embodiments where the bacterial strain used in compositions of the invention is of the species *Parabacteroides gordonii*, preferred strains have a 16s rRNA gene sequence that is (in increasing preference) at least 98%, 99%, 99.5% or 99.9% identical to SEQ ID NO: 33, or more preferably have the 16s rRNA gene sequence represented by SEQ ID NO: 33.

In preferred embodiments, the composition of the invention comprises live bacteria. In preferred embodiments, the composition of the invention comprises live bacteria in an active state, preferably lyophilised.

In preferred embodiments, the *Parabacteroides* bacterial strain in compositions of the invention has the effect of inhibiting ERK signalling. This effect may be identified by culturing bacterial strains or supernatant therefrom with cancer cell lines comprising oncogenic ERK signalling (such as 451Lu or HT29 as used in the Examples), and measuring inhibitory effects on ERK signalling, for example by quantifying cellular levels of phosphorylated ERK relative to total ERK. This can be performed by western blot analysis, using a primary antibody specific for phosphorylated ERK and a primary antibody specific for ERK irrespective of phosphorylation status, as performed in the Examples. A secondary antibody specific for the primary antibody, which is linked to an agent capable of catalysing a chromogenic reaction (such as horseradish peroxidase), can then be used to visualise and quantify levels of phosphorylated ERK relative to total ERK, as performed in the Examples. "Inhibiting" ERK signalling refers to the administration of the *Parabacteroides* bacterial strain to a cancer cell line reducing cellular levels of phosphorylated ERK (relative to total ERK), as compared to the absence of said administration.

In certain embodiments, a composition of the invention comprises a biotype of the bacterium deposited under accession number NCIMB 42382. Bacterial strains that are biotypes of the bacterium deposited under accession number 42382 are also expected to be effective for treating or preventing cancer comprising oncogenic ERK signalling. A biotype is a closely related strain that has the same or very similar physiological and biochemical characteristics.

Strains that are biotypes of the bacterium deposited under accession number NCIMB 42382 and that are suitable for use in the invention may be identified by sequencing other nucleotide sequences for the bacterium deposited under accession number NCIMB 42382. For example, substantially the whole genome may be sequenced and a biotype strain for use in the invention may have at least 95%, 96%, 97%, 98%, 99%, 99.5% or 99.9% sequence identity across at least 80% of its whole genome (e.g. across at least 85%, 90%, 95% or 99%, or across its whole genome). Other suitable sequences for use in identifying biotype strains may include hsp60 or repetitive sequences such as BOX, ERIC, $(GTG)_5$, or REP or [24]. Biotype strains may have sequences with at least 95%, 96%, 97%, 98%, 99%, 99.5% or 99.9% sequence identity to the corresponding sequence of the bacterium deposited under accession number NCIMB 42382.

In certain embodiments, the bacterial strain for use in the invention has a genome with sequence identity to SEQ ID NO:10 of WO 2016/203220. In preferred embodiments, the bacterial strain for use in the invention has a genome with at least 90% sequence identity (e.g. at least 92%, 94%, 95%, 96%, 97%, 98%, 99% or 100% sequence identity) to SEQ ID NO:10 of WO 2016/203220 across at least 60% (e.g. at least 65%, 70%, 75%, 80%, 85%, 95%, 96%, 97%, 98%, 99% or 100%) of SEQ ID NO:10 of WO 2016/203220. For example, the bacterial strain for use in the invention may have a genome with at least 90% sequence identity to SEQ ID NO:10 of WO 2016/203220 across 70% of SEQ ID NO:10, or at least 90% sequence identity to SEQ ID NO:10 of WO 2016/203220 across 80% of SEQ ID NO:10 of WO 2016/203220, or at least 90% sequence identity to SEQ ID NO:10 of WO 2016/203220 across 90% of SEQ ID NO:10 of WO 2016/203220, or at least 90% sequence identity to SEQ ID NO:10 of WO 2016/203220 across 100% of SEQ ID NO:10 of WO 2016/203220, or at least 95% sequence identity to SEQ ID NO:10 of WO 2016/203220 across 70% of SEQ ID NO:10 of WO 2016/203220, or at least 95% sequence identity to SEQ ID NO:10 of WO 2016/203220 across 80% of SEQ ID NO:10 of WO 2016/203220, or at least 95% sequence identity to SEQ ID NO:10 of WO 2016/203220 across 90% of SEQ ID NO:10 of WO 2016/203220, or at least 95% sequence identity to SEQ ID NO:10 of WO 2016/203220 across 100% of SEQ ID NO:10 of WO 2016/203220, or at least 98% sequence identity to SEQ ID NO:10 of WO 2016/203220 across 70% of SEQ ID NO:10 of WO 2016/203220, or at least 98% sequence identity to SEQ ID NO:10 of WO 2016/203220 across 80% of SEQ ID NO:10 of WO 2016/203220, or at least 98% sequence identity to SEQ ID NO:10 of WO 2016/203220 across 90% of SEQ ID NO:10 of WO 2016/203220, or at least 98% sequence identity to SEQ ID NO:10 of WO 2016/203220 across 100% of SEQ ID NO:10 of WO 2016/203220.

Alternatively, strains that are biotypes of the bacterium deposited under accession number NCIMB 42382 and that are suitable for use in the invention may be identified by using the accession number NCIMB 42382 deposit and restriction fragment analysis and/or PCR analysis, for example by using fluorescent amplified fragment length polymorphism (FAFLP) and repetitive DNA element (rep)-PCR fingerprinting, or protein profiling, or partial 16S or 23S rDNA sequencing. In preferred embodiments, such techniques may be used to identify other *Parabacteroides distasonis* strains.

In certain embodiments, strains that are biotypes of the bacterium deposited under accession number NCIMB 42382 and that are suitable for use in the invention are strains that provide the same pattern as the bacterium deposited under accession number NCIMB 42382 when analysed by amplified ribosomal DNA restriction analysis (ARDRA), for example when using Sau3AI restriction enzyme (for exemplary methods and guidance see, for example [25]).

Figure 23:
FIG. 23: Fermentation profile of NCIMB 42382 obtained using the (A) Rapid ID 32 A and (B) API 50 CHL systems.
Figure 24:
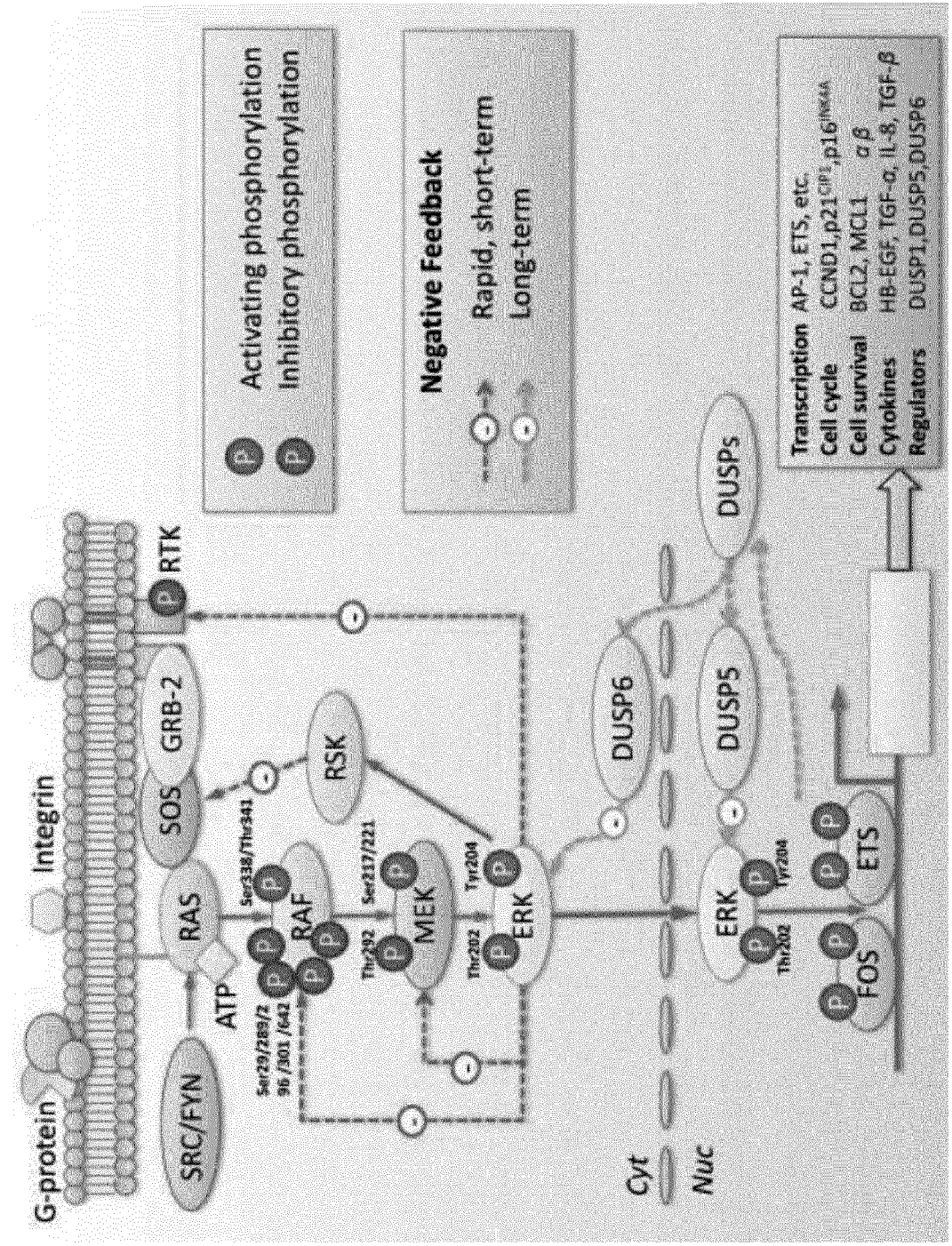
FIG. 24: Overview of the MAPK pathway (from [26]).

Alternatively, biotype strains are identified as strains that have the same carbohydrate fermentation patterns as the bacterium deposited under accession number NCIMB 42382 (see Example 8 and FIG. 23). Alternatively, biotype strains are identified as strains that have the same amino acid fermentation patterns as the bacterium deposited under accession number NCIMB 42382 (see Example 8 and FIG. 23).

In preferred embodiments, the biotype bacterial strain (in particular, a *Parabacteroides distasonis* bacterial strain) used in the invention exhibits enzymatic activity for one or more, such as (in increasing preference) 2, 3, 4 or all 5 of: α-galactosidase, β-galactosidase, α-glucosidase, β-glucosidase and alkaline phosphatase, for example when cultured in an appropriate suspension medium (such as API suspension medium) at 37° C. for 4 hours. The biotype bacterial strain (in particular, a *Parabacteroides distasonis* bacterial strain) used in the invention is preferably able to ferment one or more, such as (in increasing preference) 2, 3, 4, 5 or all 6 of: arginine, leucyl-glycine, leucine, alanine, histidine and glutamyl glutamic acid, for example when cultured in an appropriate suspension medium (such as API suspension medium) at 37° C. for 4 hours. The biotype bacterial strain (in particular, a *Parabacteroides distasonis* bacterial strain) used in the invention is more preferably able to ferment one or more, such as (in increasing preference) 2, 3, 4, 5 or all 6 of: arginine, leucyl-glycine, leucine, alanine, histidine and glutamyl glutamic acid and exhibits enzymatic activity for one or more, such as (in increasing preference) 2, 3, 4 or all 5 of: α-galactosidase, β-galactosidase, α-glucosidase, β-glucosidase and alkaline phosphatase, for example when cultured in an appropriate suspension medium (such as API suspension medium) at 37° C. for 4 hours. Any suitable assay known in the art may be used to assess the ability of a bacterium to ferment a carbohydrate source or amino acid. Preferably, the Rapid ID 32A analysis is used (preferably using the Rapid ID 32A system from bioMérieux).

In alternative preferred embodiments, the biotype bacterial strain (in particular, a *Parabacteroides distasonis* bacterial strain) used in the invention is able to ferment one or more, such as (in increasing preference) 2, 3, 4, 5, 6, 7, 8, 9, 10, 11, 12, 13, 14 or all 15 of: fructose, mannose, mannitol, sorbitol, arbutin, esculin, maltose, lactose, melibiose, sucrose, raffinose, starch, glycogen, turanose and fucose. The biotype bacterial strain (in particular, a *Parabacteroides distasonis* bacterial strain) used in the invention preferably furthermore exhibits intermediate fermentation of one or more, such as (in increasing preference) 2, 3, 4, 5, 6, 7 or all 8 of: xylose, N-acetylglucosamine, amygdalin, salicin, cellobiose, trehalose, melezitose and gentiobiose. In such embodiments, any suitable assay known in the art may be used to assess the ability of a bacterium to ferment a carbohydrate source. Preferably, the API 50 CH analysis is used (preferably using the API 50 CH system from bioMérieux).

An especially preferred biotype bacterial strain (in particular, a *Parabacteroides distasonis* bacterial strain) used in the invention (i) exhibits enzymatic activity for α-galactosidase, β-galactosidase, α-glucosidase, β-glucosidase and alkaline phosphatase; (ii) is able to ferment arginine, leucylglycine, leucine, alanine, histidine and glutamyl glutamic acid; and (iii) is able to ferment fructose, mannose, mannitol, sorbitol, arbutin, esculin, maltose, lactose, melibiose, sucrose, raffinose, starch, glycogen, turanose and fucose. The biotype bacterial strain preferably furthermore (iv) exhibits intermediate fermentation of xylose, N-acetylglucosamine, amygdalin, salicin, cellobiose, trehalose, melezitose and gentiobiose. (i) and (ii) are preferably assessed when the bacterial strain is cultured in an appropriate suspension medium (such as API suspension medium) at 37° C. for 4 hours, and assessed by Rapid ID 32A analysis (preferably using the Rapid ID 32A system from bioMérieux). (iii) and (iv) are preferably assessed by API 50 CH analysis (preferably using the API 50 CH system from bioMérieux).

In addition or alternatively, a biotype of strain NCIMB 42382 will increase the proliferation of splenocytes, e.g. to a greater extent than untreated splenocytes or splenocytes treated with a control media (e.g. YCFA+ media), which may be determined using an assay which measures the conversion of 3-[4,5-dimethylthiazole-2-yl]-2,5-diphenyltetrazolium bromide (MTT) to MTT-formazan, e.g. by colourimetric detection of MTT-formazan (e.g. as in Example 10). In addition or alternatively, a biotype of strain NCIMB 42382 will increase the production of one or more, preferably all of, the cytokines TNF-α, IL-1β, IL-27, IL-10, MIP-2, MIP-1α, MIP-1β, IL-22, IL-5, IL-18, IL-23, CXCL1, IL-2, GM-CSF, IFN-γ, IL-6, IP-10 and/or RANTES from splenocytes, e.g. to a greater extent than untreated splenocytes or splenocytes treated with a control media (e.g. YCFA+ media), which may be determined by a cytokine immunoassay (e.g. the 26-plex Mouse ProcartaPlex™ multiplex immunoassay from Thermo Fischer Scientific as used in Examples 11 and 12).

Other *Parabacteroides* strains that are useful in the compositions and methods of the invention, such as biotypes of the bacteria deposited under accession number NCIMB 42382, may be identified using any appropriate method or strategy, including the assays described in the examples. Preferably, biotypes will have the effect of inhibiting ERK signalling, which can be determined as described above and in the Examples. Bacterial strains that have similar growth patterns, metabolic type and/or surface antigens to the bacterium deposited under accession number NCIMB 42382 may also be useful in the invention. A useful strain may have comparable inhibitory activity on ERK signalling in cancer cell lines such as such as 451Lu or HT29 to the NCIMB 42382 strain. A useful strain may also elicit comparable effects on the clonogenic survival of cancer cell lines such as such as 451Lu or HT29 to the NCIMB 42382 strain. A useful strain may also elicit comparable upregulation of MAP2 gene expression in cancer cell lines such as SKMEL2 to the NCIMB 42382 strain.

In addition or alternatively, a derivative of strain NCIMB 42382 will increase the proliferation of splenocytes, e.g. to a greater extent than untreated splenocytes or splenocytes treated with a control media (e.g. YCFA+ media), which may be determined using an assay which measures the conversion of 3-[4,5-dimethylthiazole-2-yl]-2,5-diphenyltetrazolium bromide (MTT) to MTT-formazan, e.g. by colourimetric detection of MTT-formazan (e.g. as in Example 10). In addition or alternatively, a derivative of strain NCIMB 42382 will increase the production of one or more, preferably all of, the cytokines TNF-α, IL-1β, IL-27, IL-10, MIP-2, MIP-1α, MIP-1β, IL-22, IL-5, IL-18, IL-23, CXCL1, IL-2, GM-CSF, IFN-γ, IL-6, IP-10 and/or RANTES from splenocytes, e.g. to a greater extent than untreated splenocytes or splenocytes treated with a control media (e.g. YCFA+ media), which may be determined by a cytokine immunoassay (e.g. the 26-plex Mouse ProcartaPlex™ multiplex immunoassay from Thermo Fischer Scientific as used in Examples 11 and 12).

In certain embodiments, a composition of the invention comprises a derivative of the bacterium deposited under accession number NCIMB 42382. A derivative of the strain deposited under accession number NCIMB 42382 may be a daughter strain (progeny) or a strain cultured (subcloned) from the original. A derivative of a strain of the invention may be modified, for example at the genetic level, without ablating the biological activity. In particular, a derivative strain of the invention is therapeutically active. A derivative strain will have comparable immune modulatory activity to the original NCIMB 42382 strain. In particular, a derivative strain will elicit comparable effects on oncogenic ERK signalling and clonogenic survival of cancer cell lines to the effects shown with the NCIMB 42382 strain, which may be identified by using the culturing and administration protocols described in the Examples. A derivative of the NCIMB 42382 strain will generally be a biotype of the NCIMB 42382 strain.

References to cells of the *Parabacteroides distasonis* strain deposited under accession number NCIMB 42382 encompass any cells that have the same safety and therapeutic efficacy characteristics as the strains deposited under accession number NCIMB 42382, and such cells are encompassed by the invention.

References to cells of the *Parabacteroides* strain deposited under accession number NCIMB 42382 encompass any cells that have the same safety and therapeutic efficacy characteristics as the strain deposited under accession number NCIMB 42382, and such cells are encompassed by the invention. The composition can therefore comprise a *Parabacteroides* strain that is not the strain deposited under accession number NCIMB 42382 but has the same safety and therapeutic efficacy characteristics as the strain deposited under accession number NCIMB 42382. The safety characteristics of a strain can be established for example by testing the resistance of the strain to antibiotics, for example distinguishing between intrinsic and transmissible resistance to antibiotics. The safety characteristics of a strain can also be established by evaluating the pathogenic properties of a strain in vitro, for example the levels of toxin production. Other safety tests include testing the acute or chronic toxicity of the bacterial strain in rat and mice models. The therapeutic efficacy of a strain can be established by functional characterization of the bacterial strain in vitro and in vivo using a relevant model.

In preferred embodiments, the bacterial strains in the compositions of the invention are viable and capable of partially or totally colonising the intestine.

In certain preferred embodiments, the bacterial strains for use in the invention are able to increase the proliferation of splenocytes. This may be determined using an assay which measures the conversion of 3-[4,5-dimethylthiazole-2-yl]-2, 5-diphenyltetrazolium bromide (MTT) to MTT-formazan, e.g. by colourimetric detection of MTT-formazan (e.g. as in Example 10).

In certain preferred embodiments, the bacterial strains for use in the invention are able to increase the production of one or more, preferably all of, TNF-α, IL-113, IL-27, IL-10, MIP-2, MIP-1α, MIP-113, IL-22, IL-5, IL-18, IL-23, CXCL1, IL-2, GM-CSF, IFN-γ, IL-6, IP-10 and/or RANTES cytokines from splenocytes. This may be determined by a cytokine immunoassay (e.g. the 26-plex Mouse ProcartaPlex™ multiplex immunoassay from Thermo Fischer Scientific as used in Examples 11 and 12).

In certain preferred embodiments, the bacterial strains for use in the invention produce acetic acid. In certain preferred embodiments, the bacterial strains for use in the invention produce propionic acid. In certain preferred embodiments, the bacterial strains for use in the invention produce acetic acid and propionic acid. The production of acetic and/or propionic acid may be determined using gas chromatography/mass spectrometry (e.g. as in Examples 13 and 14).

In some embodiments, the bacterial strain in the compositions of the invention is a bacterial strain of the genus *Parabacteroides*, wherein the bacterial strain is not of the strain deposited under accession number NCIMB 42382.

In some embodiments, the bacterial strain in the compositions of the invention is a bacterial strain of the species *Parabacteroides distasonis*, wherein the bacterial strain is not of the strain deposited under accession number NCIMB 42382.

In some embodiments, the bacterial strain in the compositions of the invention is a bacterial strain of the genus *Parabacteroides*, wherein the bacterial strain is not of the species *Parabacteroides merdae*.

In some embodiments, the bacterial strain in the compositions of the invention is a bacterial strain of the genus *Parabacteroides*, wherein the bacterial strain is not of the species *Parabacteroides goldsteinii*.

In some embodiments, the bacterial strain in the compositions of the invention is a bacterial strain of the genus *Parabacteroides*, wherein the bacterial strains is neither of the species *Parabacteroides* merdae nor of the species *Parabacteroides goldsteinii*.

Therapeutic Uses
Cancers and Characteristics Thereof

In one aspect, compositions of the invention are for use in treating or preventing cancer, wherein the cancer comprises oncogenic ERK signalling. Extracellular signal-related kinase (ERK) is a downstream effector in the mitogen-activated protein (MAP) kinase (MAPK) pathway, a highly conserved signal transduction pathway found in all eukaryotes [26]. The MAPK pathway regulates processes such as cell proliferation, differentiation, survival and apoptosis, and aberrant activation of the pathway is closely linked to cancer pathogenesis.

As used herein "oncogenic ERK signalling" refers to the cancer comprising dysregulated cellular signalling, such as stimulus-independent signalling, via the MAPK pathway, the result of which is overactive signalling by ERK (either the ERK1 or ERK2 isoform, or both), which drives increased cancer cell proliferation and/or survival. ERK1 is active (i.e. signalling) when phosphorylated at positions Thr202 and Tyr204. ERK 2 is active (i.e. signalling) when phosphorylated at positions Thr173 and Tyr185. Accordingly, "oncogenic ERK signalling" can result from the presence of oncogenic mutations in (gain of function mutations) or overexpression of positive regulators of the MAPK pathway, or oncogenic mutations in (loss of function mutations) or downregulated expression of negative regulators of the MAPK pathway.

Cancer comprising oncogenic ERK signalling may alternatively be defined as cancer "bearing", "exhibiting" or "characterised by" oncogenic ERK signalling. Cancer comprising oncogenic ERK signalling may alternatively be defined as cancer wherein the proliferation and/or survival of malignant cells is "stimulated", "induced" or "upregulated" by ERK signalling. Cancer comprising oncogenic ERK may alternatively be defined as cancer bearing, comprising, exhibiting or characterised by "stimulus-independent" ERK signalling.

"Oncogenic mutation" encompasses any amino acid variation in a protein, relative to the wild-type protein, which promotes cancer cell proliferation and/or survival, including, but not limited to, substitutions (including single amino acid substitutions), insertions and/or deletions. As noted above, oncogenic mutations may be loss of function or gain of function mutations, depending on the protein and its function within the MAPK pathway. "Overexpression" or "downregulated expression" refer respectively to increased or decreased expression of a protein in a tumour cell relative to a non-tumour cell.

Accordingly, cancers comprising oncogenic ERK signalling include those comprising an oncogenic mutation in, or overexpression of, BRAF, NRAS, ARAF, CRAF, EGFR, GRB2, SOS, HRAS, KRAS, such as KRAS4A or KRAS4B, MEK1, MEK2, ERK1 or ERK2; such as BRAF, ARAF, CRAF, EGFR, GRB2, SOS, HRAS, MEK1, MEK2, ERK1 or ERK2. These proteins are positive regulators of the MAPK pathway (i.e. oncoproteins) [26]. For example, the cancer may comprise an oncogenic mutation in BRAF, NRAS, ARAF, CRAF, EGFR, GRB2, SOS, HRAS, MEK1, MEK2, ERK1 or ERK2.

Cancers comprising oncogenic ERK signalling also include those which comprise (either alternatively, or in addition to, the above oncogenic mutations/overexpression) an oncogenic mutation in, or downregulated expression of, RSK, DUSP1, DUSP5, DUSP6 or SPRY. These proteins are negative regulators of the MAPK pathway (i.e. tumour suppressor proteins) [26].

Any cancer comprising oncogenic ERK signalling can be treated or prevented using compositions of the invention, such as solid tumours or haematological malignancies. Such cancers include, but are not limited to, colorectal cancer, melanoma, small bowel cancer such as small bowel adenocarcinoma, acute lymphoblastic leukaemia (ALL), acute myeloid leukaemia, adrenocortical carcinoma, basal-cell carcinoma, bile duct cancer, bladder cancer, bone tumour, osteosarcoma/malignant fibrous histiocytoma, brainstem glioma, brain tumour, cerebellar astrocytoma, cerebral astrocytoma/malignant glioma, ependymoma, medulloblastoma, supratentorial primitive neuroectodermal tumours, breast cancer, bronchial adenomas/carcinoids, Burkitt's lymphoma, carcinoid tumour, cervical cancer, chronic lymphocytic leukaemia, chronic myelogenous leukaemia, chronic myeloproliferative disorders, cutaneous T-cell lymphoma, endometrial cancer, ependymoma, esophageal cancer, Ewing's sarcoma, intraocular melanoma, retinoblastoma, gallbladder cancer, gastric cancer, gastrointestinal carcinoid tumour, gastrointestinal stromal tumour (GIST), germ cell tumour, glioma, childhood visual pathway and hypothalamic, Hodgkin lymphoma, islet cell carcinoma, Kaposi sarcoma, renal cell cancer, laryngeal cancer, leukaemias, lymphomas, mesothelioma, neuroblastoma, non-Hodgkin lymphoma, oropharyngeal cancer, osteosarcoma, ovarian cancer, pancreatic cancer, parathyroid cancer, pharyngeal cancer, pituitary adenoma, plasma cell neoplasia, prostate cancer, renal cell carcinoma, retinoblastoma, sarcoma, testicular cancer, thyroid cancer, or uterine cancer.

Preferably, cancers comprising oncogenic ERK signalling which can be treated or prevented using compositions of the invention (in particular, those comprising a bacterial strain of the species *Parabacteroides distasonis*) include, but are not limited to, colorectal cancer, melanoma, small bowel cancer such as small bowel adenocarcinoma, prostate cancer, lung adenocarcinoma such as non-small cell lung adenocarcinoma, pancreatic cancer, bladder cancer, leukaemia such as hairy cell leukaemia or acute myeloid leukaemia, glioma, pilocytic astrocytoma, ovarian cancer, papillary or follicular thyroid cancer, seminoma, liver cancer, myelodysplastic syndrome, kidney cancer and Hodgkin's disease. Such cancers have been reported as comprising an overactive MAPK pathway (i.e. oncogenic ERK signalling) [26].

As shown in the examples, numerous *Parabacteroides* strains elicit immunostimulatory effects, such as splenocyte proliferation and cytokine secretion. Accordingly, compositions of the invention may be particularly effective in immunocompromised or immunosuppressed subjects. The subject may be immunocompromised or immunosuppressed for any reason including, but not limited to, organ recipiency, iatrogenic immunosuppression, the presence of an immunosuppressive infection (such as an HIV infection), and/or tumour-induced immunosuppression. Preferably, the subject is immunocompromised or immunosuppressed as a result of tumour-induced immunosuppression (i.e. as a result of the cancer, such as the cancer comprising oncogenic ERK signalling).

Subjects that are immunocompromised or immunosuppressed, in particular as a result of tumour-induced immunosuppression, may exhibit elevated numbers of regulatory T cells (Tregs) within the lymph nodes (in particular, metastatic lymph nodes) and/or within a volume of peripheral blood mononuclear cells (PBMCs), compared to subjects free of cancer (see, e.g. [27], [28]). Accordingly, compositions of the invention are preferably for use in a subject having an elevated number of regulatory T cells (Tregs) within a lymph node (such as a metastatic lymph node), compared to a lymph node of a subject free of cancer. For example, compositions of the invention are preferably for use in a subject who exhibits a frequency of (in increasing preference) at least 7%, at least 8%, at least 9% or at least 10% (e.g. between 7% and 12%) Tregs (e.g. CD25+CD4+ T cells) within a population of CD4+ T cells obtained from a lymph node, such as a metastatic lymph node (see, e.g. [28]). In addition or alternatively to the above, preferably the subject has an elevated number of Tregs within a volume of PBMCs, compared to the same volume of PBMCs from a subject free of cancer. In these embodiments, Tregs may alternatively be defined as CD4+CD25+ cells, FOXP3+ cells, or CD4+CD25+ and Foxp3+ cells (see [34]) Immunocompromised or immunosuppressed subjects may, in addition or alternatively to the above, exhibit a higher number of myeloid dendritic cells (mDCs) and/or plasmacytoid dendritic cells (pDCs), compared to subjects free of cancer (see, e.g. [29]). Accordingly, in addition or alternatively to the above, preferably the subject has an elevated number of mDCs within a volume of PBMCs, compared to the same volume of PBMCs from a subject free of cancer. In addition or alternatively to the above, preferably the subject has an elevated number of pDCs within a volume of PBMCs, compared to the same volume of PBMCs from a subject free of cancer. In these embodiments, pDCs may alternatively be defined as CD11c+ cells, and/or mDCs may alternatively be defined as CD123+ cells (see [35]). Cell numbers and the expression of cell surface markers may be determined using standard methods available in the art, such as flow cytometry (see e.g. [28]).

In a particular embodiment, compositions of the invention are for use in treating or preventing cancer comprising an oncogenic mutation in BRAF or NRAS, optionally wherein the cancer further comprises overexpression of BRAF or NRAS. Preferably, compositions of the invention (in particular, those comprising a bacterial strain of the species *Parabacteroides distasonis*) are for use in treating or preventing cancer which comprises an oncogenic mutation in BRAF, and optional overexpression of BRAF.

Oncogenic mutations in BRAF include Class I, II and III mutations, as reported in [30]. In some embodiments, compositions of the invention (in particular, those comprising a bacterial strain of the species *Parabacteroides distasonis*) are for use in treating or preventing cancer comprising a class II mutation in BRAF, such as the mutations R462I, I463S, G464E/V/R, G469A/V/S, E586K, F595L, L597Q/R/SN, A598V, T599I, K601E/N/T, and/or A727V, and/or BRAF fusion proteins. In other embodiments, compositions of the invention (in particular, those comprising a bacterial strain of the species *Parabacteroides distasonis*) are for use in treating or preventing cancer comprising a class III mutation in BRAF, such as the mutations G466A/EN/R, S467A/E/L, G469E, K483M, N581I/S, D594A/E/G/H/N/V, G596A/C/D/R. In other embodiments (which are preferred), compositions of the invention (in particular, those comprising a bacterial strain of the species *Parabacteroides distasonis*) are for use in treating or preventing cancer comprising a class I mutation in BRAF, such as the mutations V600E/K/D/R.

Oncogenic mutations in BRAF include V600E, K601E, G469A, G469V, L597R, K601N, G464V, N581S, L597Q, A598V, G464R, G466A or G469E, which have been identified in colorectal cancers [31], and compositions of the invention compositions (in particular, those comprising a bacterial strain of the species *Parabacteroides distasonis*) may be used to treat or prevent such cancers. Further oncogenic mutations in BRAF include V600E, V600K, V600R or V600D, which have been identified in melanomas [32], and compositions of the invention compositions (in particular, those comprising a bacterial strain of the species *Parabacteroides distasonis*) may be used to treat or prevent such cancers. Amino acids in BRAF are numbered according to UniProt entry P15056 [33] (wild-type BRAF).

In an especially preferred embodiment, compositions of the invention (in particular, those comprising a bacterial strain of the species *Parabacteroides distasonis*) are for use in treating or preventing cancer which comprises the mutation BRAF V600E. The cancer cell lines SKMEL28, 451Lu and HT29 comprise this mutation in BRAF, and a strain of *Parabacteroides* was found in the Examples to inhibit clonogenic survival, inhibit ERK signalling and induce MAP2 gene expression in such cell lines. The cancer may further comprise the oncogenic mutation NRAS Q61R. The cancer cell line SKMEL2 comprises this mutation in NRAS, and a strain of *Parabacteroides* was found in the Examples to induce MAP2 gene expression in this cell line.

The HT29 cell line used in the Examples is a colorectal cancer cell line, and a strain of *Parabacteroides* was found to inhibit clonogenic survival and inhibit ERK signalling in this cell line. A strain of *Parabacteroides* was also found to inhibit ERK signalling in a further colorectal cancer cell line (HCT116). Therefore, in especially preferred embodiments, compositions of the invention (in particular, those comprising a bacterial strain of the species *Parabacteroides distasonis*) are used to treat or prevent colorectal cancer, such as colorectal cancer which comprises the mutation BRAF V600E. In other embodiments, compositions of the invention (in particular, those comprising a bacterial strain of the species *Parabacteroides distasonis*) are used to treat or prevent colorectal cancer which comprises the mutation KRAS G13D.

The SKMEL2 and SKMEL28 and 451Lu cell lines used in the Examples are melanoma cell lines, and a strain of *Parabacteroides* was found to inhibit clonogenic survival, inhibit ERK signalling and induce MAP2 gene expression in such cell lines. Furthermore, interleukin-2 (IL-2) is an approved therapy for melanoma [64], and numerous *Parabacteroides* strains are shown in the Examples to stimulate IL-2 secretion from murine splenocytes, further indicating the utility of *Parabacteroides* strains in the therapy of melanoma. Therefore, in especially preferred embodiments, compositions of the invention (in particular, those comprising a bacterial strain of the species *Parabacteroides distasonis*) are used to treat or prevent melanoma, such as melanoma which comprises the mutation BRAF V600E. Melanoma, in particular metastatic melanoma, has been reported as inducing immunosuppression [27]. As shown in the examples, *Parabacteroides* strains elicit immunostimulatory effects, such as splenocyte proliferation and cytokine secretion. Accordingly, in embodiments concerning the treatment or prevention of melanoma (in particular metastatic melanoma), compositions of the invention may be especially effective in an immunocompromised or immunosuppressed subject (as defined above).

The methotrexate-treated HT29 cell line used in Example 6 has a phenotype resembling epithelial cells of the small intestine. A strain of *Parabacteroides* was found to induce GPR109a expression in this cell line. Therefore, in some embodiments, compositions of the invention (in particular, those comprising a bacterial strain of the species *Parabacteroides distasonis*) are used to treat or prevent small bowel cancer, preferably to treat metastatic small bowel cancer; preferably wherein the small bowel cancer is small bowel adenocarcinoma. In some embodiments, compositions of the invention (in particular, those comprising a bacterial strain of the species *Parabacteroides distasonis*) are used to promote apoptosis in the treatment or prevention of the small bowel cancer. In some embodiments, compositions of the invention (in particular, those comprising a bacterial strain of the species *Parabacteroides distasonis*) are used to induce GPR109a gene expression in the treatment or prevention of the small bowel cancer.

In another aspect, the composition of the invention comprises a bacterial strain of the species *Parabacteroides distasonis*, for use in a method of treating colorectal cancer. In another aspect, the composition of the invention comprises a bacterial strain of the species *Parabacteroides distasonis*, for use in a method of treating melanoma.

In any of the aspects and embodiments detailed above, the composition of the invention (in particular, a composition comprising a bacterial strain of the species *Parabacteroides distasonis*) is preferably for use in treating a metastatic cancer. As reported in the Examples, a strain of *Parabacteroides* was found to upregulated MAP2 gene expression. MAP2 has been found to be highly expressed in primary cutaneous melanomas, but has reduced expression in metastatic melanomas [34]. It has been proposed that increased expression of microtubule-stabilizing proteins or treatment with microtubule stabilizing proteins such as MAP2 may interfere with the dynamic instability of microtubules which is required during cell division. Therefore, upregulation of MAP2 is thought to hamper cell division and delay tumour growth in cancer [34], indicating that compositions of the invention may have particular use in treating metastatic cancers.

Effects of *Parabacteroides* Strains in the Therapy of Cancer

As demonstrated in the Examples, compositions of the invention comprising a *Parabacteroides* strain have the effects of inducing MAP2 gene expression and inhibiting ERK signalling in melanoma and colorectal cancer cell lines. Therefore, compositions of the invention are useful in methods of inhibiting ERK signalling, such as ERK1 and/or ERK2 signalling, in the treatment or prevention of cancers comprising oncogenic ERK signalling, as defined above. Compositions of the invention are also useful in methods of inhibiting ERK phosphorylation, such as ERK1 and/or ERK2 phosphorylation, in the treatment or prevention of such cancers. Compositions of the invention are also useful in methods of inducing MAP2 gene expression in the treatment or prevention of such cancers. MAP2 gene expression has been associated with increased cancer sensitivity to microtubule-targeting compounds such as Paclitaxel [35]. Therefore, compositions of the invention may be used to increase the susceptibility of such cancers to a tubulin polymerisation or depolymerisation inhibitor, in particular Paclitaxel. Compositions of the invention are also useful in methods of reducing tumour size, reducing tumour growth, preventing or inhibiting metastasis, or preventing angiogenesis in the treatment or prevention of cancers comprising oncogenic ERK signalling. Due to the effects on MAP2 gene expression demonstrated in the Examples, compositions of the invention are preferably for use in methods of inhibiting metastasis in the treatment of such cancers.

Compositions of the invention are also useful in methods of inducing TNF-α cytokine production, in the treatment or prevention of a cancer comprising oncogenic ERK signalling, as defined above. Compositions of the invention are also useful in methods of inducing IL-1ß cytokine production, in the treatment or prevention of a cancer comprising oncogenic ERK signalling, as defined above. Compositions of the invention are also useful in methods of inducing IL-2 cytokine production, in the treatment or prevention of a cancer comprising oncogenic ERK signalling, as defined above. Compositions of the invention are also useful in methods of inducing GM-CSF cytokine production, in the treatment or prevention of a cancer comprising oncogenic ERK signalling, as defined above. Compositions of the invention are also useful in methods of inducing IFN-γ cytokine production, in the treatment or prevention of a cancer comprising oncogenic ERK signalling, as defined above. Compositions of the invention are also useful in methods of inducing IL-27 cytokine production, in the treatment or prevention of a cancer comprising oncogenic ERK signalling, as defined above. Compositions of the invention are also useful in methods of inducing IP-10 cytokine production, in the treatment or prevention of a cancer comprising oncogenic ERK signalling, as defined above. Compositions of the invention are also useful in methods of inducing RANTES cytokine production, in the treatment or prevention of a cancer comprising oncogenic ERK signalling, as defined above. Compositions of the invention are also useful in methods of inducing MIP-1α cytokine production, in the treatment or prevention of a cancer comprising oncogenic ERK signalling, as defined above. Compositions of the invention are also useful in methods of inducing MIP-1ß cytokine production, in the treatment or prevention of a cancer comprising oncogenic ERK signalling, as defined above. Compositions of the invention are also useful in methods of inducing MIP-2 cytokine production, in the treatment or prevention of a cancer comprising oncogenic ERK signalling, as defined above. Compositions of the invention are also useful in methods of inducing IL-10 cytokine production, in the treatment or prevention of a cancer comprising oncogenic ERK signalling, as defined above. Compositions of the invention are also useful in methods of inducing IL-22 cytokine production, in the treatment or prevention of a cancer comprising oncogenic ERK signalling, as defined above. Compositions of the invention are also useful in methods of inducing IL-5 cytokine production, in the treatment or prevention of a cancer comprising oncogenic ERK signalling, as defined above. Compositions of the invention are also useful in methods of inducing IL-18 cytokine production, in the treatment or prevention of a cancer comprising oncogenic ERK signalling, as defined above. Compositions of the invention are also useful in methods of inducing IL-23 cytokine production, in the treatment or prevention of a cancer comprising oncogenic ERK signalling, as defined above. Compositions of the invention are also useful in methods of inducing CXCL1 cytokine production, in the treatment or prevention of a cancer comprising oncogenic ERK signalling, as defined above. Compositions of the invention are also useful in methods of inducing IL-6 cytokine production, in the treatment or prevention of a cancer comprising oncogenic ERK signalling, as defined above.

In a further aspect, a composition comprising a bacterial strain of the genus *Parabacteroides* (in particular, a composition comprising a bacterial strain of the species *Parabacteroides distasonis*) is for use in a method of inhibiting ERK1 and/or ERK2 signalling in the treatment or prevention of cancer. In a further aspect, a composition comprising a bacterial strain of the genus *Parabacteroides* (in particular, a composition comprising a bacterial strain of the species *Parabacteroides distasonis*) is for use in a method of inhibiting ERK1 and/or ERK2 phosphorylation in the treatment or prevention of cancer. In a further aspect, a composition comprising a bacterial strain of the genus *Parabacteroides* (in particular, a composition comprising a bacterial strain of the species *Parabacteroides distasonis*) is for use in a method of inducing MAP2 gene expression in the treatment or prevention of cancer. In a further aspect, a composition comprising a bacterial strain of the genus *Parabacteroides* (in particular, a composition comprising a bacterial strain of the species *Parabacteroides distasonis*) is for use in a method of inducing GPR109a gene expression in the treatment or prevention of cancer. In a further aspect, a composition comprising a bacterial strain of the genus *Parabacteroides* is for use in a method of inducing TNF-α cytokine production, in the treatment or prevention of cancer. In a further aspect, a composition comprising a bacterial strain of the genus *Parabacteroides* is for use in a method of inducing IL-1B cytokine production, in the treatment or prevention of cancer. In a further aspect, a composition comprising a bacterial strain of the genus *Parabacteroides* is for use in a method of inducing IL-2 cytokine production, in the treatment or prevention of cancer. In a further aspect, a composition comprising a bacterial strain of the genus *Parabacteroides* is for use in a method of inducing GM-CSF cytokine production, in the treatment or prevention of cancer. In a further aspect, a composition comprising a bacterial strain of the genus *Parabacteroides* is for use in a method of inducing IFN-γ cytokine production, in the treatment or prevention of cancer. In a further aspect, a composition comprising a bacterial strain of the genus *Parabacteroides* is for use in a method of inducing IL-27 cytokine production, in the treatment or prevention of cancer. In a further aspect, a composition comprising a bacterial strain of the genus *Parabacteroides* is for use in a method of inducing IP-10 cytokine production, in the treatment or prevention of cancer. In a further aspect, a composition comprising a bacterial strain of the genus *Parabacteroides* is for use in a method of inducing RANTES cytokine production, in the treatment or prevention of cancer. In a further aspect, a composition comprising a bacterial strain of the genus *Parabacteroides* is for use in a method of inducing MIP-1α cytokine production, in the treatment or prevention of cancer. In a further aspect, a composition comprising a bacterial strain of the genus *Parabacteroides* is for use in a method of inducing MIP-1ß cytokine production, in the treatment or prevention of cancer. In a further aspect, a composition comprising a bacterial strain of the genus *Parabacteroides* is for use in a method of inducing MIP-2 cytokine production, in the treatment or prevention of cancer. In a further aspect, a composition comprising a bacterial strain of the genus *Parabacteroides* is for use in a method of inducing IL-10 cytokine production, in the treatment or prevention of cancer. In a further aspect, a composition comprising a bacterial strain of the genus *Parabacteroides* is for use in a method of inducing IL-22 cytokine production, in the treatment or prevention of cancer. In a further aspect, a composition comprising a bacterial strain of the genus *Parabacteroides* is for use in a method of inducing IL-5 cytokine production, in the treatment or prevention of cancer. In a further aspect, a composition comprising a bacterial strain of the genus *Parabacteroides* is for use in a method of inducing IL-18 cytokine production, in the treatment or prevention of cancer. In a further aspect, a composition comprising a bacterial strain of the genus *Parabacteroides* is for use in a method of inducing IL-23 cytokine production, in the treatment or prevention of cancer. In a further aspect, a composition comprising a bacterial strain of the genus *Parabacteroides* is for use in a method of inducing CXCL1 cytokine production, in the treatment or prevention of cancer. In a further aspect, a composition comprising a bacterial strain of the genus *Parabacteroides* is for use in a method of inducing IL-6 cytokine production, in the treatment or prevention of cancer. In said further aspects, preferably the cancers are characterised as detailed above ("Cancers and characteristics thereof").

Combination Therapies

The compositions of the invention comprising a *Parabacteroides* bacterial strain may be particularly effective when used in combination with further therapeutic agents, such as direct anti-cancer agents.

Therefore, in certain embodiments, the invention provides a composition of the invention and an anticancer agent, for use in treating or preventing a cancer comprising oncogenic ERK signalling, such as colorectal cancer or melanoma. In certain embodiments, the composition of the invention is for use in priming a cancer comprising oncogenic ERK signalling, such as colorectal cancer or melanoma, to enhance its susceptibility to treatment with a second anti-cancer agent. In certain embodiments, the composition of the invention is for use in treating a cancer comprising oncogenic ERK signalling, such as colorectal cancer or melanoma, by enhancing its susceptibility to treatment with a second anti-cancer agent. The second anti-cancer agent may be administered concurrently, or may be administered after the composition of the invention, such as at least a day, a week, or a month after.

The anticancer agent may be an immune checkpoint inhibitor, a targeted antibody immunotherapy, a CAR-T cell therapy, an oncolytic virus, or a cytostatic drug. Anti-cancer agents include, but are not limited to, those selected from the group consisting of: YERVOY® (ipilimumab, BMS); KEYTRUDA® (pembrolizumab, Merck); OPDIVO® (nivolumab, BMS); MEDI4736 (Durvalumab, AZ/MedImmune); MPDL3280A (Atezolizumab, Roche/Genentech); Tremelimumab (AZ/MedImmune); CT-011 (pidilizumab, CureTech); BMS-986015 (lirilumab, BMS); MEDI0680 (Durvalumab, AZ/MedImmune); MSB-0010718C (Avelumab, Merck); PF-05082566 (Utomilumab, Pfizer); MEDI6469 (AZ/MedImmune); BMS-986016 (Relatlimab, BMS); BMS-663513 (urelumab, BMS); IMP321 (Eftilagimod alpha, Prima Biomed); LAG525 (Ieramilimab, Novartis); ARGX-110 (Cusatuzumab, arGEN-X); PF-05082466 (Pfizer); CDX-1127 (varlilumab; CellDex Therapeutics); TRX-518 (GITR Inc.); MK-4166 (Merck); JTX-2011 (vopratelimab, Jounce Therapeutics); ARGX-115 (arGEN-X); NLG-9189 (indoximod, NewLink Genetics); INCB024360 (Epacadostat, Incyte); IPH2201 (Monalizumab, Innate Immotherapeutics/AZ); NLG-919 (NewLink Genetics); anti-VISTA (JnJ); Epacadostat (INCB24360, Incyte); F001287 (*Flexus*/BMS); CP 870893 (University of Pennsylvania); MGA271 (Macrogenix); Emactuzumab (Roche/Genentech); Galunisertib (Eli Lilly); Ulocuplumab (BMS); BKT140/BL8040 (Biokine Therapeutics); Bavituximab (Peregrine Pharmaceuticals); CC 90002 (Celgene); 852A (Pfizer); VTX-2337 (VentiRx Pharmaceuticals); IMO-2055 (Hybridon, Idera Pharmaceuticals); LY2157299 (Eli Lilly); EW-7197 (Ewha Women's University, Korea); BMS-777607 (BMS); BLZ945 (Memorial Sloan-Kettering Cancer Centre); UNITUXIN® (dinutuximab, United Therapeutics Corporation); BLINCYTO® (blinatumomab, Amgen); CYRAMZA® (ramucirumab, Eli Lilly); GAZYVA® (obinutuzumab, Roche/Biogen); KADCYLA® (ado-trastuzumab emtansine, Roche/Genentech); PERJETA® (pertuzumab, Roche/Genentech); ADCETRIS® (brentuximab vedotin, Takeda/Millennium); ARZERRA® (ofatumumab, GSK); VECTIBIX® (panitumumab, Amgen); AVASTIN® (bevacizumab, Roche/Genentech); ERBITUX® (cetuximab, BMS/Merck); BEXXAR® (tositumomab-I131, GSK); ZEVALIN® (ibritumomab tiuxetan, Biogen); CAMPATH® (alemtuzumab, Bayer); Mylotarg™ (gemtuzumab ozogamicin, Pfizer); Herceptin® (trastuzumab, Roche/Genentech); Rituxan® (rituximab, Genentech/Biogen); volociximab (Abbvie); Enavatuzumab (Abbvie); ABT-414 (Abbvie); Elotuzumab (Abbvie/BMS); ALX-0141 (Ablynx); Ozaralizumab (Ablynx); Actimab-C (Actinium); Actimab-P (Actinium); Milatuzumab-dox (Actinium); Emab-SN-38 (Actinium); Naptumonmab estafenatox (Active Biotech); AFM13 (Affimed); AFM11 (Affimed); AGS-16C3F (Agensys); AGS-16M8F (Agensys); AGS-22ME (Agensys); AGS-15ME (Agensys); GS-67E (Agensys); ALXN6000 (samalizumab, Alexion); ALT-836 (Altor Bioscience); ALT-801 (Altor Bioscience); ALT-803 (Altor Bioscience); AMG780 (Amgen); AMG 228 (Amgen); AMG820 (Amgen); AMG172 (Amgen); AMG595 (Amgen); AMG110 (Amgen); AMG232 (adecatumumab, Amgen); AMG211 (Amgen/Me dImmune); BAY20-10112 (Amgen/Bayer); Rilotumumab (Amgen); Deno sumab (Amgen); AMP-514 (Amgen); MEDI575 (AZ/MedImmune); MEDI3617 (AZ/MedImmune); MEDI6383 (AZ/MedImmune); MEDI551 (AZ/MedImmune); Moxetumomab pasudotox (AZ/MedImmune); MEDI565 (AZ/MedImmune); MEDI0639 (AZ/MedImmune); MEDI0680 (AZ/MedImmune); MEDI562 (AZ/MedImmune); AV-380 (AVEO); AV203 (AVEO); AV299 (AVEO); BAY79-4620 (Bayer); Anetumab ravtansine (Bayer); vantictumab (Bayer); BAY94-9343 (Bayer); Sibrotuzumab (Boehringer Ingleheim); BI-836845 (Xentuzumab, Boehringer Ingleheim); B-701 (vofatamab, BioClin); BIIB015 (Biogen); Obinutuzumab (Biogen/Genentech); BI-505 (Bioinvent); BI-1206 (Bioinvent); TB-403 (Bioinvent); BT-062 (Biotest) BIL-010t (Biosceptre); MDX-1203 (BMS); MDX-1204 (BMS); Necitumumab (BMS); CAN-4 (Cantargia AB); CDX-011 (Celldex); CDX1401 (Celldex); CDX301 (Celldex); U3-1565 (Daiichi Sankyo); patritumab (Daiichi Sankyo); tigatuzumab (Daiichi Sankyo); nimotuzumab (Daiichi Sankyo); DS-8895 (Daiichi Sankyo); DS-8873 (Daiichi Sankyo); DS-5573 (Daiichi Sankyo); MORab-004 (Eisai); MORab-009 (Eisai); MORab-003 (Eisai); MORab-066 (Eisai); LY3012207 (Eli Lilly); LY2875358 (Eli Lilly); LY2812176 (Eli Lilly); LY3012217(Eli Lilly); LY2495655 (Eli Lilly); LY3012212 (Eli Lilly); LY3012211 (Eli Lilly); LY3009806 (Eli Lilly); cixutumumab (Eli Lilly); Flanvotumab (Eli Lilly); IMC-TR1 (Eli Lilly); Ramucirumab (Eli Lilly); Tabalumab (Eli Lilly); Zanolimumab (Emergent Biosolution); FG-3019 (FibroGen); FPA008 (Five Prime Therapeutics); FP-1039 (Five Prime Therapeutics); FPA144 (Five Prime Therapeutics); catumaxomab (Fresenius Biotech); IMAB362 (Ganymed); IMAB027 (Ganymed); HUMAX®-CD74 (Genmab); HUMAX®-TFADC (Genmab); GS-5745 (Gilead); GS-6624 (Gilead); OMP-21M18 (demcizumab, GSK); mapatumumab (GSK); IMGN289 (ImmunoGen); IMGN901 (ImmunoGen); IMGN853 (ImmunoGen); IMGN529 (ImmunoGen); IMMU-130 (Immunomedics); milatuzumab-dox (Immunomedics); IMMU-115 (Immunomedics); IMMU-132 (Immunomedics); IMMU-106 (Immunomedics); IMMU-102 (Immunomedics); Epratuzumab (Immunomedics); Clivatuzumab (Immunomedics); IPH41 (Innate Immunotherapeutics); Daratumumab (Janssen/Genmab); CNTO-95 (Intetumumab, Janssen); CNTO-328 (siltuximab, Janssen); KB004 (KaloBios); mogamulizumab (Kyowa Hakko Kirrin); KW-2871 (ecromeximab, Life Science); Sonepcizumab (Lpath); Margetuximab (Macrogenics); Enoblituzumab (Macrogenics); MGD006 (Macrogenics); MGF007 (Macrogenics); MK-0646 (dalotuzumab, Merck); MK-3475 (Merck); Sym004 (Symphogen/Merck Serono); DI17E6 (Merck Serono); MOR208 (Morphosys); MOR202 (Morphosys); Xmab5574 (Morphosys); BPC-1C (ensituximab, Precision Biologics); TAS266 (Novartis); LFA102 (Novartis); BH Q 880 (Novartis/Morphosys); QGE031 (Novartis); HCD122 (lucatumumab, Novartis); LJM716 (Novartis); AT355 (Novartis); OMP-21M18 (Demcizumab, OncoMed); OMP52M51 (Oncomed/GSK); OMP-59R5 (Oncomed/GSK); vantictumab (Oncomed/Bayer); CMC-544 (inotuzumab ozogamicin, Pfizer); PF-03446962 (Pfizer); PF-04856884 (Pfizer); PSMA-ADC (Progenics); REGN1400 (Regeneron); REGN910 (nesvacumab, Regeneron/Sanofi); REGN421 (enoticumab, Regeneron/Sanofi); RG7221, RG7356, RG7155, RG7444, RG7116, RG7458, RG7598, RG7599, RG7600, RG7636, RG7450, RG7593, RG7596, DCDS3410A, RG7414 (parsatuzumab), RG7160 (imgatuzumab), RG7159 (obintuzumab), RG7686, RG3638 (onartuzumab), RG7597 (Roche/Genentech); SAR307746 (Sanofi); SAR566658 (Sanofi); SAR650984 (Sanofi); SAR153192(Sanofi); SAR3419 (Sanofi); SAR256212 (Sanofi), SGN-LIV1A (lintuzumab, Seattle Genetics); SGN-CD33A (Seattle Genetics); SGN-75 (vorsetuzumab mafodotin, Seattle Genetics); SGN-19A (Seattle Genetics) SGN-CD70A (Seattle Genetics); SEA-CD40 (Seattle Genetics); ibritumomab tiuxetan (Spectrum); MLN0264 (Takeda); ganitumab (Takeda/Amgen); CEP-37250 (Teva); TB-403 (Thrombogenic); VB4-845 (Viventia); Xmab2512 (Xencor); Xmab5574 (Xencor); nimotuzumab (YM Biosciences); Carlumab (Janssen); NY-ESO TCR (Adaptimmune); MAGE-A-10 TCR (Adaptimmune); CTL019 (Novartis); JCAR015 (Juno Therapeutics); KTE-C19 CAR (Kite Pharma); UCART19 (Cellectis); BPX-401 (Bellicum Pharmaceuticals); BPX-601 (Bellicum Pharmaceuticals); ATTCK20 (Unum Therapeutics); CAR-NKG2D (Celyad); Onyx-015 (Onyx Pharmaceuticals); H101 (Shanghai Sunwaybio); DNX-2401 (DNAtrix); VCN-01 (VCN Biosciences); Colo-Adl (PsiOxus Therapeutics); PROSTATAK® (Advantagene); ONCOS-102 (Oncos Therapeutics); CG0070 (Cold Genesys); PEXA-VAC (JX-594, Jennerex Biotherapeutics); GL-ONC1 (Genelux); T-VEC (Amgen); G207 (Medigene); HF10 (Takara Bio); SEPREHVIR (HSV1716, Virttu Biologics); ORIENX010 (OrienGene Biotechnology); REOLYSIN® (Oncolytics Biotech); SVV-001 (Neotropix); CACATAK (CVA21, Viralytics); ALIMTA® (pemetrexed, Eli Lilly), cisplatin, oxaliplatin, irinotecan, folinic acid, methotrexate, cyclophosphamide, 5-fluorouracil, ZYKADIA™ (Novartis), TAFINLAR (dabrafenib, GSK), XALKORI® (crizotinib, Pfizer), IRESSA® (Gefitinib, AZ), (GILOTRIF™ (Afatinib, Boehringer Ingelheim), (TARCEVA® (Erlotinib, Astellas Pharma), HALAVEN® (Eribulin, Eisai Pharma), Veliparib (Abbvie), AZD9291 (AZ), Alectinib (Chugai), LDK378 (Novartis), Genetespib (Synta Pharma), Tergenpumatucel-L (NewLink Genetics), GV1001 (Kael-GemVax), Tivantinib (ArQule); CYTOXAN (BMS); ONCOVIN (Eli Lilly); ADRIAMYCIN (Doxorubicin, Pfizer); GEMZAR (Gemcitabine, Eli Lilly); (XELODA® (Capecitabine, Roche); IXEMPRA® (Ixabepilone, BMS); TRELSTAR® (triptorelin pamoate, Debiopharm); TAXOTERE (docetaxel, Sanofi); NEXAVAR® (sorafenib, Bayer); IMMU-132 (Sacituzumab govitecan, Immunomedics); E7449 (Stenoparib, Eisai); (THERMODOX® (doxorubicin, Celsion); (COMETRIQ™ (cabozantinib, Exellxis); LONSURF® (Trifluridine/tipiricil, Taiho Pharmaceuticals); CAMPTOSAR® (irinotecan, Pfizer); UFT (Tegafur/uracil, Taiho Pharmaceuticals); and TS-1 (Tegafur/gimeracil/oteracil, Taiho Pharmaceuticals).

In preferred embodiments, a BRAF inhibitor is administered simultaneously, separately or sequentially, relative to administration of the composition of the invention comprising a bacterial strain of the genus *Parabacteroides* (in particular, a composition comprising a bacterial strain of the species *Parabacteroides distasonis*). Preferably, the BRAF inhibitor is selected from Vemurafenib, Dabrafinib or Encorafenib which are selective inhibitors of BRAF$^{V600E}$, and which are preferably used in the treatment or prevention of cancer comprising the BRAF V600E mutation. More preferably, the BRAF inhibitor is Vemurafenib (dosing and administration guidance for which can be found at [36]).

As shown in the Examples, Vemurafenib can enhance the effects of the *Parabacteroides* strain in inhibiting the clonogenic survival, soft agar growth and ERK signalling of melanoma cell lines. Therefore, in a preferred embodiment, Vemurafenib and a composition comprising a *Parabacteroides* strain are for simultaneous, separate or sequential use in the treatment or prevention of melanoma, preferably melanoma comprising the BRAF V600E mutation. As shown in the Examples, Vemurafenib can also enhance MAP2 gene expression elicited by the *Parabacteroides* strain in a colorectal cancer cell line. Therefore, in a preferred embodiment, Vemurafenib and a composition comprising a *Parabacteroides* strain are for simultaneous, separate or sequential use in the treatment or prevention of colorectal cancer, preferably metastatic colorectal cancer. Oral administration of BRAF inhibitors such as Vemurafenib is recommended (see [36]). Therefore, advantageously, a bacterial strain of the genus *Parabacteroides* (in particular, a bacterial strain of the species *Parabacteroides distasonis*) and BRAF inhibitor (in particular, Vemurafenib) may be formulated into a single composition for oral administration (such as a tablet, capsule or powder), to improve patient compliance.

The BRAF inhibitor (preferably Vemurafenib) may be further combined with other combination partners such as a cytidine analogue; preferably Azacytidine-c, Decitabine, or Zebularine; more preferably Azacytidine-c (dosing and administration guidance for which can be found at [37]). As shown in the Examples, Vemurafenib in combination with Azacytidine-c can enhance the effects of the *Parabacteroides* strain in inhibiting the clonogenic survival and soft agar growth of melanoma cell lines. Therefore, in a preferred embodiment, Vemurafenib, Azacytidine-c and a composition comprising a *Parabacteroides* strain (in particular, a composition comprising a bacterial strain of the species *Parabacteroides distasonis*) are for simultaneous, separate or sequential use in the treatment or prevention of melanoma, preferably melanoma comprising the BRAF V600E mutation. As shown in the Examples, Vemurafenib and Azacytidine-c can also enhance MAP2 gene expression elicited by the *Parabacteroides* strain in a colorectal cancer cell line. Therefore, in a preferred embodiment, Vemurafenib, Azacytidine-c and a composition comprising a *Parabacteroides* strain are for simultaneous, separate or sequential use in the treatment or prevention colorectal cancer, preferably metastatic colorectal cancer.

In other preferred embodiments, a cytidine analogue is administered simultaneously, separately or sequentially, relative to administration of the composition of the invention comprising a bacterial strain of the genus *Parabacteroides* (in particular, a composition comprising a bacterial strain of the species *Parabacteroides distasonis*). Preferably, the cytidine analogue is selected from Azacytidine-c, Decitabine, or Zebularine. More preferably, the cytidine analogue is Azacytidine-c. As shown in the Examples, Azacytidine-c can enhance the effects of the *Parabacteroides* strain in inhibiting the clonogenic survival and soft agar growth of melanoma cell lines. Therefore, in a preferred embodiment, Azacytidine-c and a composition comprising a *Parabacteroides* strain (in particular, a composition comprising a bacterial strain of the species *Parabacteroides distasonis*) are for simultaneous, separate or sequential use in the treatment or prevention of melanoma. As shown in the Examples, Azacytidine-c can also enhance MAP2 gene expression elicited by the *Parabacteroides* strain, and enhance the effects of the *Parabacteroides* strain in inhibiting clonogenic survival, in a colorectal cancer cell line. Therefore, in a preferred embodiment, Azacytidine-c and a composition comprising a *Parabacteroides* (in particular, a composition comprising a bacterial strain of the species

*Parabacteroides distasonis*) strain are for simultaneous, separate or sequential use in the treatment or prevention of colorectal cancer, preferably metastatic colorectal cancer.

In other preferred embodiments, a tubulin polymerisation inhibitor or tubulin depolymerisation inhibitor is administered simultaneously, separately or sequentially, relative to administration of the composition comprising a bacterial strain of the genus *Parabacteroides* (in particular, a composition comprising a bacterial strain of the species *Parabacteroides distasonis*). Preferably, the tubulin polymerisation inhibitor or tubulin depolymerisation inhibitor is selected from Paclitaxel, Abraxane, Docetaxel, Epothilone, (+)-Discodermolide, Colchicine, Combretastatin, 2-Methoxyestradiol, E7010, Vincristine, Vinblastine, Vinorelbine or Vinflunine; more preferably, the tubulin polymerisation inhibitor or tubulin depolymerisation inhibitor is Paclitaxel (dosing and administration guidance for which can be found at [38]). As noted above, MAP2 gene expression has been associated with increased melanoma sensitivity to microtubule-targeting compounds such as Paclitaxel [35]. Furthermore, the ability of *Parabacteroides* strains to induce MAP2 gene expression indicates particular utility in treating metastatic cancers. Therefore, in a preferred embodiment, the tubulin polymerisation inhibitor or tubulin depolymerisation inhibitor (in particular, Paclitaxel) and a composition comprising a *Parabacteroides* strain (in particular, a composition comprising a bacterial strain of the species *Parabacteroides distasonis*) are for simultaneous, separate or sequential use in the treatment or prevention of metastatic cancer, preferably metastatic melanoma or colorectal cancer. In another preferred embodiment, the composition comprising a *Parabacteroides* strain (in particular, a composition comprising a bacterial strain of the species *Parabacteroides distasonis*) is for use in treating a cancer comprising oncogenic ERK signalling by enhancing its susceptibility to treatment with a tubulin polymerisation inhibitor or tubulin depolymerisation inhibitor (in particular, Paclitaxel), preferably melanoma or colorectal cancer, more preferably metastatic melanoma or colorectal cancer.

Combinations of a *Parabacteroides* strain with further therapeutics such as BRAF inhibitors, cytidine analogues and tubulin polymerisation or depolymerisation inhibitors, as described above, may be especially useful to enhance the antineoplastic effects of the *Parabacteroides* strain and enhance MAP2 gene expression as induced by the strain. Furthermore, combinations of therapeutic agents may reduce the emergence of acquired resistance to treatment through new somatic mutation(s) in cancer cells, which is problem encountered with BRAF inhibitors [39].

Administration of Compositions of the Invention

Preferably, the compositions of the invention are to be administered to the gastrointestinal tract in order to enable delivery to and/or partial or total colonisation of the intestine with the bacterial strain of the invention. Generally, the compositions of the invention are administered orally, but they may be administered rectally, intranasally, intratumourally or via buccal or sublingual routes.

In certain embodiments, the compositions of the invention may be administered as a foam, as a spray or a gel.

In certain embodiments, the compositions of the invention may be administered as a suppository, such as a rectal suppository, for example in the form of a theobroma oil (cocoa butter), synthetic hard fat (e.g. suppocire, witepsol), glycero-gelatin, polyethylene glycol, or soap glycerin composition.

In certain embodiments, the composition of the invention is administered to the gastrointestinal tract via a tube, such as a nasogastric tube, orogastric tube, gastric tube, jejunostomy tube (J tube), percutaneous endoscopic gastrostomy (PEG), or a port, such as a chest wall port that provides access to the stomach, jejunum and other suitable access ports.

The compositions of the invention may be administered once, or they may be administered sequentially as part of a treatment regimen. In certain embodiments, the compositions of the invention are to be administered daily.

In certain embodiments of the invention, treatment according to the invention is accompanied by assessment of the patient's gut microbiota. Treatment may be repeated if delivery of and/or partial or total colonisation with the strain of the invention is not achieved such that efficacy is not observed, or treatment may be ceased if delivery and/or partial or total colonisation is successful, and efficacy is observed.

The compositions of the invention may be administered to a subject that has been diagnosed with cancer comprising oncogenic ERK signalling. In one embodiment, the mutation status of the cancer in a subject has been determined prior to administration of the composition to the subject. For example, a biopsy of the tumour may be taken from the subject and nucleotide sequencing used to determine that the cancer comprises an oncogenic mutation in BRAF, NRAS, ARAF, CRAF, EGFR, GRB2, SOS, HRAS, KRAS, such as KRAS4A or KRAS4B, MEK1, MEK2, ERK1 or ERK2, and/or an oncogenic mutation in RSK, DUSP1, DUSP5, DUSP6 or SPRY. In particular, the the cancer may be determined as comprising an oncogenic mutation in BRAF or NRAS, an oncogenic mutation in BRAF, or preferably an oncogenic mutation at position 600 of the BRAF protein. Wherein the cancer is colorectal cancer, the cancer may be determined as comprising an oncogenic mutation selected from BRAF V600E, K601E, G469A, G469V, L597R, K601N, G464V, N581S, L597Q, A598V, G464R, G466A or G469E. Wherein the cancer is melanoma, the cancer may be determined as comprising an oncogenic mutation selected from BRAF V600E, V600K, V600R or V600D. In especially preferred embodiments, the cancer, such as colorectal cancer or melanoma, has been determined as comprising the mutation BRAF V600E. The presence of BRAF V600E may identified by detecting a T to A mutation in nucleotide 1799 of the BRAF gene, for example using the Cobas® 4800 BRAF V600 Mutation Test (Roche).

The compositions of the invention may be administered to a patient that has been identified as having an abnormal gut microbiota. For example, the patient may have reduced or absent colonisation by *Parabacteroides*, and in particular *Parabacteroides* distasonis.

The compositions of the invention may be administered as a food product, such as a nutritional supplement.

Generally, the compositions of the invention are for the treatment of humans, although they may be used to treat animals including monogastric mammals such as poultry, pigs, cats, dogs, horses or rabbits. If administered to animals, oral gavage may be used.

Compositions

The composition of the invention comprises bacteria. As detailed above, the invention provides a composition comprising a bacterial strain of the genus *Parabacteroides*, for use in a method of treating or preventing cancer as defined above.

In preferred embodiments of the invention, the compositions are formulated in freeze-dried form. For example, the compositions of the invention may comprise granules or gelatin capsules, for example hard gelatin capsules, comprising a bacterial strain of the invention.

Preferably, the compositions of the invention comprise lyophilised bacteria. Lyophilisation of bacteria is a well-established procedure and relevant guidance is available in, for example, references 140-421.

Alternatively, the compositions of the invention may comprise a live, active bacterial culture.

In preferred embodiments, the compositions of the invention are encapsulated to enable delivery of the bacterial strain to the intestine. Encapsulation protects the composition from degradation until delivery at the target location through, for example, rupturing with chemical or physical stimuli such as pressure, enzymatic activity, or physical disintegration, which may be triggered by changes in pH. Any appropriate encapsulation method may be used. Exemplary encapsulation techniques include entrapment within a porous matrix, attachment or adsorption on solid carrier surfaces, self-aggregation by flocculation or with cross-linking agents, and mechanical containment behind a microporous membrane or a microcapsule. Guidance on encapsulation that may be useful for preparing compositions of the invention is available in, for example, references [43] and [44].

The compositions may be administered orally and may be in the form of a tablet, capsule or powder. Encapsulated products are preferred. Other ingredients (such as vitamin C, for example), may be included as oxygen scavengers and prebiotic substrates to improve the delivery and/or partial or total colonisation and survival in vivo. Alternatively, the probiotic compositions of the invention may be administered orally as a food or nutritional product, such as milk or whey based fermented dairy product, or as a pharmaceutical product.

The compositions may be formulated as a probiotic.

Compositions of the invention includes a therapeutically effective amount of a bacterial strain of the invention. A therapeutically effective amount of a bacterial strain is sufficient to exert a beneficial effect upon a patient. A therapeutically effective amount of a bacterial strain may be sufficient to result in delivery to and/or partial or total colonisation of the patient's intestine.

A suitable daily dose of the bacteria, for example for an adult human, may be from about $1 \times 10^3$ to about $1 \times 10^{11}$ colony forming units (CFU); for example, from about $1 \times 10^7$ to about $1 \times 10^{10}$ CFU; in another example from about $1 \times 10^6$ to about $1 \times 10^{10}$ CFU; in another example from about $1 \times 10^7$ to about $1 \times 10^{11}$ CFU; in another example from about $1 \times 10^8$ to about $1 \times 10^{10}$ CFU; in another example from about $1 \times 10^8$ to about $1 \times 10^{11}$ CFU.

In certain embodiments, the dose of the bacteria is at least $10^9$ cells per day, such as at least $10^{10}$, at least $10^{11}$, or at least $10^{12}$ cells per day.

In certain embodiments, the compositions contain the bacterial strain in an amount of from about $1 \times 10^6$ to about $1 \times 10^{11}$ CFU/g, respect to the weight of the composition; for example, from about $1 \times 10^8$ to about $1 \times 10^{10}$ CFU/g. The dose may be, for example, 1 g, 3 g, 5 g, and 10 g.

In certain embodiments, the invention provides the above compositions, wherein the amount of the bacterial strain is from about $1 \times 10^3$ to about $1 \times 10^{11}$ colony forming units per gram with respect to a weight of the composition.

In certain embodiments, the pharmaceutical composition comprises 16, 15, 14, 13, 12, 11, 10, 9, 8, 7, 6, 5 or fewer distinct bacterial species. In certain embodiments, the pharmaceutical composition comprises 4 or fewer distinct bacterial species. In certain embodiments, the pharmaceutical composition comprises 3 or fewer distinct bacterial species. In certain embodiments, the pharmaceutical composition comprises 2 or fewer distinct bacterial species. In certain embodiments, the pharmaceutical composition comprises *Parabacteroides distasonis*, merdae, *johnsonii* or goldsteinii (in particular, *Parabacteroides distasonis*) and no other bacterial species. In preferred embodiments, the compositions of the invention comprise a single strain of *Parabacteroides distasonis*, merdae, *johnsonii* or goldsteinii (in particular *Parabacteroides distasonis*) and no other bacterial strains or species. Such compositions may comprise only de minimis or biologically irrelevant amounts of other bacterial strains or species. Strikingly, the examples demonstrate that compositions comprising only a single strain of the invention can have potent effects, with no reliance on co-administration with other strains or species.

In certain embodiments, compositions of the invention may comprise more than one bacterial strain (such as a consortium of different bacterial strains). In such embodiments, compositions of the invention may comprise (in increasing preference) at least 3, at least 4, at least 5, at least 6, at least 7, at least 8, at least 9, at least 10, or at least 11 different bacterial strains. In such embodiments, the consortium may comprise at least three different *Parabacteroides* strains, such as a strain of *Parabacteroides distasonis*, a strain of *Parabacteroides johnsonii*, and a strain of *Parabacteroides gordonii*. In such embodiments, compositions of the invention preferably comprise at least 11 different bacterial strains, wherein said at least 11 different bacterial strains comprise a strain of *Parabacteroides distasonis*, a strain of *Parabacteroides johnsonii*, and a strain of *Parabacteroides* gordonii.

In certain embodiments, the invention provides the above compositions, wherein the composition is administered at a dose of 1 g, 3 g, 5 g or 10 g.

In certain embodiments, the invention provides the above compositions, wherein the composition is administered at a dose of between 500 mg and 1000 mg, between 600 mg and 900 mg, between 700 mg and 800 mg, between 500 mg and 750 mg or between 750 mg and 1000 mg. In certain embodiments, the invention provides the above compositions, wherein the lyophilised bacteria in the pharmaceutical composition is administered at a dose of between 500 mg and 1000 mg, between 600 mg and 900 mg, between 700 mg and 800 mg, between 500 mg and 750 mg or between 750 mg and 1000 mg.

Typically, a probiotic, such as the composition of the invention, is optionally combined with at least one suitable prebiotic compound. A prebiotic compound is usually a non-digestible carbohydrate such as an oligo- or polysaccharide, or a sugar alcohol, which is not degraded or absorbed in the upper digestive tract. Known prebiotics include commercial products such as inulin and transgalacto-oligosaccharides.

In certain embodiments, the probiotic composition of the present invention includes a prebiotic compound in an amount of from about 1 to about 30% by weight, respect to the total weight composition, (e.g. from 5 to 20% by weight). Carbohydrates may be selected from the group consisting of: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. In one aspect, the prebiotics are the short-chain fructo-oligosaccharides (for simplicity shown herein below as FOSs-c.c); said FOSs-c.c. are not digestible carbohydrates, generally obtained by the conversion of the beet sugar and including a saccharose molecule to which three glucose molecules are bonded.

The compositions of the invention may comprise pharmaceutically acceptable excipients or carriers. Examples of such suitable excipients may be found in the reference [45]. Acceptable carriers or diluents for therapeutic use are well known in the pharmaceutical art and are described, for example, in reference [46]. Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

The compositions of the invention may be formulated as a food product. For example, a food product may provide nutritional benefit in addition to the therapeutic effect of the invention, such as in a nutritional supplement. Similarly, a food product may be formulated to enhance the taste of the composition of the invention or to make the composition more attractive to consume by being more similar to a common food item, rather than to a pharmaceutical composition. In certain embodiments, the composition of the invention is formulated as a milk-based product. The term "milk-based product" means any liquid or semi-solid milk- or whey-based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products.

Another important group includes milk beverages, such as whey beverages, fermented milks, condensed milks, infant or baby milks; flavoured milks, ice cream; milk-containing food such as sweets.

In certain embodiments, the compositions of the invention contain a single bacterial strain or species and do not contain any other bacterial strains or species. Such compositions may comprise only de minimis or biologically irrelevant amounts of other bacterial strains or species. Such compositions may be a culture that is substantially free from other species of organism. In some embodiments, the bacterial strain of *Parabacteroides* is the only therapeutically active agent in a composition of the invention.

The compositions for use in accordance with the invention may or may not require marketing approval.

In some cases, the lyophilised bacterial strain is reconstituted prior to administration. In some cases, the reconstitution is by use of a diluent described herein.

The compositions of the invention can comprise pharmaceutically acceptable excipients, diluents or carriers.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is cancer comprising oncogenic ERK signalling, such as colorectal cancer, melanoma, small bowel cancer such as small bowel adenocarcinoma, prostate cancer, lung adenocarcinoma such as non-small cell lung adenocarcinoma, pancreatic cancer, bladder cancer, leukaemia such as hairy cell leukaemia or acute myeloid leukaemia, glioma, pilocytic astrocytoma, ovarian cancer, papillary or follicular thyroid cancer, seminoma, liver cancer, myelodysplastic syndrome, kidney cancer or Hodgkin's disease.

In certain embodiments, the invention provides the above pharmaceutical composition, wherein the composition is administered by a method selected from the group consisting of oral, rectal, subcutaneous, nasal, buccal, and sublingual.

In certain embodiments, the invention provides the above pharmaceutical composition, comprising a carrier selected from the group consisting of lactose, starch, glucose, methyl cellulose, magnesium stearate, mannitol and sorbitol.

In certain embodiments, the invention provides the above pharmaceutical composition, comprising a diluent selected from the group consisting of ethanol, glycerol and water.

In certain embodiments, the invention provides the above pharmaceutical composition, comprising an excipient selected from the group consisting of starch, gelatin, glucose, anhydrous lactose, free-flow lactose, beta-lactose, corn sweetener, acacia, tragacanth, sodium alginate, carboxymethyl cellulose, polyethylene glycol, sodium oleate, sodium stearate, magnesium stearate, sodium benzoate, sodium acetate and sodium chloride.

In certain embodiments, the invention provides the above pharmaceutical composition, further comprising at least one of a preservative, an antioxidant and a stabilizer.

In certain embodiments, the invention provides the above pharmaceutical composition, comprising a preservative selected from the group consisting of sodium benzoate, sorbic acid and esters of p-hydroxybenzoic acid.

In certain embodiments, the invention provides the above pharmaceutical composition, wherein said bacterial strain is lyophilised.

In certain embodiments, the invention provides the above pharmaceutical composition, wherein when the composition is stored in a sealed container at about 4.0 or about 25.0 and the container is placed in an atmosphere having 50% relative humidity, at least 80% of the bacterial strain as measured in colony forming units, remains after a period of at least about: 1 month, 3 months, 6 months, 1 year, 1.5 years, 2 years, 2.5 years or 3 years.

Culturing Methods

The bacterial strains for use in the present invention can be cultured using standard microbiology techniques as detailed in, for example, references [47-49].

The solid or liquid medium used for culture may be YCFA agar, YCFA medium or YCFA+ medium. YCFA medium may include (per 100 ml, approximate values): Casitone (1.0 g), yeast extract (0.25 g), NaHCO$_3$ (0.4 g), cysteine (0.1 g), K$_2$HPO$_4$ (0.045 g), KH$_2$PO$_4$ (0.045 g), NaCl (0.09 g), (NH4)$_2$SO$_4$ (0.09 g), MgSO$_4$.7H$_2$O (0.009 g), CaCl$_2$) (0.009 g), resazurin (0.1 mg), hemin (1 mg), biotin (1 μg), cobalamin (1 µg), p-aminobenzoic acid (3 µg), folic acid (5 µg), and pyridoxamine (15 µg). YCFA+ medium has the following composition:

| | |
|---|---|
| Bacto casitione | 1.0 g |
| Yeast extract | 0.25 g |
| Sodium hydrogen carbonate | 0.4 g |
| Glucose | 0.2 g |
| Cellobiose | 0.2 g |
| Soluble starch | 0.2 g |
| Mineral solution 1 | 15 ml |
| Mineral solution 2 | 15 ml |
| SCFA solution | 0.31 ml |
| Haemin solution | 1 ml |
| Vitamin solution 1 | 100 µl |
| Vitamin solution 2 | 100 µl |
| Resazurin solution | 0.1 ml |
| Cysteine | 0.1 g |
| d. H2O to a total volume of: | 100 m |

Mineral solution 1: $K_2HPO_4$ –3.0 g; $d.H_2O$ to a total volume of 1l

Mineral solution 2: $KH_2PO_4$ –3.0 g; $(NH_4)_2SO_4$ –6.0 g; NaCl-6.0 g; $MgSO_4$ –0.6 g; $CaCl_2$ –0.6 g; d. $H_2O$ to a total volume of 1l Resazurin solution: 0.1% powdered resazurin in 100 ml distilled water.

Short chain fatty acid solution: Acetic acid –17 ml; Propionic acid-6 ml; n-Valeric acid-1 ml; Iso-Valeric acid-1 ml; Iso-Butyric acid-1 ml Haemin solution: KOH-0.28 g Ethanol 95%-25 ml; Haemin-100 mg; d. $H_2O$ to a total volume of 100 ml Vitamin solution 1: Biotin-1 mg; Cobalamin-1 mg; p-Aminobenzoic acid-3 mg; Folic acid-5 mg; Pyridoxamine-15 mg; d. $H_2O$ to a total volume of 100 ml Vitamin solution 2: Thiamine-5 mg; Riboflavin-5 mg; d. $H_2O$ to a total volume of 100 ml General The practice of the present invention will employ, unless otherwise indicated, conventional methods of chemistry, biochemistry, molecular biology, immunology and pharmacology, within the skill of the art. Such techniques are explained fully in the literature. See, e.g., references [50] and [51-57], etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two nucleotide sequences means that, when aligned, that percentage of nucleotides are the same in comparing the two sequences. This alignment and the percent homology or sequence identity can be determined using software programs known in the art, for example those described in section 7.7.18 of ref. [58]. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref [59].

Unless specifically stated, a process or method comprising numerous steps may comprise additional steps at the beginning or end of the method, or may comprise additional intervening steps. Also, steps may be combined, omitted or performed in an alternative order, if appropriate.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

MODES FOR CARRYING OUT THE INVENTION

Materials and Methods

RNA Extraction and MAP2 qPCR Analysis

Cells were plated in 12-well plates at density of $2 \times 10^5$ cells/well. After 24h cells were treated with either DMSO or Vemurafenib (662005; EMD Millipore; VEMU; SKMEL28, SKMEL31, 451Lu, HT29 (1 µM) SKMEL2 (10 µM) or Azacytidine-C (A3656; Sigma Aldrich; AzaC; 5 µg/ml) or both drugs (VEMU+Aza) together, in presence of 10% bacteria supernatants or absence of it (YCFA+). Total RNA was extracted using the RNeasy mini kit (Qiagen, Manchester, UK) according to the manufacturer's instructions, and the RNA concentration was determined by spectrophotometer at 260/280 nm (NanoDrop ND-1000; Thermo Fisher Scientific, Loughborough). For mRNA expression analysis, cDNA was prepared from 2000 ng of total RNA using the High-Capacity cDNA reverse transcription kit (Thermo Fisher, Loughborough) according to the manufacturer's instructions. The reverse transcription reactions were performed in a thermocycler (Biometra, Germany) at 25° C. for 10 min, 37° C. for 120 min, and 85° C. for 5 min. Resulting cDNA was amplified in duplicates by the SYBR-Green PCR assay, and products were detected on QuantStudio 6 flex real-time PCR machine (Applied Biosystems, UK) using a standardised profile (initial denaturation of 95° C. for 10 minutes, followed by 40 cycles of 10 seconds of denaturation at 95° C. and 30 seconds of annealing/extension at 65° C.). A dissociation stage was added after the 40 cycles to generate a melting curve. Analysis was performed using the Applied Biosystems QuantStudio Real-Time PCR Software v1.2. The primer sequences for GAPDH, and MAP2 are shown below.

| Name | Forward sequence | Reverse sequence |
|---|---|---|
| GAPDH | GGTATCGTGGA AGGACTCATG (SEQ ID NO: 12) | ATGCCAGTGAGC TTCCCGTTC (SEQ ID NO: 13) |
| MAP2 | CTCAGCACCGC TAACAGAGG (SEQ ID NO: 14) | CATTGGCGCTTC TCTCCTC (SEQ ID NO: 15) |

Western Blot Analysis

Following 24h treatment with the appropriate drugs either in presence of 10% bacterial supernatant or absence (YCFA+), protein extracts were obtained by lysing cells in RIPA buffer (R0278; Sigma Aldrich) supplemented with protease inhibitors (cOmplete Protease Inhibitor Cocktail Tablets; Roche, Switzerland) and 1 mM/L sodium orthovanadate, 0.5 mM/L PMSF. Protein quantification was done by the BCA protein assay. Equal amounts of total protein (20

μg/lane) were then separated by SDS-PAGE on 4-15% gradient gel (BioRad) and transferred to polyvinylidene difluoride (PVDF) membranes (Thermo Fisher Scientific, Loughborough). After blocking with 5% BSA or nonfat dry milk in TBST (10 mM Tris, pH 7.5, 150 mM NaCl, 0.5% Tween 20) for 60 min, membranes were probed with primary antibodies against phospho-ERK (9101S, 1:1000, Cell Signalling; New England Biolabs (UK)) or total ERK (4696S, 1:1000, Cell signalling; New England Biolabs (UK)).

Proteins of interest were detected with the appropriate HRP-conjugated secondary antibody (1:10,000, Thermo Fisher Scientific, Loughborough), developed with the ECL Western blotting Super Signal PicoPlus substrate (34577; Thermo Fisher Scientific, Loughborough), and visualised in Chemidoc XRS Imager (BioRad).

Anchorage-Independent Growth (Soft Agar Growth Assay) in 96-Well Plates

A mixture of 25 μL prewarmed (37° C.) 2× appropriate growth medium (EMEM for melanoma cell lines; DMEM high glucose for HT29) containing 20% FBS, 4 mM L-Glu, 2×NEAA, 0.6% sodium bicarbonate, 200 U/mL penicillin/streptomycin (Invitrogen), and 25 μL prewarmed (47° C.) 1.2% Noble Agar (A5431; Sigma Aldrich) were plated onto each well of a 96-well microplate to serve as a prelayer for the assay. Ten microliters of cell suspensions containing $0-2 \times 10^3$ cells were mixed with 25 μL 2× growth media and 35 μL 0.8% Noble Agar in a 96-well round-bottom polypropylene microplate and transferred to the 96-well microplate containing the solidified prelayers. The cells were allowed to grow for 2 days and then fed with media containing drugs in presence of 10% bacterial supernatants or YCFA+ every three days. They left to grow in the humidified 37° C. incubator with 5% $CO_2$ for 1-2 weeks before soft agar growth was scored using the CytoSelect 96 well cell transformation assay (CBA-130; Cell Biolabs) according to the manufacturer's protocol. Cell growth was measured using a Tecan Infinite F200 Pro Series Multi-Well Plate Reader (Tecan Biosystems), with excitation at 485 nm and emission at 530 nm.

Anchorage-Independent Growth (Soft Agar Growth Assay) in a 32-Mm Plate

A mixture of 1 mL of prewarmed (37° C.) 2× appropriate growth media (EMEM for melanoma cell lines; DMEM high glucose for HT29) and 1 mL prewarmed (47° C.) 0.8% Noble Agar per plate (0.4% final agar) were mixed with 1 mL cell suspension and seeded over a 0.6% agar/cell growth prelayer (2 mL) in a 6-well plate. The cells were allowed to grow in the humidified 37° C. incubator with 5% CO2 for 21-28 days. They fed with drugs in absence (YCFA+) or presence of 10% bacterial supernatant every three days. Colonies were photographed using Evos XL Core microscope (Thermo Fisher Scientific, Loughborough).

Clonogenic Assay

Cells were trypsinized and 200 cells/well were seeded in 12-well plates. After 48h cells were treated with the appropriate drugs in absence (YCFA+) or presence of 10% bacterial supernatant and were re-fed every three days. On day 21 after seeding, cells were fixed in ice-cold methanol and stained with Crystal Violet blue. Colonies (0.50 cells) were counted and survival fraction was calculated as number of colonies divided by the number of plated cells (plating efficiency) of treated divided by the plating efficiency of control.

GPR109a RNA Expression Assay

HT29mtx cells seeded on 12 well plates and differentiated for 10 days; then they were serum-starved for 12 hours and subsequently exposed to 10% supernatant derived from stationary phase bacteria for 24h. Cells were collected, and total RNA was isolated according to the RNeasy mini kit protocol (Qiagen). cDNA was made using the high capacity cDNA reverse transcription kit (Applied Biosystems). Gene expression was measured by qPCR. βactin was used as internal control. Fold change was calculated according to the $2^{\wedge}(-\Delta\Delta ct)$ method [60]. The sequences of the forward and reverse primers used are provided as SEQ ID NO: 15 and 16, respectively.

TNF-α Secretion Assay

Differentiated HT29 cells were plated in 12 well plates at a density of 200,000 cells/well. Cells were differentiated for 10 days (media change every 2 days). The day of the experiment cells were placed in the anaerobic hood and washed with anaerobic equilibrated HANKs solution. Then 900 μl of growth media (without FBS and antibiotics) was added to the cells. Bacterial cells were resuspended growth media (without FBS and antibiotics) and were then added at $10^{\wedge}7$ in total in 100 μl. Cells were co-incubated with bacteria for 2 hr in an anaerobic hood. Afterwards cells were washed in growth media without FBS but containing antibiotics. Cells were left to rest in 1 ml of ThP1 condition media for 24 h. After 24 h incubation the supernatant was collected and spun down at 10,000 g for 3 min and 4° C. Samples were frozen at −80° C. until further use.

ThP1 condition media: Thp1 were seeded on T25 flask at density of $4\times10^{\wedge}6$/flask. Cells were treated in RPMI media (contain 2 mM L-glutamine without FBS) with 1 ug/ml LPS or LPS+5 mM ATP (ATP added 3 hours after LPS). Cells were left to rest for 24 hr. Thereafter Condition Media (CM) was collected by spinning down the cells at 250 g for 5 min and RT. Different CMs were used to treat HT29 Cells. A small aliquot was frozen at 80° C. for ELISA.

Supernatants from the different samples were collected and cytokine analysis performed according to manufacturer's instruction using the human TNF-α ELISA kit from Peprotech. GraphPad Prism7 was used to plot and analysed the data.

Fermentation Profile of NCIMB 42382

Rapid ID 32A testing was carried out on NCIMB 42382 colonies as per manufacturer's instructions. A single bead from an NCIMB 42382 bead stock generated on 26 Jun. 2015 was used to inoculate an YCFA agar plate (E&O Labs) which was incubated for 24 hours at 37° C. in an anaerobic workstation. Colonies were removed from the plate and resuspended in a 2 ml ampoule of API® Suspension Medium (bioMérieux), and this suspension was used to inoculate a Rapid ID 32A strip (bioMérieux) as per manufacturer's instructions. The strip was incubated and developed according to manufacturer's instructions, and the colour of each cupule was recorded and assigned a value of negative, intermediate or positive.

API® 50 CHL testing was carried out as per manufacturer's instructions with some slight alterations. A single bead from an NCIMB 42382 glycerol stock generated on 14 Aug. 2015 was used to inoculate an YCFA agar plate (E&O Labs) which was incubated for 24 hours at 37° C. in an anaerobic workstation. A single colony from this plate was used to inoculate a culture in YCFA broth (E&O Labs) and this was incubated for 16-18 hours at 37° C. anaerobically. This culture was diluted tenfold in API® CHL Medium (bioMérieux) to create a suspension that was used to inoculate each cupule on an API® 50 CH test panel (bioMérieux). Test strips were incubated in a humidified incubation box at 37° C. anaerobically for 48 hours, following which the colour of each cupule was recorded and assigned a value of negative, intermediate or positive.

Splenocyte Proliferation and Cytokine Secretion

Splenocytes were freshly prepared from spleen dissected from female C57BL/6 mice between 6 and 8 weeks of age. Briefly, splenocytes were plated at 900,000 cells/well in 96 well plates in RPMI 1640 with 10% FBS, 2 mM L-Glutamine, 100U/ml penicillin, 100 µg/ml streptomycin and 55 µM of f3-mercaptoethanol. Cells were left untreated (resting) or treated with 10% bacterial media YCFA+ (blank media) or 10% cell-free bacterial supernatant from stationary culture of various strains and incubated for 72h in a $CO_2$ incubator at 37° C. Afterwards the cells were spun down for 5 minutes at 500 g at 4° C. and cell free supernatants were collected, and stored at −80° C. for cytokine analysis. Each *Parabacteroides* strain was cultured and supernatant prepared as follows: 100 µL of a Research Cell Bank vial was used to inoculate 10 mL of YCFA+ broth. The culture was incubated overnight in an anaerobic workstation at 37° C. Each overnight culture was used to inoculate five Hungate tubes containing 10 mL of fresh growth medium with a 10% subculture. Culture tubes were incubated until they reached early stationary phase, following which cell-free supernatants (CFS) were collected as follows. Individual culture tubes were combined and the bacterial density (O.D. 600 nm) was recorded. Cell-free supernatant of the *Parabacteroides* strain was obtained by centrifugation (5000×g for 15 minutes) and filtration through a 0.45 µm followed by a 0.22 µm filter.

MTT assay kit was purchased from Merck Millipore (Cat n. CT01). After 72h incubation, 10 µl of MTT solution was added to each well, cells were incubated in a $CO_2$ incubator for 4h. Afterwards 100 µl of isopropanol/0.04 M HCL solution was added to each well and the absorbance was measured at 560 nm wavelength with a reference wavelength of 655 nm.

Cytokine quantification was conducted using a 26-plex Mouse ProcartaPlex multiplex immunoassay following the manufacturers recommendations (Thermo Fischer Scientific). Briefly, 50 µl of cell-free co-culture supernatants were used for cytokine quantification using a MAGPIX® MILLIPLEX® system (Merck) with the xPONENT software (Luminex, Austin, Tex., USA). Data was analysed using the MILLIPLEX® analyst software (Merck) using a 5-parameter logistic curve and background subtraction to convert mean fluorescence intensity to pg/ml values.

Short/Medium Chain Fatty Acid Quantification

A pure culture of *P. distasonis* strain DSM 20701 was grown anaerobically in YCFA+ broth [Per litre: Casein hydrolysate 10.0 g, Yeast Extract 2.5 g, Sodium hydrogen carbonate 4.0 g, Glucose 2.0 g, Cellobiose 2.0 g, Soluble starch 2.0 g, Di-potassium hydrogen phosphate 0.45 g, Potassium di-hydrogen phosphate 0.45 g, Resazurin 0.001 g, L-Cysteine HCl 1.0 g, Ammonium sulphate 0.9 g, Sodium chloride 0.9 g, Magnesium sulphate 0.09 g, Calcium chloride 0.09 g, Haemin 0.01 g, SCFA 3.1 ml (Acetic acid 2.026 ml/L, Propionic acid 0.715 ml/L, n-Valeric acid 0.119 ml/L, Iso-Valeric acid 0.119 ml/L, Iso-Butyric acid 0.119 ml/L), vitamin mix 1:1 ml (Biotin 1 mg/100 ml, Cyanocobalamine 1 mg/100 ml, p-Aminobenzoic acid 3 mg/100 ml, Pyridoxine 15 mg/100 ml), vitamin mix 2:1 ml (Thiamine 5 mg/100 ml, Riboflavin 5 mg/100 ml), vitamin mix 3:1 ml (Folic acid 5 mg/100 ml)] until they reached their stationary growth phase. Cultures were centrifuged at 5000×g for 10 minutes and the cell-free supernatant (CFS) was filtered using a 0.45 µM followed by a 0.2 µM filter (Millipore, UK), after which 1 mL aliquots of the CFS were stored at −80° C. until use.

Short chain fatty acids (SCFAs) and medium chain fatty acids (MCFAs) from bacterial supernatants were analysed and quantified by MS Omics APS, Denmark. Samples were acidified using hydrochloride acid, and deuterium labelled internal standards were added. All samples were analyzed in a randomized order. Analysis was performed using a high polarity column (Zebron™ ZB-FFAP, GC Cap. Column 30 m×0.25 mm×0.25 µm) installed in a gas chromatograph (7890B, Agilent) coupled with a quadropole detector (5977B, Agilent). The system was controlled by ChemStation (Agilent). Raw data was converted to netCDF format using Chemstation (Agilent), before the data was imported and processed in Matlab R2014b (Mathworks, Inc.) using the PARADISe software.

Phospho-ERK Staining Intensity Assay (Indirect Immunofluorescence)

Cells (HT29 and HCT116) were seeded in black 96 well plates at a density of 10,000 cells/well overnight and were treated with 10% bacterial supernatant for 24h. Afterwards, the cells were fixed with 4% paraformaldehyde in PBS (pH 7.3) for 20 min at room temperature (RT). Fixed cells were washed with PBS, and permeabilized with 0.5% Triton X-100 in PBS for 10 min. After washing with PBS, the plates were incubated with blocking buffer (4% BSA/PBS) for 1 h at RT before adding the primary antibody for 12h at 4° C. (anti-p44/42 MAPK mouse antibody (4696S, Cell Signalling) anti-phospho-p44/42 (T202/Y204) MAPK rabbit antibody (9101S, Cell signalling) both at 1:100, diluted in 1% BSA/PBS. They were then washed twice with PBS, followed by incubation with secondary antibodies Alexa Flour 488 conjugated anti-rabbit (Molecular Probes Inc) and Alexa Flour 594 ((Molecular Probes Inc) conjugated for 1 h at RT. After washing 3× with PBS, DAPI was added for 10 min followed by washing with PBS 3×. Plates were then viewed using ImageExpress Plco microscope (Molecular Devices) equipped with a 20× objective and filter sets suitable for detection of the fluorochromes used. Raw analysis data generated by the PICO analysis module were plotted and analysed using GraphPad Prism 7 software.

Example 1—SKMEL2 Melanoma Cell Line

The effects of the following treatments were assessed on the SKMEL2 melanoma cell line (WT BRAF; N61R oncogenic mutation in Nras): (1) the strain deposited under accession no. NCIMB 42382 ("NCIMB 42382"); (2) Vemurafenib (VEMU) in YCFA medium; (3) VEMU and NCIMB 42382; (4) Azacytidine-C (Aza-c) in YCFA medium; (5) Aza-c and NCIMB 42382; (6) VEMU, Aza-c and NCIMB 42382.

MAP2 gene expression in the SKMEL2 cell line was assessed using the protocol in Materials and Methods, and the results are shown in FIG. 1. All treatments with NCIMB 42382 (alone or in combination with VEMU and/or Aza-c) increased MAP2 gene expression relative to both negative controls (cell line only, and YCFA+). Clonogenic survival of the SKMEL2 cell line was assessed using the protocol in Materials and Methods, and the results are shown in FIG. 2. Soft agar growth of the SKMEL2 cell line was assessed using the protocol in Materials and Methods, and the results are shown in FIG. 3. VEMU+Aza-c improved soft agar growth inhibition by NCIMB 42382. ERK signalling in the SKMEL2 cell line was assessed using the protocol in Materials and Methods, and the results are shown in FIG. 4 (VEMU, Aza-c and NCIMB 42382 was not assessed). ERK signalling in the SKMEL2 cell line was further assessed by a different assay (phospho-ERK staining intensity) using the protocol in Materials and Methods, and the results are shown in FIG. 27. NCIMB 42382 alone or in combination with VEMU or Aza-c reduced phospho-ERK staining intensity compared to the cells only and YCFA+ controls.

These results indicate that NCIMB 42382 alone or in combination with Vemurafenib and/or Azacytidine-C may have the effects of inducing MAP2 gene expression in a melanoma cell line (SKMEL2). Furthermore, Vemurafenib+ Azacytidine-C enhanced soft agar growth inhibition by NCIMB 42382. Furthermore, NCIMB 42382 alone or in combination with Vemurafenib or Azacytidine-C may have the effect of inhibiting ERK signalling in this cell line. On this basis, compositions of the invention are expected to be useful in the treatment or prevention of various metastatic cancers, in particular metastatic melanoma. Compositions of the invention may also be useful in the treatment or prevention of cancers comprising oncogenic ERK signalling, such as cancers comprising an oncogenic mutation in NRAS, especially the mutation NRAS N61R.

Example 2—SKMEL28 Melanoma Cell Line

The effects of the following treatments were assessed on the SKMEL28 melanoma cell line (V600E oncogenic mutation in BRAF): (1) NCIMB 42382; (2) Vemurafenib (VEMU) in YCFA medium; (3) VEMU and NCIMB 42382; (4) Azacytidine-C (Aza-c) in YCFA medium; (5) Aza-c and NCIMB 42382; (6) VEMU, Aza-c and NCIMB 42382.

MAP2 gene expression in the SKMEL28 cell line was assessed using the protocol in Materials and Methods, and the results are shown in FIG. 5. Clonogenic survival of the SKMEL28 cell line was assessed using the protocol in Materials and Methods, and the results are shown in FIG. 6. NCIMB 42382 in combination with VEMU and/or Aza-c decreased clonogenic survival relative to both negative controls (YCFA and cell line only). Soft agar growth of the SKMEL28 cell line was assessed using the protocol in Materials and Methods, and the results are shown in FIG. 7. ERK signalling in the SKMEL28 cell line was assessed using the protocol in Materials and Methods, and the results are shown in FIG. 8 (VEMU, Aza-c and NCIMB 42382 was not assessed). All treatments with NCIMB 42382 (alone or in combination with VEMU or Aza-c) reduced ERK signalling relative to the negative control (YCFA). ERK signalling in the SKMEL28 cell line was further assessed by a different assay (phospho-ERK staining intensity) using the protocol in Materials and Methods, and the results are shown in FIG. 28. NCIMB 42382 alone or in combination with VEMU or Aza-c reduced phospho-ERK staining intensity compared to the cells only and YCFA+ controls.

These results indicate that NCIMB 42382 alone or in combination with Vemurafenib and/or Azacytidine-C may have the effects of inhibiting ERK signalling and decreasing clonogenic survival of a melanoma cell line comprising the BRAF V600E mutation (SKMEL28). On this basis, compositions of the invention are expected to be useful in the treatment or prevention of cancers comprising oncogenic ERK signalling, especially melanomas. In particular, compositions of the invention are expected to be useful in the treatment or prevention of such cancers comprising an oncogenic mutation in BRAF, in particular at position 600, and especially the mutation BRAF V600E.

Example 3—SKMEL31 Melanoma Cell Line

The effects of the following treatments were assessed on the SKMEL31 melanoma cell line (heterozygous for BRAF V600E): (1) NCIMB 42382; (2) Vemurafenib (VEMU) in YCFA medium; (3) VEMU and NCIMB 42382; (4) Azacytidine-C (Aza-c) in YCFA medium; (5) Aza-c and NCIMB 42382; (6) VEMU, Aza-c and NCIMB 42382.

Figure 11:
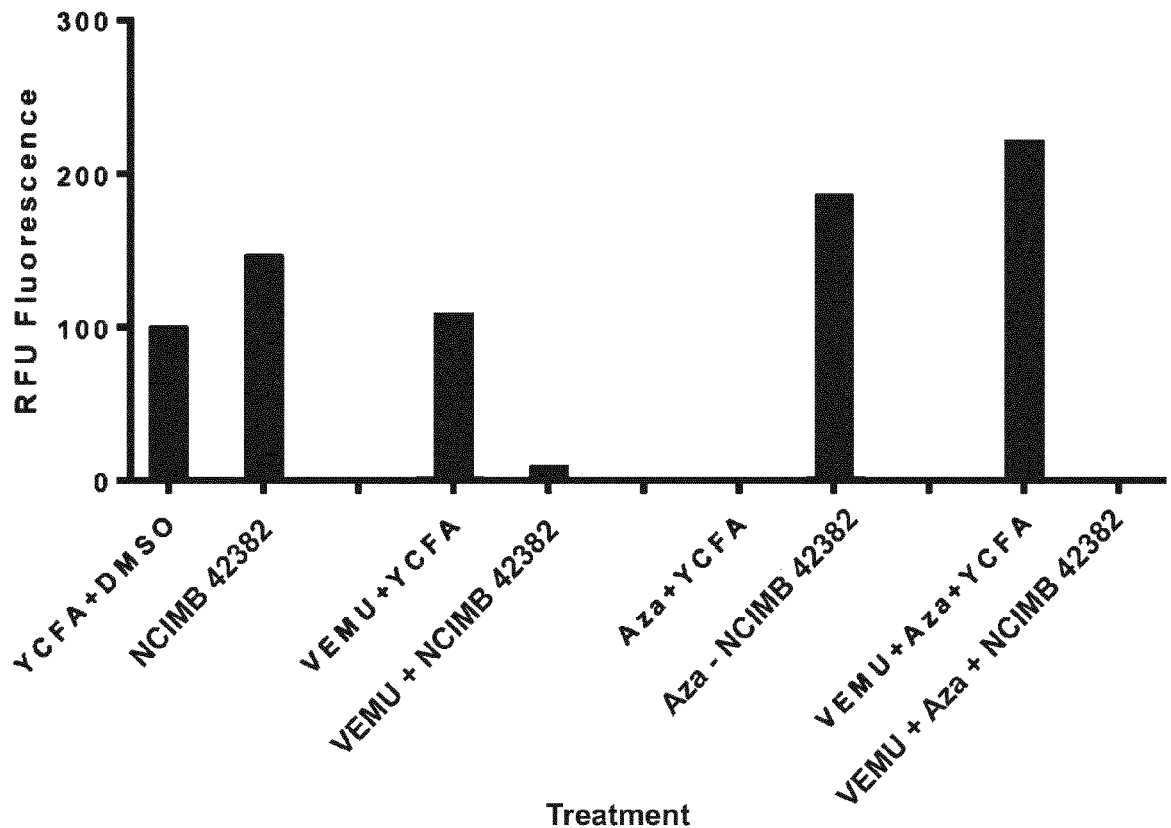
FIG. 11: Soft agar growth of the SKMEL31 cell line following various treatments ("YCFA"=YCFA+).
Figure 29:
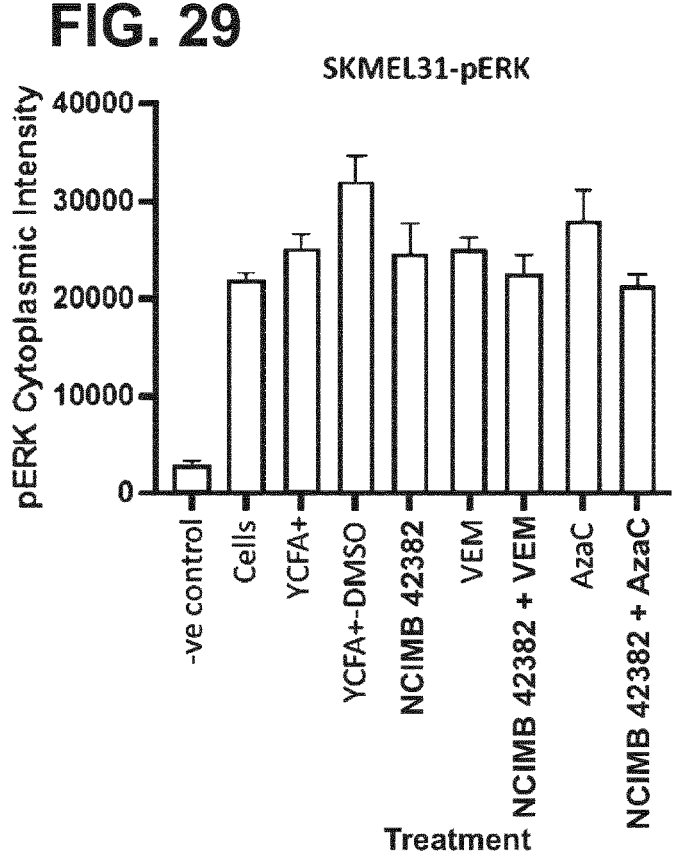
FIG. 29: Phospho-ERK (pERK) staining intensity in the SKMEL31 melanoma cell line, following various treatments ("VEM"=Vemurafenib, "AzaC"=Azacytidine C).

MAP2 gene expression in the SKMEL31 cell line was assessed using the protocol in Materials and Methods, and the results are shown in FIG. 9. Clonogenic survival of the SKMEL31 cell line was assessed using the protocol in Materials and Methods, and the results are shown in FIG. 10. Soft agar growth of the SKMEL31 cell line was assessed using the protocol in Materials and Methods, and the results are shown in FIG. 11. VEMU, Aza-c and VEMU+Aza-c improved soft agar growth and clonogenic survival inhibition by NCIMB 42382. ERK signalling in the SKMEL31 cell line was assessed using the protocol in Materials and Methods, and the results are shown in FIG. 12 (VEMU, Aza-c and NCIMB 42382 in combination was not assessed). All treatments with NCIMB 42382 (alone or in combination with VEMU or Aza-c) reduced ERK signalling relative to the negative control (YCFA). ERK signalling in the SKMEL31 cell line was further assessed by a different assay (phospho-ERK staining intensity) using the protocol in Materials and Methods, and the results are shown in FIG. 29.

Example 4—451Lu Melanoma Cell Line

The effects of the following treatments were assessed on the 451Lu melanoma cell line (V600E oncogenic mutation in BRAF): (1) NCIMB 42382; (2) Vemurafenib (VEMU) in YCFA medium; (3) VEMU and NCIMB 42382; (4) Azacytidine-C (Aza-c) in YCFA medium; (5) Aza-c and NCIMB 42382; (6) VEMU, Aza-c and NCIMB 42382.

Figure 30:
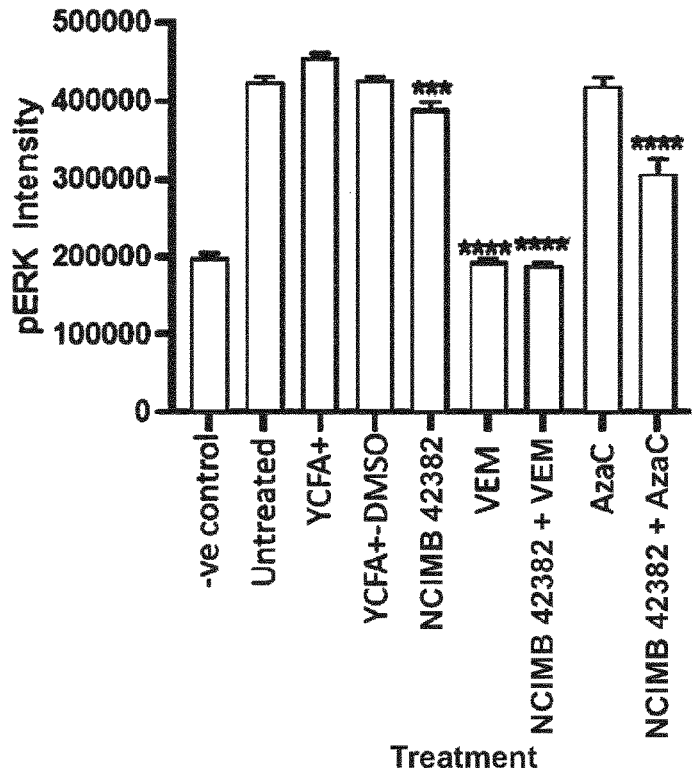
FIG. 30: Phospho-ERK (pERK) staining intensity in the 451Lu melanoma cell line, following various treatments ("VEM"=Vemurafenib, "AzaC"=Azacytidine C).

MAP2 gene expression in the 451Lu cell line was assessed using the protocol in Materials and Methods, and the results are shown in FIG. 13. All treatments with NCIMB 42382 (alone or in combination with VEMU and/or Aza-c) increased MAP2 gene expression relative to the cell line only negative control. Clonogenic survival of the 451Lu cell line was assessed using the protocol in Materials and Methods, and the results are shown in FIG. 14. All treatments with NCIMB 42382 (alone or in combination with VEMU and/or Aza-c) decreased clonogenic survival relative to both negative controls (cell line only, and YCFA+ +DMSO). Soft agar growth of the 451Lu cell line was assessed using the protocol in Materials and Methods, and the results are shown in FIG. 15. Azacytidine C enhanced soft agar growth inhibition by NCIMB 42382. ERK signalling in the 451Lu cell line was assessed using the protocol in Materials and Methods, and the results are shown in FIG. 16 (VEMU, Aza-c and NCIMB 42382 in combination was not assessed). NCIMB 42382 in combination with VEMU or Aza-c reduced ERK signalling relative to the negative control (YCFA+DMSO). ERK signalling in the 451Lu cell line was further assessed by a different assay (phospho-ERK staining intensity) using the protocol in Materials and Methods, and the results are shown in FIG. 30. NCIMB 42382 alone or in combination with VEMU or Aza-c reduced phospho-ERK staining intensity compared to the untreated (cells only), YCFA+ and YCFA+ with DMSO controls, with a greater effect observed when NCIMB 42382 was combined with either VEMU or Aza-C.

These results indicate that NCIMB 42382 alone or in combination with Vemurafenib and/or Azacytidine-C has the effects of inducing MAP2 gene expression, and decreasing clonogenic survival and growth of a melanoma cell line carrying a BRAF V600E oncogenic mutation (451Lu). NCIMB 42382 alone or in combination with Vemurafenib and/or Azacytidine-C also has the effects of inhibiting ERK signalling in this cell line. On this basis, compositions of the invention are expected to be useful in the treatment or prevention of cancers comprising oncogenic ERK signalling, especially melanomas such as metastatic melanomas. In particular, compositions of the invention are expected to be useful in the treatment or prevention of such cancers comprising an oncogenic mutation in BRAF, in particular at position 600, and especially the mutation BRAF V600E.

Example 5—HT29 Colorectal Cancer Cell Line

The effects of the following treatments were assessed on the HT29 colorectal cancer cell line (V600E oncogenic mutation in BRAF): (1) NCIMB 42382; (2) Vemurafenib (VEMU) in YCFA medium; (3) VEMU and NCIMB 42382; (4) Azacytidine-C (Aza-c) in YCFA medium; (5) Aza-c and NCIMB 42382; (6) VEMU, Aza-c and NCIMB 42382.

Figure 19B:
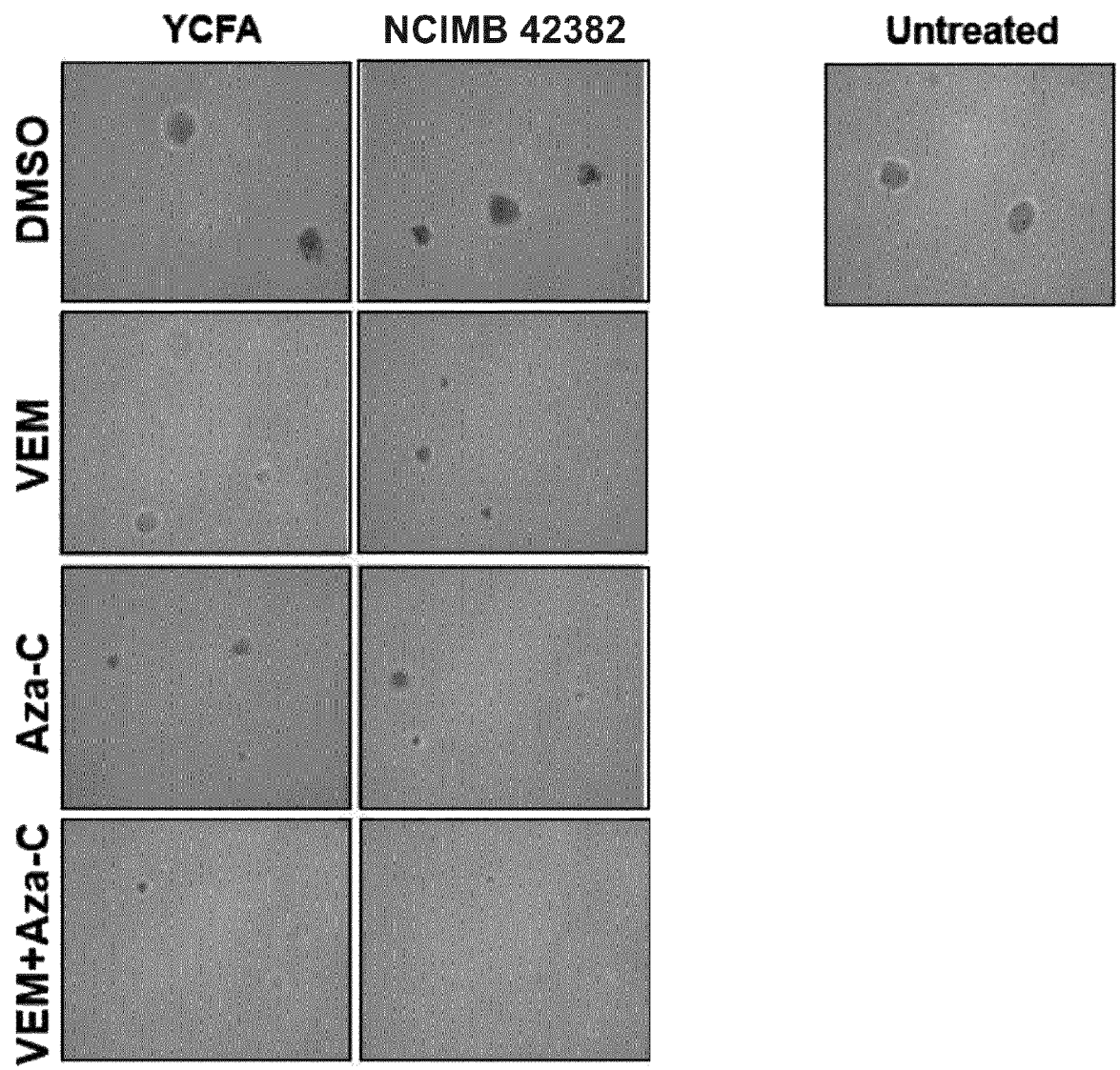
FIG. 19B: Soft agar growth of the HT-29 cell line following various treatments (photograph of agar plates) ("YCFA"=YCFA+).
Figure 31:
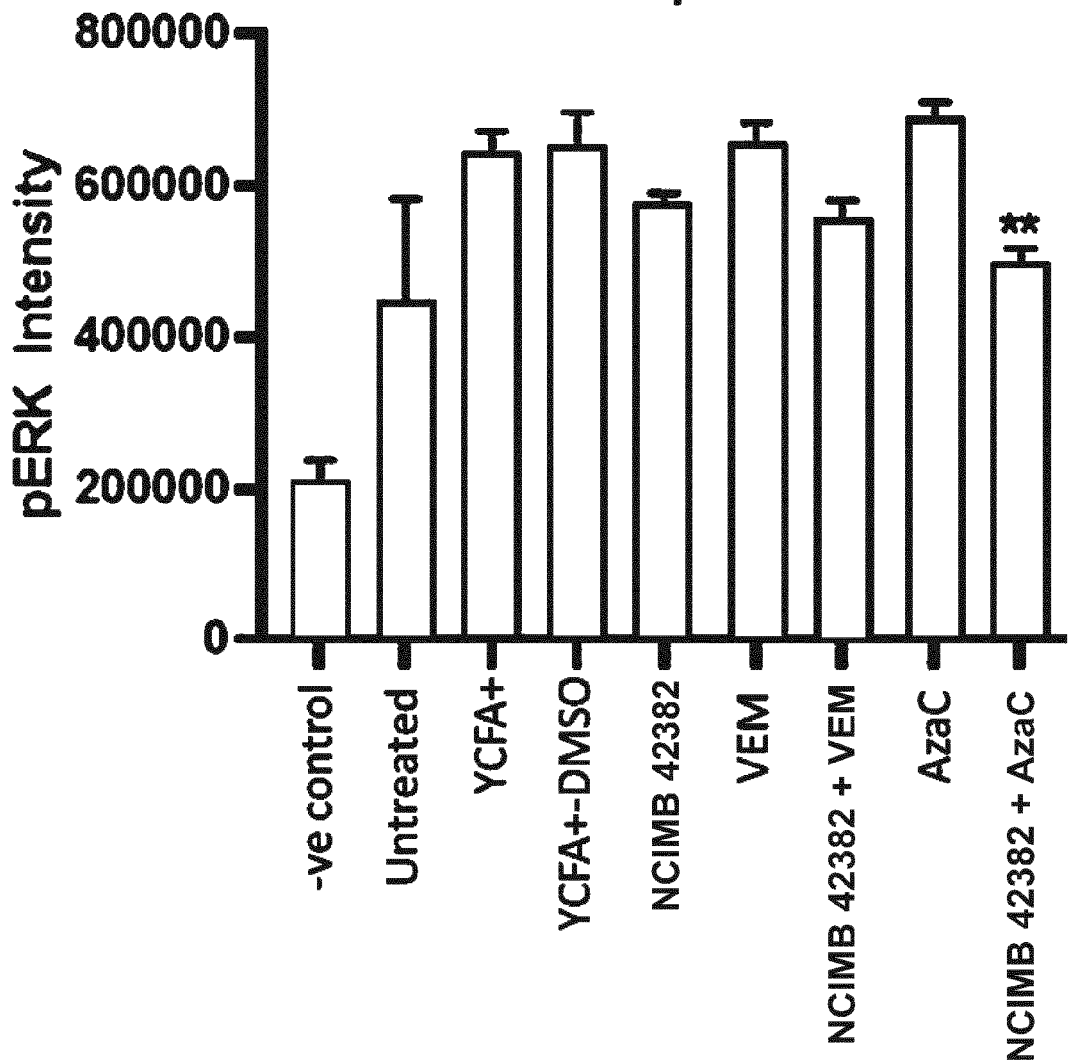
FIG. 31: Phospho-ERK (pERK) staining intensity in the HT29 colorectal cancer cell line, following various treatments ("VEM"=Vemurafenib, "AzaC"=Azacytidine C).

MAP2 gene expression in the HT29 cell line was assessed using the protocol in Materials and Methods, and the results are shown in FIG. 17. NCIMB 42382 in combination with VEMU and/or Aza-c increased MAP2 gene expression relative to both negative controls (cell line only and YCFA+). Clonogenic survival of the HT29 cell line was assessed using the protocol in Materials and Methods, and the results are shown in FIG. 18. All treatments with NCIMB 42382 (alone or in combination with VEMU and/or Aza-c) decreased clonogenic survival relative to both negative controls (cell line only, and YCFA+ +DMSO). Aza-c improved the effects of NCIMB 42382 in inhibiting clonogenic survival. Soft agar growth of the HT29 cell line was assessed using the protocol in Materials and Methods, and the results are shown in FIGS. 19a and b. ERK signalling in the HT29 cell line was assessed using the protocol in Materials and Methods, and the results are shown in FIG. 20 (VEMU, Aza-c and NCIMB 42382 in combination was not assessed). NCIMB 42382 alone ERK signalling relative to the negative control (YCFA+DMSO). ERK signalling in the HT29 cell line was further assessed by a different assay (phospho-ERK staining intensity) using the protocol in Materials and Methods, and the results are shown in FIG. 31. NCIMB 42382 alone or in combination with VEMU or Aza-c reduced phospho-ERK staining intensity compared to the YCFA+ and YCFA+DMSO controls, with a greater effect observed when NCIMB 42382 was combined with Aza-C.

These results indicate that NCIMB 42382 alone or in combination with Vemurafenib and/or Azacytidine-C has the effects of inducing MAP2 gene expression, decreasing clonogenic survival and inhibiting ERK signalling in a cell line carrying the V600E oncogenic mutation (HT29). On this basis, compositions of the invention are expected to be useful in the treatment or prevention of cancers comprising oncogenic ERK signalling, especially colorectal cancers such as metastatic colorectal cancer. In particular, compositions of the invention are expected to be useful in the treatment or prevention of such cancers comprising an oncogenic mutation in BRAF, in particular at position 600, and especially the mutation BRAF V600E.

Example 6—HCT116 Cell Line

The effects of the following treatments were assessed on the HCT116 colorectal cancer cell line (which is heterozygous for the G13D mutation in KRAS): (1) NCIMB 42382; (2) Vemurafenib (VEMU); (3) VEMU and NCIMB 42382; (4) Azacytidine-C (Aza-c); (5) Aza-c and NCIMB 42382; (6) VEMU, Aza-c and NCIMB 42382.

Figure 32:
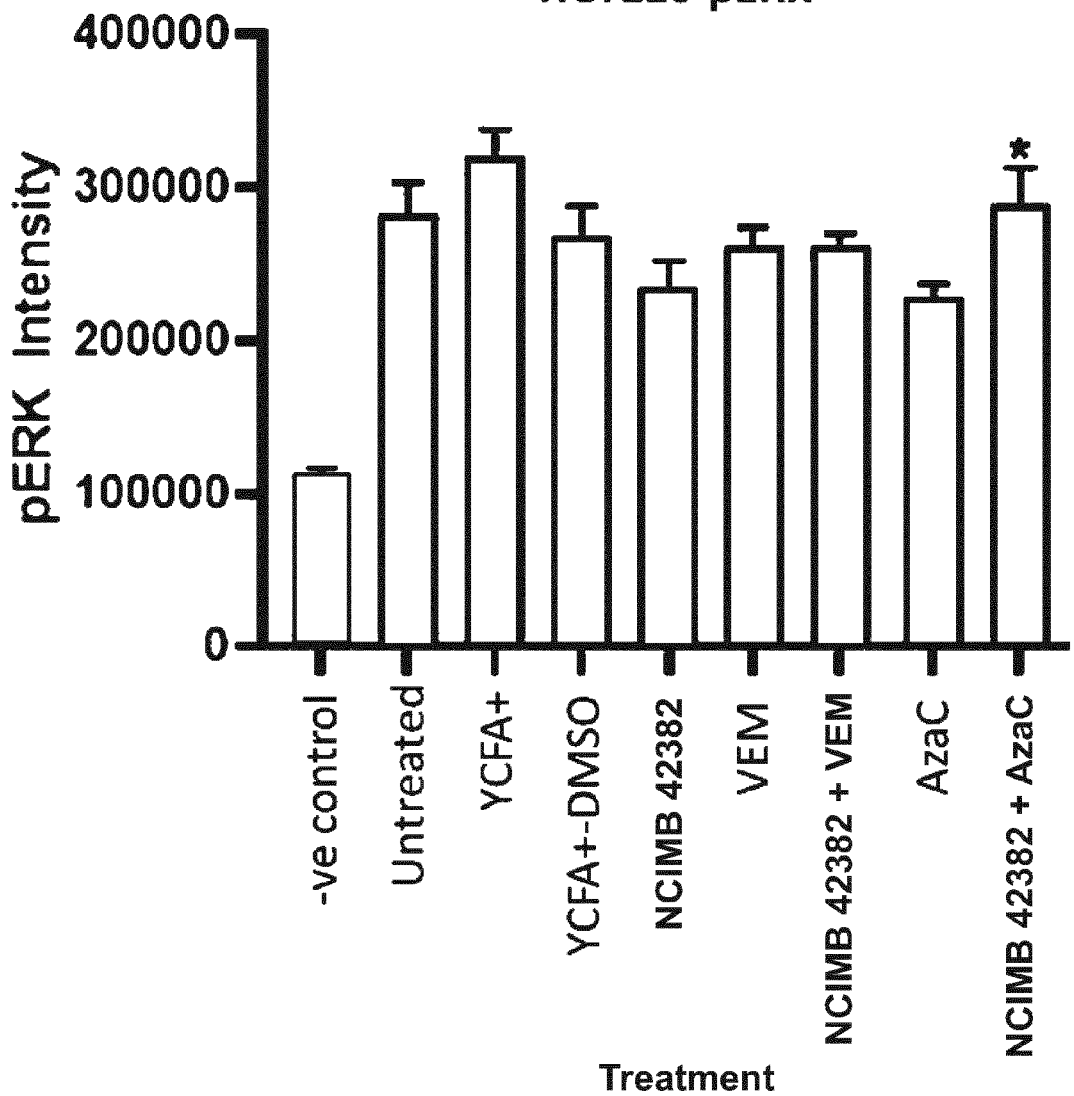
FIG. 32: Phospho-ERK (pERK) staining intensity in the HCT116 colorectal cancer cell line, following various treatments ("VEM"=Vemurafenib, "AzaC"=Azacytidine C).
Figure 33D:
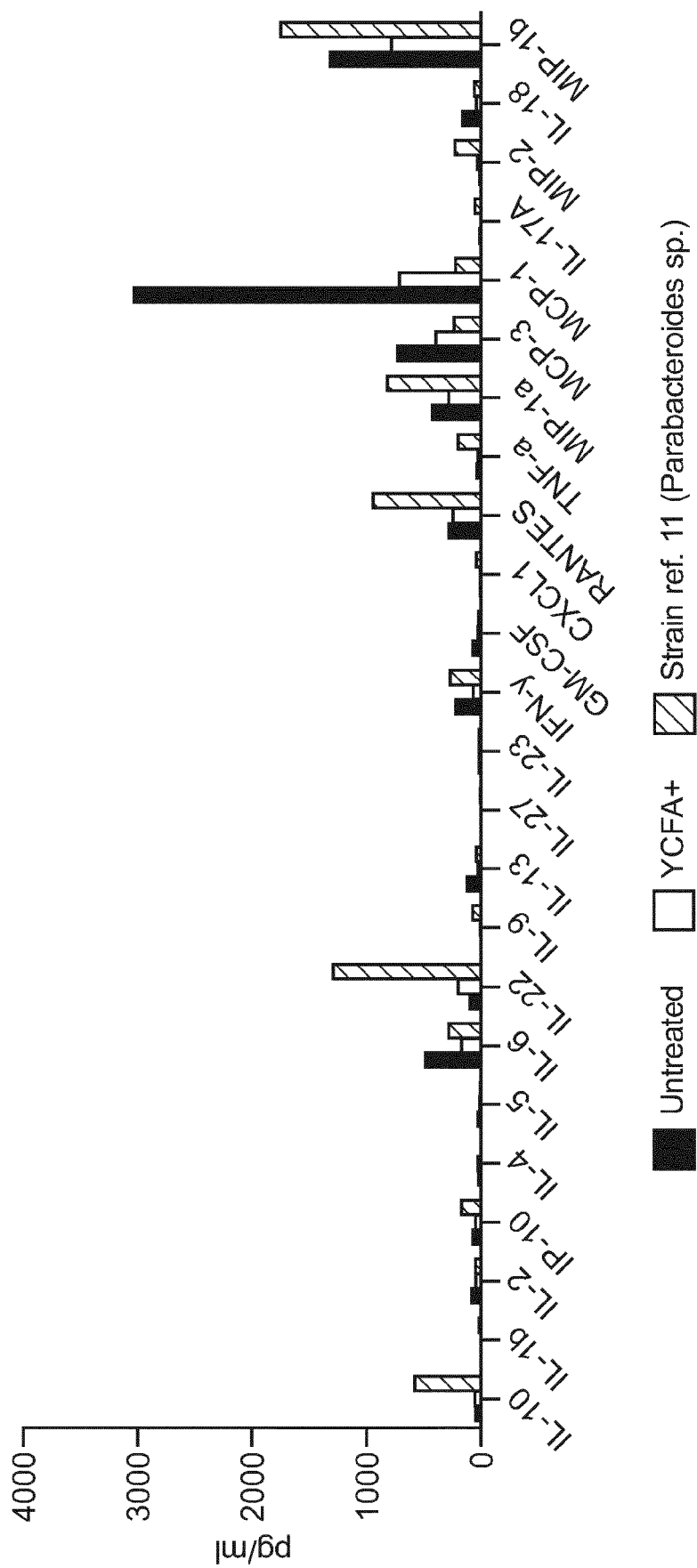
Figure 33F:
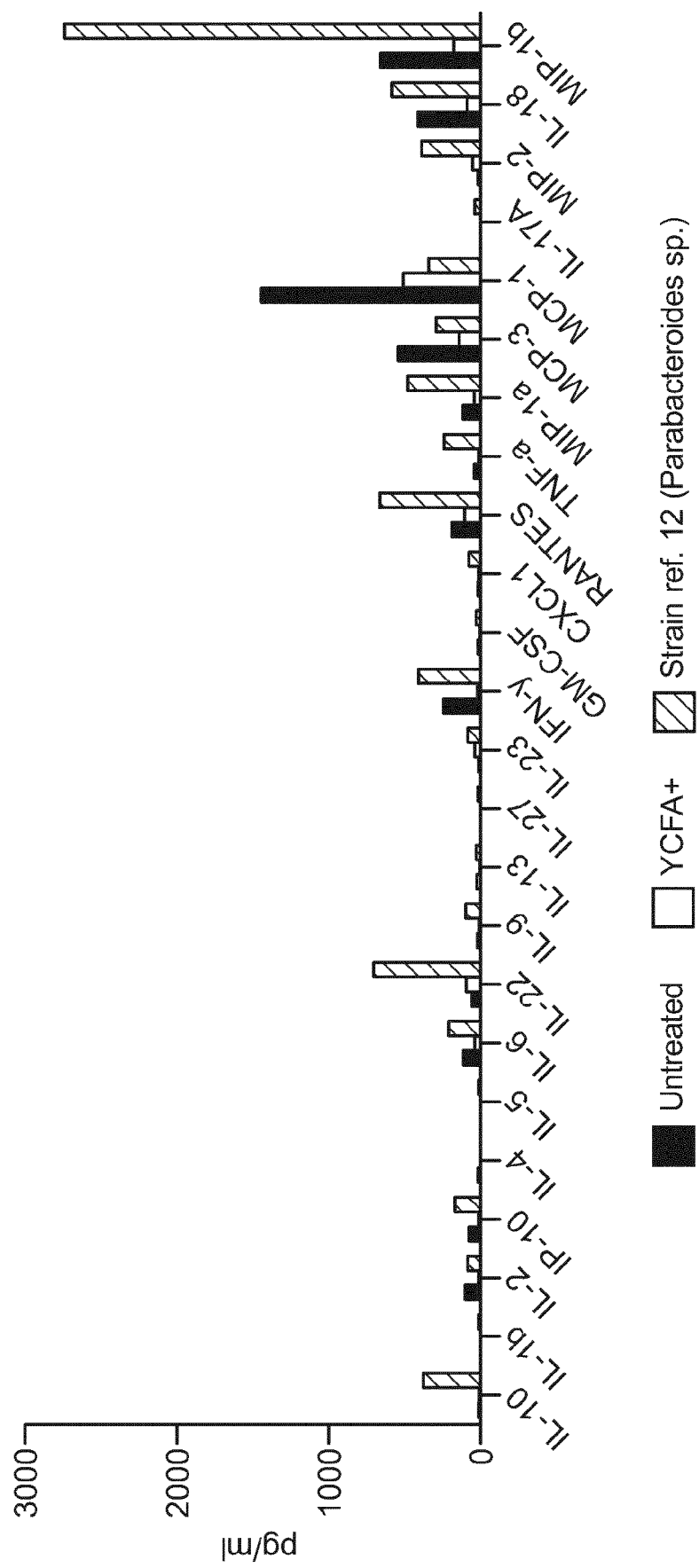
Figure 33G:
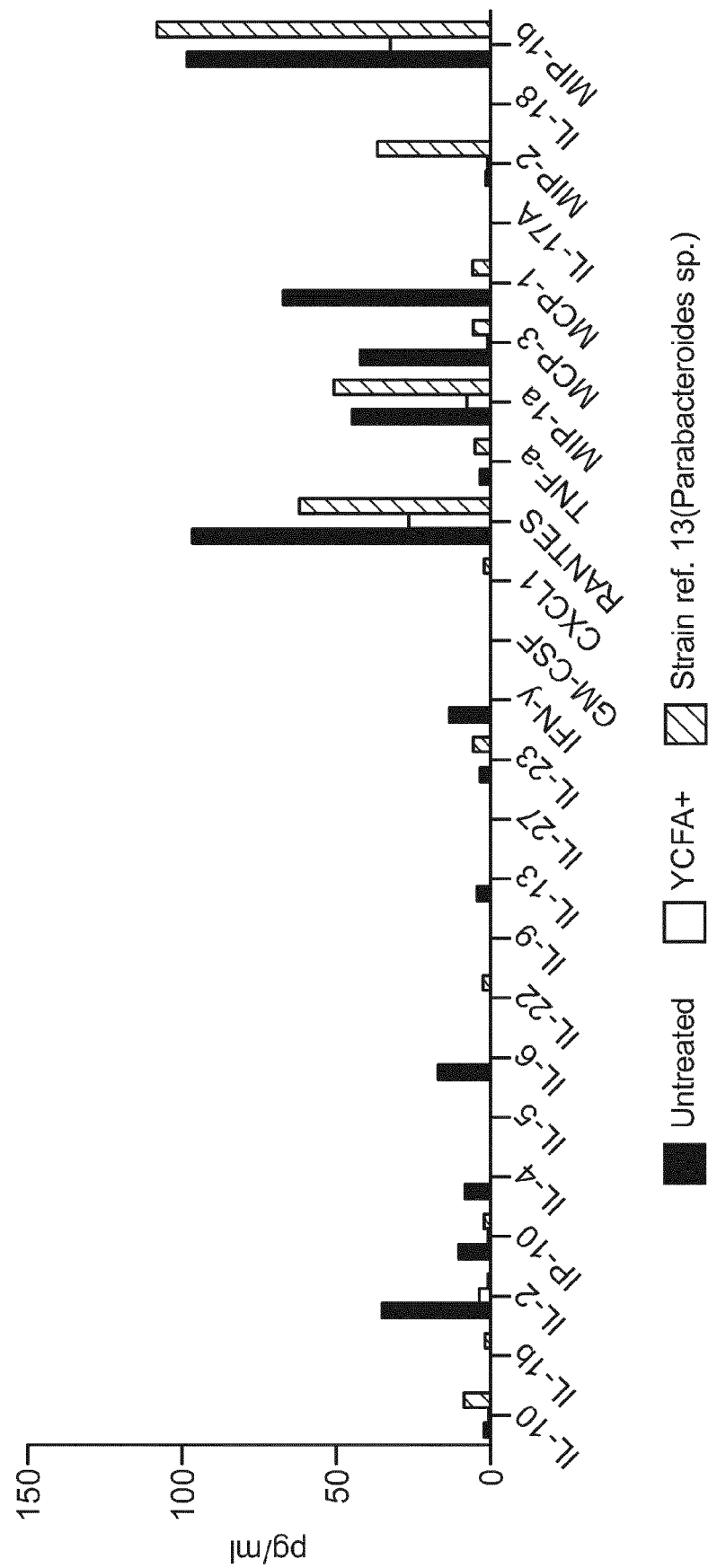
Figure 33H:
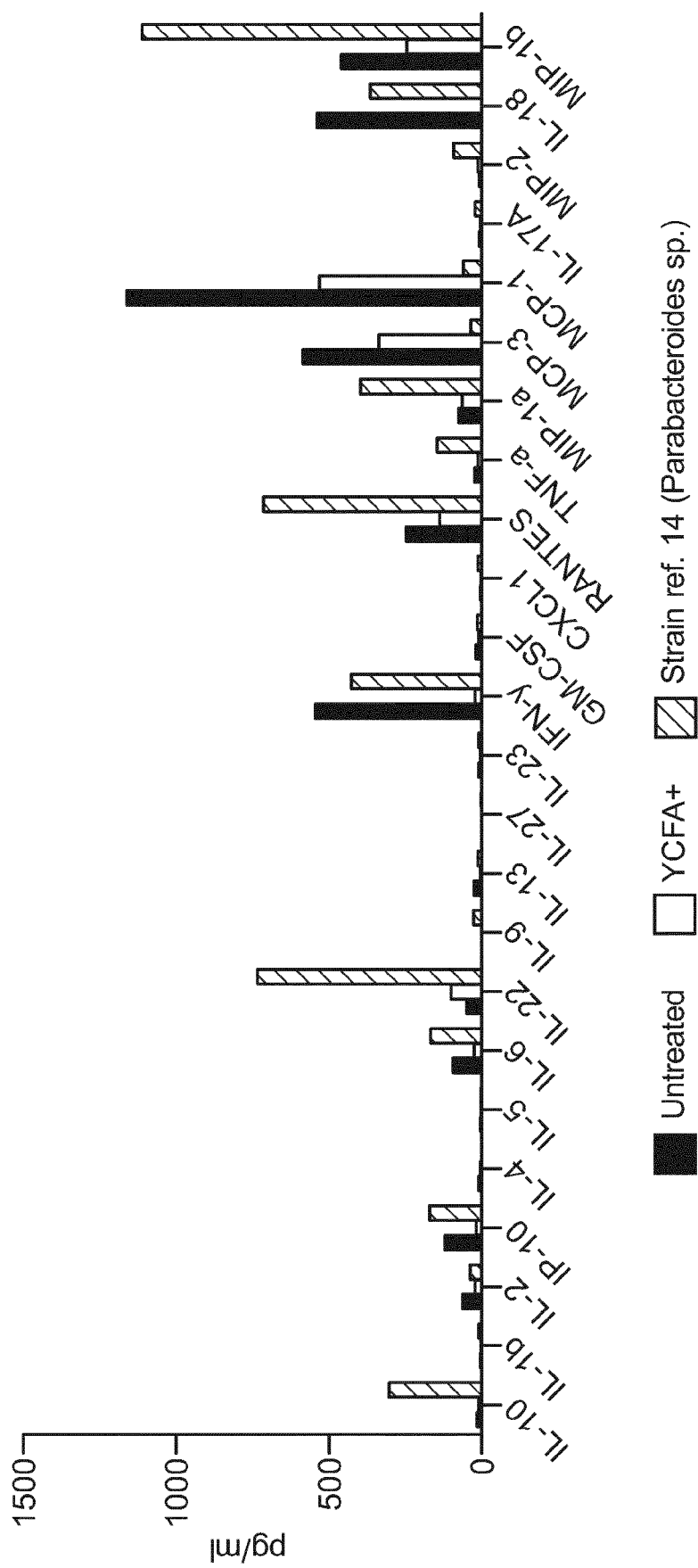
Figure 33I:
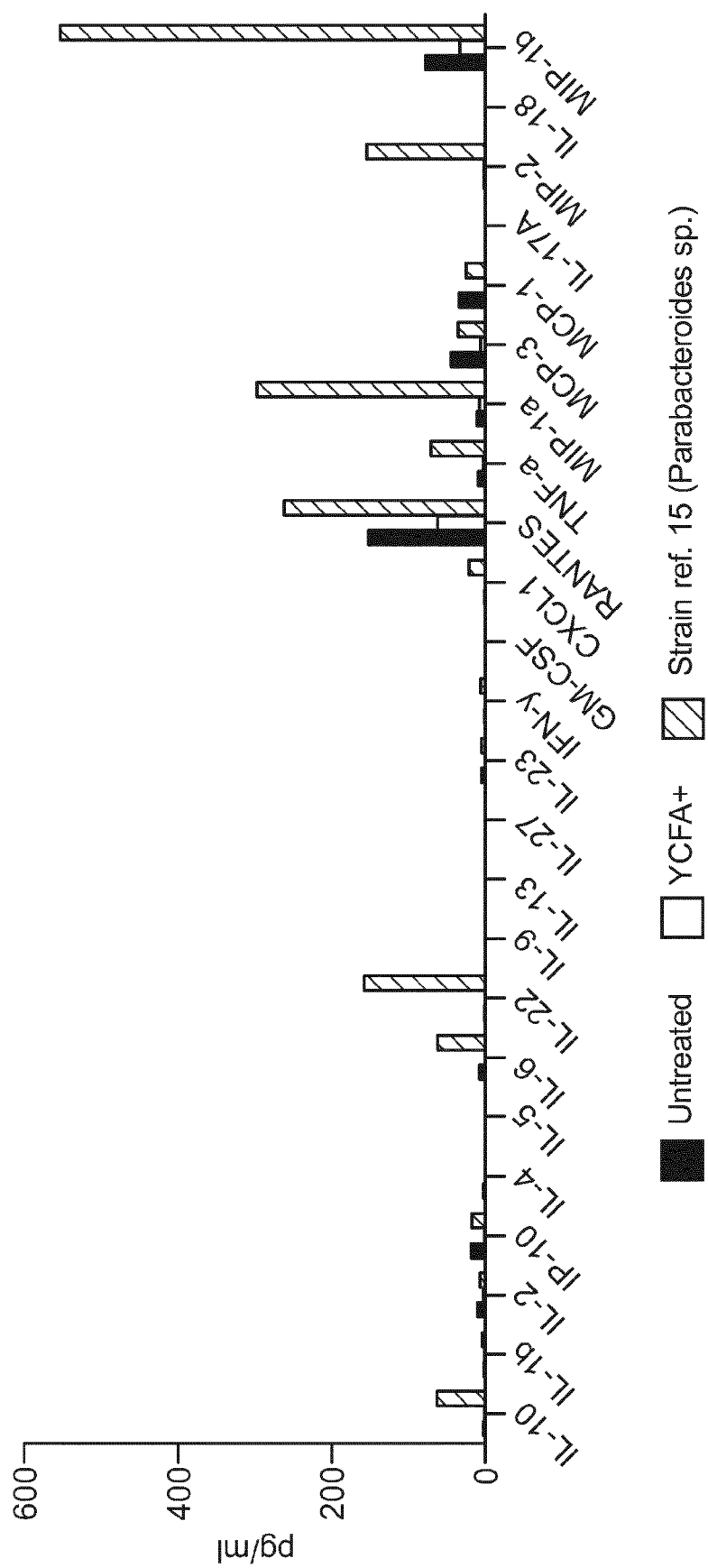

ERK signalling in the HCT116 cell line was assessed by the phospho-ERK staining intensity assay using the protocol in Materials and Methods, and the results are shown in FIG. 32. NCIMB 42382 alone reduced phospho-ERK staining intensity compared to the untreated, YCFA+ and YCFA+ with DMSO controls.

Example 7—GPR109a RNA Expression in Differentiated HT29 (HT29mtx) Cells

GPR109a is a G-protein coupled receptor expressed in the lumen-facing apical membrane of colonic and intestinal epithelial cells. GPR109a expression silencing is found in colon cancers cell lines, and the induction of its expression has been reported to induce tumour cell apoptosis in the presence of bacterial fermentation products such as butyrate [61].

Figure 21A:
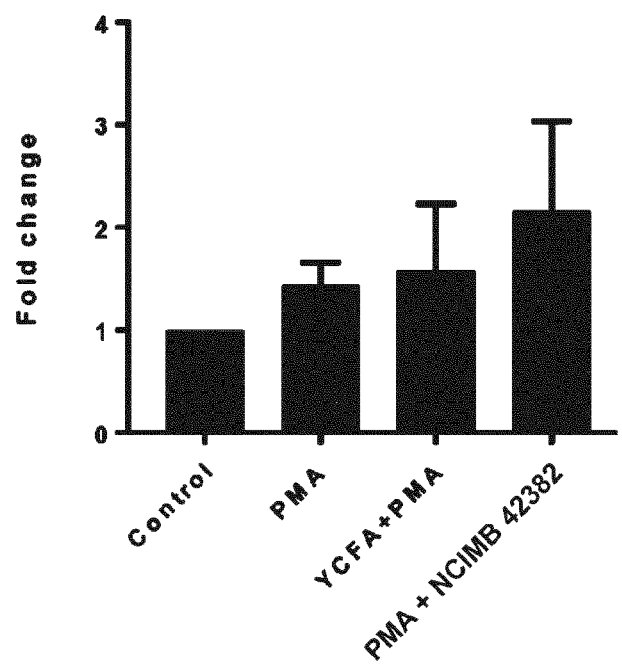
FIGS. 21A-21B: GPR109a RNA expression in methotrexate-treated HT29 cells (FIG. 21A) with, and (FIG. 21B) without phorbol-12-myristate-13-acetate treatment in addition to NCIMB 42382 ("YCFA"=YCFA+).
Figure 21B:
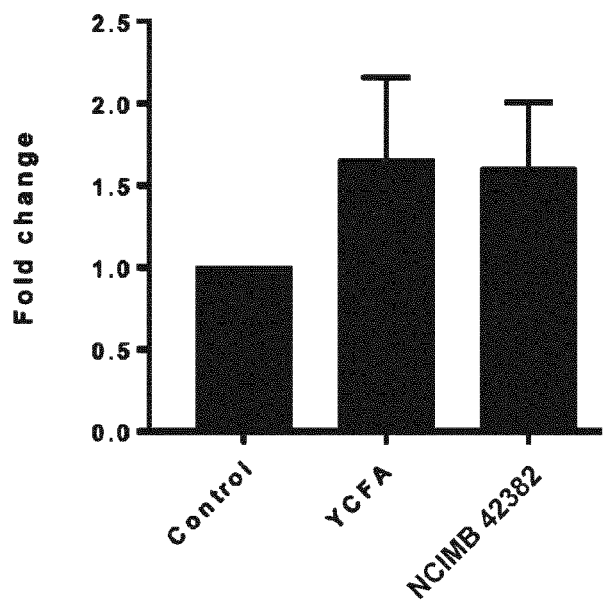

Differentiated HT29 cells resulting from methotrexate treatment (HT29mtx cells) form polarised apical/mucosal and basolateral/serosal membranes that are impermeable and are structurally and functionally similar to epithelial cells of the small intestine. HT-29mtx cells treated with phorbol-12-myristate-13-acetate (PMA) and NCIMB 42382 supernatant exhibited greater expression of GPR109a RNA, than treatment with PMA alone (or PMA in YCFA+ medium)—see FIG. 21A. PMA treatment of HT29 cells induces a metastatic phenotype, including increased migration and invasion capacity [62]. Therefore, these data suggest that compositions of the invention may be useful in the treatment of metastatic cancers, in particular metastatic colorectal cancer or small bowel cancer such as small bowel adenocarcinoma, and in particular those comprising oncogenic ERK signalling. These data also suggest that compositions of the invention may effect such treatment through the mechanism of inducing apoptosis, as a result of GPR109a expression.

Example 8—Effect of NCIMB 42382 on TNF-Alpha Secretion by the HT29 Cell Line

Figure 22A:
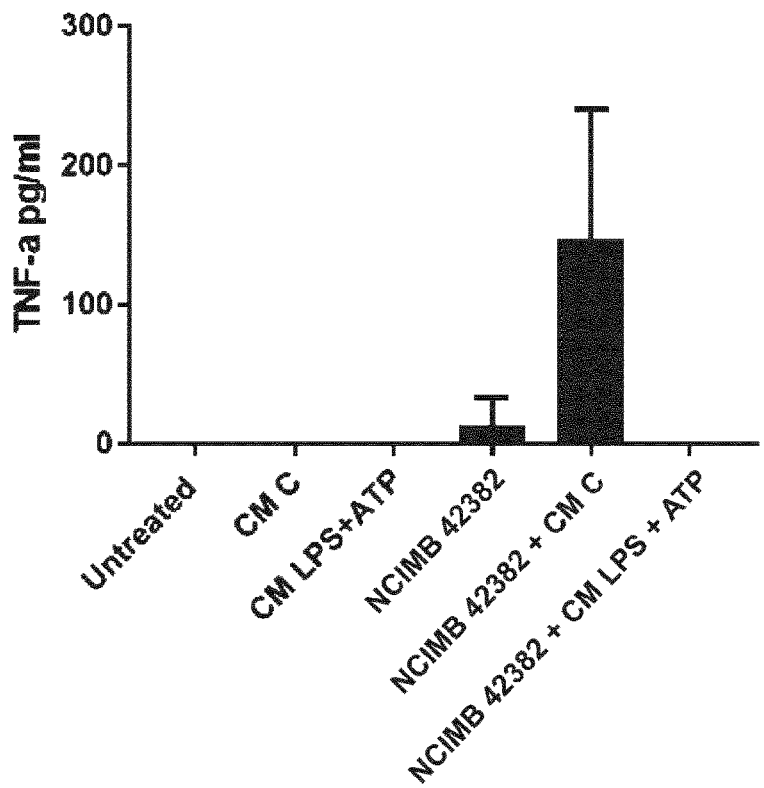
FIGS. 22A-22B: Induction of TNF-α secretion from HT29 cells by (FIG. 22A) NCIMB 42382 with conditioned media and (FIG. 22B) NCIMB 42382 alone.
Figure 22B:
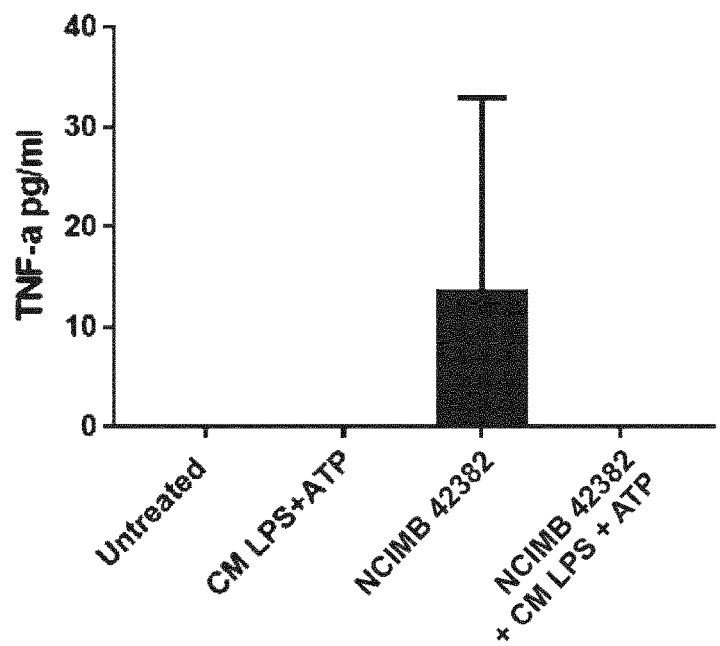

NCIMB 42382 supernatant either alone or with Thp1 conditioned media (CM) induced TNF-α secretion from the HT29 cancer cell line (colorectal cancer)—see FIGS. 22B and 22A respectively.

Example 9—Fermentation Profile of NCIMB 42382

Using Rapid ID 32A analysis, NCIMB 42382 tested positive for fermentation of α-galactosidase, β-galactosidase, α-glucosidase, β-glucosidase, alkaline phosphatase, and utilisation of arginine, leucyl-glycine, leucine, alanine, histidine and glutamyl glutamic acid (FIG. 23A). Using API® 50 CHL, NCIMB 42382 tested positive for utilisation of the following carbohydrate sources: fructose, mannose, mannitol, sorbitol, arbutin, esculin, maltose, lactose, melibiose, sucrose, raffinose, starch, glycogen, turanose and fucose (FIG. 23B). Intermediate reactions were observed for xylose, N-acetylglucosamine, amygdalin, salicin, cellobiose, trehalose, melezitose and gentiobiose. Bacterial strains exhibiting either a highly similar or the same fermentation profile as NCIMB 42382, for carbohydrates and/or amino acids (in particular, for carbohydrates), are expected to be useful in the treatment or prevention of cancers comprising oncogenic ERK signalling.

Example 10—Effect of *Parabacteroides* Strains on Splenocyte Proliferation

Figure 25:
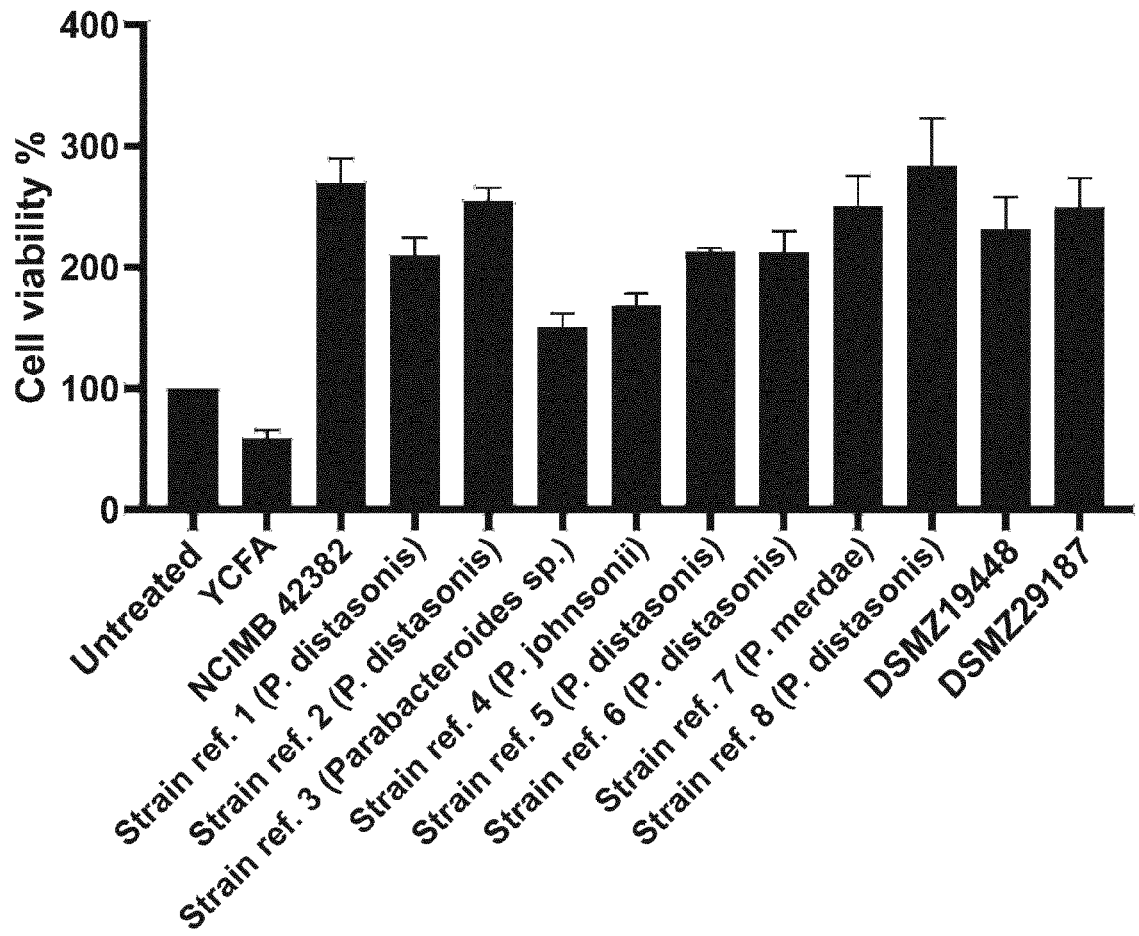
FIG. 25: Splenocyte proliferation following treatment with *Parabacteroides* strains ("YCFA"=YCFA+).
Figure 26A:
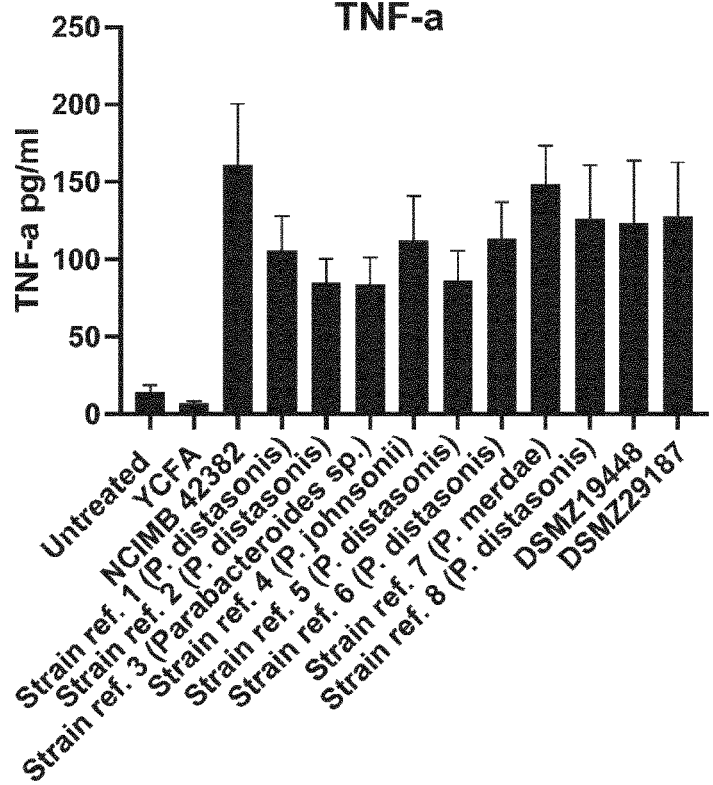
FIGS. 26A-26W: Cytokine secretion from splenocytes following treatment with various *Parabacteroides* strains— (FIG. 26A) TNF-α, (FIG. 26B) IL-1ß, (FIG. 26C) IL-2, (FIG. 26D) GM-CSF, (FIG. 26E) IFN-γ, (FIG. 26F) IL-27, (FIG. 26G) IL-10, (FIG. 26H) IL-6, (FIG. 26I) MIP-2, (FIG. 26J) MIP-1α, (FIG. 26K) MIP-1ß, (FIG. 26L) IL-22, (FIG. 26M) RANTES, (FIG. 26N) IP-10, (FIG. 26O) IL-4, (FIG. 26P), IL-5, (FIG. 26Q), IL-18, (FIG. 26R) IL-23, (FIG. 26S) IL-9, (FIG. 26T) CXCL1, (FIG. 26U) MCP-3, (FIG. 26V) MCP-1 and (FIG. 26W) IL-17A ("YCFA"=YCFA+).
Figure 26B:
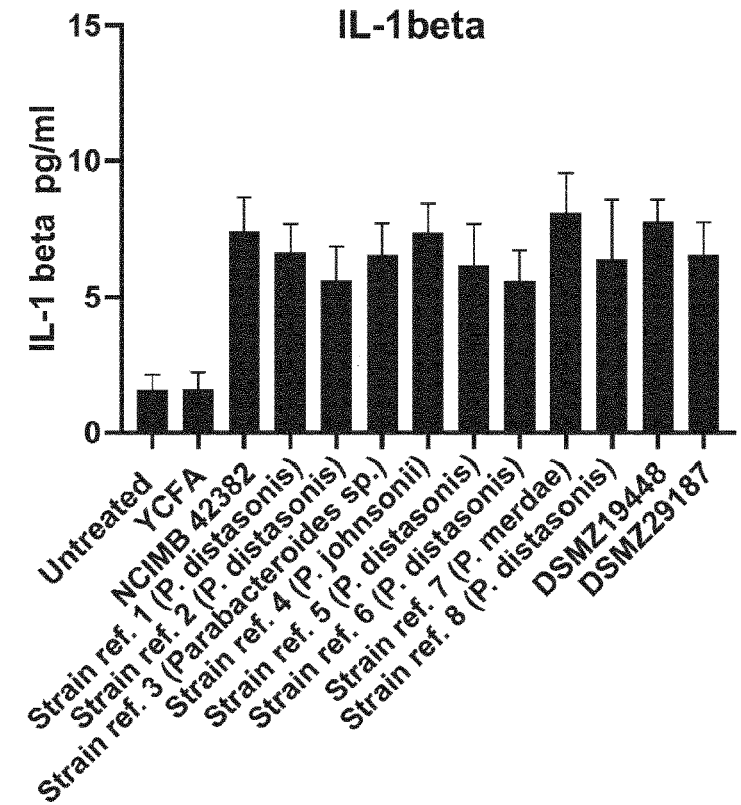
Figure 26C:
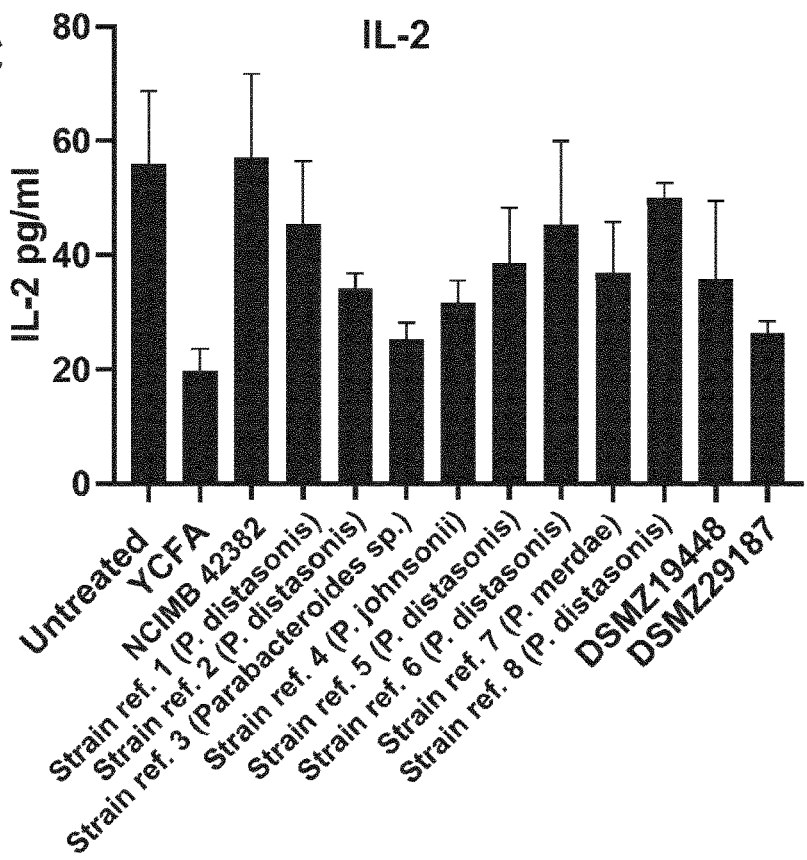
Figure 26D:
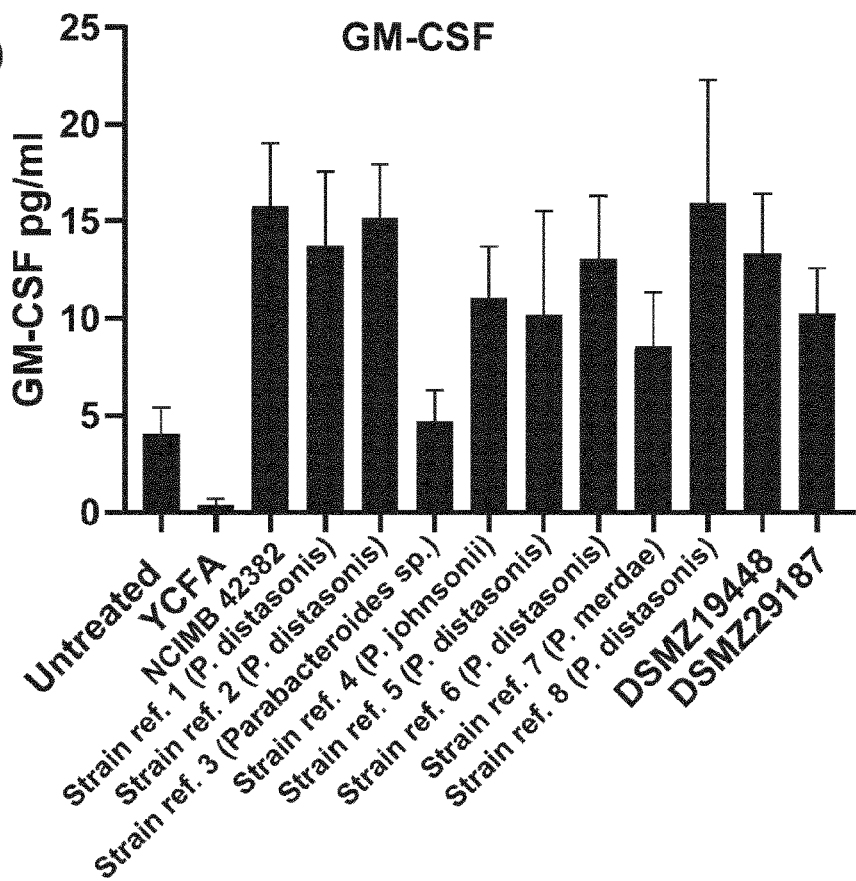
Figure 26E:
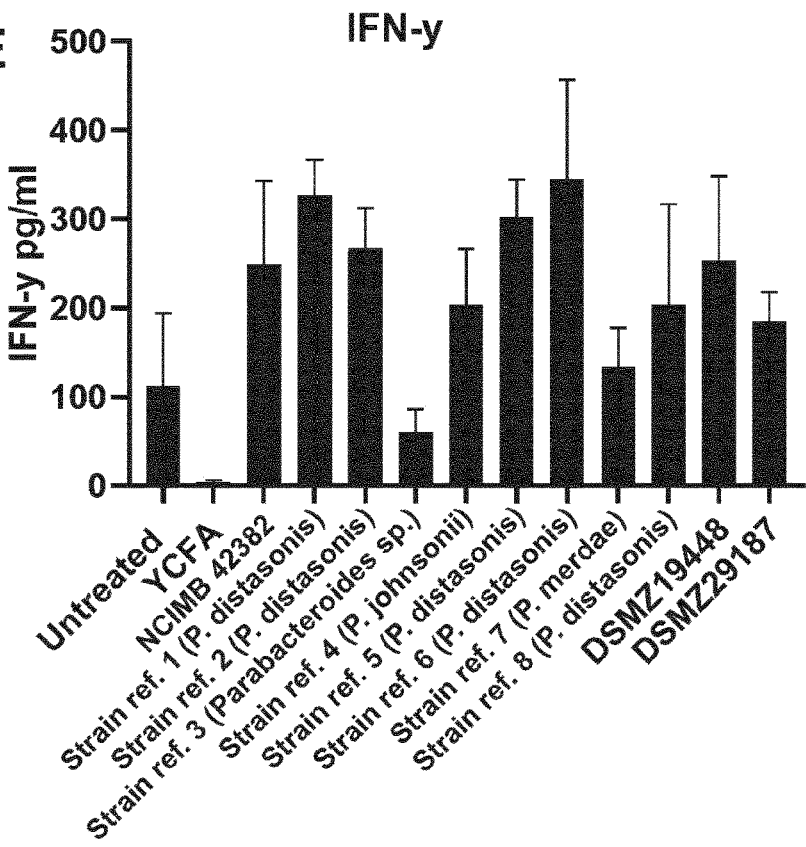
Figure 26F:
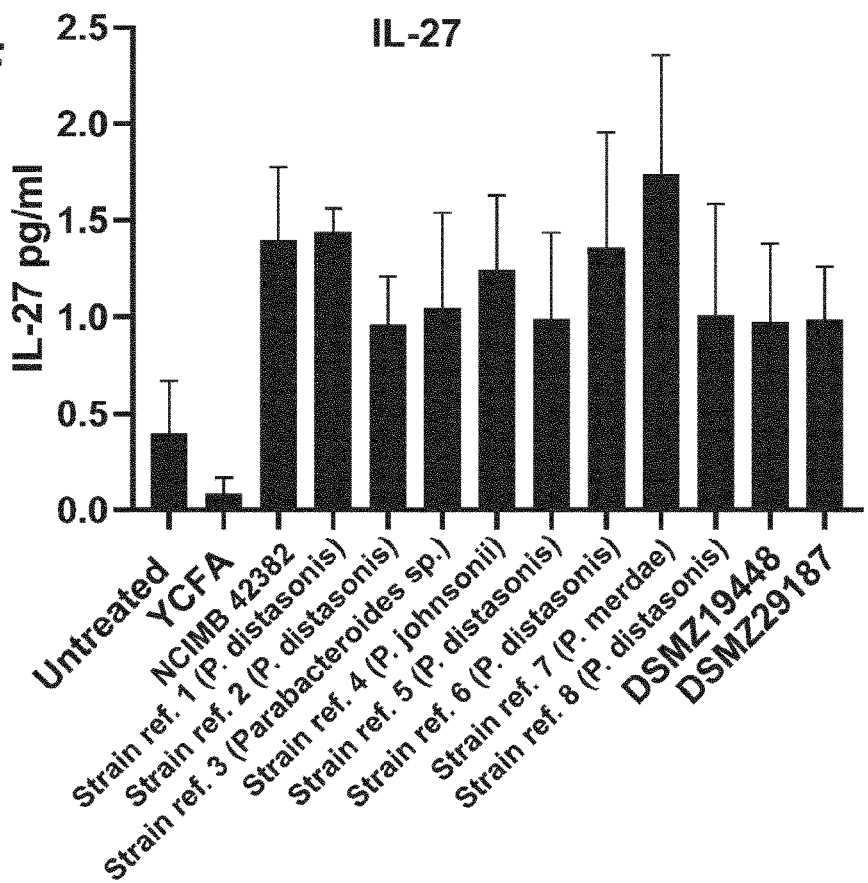
Figure 26G:
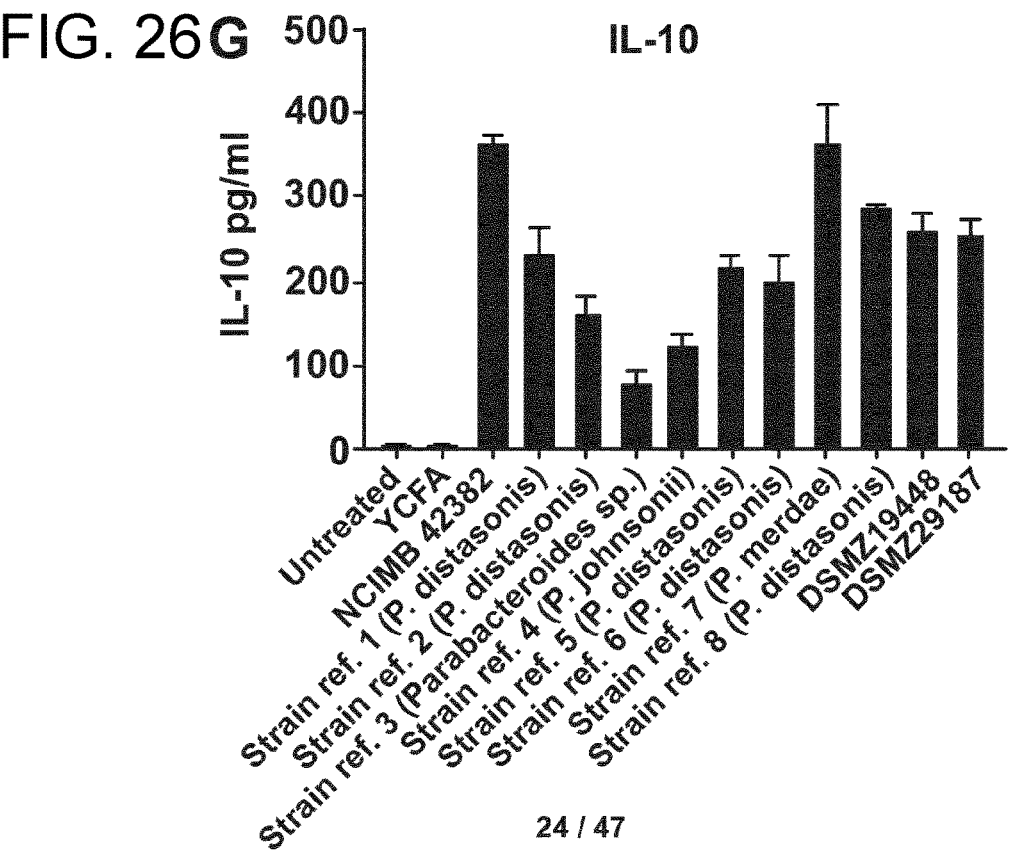
Figure 26H:
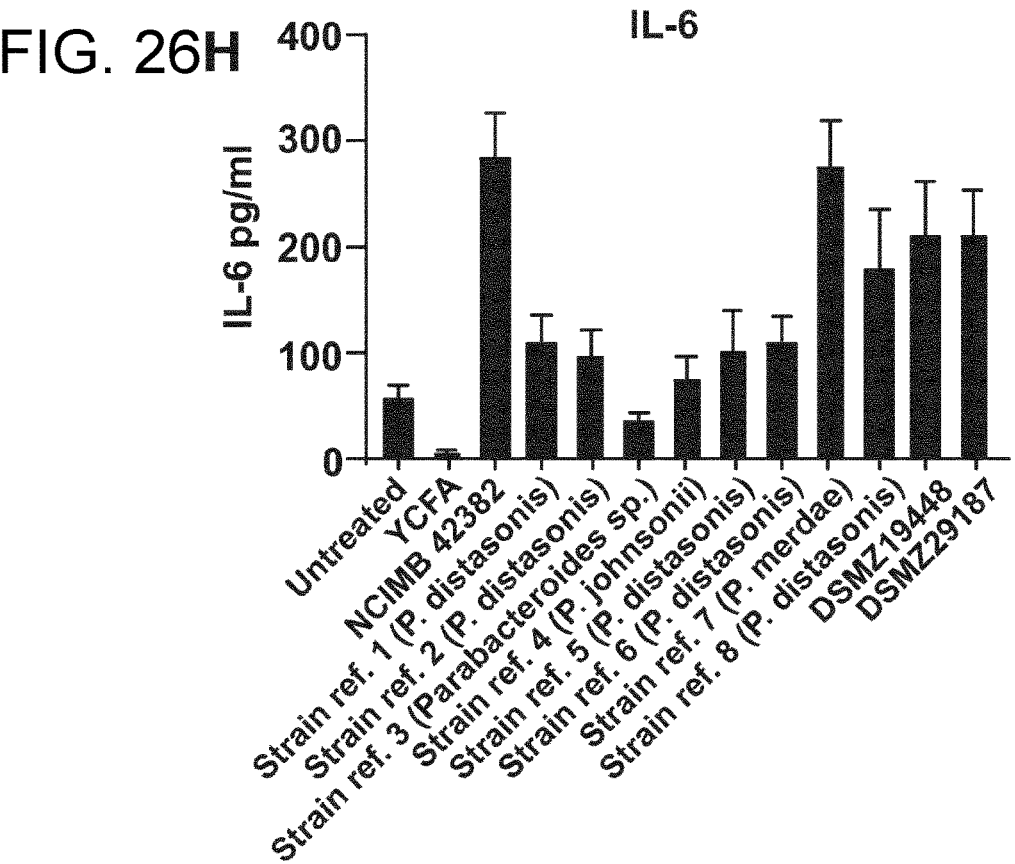
Figure 26I:
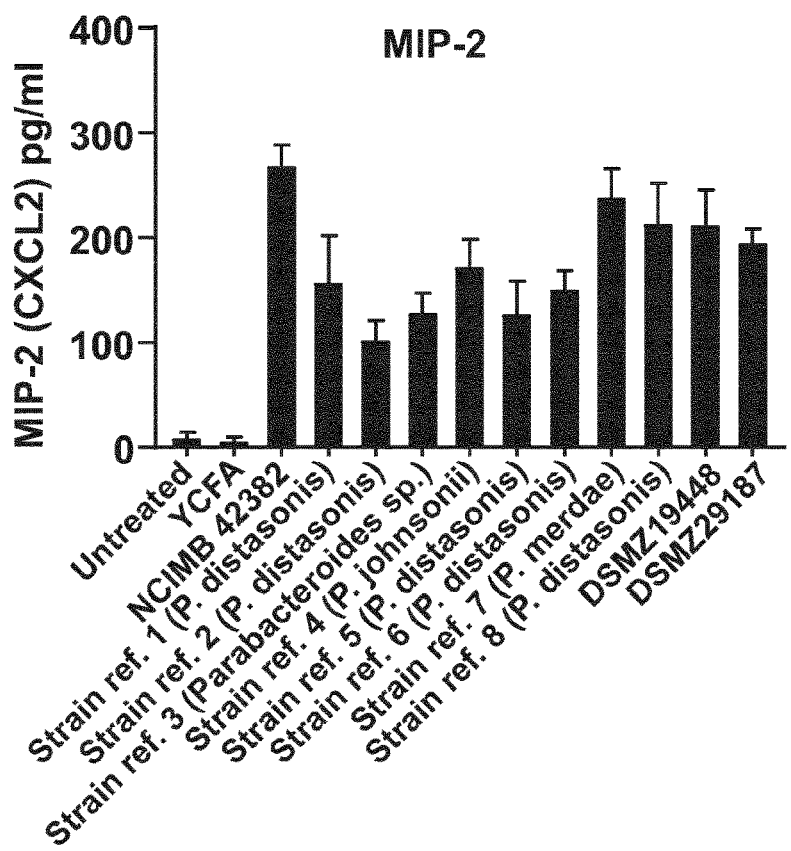
Figure 26J:
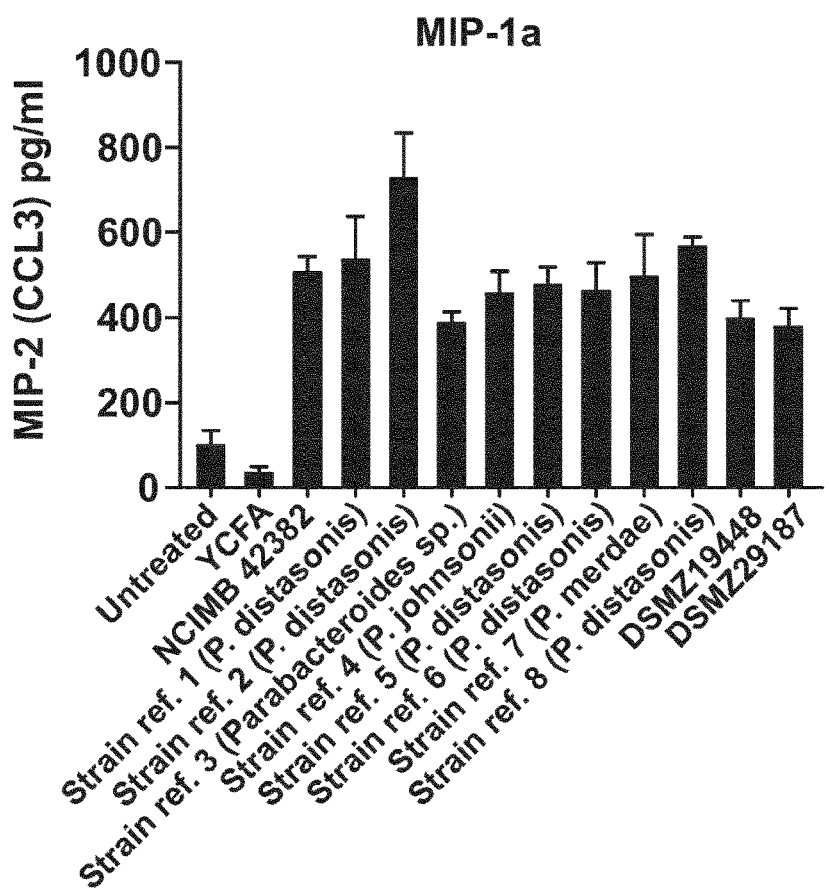
Figure 26K:
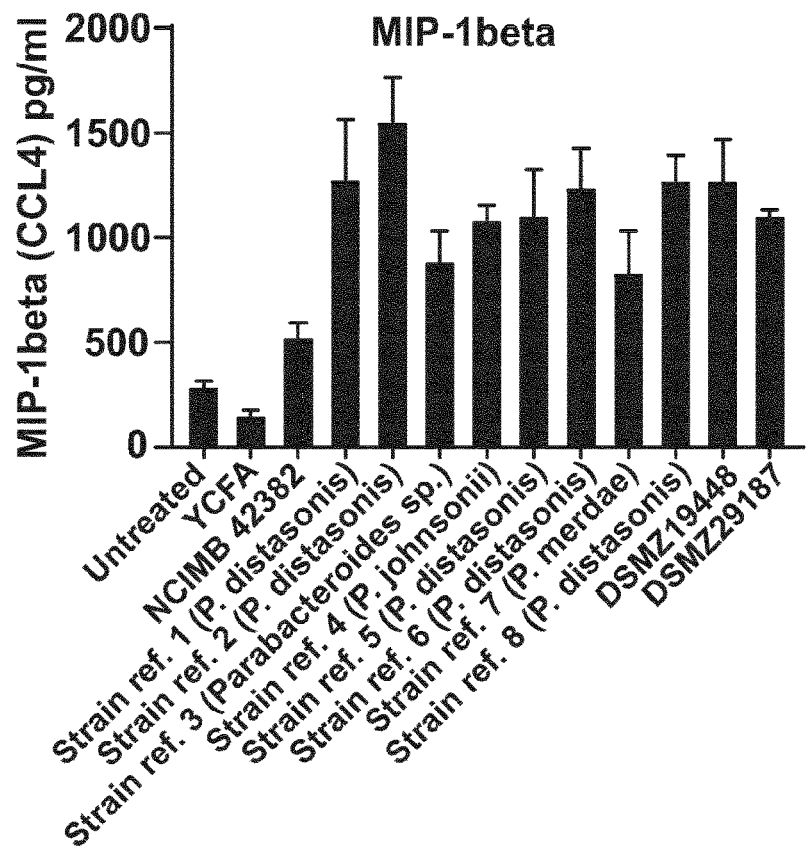
Figure 26L:
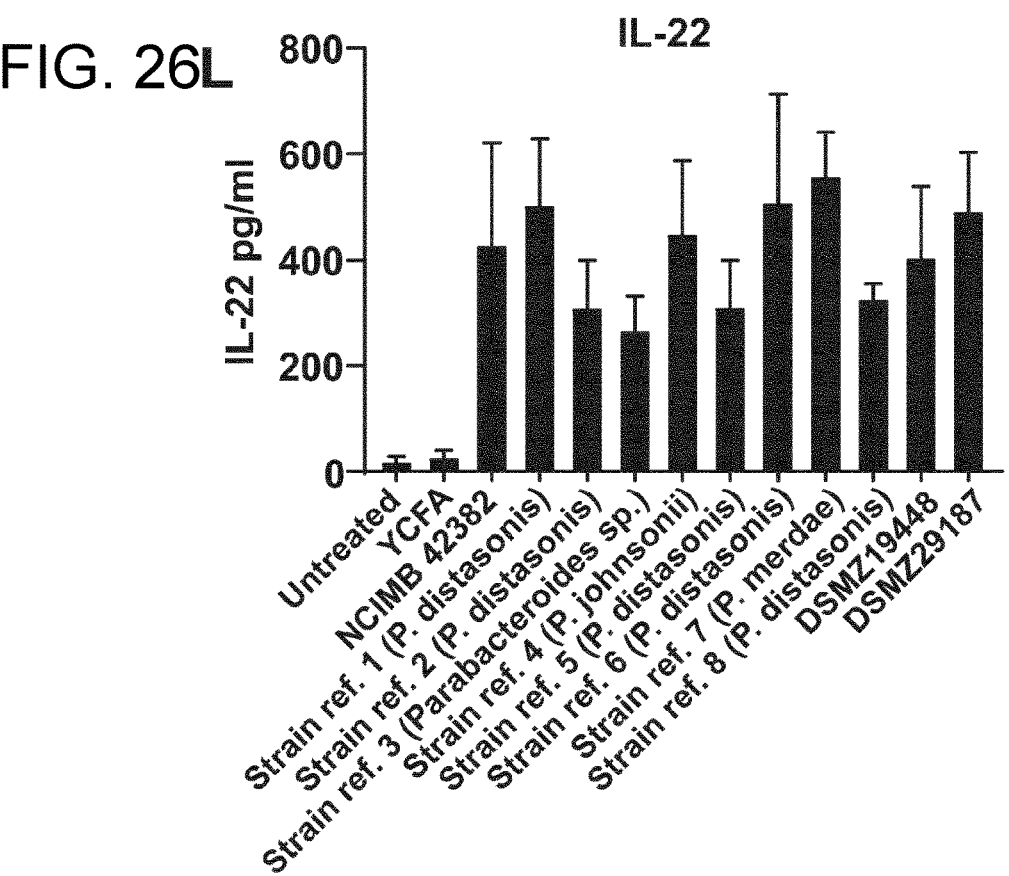
Figure 26M:
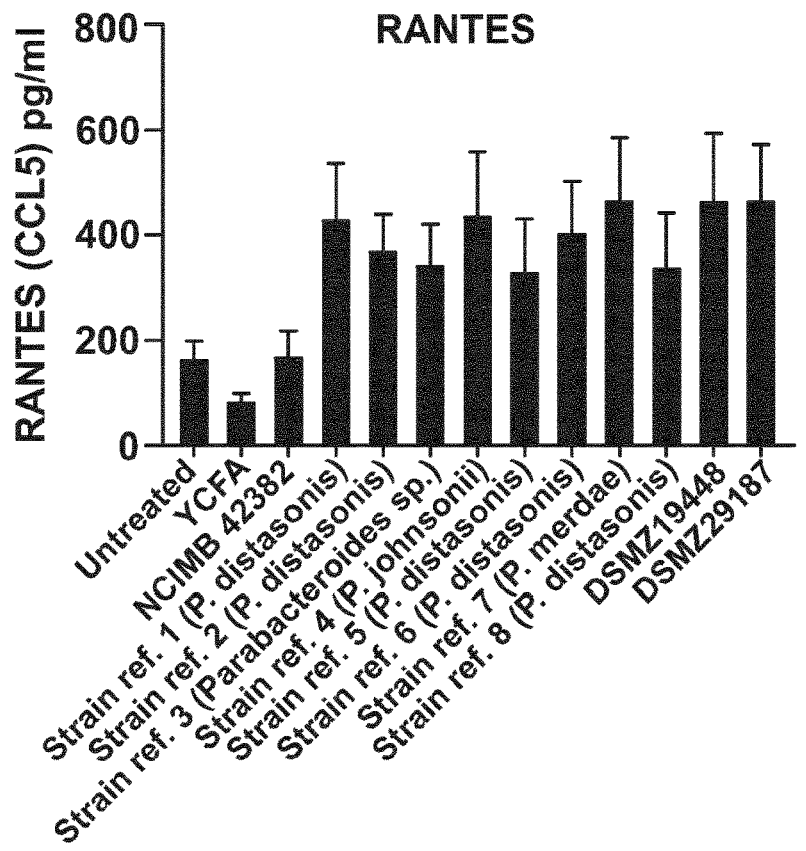
Figure 26N:
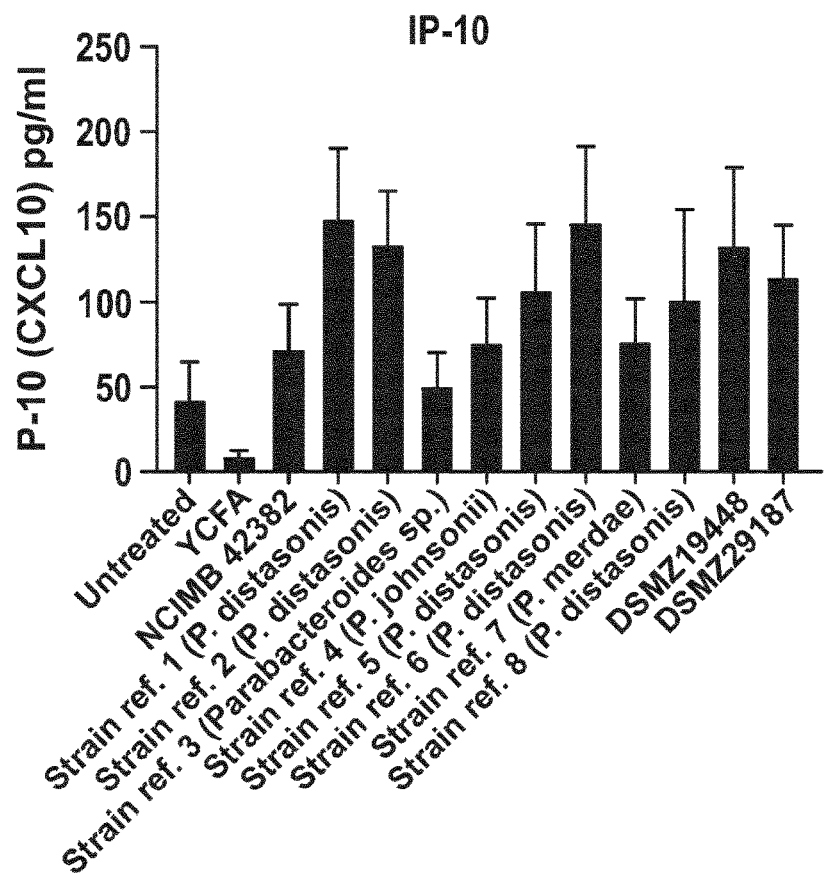
Figure 26O:
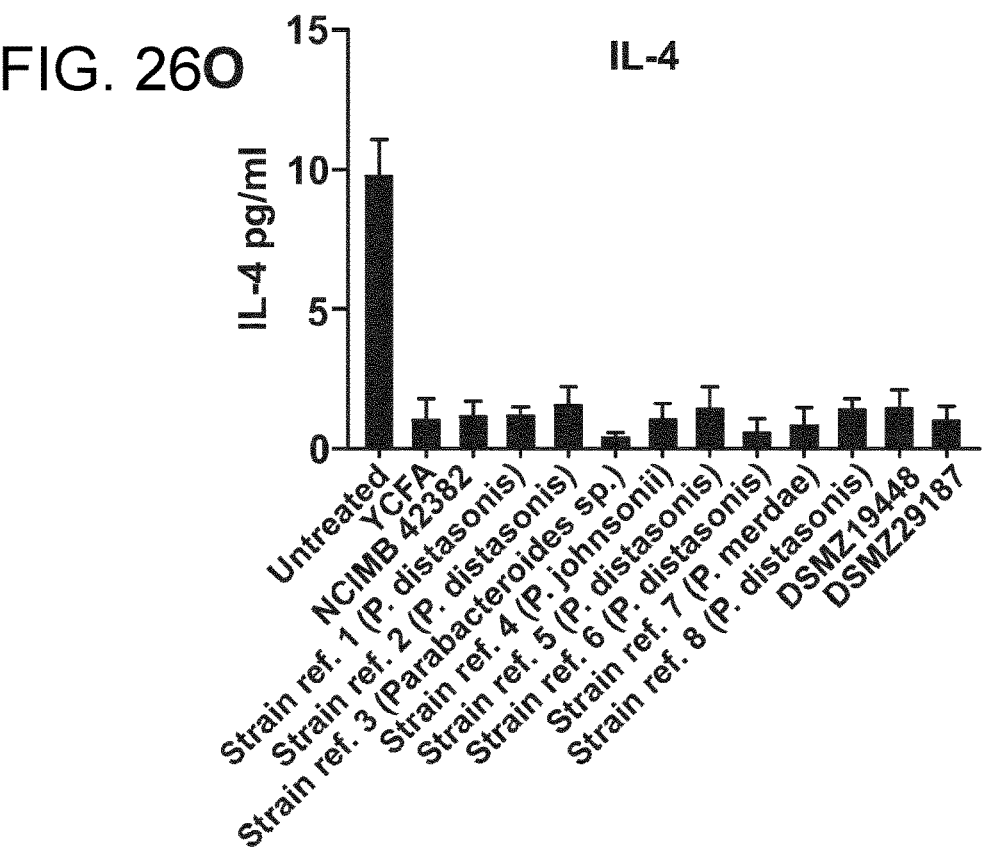
Figure 26P:
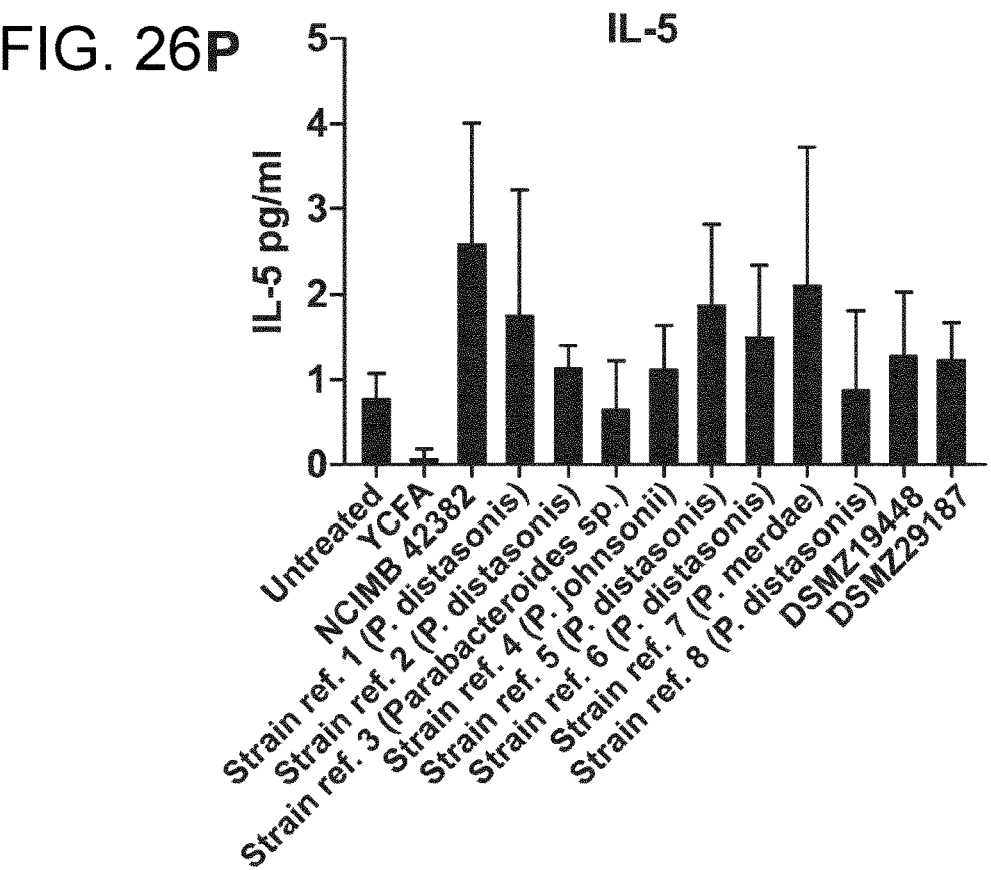
Figure 26Q:
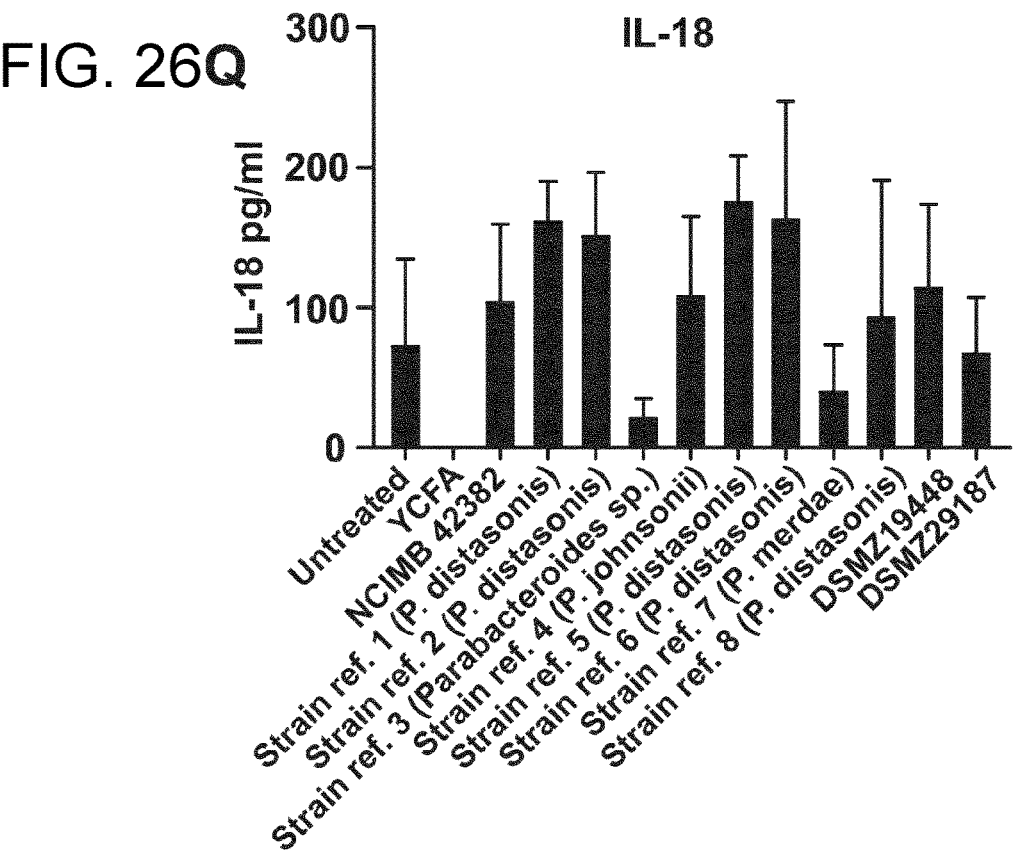
Figure 26R:
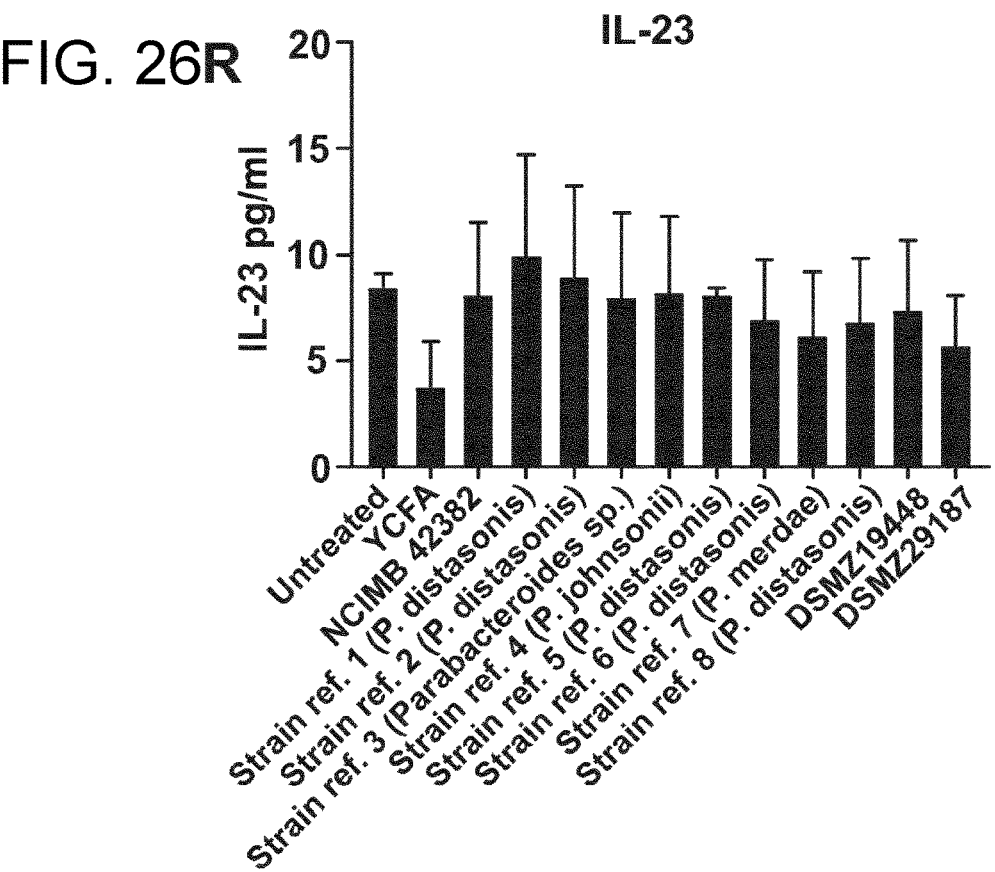
Figure 26S:
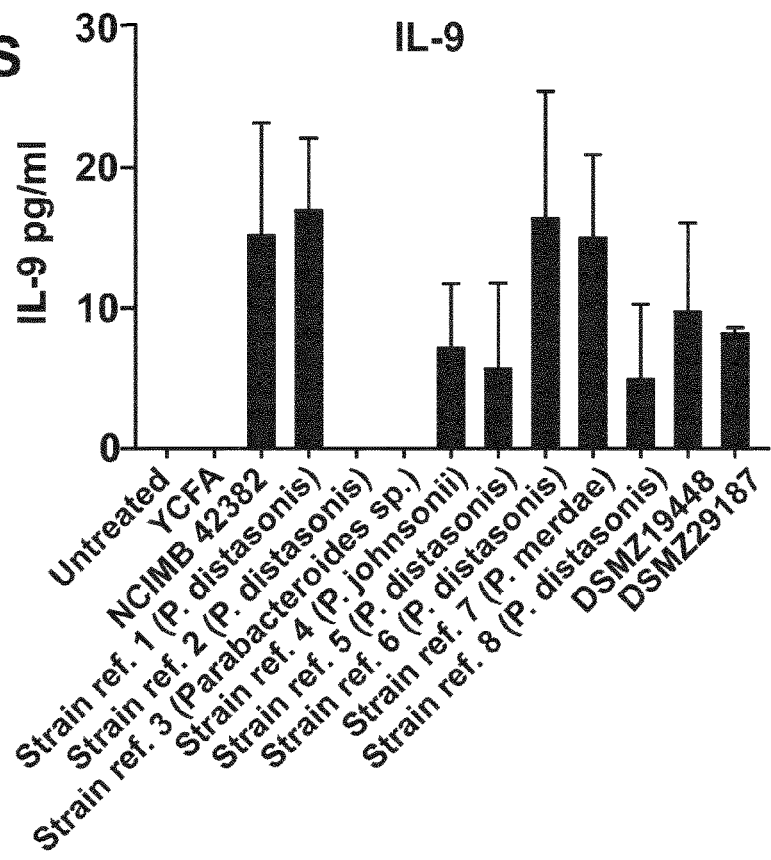
Figure 26T:
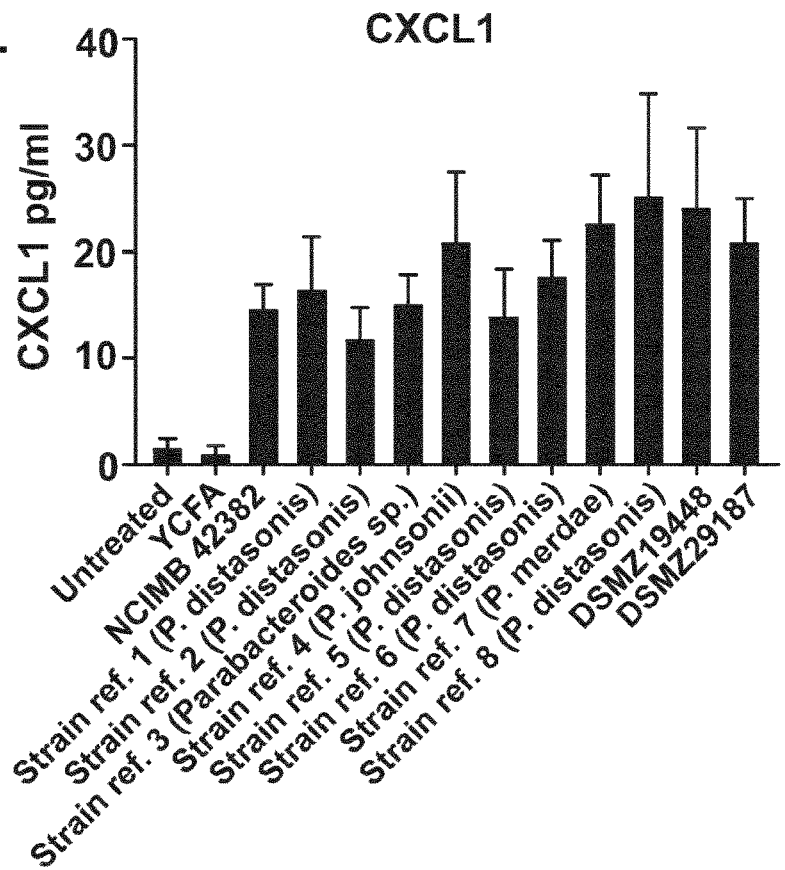
Figure 26U:
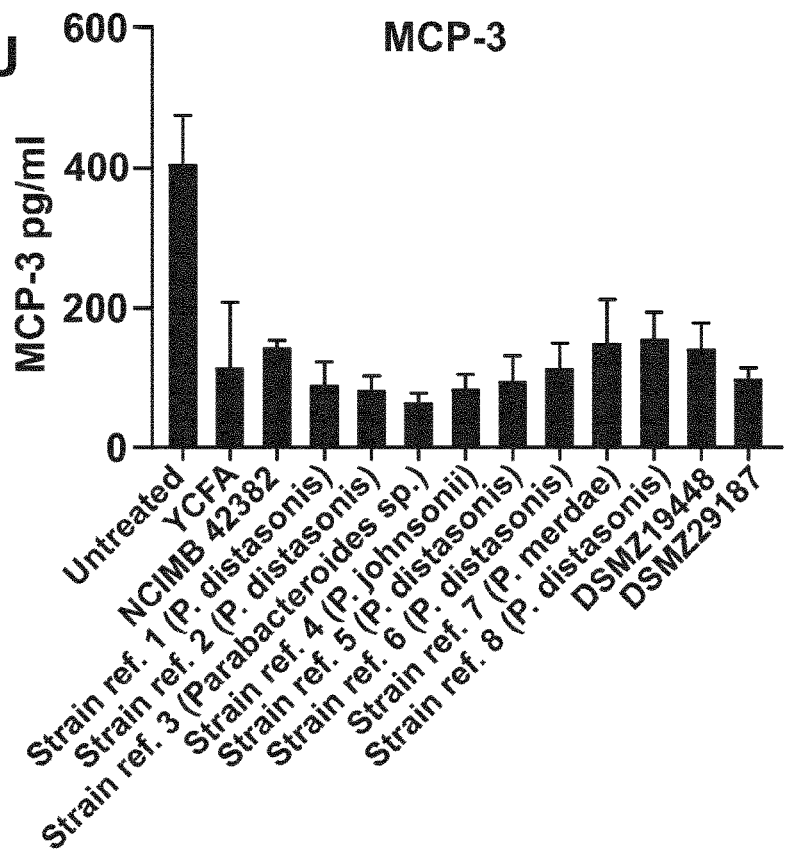
Figure 26V:
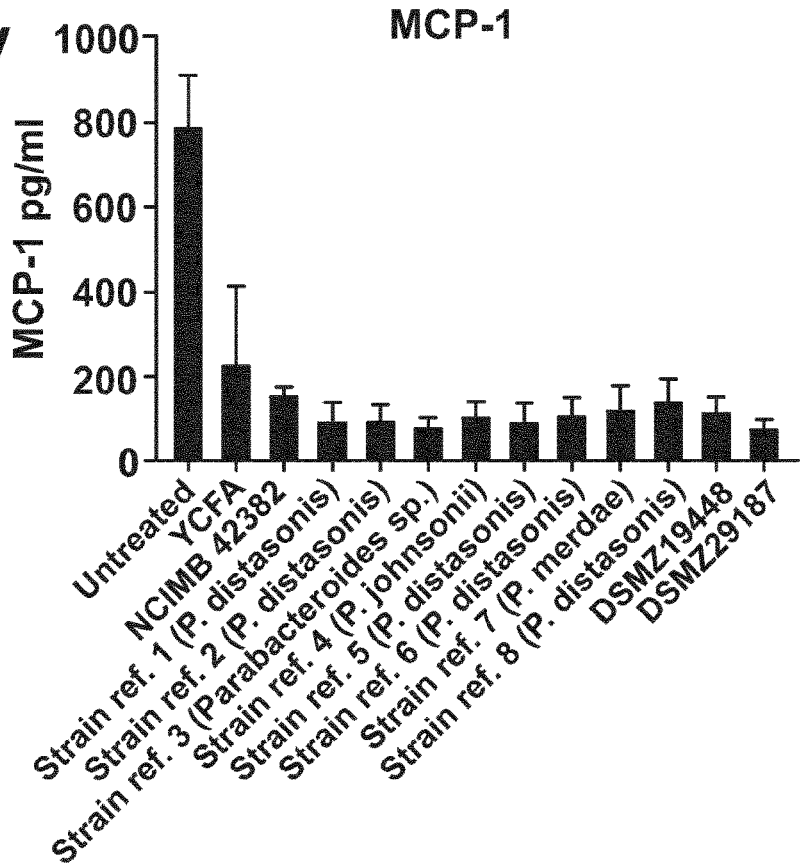

The *Parabacteroides* strains tested were NCIMB 42382 (*P. distasonis*), strain ref 1 (*P. distasonis*), strain ref 2 (*P. distasonis*), strain ref 3 (*Parabacteroides* sp.), strain ref 4 (*P. johnsonii*), strain ref 5 (*P. distasonis*), strain ref 6 (*P. distasonis*), strain ref 7 (*P. merdae*), strain ref 8 (*P. distasonis*), the strain deposited under accession no. DSMZ19448 (*P. goldsteinii*), the strain deposited under accession no. DSMZ29187 (*P. goldsteinii*). All strains induced proliferation of the splenocytes after 72h culture when compared to YCFA+ or untreated cells (FIG. 25). Splenocytes include various subsets of T cells, B cells and macrophages [63], responsible for cell-mediated and humoural immunity. Accordingly, these data indicated that treatment with *Parabacteroides* strains may enhance cell-mediated and humoural immunity, for example in response to tumour antigens. Moreover, *Parabacteroides* strains may be of particular use in immunocompromised or immunosuppressed cancer subjects, for example resulting from melanoma (see, e.g. [27]).

Example 11—Effect of *Parabacteroides* Strains on Cytokine Secretion from Splenocytes The *Parabacteroides* strains tested were NCIMB 42382 (*P. distasonis*), strain ref 1 (*P. distasonis*), strain ref 2 (*P. distasonis*), strain ref 3 (*Parabacteroides* sp.), strain ref 4 (*P. johnsonii*), strain ref 5 (*P. distasonis*), strain ref 6 (*P. distasonis*), strain ref 7 (*P. merdae*), strain ref 8 (*P. distasonis*), DSMZ19448 (*P. goldsteinii*), DSMZ29187 (*P. goldsteinii*), and the results are shown in FIG. 26. All *Parabacteroides* strains tested elicited greater secretion of TNF-α, IL-1B, IL-27, IL-10, MIP-2, MIP-1α, MIP-1ß, IL-22, IL-5 and CXCL1 than the YCFA+ media and untreated controls. Furthermore, all *Parabacteroides* strains tested elicited greater secretion of IL-2, GM-CSF, IFN-γ, IL-6, IP-10, IL-18, IL-23 and RANTES than the YCFA+ media control. Accordingly, these data further indicate that treatment with *Parabacteroides* strains may enhance cell-mediated and humoural immunity, for example in response to tumour antigens, and may be of particular use in immunocompromised or immunosuppressed cancer subjects. Moreover, anticancer effects have been reported for inter alia, IL-2 [64], GM-CSF [65], IFN-γ [66] and IL-27 [67], further indicating the utility of *Parabacteroides* strains in the therapy of cancer characterised by oncogenic ERK signaling.

Example 12—Effect of Additional *Parabacteroides* Strains on Cytokine Secretion from Splenocytes The *Parabacteroides* strains tested were: strain ref 2 (*P. distasonis*), strain ref 7 (*P. merdae*), strain ref 9 (*P. distasonis*), strain ref 10 (*P. johnsonii*), strain ref 11 (*Parabacteroides* sp.), strain ref 12 (*Parabacteroides* sp.), strain ref 13 (*Parabacteroides* sp.), strain ref 14 (*Parabacteroides* sp.) and strain ref 15 (*Parabacteroides* sp.). The results are shown in FIG. 33. Treatment of mouse splenocytes with supernatants from most *Parabacteroides* strains tested elicited greater secretion of the pro-inflammatory cytokines/chemokines IP-10, RANTES, TNF-α, MIP-1α, MIP-1ß and MIP2 compared to the YCFA+ media and untreated controls. Overall, these results demonstrate that treatment with *Parabacteroides* strains elicits immunostimulatory effects, indicating that they may enhance cell-mediated and humoural immunity, for example in response to tumour antigens, and may be of particular use in immunocompromised or immunosuppressed cancer subjects. Notably, several of the upregulated cytokines/chemokines (RANTES, MIP-1α, TNF-α, MIP-2, MIP-1ß) are produced by natural killer T-cells (NK-cells) [68], and it is possible that the *Parabacteroides* strains tested may stimulate the activation of these cells within the splenocyte population. NK-cells can directly detect and eliminate cancer cells, as well as coordinate a wider immune response. Thus, they are an attractive target for manipulation in cancer immunotherapy [69]. Enhancing the activation of NK-cells is additionally desirable because their function is decreased in many cancer subjects [69], suggesting scope for therapeutic intervention. The potential ability of *Parabacteroides* strains to bring about this effect further indicates their utility in cancer therapy (e.g. therapy of cancer comprising oncogenic ERK signalling), particularly in immunocompromised or immunosuppressed cancer subjects.

Example 13—Short/Medium Chain Fatty Acid Production Profile of *Parabacteroides distasonis* Strain DSM20701

*P. distasonis* strain DSM 20701 gave the following profile of short/medium chain fatty acids:

| | | | | | | | | | |
|---|---|---|---|---|---|---|---|---|---|
| | | | Short/medium chain fatty acid concentration (mM) | | | | | | |
| Acetic acid | Formic acid | Propanoic acid | 2-methyl-propanoic acid | Butanoic acid | 3-methyl-butanoic acid | Pentanoic acid | 4-methyl-pentanoic acid | Hexanoic acid | Heptanoic acid |
| 0.9 | 0.5 | 5.2 | 0.2 | 0.0 | 0.3 | −0.1 | 0.0 | −0.1 | 0.0 |

Example 14—Short/Medium Chain Fatty Acid Production Profile of Additional *Parabacteroides* Strains Method Short/medium chain fatty acid production profiles for the strains detailed below were measured as per Example 13.

Results

| Strain ref. | Species | Short/medium chain fatty acid concentration (mM) | | | | | | |
|---|---|---|---|---|---|---|---|---|
| | | Succinic acid | Formic acid | Acetic acid | Propionic acid | Butyric acid | Valeric acid | Hexanoic acid |
| 2 | *Parabacteroides* sp. | Not detected | Not detected | 26.42 | 4.17 | Not detected | Not detected | Not detected |
| 7 | *P. merdae* | 8.55 | Not detected | 20.34 | 8.73 | Not detected | Not detected | Not detected |
| 9 | *P. distasonis* | Not detected | Not detected | 44.10 | 1.41 | Not detected | Not detected | Not detected |
| 10 | *P. johnsonii* | Not detected | Not detected | 45.45 | 5.98 | Not detected | Not detected | Not detected |
| 11 | *Parabacteroides* sp. | 6.74 | Not detected | 50.04 | 12.76 | Not detected | Not detected | Not detected |
| 12 | *Parabacteroides* sp. | 14.70 | Not detected | 32.77 | 5.78 | Not detected | Not detected | Not detected |
| 13 | *Parabacteroides* sp. | Not detected | Not detected | 43.11 | 17.70 | Not detected | Not detected | Not detected |
| 14 | *Parabacteroides* sp. | 14.43 | Not detected | 10.99 | 5.96 | Not detected | Not detected | Not detected |
| 15 | *Parabacteroides* sp. | 16.63 | 0.98 | 4.36 | 5.36 | Not detected | Not detected | Not detected |

As can be seen, the different *Parabacteroides* strains tested consistently produced both acetic acid and propionic acid.

Sequences

SEQ ID NO: 1 (*Parabacteroides distasonis* gene for 16S ribosomal RNA, partial sequence, strain: JCM5825-AB238922)

```
   1 agagtttgat cctggctcag gatgaacgct agcgacaggc ttaacacatg caagtcgagg
  61 ggcagcgggg tgtagcaata caccgccggc gaccggcgca cgggtgagta acgcgtatgc
 121 aacttgccta tcagaggggg ataacccggc gaaagtcgga ctaataccgc atgaagcagg
 181 gatcccgcat gggaatattt gctaaagatt catcgctgat agataggcat gcgttccatt
 241 aggcagttgg cggggtaacg gcccaccaaa ccgacgatgg atagggttc tgagaggaag
 301 gtcccccaca ttggtactga gacacggacc aaactcctac gggaggcagc agtgaggaat
 361 attggtcaat gggcgtaagc ctgaaccagc caagtcgcgt gagggatgaa ggttctatgg
 421 atcgtaaacc tcttttataa gggaataaag tgcgggacgt gtcccgtttt gtatgtacct
 481 tatgaataag gatcggctaa ctccgtgcca gcagccgcgg taatacggag gatccgagcg
 541 ttatccggat ttattgggtt taaagggtgc gtaggcggcc ttttaagtca gcggtgaaag
 601 tctgtggctc aaccatagaa ttgccgttga aactgggggg cttgagtatg tttgaggcag
 661 gcggaatgcg tggtgtagcg gtgaaatgca tagatatcac gcagaacccc gattgcgaag
 721 gcagcctgcc aagccattac tgacgctgat gcacgaaagc gtgggatca aacaggatta
 781 gataccctgg tagtccacgc agtaaacgat gatcactagc tgtttgcgat acactgtaag
 841 cggcacagcg aaagcgttaa gtgatccacc tggggagtac gccggcaacg tgaaactca
 901 aaggaattga cggggcccg cacaagcgga ggaacatgtg gtttaattcg atgatacgcg
 961 aggaacctta cccgggtttg aacgcattcg gaccgaggtg gaaacacctt ttctagcaat
1021 agccgttttgc gaggtgctgc atggttgtcg tcagctcgtg ccgtgaggtg tcggcttaag
1081 tgccataacg agcgcaaccc ttgccactag ttactaacag gttaggctga ggactctggt
1141 gggactgcca gcgtaagctg cgaggaaggc ggggatgacg tcaaatcagc acggcccta
1201 catccggggc gacacacgtg ttacaatggc gtggacaaag ggaggccacc tggcgacagg
1261 gagcgaatcc ccaaaccacg tctcagttcg gatcggagtc tgcaacccga ctccgtgaag
1321 ctggattcgc tagtaatcgc gcatcagcca tggcgcggtg aatacgttcc cgggccttgt
1381 acacaccgcc cgtcaagcca tgggagccgg gggtacctga agtccgtaac cgaaaggatc
1441 ggcctagggt aaaactggtg actggggcta agtcgtaaca aggtaacc
```

SEQ ID NO: 2 (*Parabacteroides distasonis* gene for 16S ribosomal RNA, partial sequence, strain: JCM13400-AB238923)

```
   1 agagtttgat cctggctcag gatgaacgct agcgacaggc ttaacacatg caagtcgagg
  61 ggcagcacag gtagcaatac cgggtggcga ccggcgcacg ggtgagtaac ggtgatgcaa
 121 cttacctatc agaggggggat aacccggcga aagtcggact aataccgcat gaagcagggg
 181 ccccgcatgg ggatatttgc taaagattca tcgctgatag ataggcatgc gttccattag
 241 gcagttggcg gggtaacggc ccaccaaacc gacgatggat aggggttctg agaggaaggt
 301 cccccacatt ggtactgaga cacggaccaa actcctacgg gaggcagcag tgaggaatat
 361 tggtcaatgg gcgtaagcct gaaccagcca gtcgcgtga gggatgaagg ttctatggat
```

```
    421 cgtaaacctc ttttataagg gaataaagtg cgggacgtgt cctgttttgt atgtacctta
    481 tgaataagga tcggctaact ccgtgccagc agccgcggta atacggagga tccgagcgtt
    541 atccggattt attgggttta aagggtgcgt aggcggactt ttaagtcagc ggtgaaagtc
    601 tgtggctcaa ccatagaatt gccgttgaaa ctgggggggct tgagtatgtt tgaggcaggc
    661 ggaatgcgtg gtgtagcggt gaaatgctta gatatcacgc agaacccga ttgcgaaggc
    721 agcctgccaa gccatgactg acgctgatgc acgaaagcgt ggggatcaaa caggattaga
    781 taccctggta gtccacgcag taaacgatga tcactagctg tttgcgatac agtgtaagcg
    841 gcacagcgaa agcgttaagt gatccacctg gggagtacgc cggcaacggt gaaactcaaa
    901 ggaattgacg ggggcccgca caagcggagg aacatgtggt ttaattcgat gatacgcgag
    961 gaaccttacc cgggtttgaa cgcattcgga ccgaggtgga aacacctttt ctagcaatag
   1021 ccgtttgcga ggtgctgcat ggttgtcgtc agctcgtgcc gtgaggtgtc ggcttaagtg
   1081 ccataacgag cgcaaccctt gccactagtt actaacaggt aaagctgagg actctggtgg
   1141 gactgccagc gtaagctgcg aggaaggcgg ggatgacgtc aaatcagcac ggcccttaca
   1201 tccggggcga cacacgtgtt acaatggcgt ggacaaaggg aagccacctg cgacaggga
   1261 gcgaatcccc aaaccacgtc tcagttcgga tcggagtctg caacccgact ccgtgaagct
   1321 ggattcgcta gtaatcgcgc atcagccatg gcgcggtgaa tacgttcccg ggccttgtac
   1381 acaccgcccg tcaagccatg ggagccgggg gtacctgaag tccgtaaccg aaaggatcgg
   1441 cctagggtaa aactggtgac tggggctaag tcgtaacaag gtaacc SEQ ID NO: 3 (Parabacteroides distasonis gene for 16S ribosomal RNA, partial sequence,
strain: JCM13401-AB238924)
      1 agagtttgat cctggctcag gatgaacgct agcgacaggc ttaacacatg caagtcgagg
     61 ggcagcacag gtagcaatac ccgccggcga ccggcgcacg ggtgagtaac gcgtatgcaa
    121 cttgcctatc agaggggggat aacccggcga aagtcggact aataccgcat gaagcagggg
    181 ccccgcatgg ggatatttgc taaagattca tcgctgatag ataggcatgc gttccattag
    241 gcagttggcg gggtaacggc ccaccaaacc gacgatggat aggggttctg agaggaaggt
    301 cccccacatt ggtactgaga cacggaccaa actcctacgg gaggcagcag tgaggaatat
    361 tggtcaatgg gcgtaagcct gaaccagcca agtcgcgtga gggatgaagg ttctatggat
    421 cgtaaacctc ttttataagg gaataaagtg tgggacgtgt cctgttttgt atgtaccta
    481 tgaataagga tcggctaact ccgtgccagc agccgcggta atacggagga tccgagcgtt
    541 atccggattt attgggttta aagggtgcgt aggcggcctt ttaagtcagc ggtgaaagtc
    601 tgtggctcaa ccatagaatt gccgttgaaa ctgggaggct tgagtatgtt tgaggcaggc
    661 ggaatgcgtg gtgtagcggt gaaatgctta gatatcacgc agaacccga ttgcgaaggc
    721 agcctgccaa gccatgactg acgctgatgc acgaaagcgt ggggatcaaa caggattaga
    781 taccctggta gtccacgcag taaacgatga tcactagctg tttgcgatac actgtaagcg
    841 gcacagcgaa agcgttaagt gatccacctg gggagtacgc cggcaacggt gaaactcaaa
    901 ggaattgacg ggggcccgca caagcggagg aacatgtggt ttaattcgat gatacgcgag
    961 gaaccttacc cgggtttgaa cgcattcgga ccgaggtgga aacacctttt ctagcaatag
   1021 ccgtttgcga ggtgctgcat ggttgtcgtc agctcgtgcc gtgaggtgtc ggcttaagtg
   1081 ccataacgag cgcaaccctt gccactagtt actaacaggt gatgctgagg actctggtgg
   1141 gactgccagc gtaagctgcg aggaaggcgg ggatgacgtc aaatcagcac ggcccttaca
   1201 tccggggcga cacacgtgtt acaatggcgt ggacaaaggg atgccacctg cgacaggga
   1261 gcgaatcccc aaaccacgtc tcagttcgga tcggagtctg caacccgact ccgtgaagct
   1321 ggattcgcta gtaatcgcgc atcagccatg gcgcggtgaa tacgttcccg ggccttgtac
   1381 acaccgcccg tcaagccatg ggagccgggg gtacctgaag tccgtaaccg aaaggatcgg
   1441 cctagggtaa aactggtgac tggggctaag tcgtaacaag gtaacc SEQ ID NO: 4 (Parabacteroides distasonis gene for 16S ribosomal RNA, partial sequence,
strain: JCM13402-AB238925)
      1 agagtttgat cctggctcag gatgaacgct agcgacaggc ttaacacatg caagtcgagg
     61 ggcagcacag gtagcaatac cgggtggcga ccggcgcacg ggtgagtaac gcgtatgcaa
    121 cttacctatc agaggggggat aacccggcga aagtcggact aataccgcat gaagcagggg
    181 ccccgcatgg ggatatttgc taaagattca tcgctgatag ataggcatgc gttccattag
    241 gcagttggcg gggtaacggc ccaccaaacc gacgatggat aggggttctg agaggaaggt
    301 cccccacatt ggtactgaga cacggaccaa actcctacgg gaggcagcag tgaggaatat
    361 tggtcaatgg gcgtaagcct gaaccagcca agtcgcgtga gggatgaagg ttctatggat
    421 cgtaaacctc ttttataagg gaataaagtg cgggacgtgt cccgttttgt atgtaccta
    481 tgaataagga tcggctaact ccgtgccagc agccgcggta atacggagga tccgagcgtt
    541 atccggattt attgggttta aagggtgcgt aggcggcctt ttaagtcagc ggtgaaagtc
    601 tgtggctcaa ccatagaatt gccgttgaaa ctgggaggct tgagtatgtt tgaggcaggc
    661 ggaatgcgtg gtgtagcggt gaaatgctta gatatcacgc agaacccga ttgcgaaggc
    721 agcctgccaa gccatgactg acgctgatgc acgaaagcgt ggggatcaaa caggattaga
    781 taccctggta gtccacgcag taaacgatga tcactagctg tttgcgatac actgtaagcg
    841 gcacagcgaa agcgttaagt gatccacctg gggagtacgc cggcaacggt gaaactcaaa
    901 ggaattgacg ggggcccgca caagcggagg aacatgtggt ttaattcgat gatacgcgag
    961 gaaccttacc cgggtttgaa cgcattcgga ccgaggtgga aacacctttt ctagcaatag
   1021 ccgtttgcga ggtgctgcat ggttgtcgtc agctcgtgcc gtgaggtgtc ggcttaagtg
   1081 ccataacgag cgcaaccctt gccactagtt actaacaggt aaagctgagg actctggtgg
   1141 gactgccagc gtaagctgcg aggaaggcgg ggatgacgtc aaatcagcac ggcccttaca
   1201 tccggggcga cacacgtgtt acaatggcgt ggacaaaggg aggccacctg cgacaggga
   1261 gcgaatcccc aaaccacgtc tcagttcgga tcggagtctg caacccgact ccgtgaagct
   1321 ggattcgcta gtaatcgcgc atcagccatg gcgcggtgaa tacgttcccg ggccttgtac
   1381 acaccgcccg tcaagccatg ggagccgggg gtacctgaag tccgtaaccg aaaggatcgg
   1441 cctagggtaa aactggtgac tggggctaag tcgtaacaag gtaacc
```

SEQ ID NO: 5 (*Parabacteroides distasonis* gene for 16S ribosomal RNA, partial sequence, strain: JCM13403-AB238926)

```
   1 agagtttgat cctggctcag gatgaacgct agcgacaggc ttaacacatg caagtcgagg
  61 ggcagcacag gtagcaatac cgggtggcga ccggcgcacg ggtgagtaac gcgtatgcaa
 121 cttacctatc agaggtggat aacccggcga aagtcggact aataccgcat gaagcagggg
 181 ccccgcatgg ggatatttgc taaagattca tcgctgatag ataggcatgc gttccattag
 241 gcagttggcg gggtaacggc ccaccaaacc gacgatggat aggggttctg agaggaaggt
 301 cccccacatt ggtactgaga cacggaccaa actcctacgg gaggcagcag tgaggaatat
 361 tggtcaatgg gcgtaagcct gaaccagcca agtcgcgtga gggatgaagg ttctatggat
 421 cgtaaacctc ttttataagg gaataaagtg tgggacgtgt cccgttttgt atgtaccttä
 481 tgaataagga tcggctaact ccgtgccagc agccgcggta atacgagga tccgagcgtt
 541 atccggattt attgggttta aagggtgcgt aggcggactt ttaagtcagc ggtgaaagtc
 601 tgtggctcaa ccatagaatt gccgttgaaa ctgggaggct tgagtatgtt tgaggcaggc
 661 ggaatgcgtg gtgtagcggt gaaatgctta gatatcacgc agaacccga ttgcgaaggc
 721 agcctgccaa gccatgactg acgctgatgc acgaaagcgt ggggatcaaa caggattaga
 781 taccctggta gtccacgcag taaacgatga tcactagctg tttgcgatac attgtaagcg
 841 gcacagcgaa agcgttaagt gatccacctg gggagtacgc cggcaacggt gaaactcaaa
 901 ggaattgacg ggggcccgca caagcggagg aacatgtggt ttaattcgat gatacgcgag
 961 gaaccttacc cgggtttgaa cgcattcgga ccgaggtgga acaccttttt ctagcaatag
1021 ccgtttgcga ggtgctgcat ggttgtcgtc agctcgtgcc gtgaggtgtc ggcttaagtg
1081 ccataacgag cgcaacccct gccactagtt actaacaggt aaagctgagg actctggtgg
1141 gactgccagc gtaagctgcg aggaaggcgg ggatgacgtc aaatcagcac ggcccttaca
1201 tccggggcga cacacgtgtt acaatggcgt ggacaaaggg aggccacctg gcgacaggga
1261 gcgaatcccc aaaccacgtc tcagttcgga tcggagtctg caacccgact ccgtgaagct
1321 ggattcgcta gtaatcgcgc atcagccatg gcgcggtgaa tacgttcccg ggccttgtac
1381 acaccgcccg tcaagccatg ggagccgggg gtacctgaag tccgtaaccg aaaggatcgg
1441 cctagggtaa aactggtgac tggggctaag tcgtaacaag gtaacc
```

SEQ ID NO: 6 (*Parabacteroides distasonis* gene for 16S ribosomal RNA, partial sequence, strain: JCM13404-AB238927)

```
   1 agagtttgat cctggctcag gatgaacgct agcgacaggc ttaacacatg caagtcgagg
  61 ggcagcacag gtagcaatac cgggtggcga ccggcgcacg ggtgagtaac gcgtatgcaa
 121 cttacctatc agaggtggat aacccggcga aagtcggact aataccgcat gaagcagggg
 181 ccccgcatgg ggatatttgc taaagattca tcgctgatag ataggcatgc gttccattag
 241 gcagttggcg gggtaacggc ccaccaaacc gacgatggat aggggttctg agaggaaggt
 301 cccccacatt ggtactgaga cacggaccaa actcctacgg gaggcagcag tgaggaatat
 361 tggtcaatgg gcgtaagcct gaaccagcca agtcgcgtga gggatgaagg ttctatggat
 421 cgtaaacctc ttttataagg gaataaagtg tgggacgtgt cccgttttgt atgtacctta
 481 tgaataagga tcggctaact ccgtgccagc agccgcggta atacgagga tccgagcgtt
 541 atccggattt attgggttta aagggtgcgt aggcggcctt ttaagtcagc ggtgaaagtc
 601 tgtggctcaa ccatagaatt gccgttgaaa ctgggaggct tgagtatgtt tgaggcaggc
 661 ggaatgcgtg gtgtagcggt gaaatgctta gatatcacgc agaacccga ttgcgaaggc
 721 agcctgccaa gccatgactg acgctgatgc acgaaagcgt ggggatcaaa caggattaga
 781 taccctggta gtccacgcag taaacgatga tcactagctg tttgcgatac attgtaagcg
 841 gcacagcgaa agcgttaagt gatccacctg gggagtacgc cggcaacggt gaaactcaaa
 901 ggaattgacg ggggcccgca caagcggagg aacatgtggt ttaattcgat gatacgcgag
 961 gaaccttacc cgggtttgaa cgcattcgga ccgaggtgga acaccttttt ctagcaatag
1021 ccgtttgcga ggtgctgcat ggttgtcgtc agctcgtgcc gtgaggtgtc ggcttaagtg
1081 ccataacgag cgcaacccct gccactagtt actaacaggt aaagctgagg actctggtgg
1141 gactgccagc gtaagctgcg aggaaggcgg ggatgacgtc aaatcagcac ggcccttaca
1201 tccggggcga cacacgtgtt acaatggcgt ggacaaaggg aggccacctg gcgacaggga
1261 gcgaatcccc aaaccacgtc tcagttcgga tcggagtctg caacccgact ccgtgaagct
1321 ggattcgcta gtaatcgcgc atcagccatg gcgcggtgaa tacgttcccg ggccttgtac
1381 acaccgcccg tcaagccatg ggagccgggg gtacctgaag tccgtaaccg aaaggatcgg
1441 cctagggtaa aactggtgac tggggctaag tcgtaacaag gtaacc
```

SEQ ID NO: 7 (*Parabacteroides merdae* gene for 16S ribosomal RNA, partial sequence, strain: JCM9497-AB238928)

```
   1 agagtttgat cctggctcag gatgaacgct agcgacaggc ttaacacatg caagtcgagg
  61 ggcagcatga tttgtagcaa tacagattga tggcgaccgg cgcacgggtg agtaacgcgt
 121 atgcaactta cctatcagag ggggatagcc cggcgaaagt cggattaata ccccataaaa
 181 caggggtccc gcatgggaat atttgttaaa gattcatcgc tgatagatag gcatgcgttc
 241 cattaggcag ttggcggggt aacggccac caaaccgacg atggataggg gttctgagag
 301 gaaggtcccc cacattggta ctgagacacg gaccaaactc ctacgggagg cagcagtgag
 361 gaatattggt caatggccga gaggctgaac cagccaagtc gcgtgaagga agaaggatct
 421 atggtttgta aacttctttt ataggggaat aaagtggagg acgtgtcctt ttttgtatgt
 481 accctatgaa taagcatcgg ctaactccgt gccagcagcc gcggtaatac ggaggatgcg
 541 agcgttatcc ggatttattg ggtttaaagg gtgcgtaggc ggtgatttaa gtcagcggtg
 601 aaagtttgtg gctcaaccat aaaattgccg ttgaaactgg gttacttgag tgtgtttgag
 661 gtaggcggaa tgcgtggtgt agcggtgaaa tgcatagata tcacgcagaa ctccgattgc
 721 gaaggcagct tactaaacca taactgacac tgaagcacga aagcgtgggg atcaaacagg
 781 attagatacc ctggtagtcc acgcagtaaa cgatgattac taggagtttg cgatacaatg
 841 taagctctac agcgaaagcg ttaagtaatc cacctgggga gtacgccggc aacggtgaaa
 901 ctcaaaggaa ttgacggggg cccgcacaag cggaggaaca tgtggtttaa ttcgatgata
 961 cgcgaggaac cttacccggg tttgaacgta gtctgaccgg agtggaaaca ctccttctag
1021 caatagcaga ttacgaggtg ctgcatggtt gtcgtcagct cgtgccgtga ggtgtcggct
1081 taagtgccat aacgagcgca acccttatca ctagttacta acaggtgaag ctgaggactc
```

|   |   |   |   |   |
|---|---|---|---|---|
| 1141 | tggtgagact | gccagcgtaa | gctgtgagga | aggtggggat | dacgtcaaat | cagcacggcc |
| 1201 | cttacatccg | gggcgacaca | cgtgttacaa | tggcatggac | aaagggcagc | tacctggcga |
| 1261 | caggatgcta | atctccaaac | catgtctcag | ttcggatcgg | agtctgcaac | tcgactccgt |
| 1321 | gaagctggat | tcgctagtaa | tcgcgcatca | gccatggcgc | ggtgaatacg | ttcccgggcc |
| 1381 | ttgtacacac | cgcccgtcaa | gccatgggag | ccggggggtac | ctgaagtccg | taaccgcaag |
| 1441 | gatcggccta | gggtaaaact | ggtgactggg | gctaagtcgt | aacaaggtaa | cc |

SEQ ID NO: 8 (*Parabacteroides merdae* gene for 16S ribosomal RNA, partial sequence, strain: JCM13405-AB238929)

|   |   |   |   |   |   |
|---|---|---|---|---|---|
| 1 | agagtttgat | cctggctcag | gatgaacgct | agcgacaggc | ttaacacatg | caagtcgagg |
| 61 | ggcagcatga | tttgtagcaa | tacagattga | tggcgaccgg | cgcacgggtg | agtaacgcgt |
| 121 | atgcaactta | cctatcagag | ggggatagcc | cggcgaaagt | cggattaata | ccccataaaa |
| 181 | caggggttcc | gcatgggaat | atttgttaaa | gattcatcgc | tgatagatag | gcatgcgttc |
| 241 | cattaggcag | ttggcggggt | aacggcccac | caaaccgacg | atggataggg | ttctgagag |
| 301 | gaaggtcccc | cacattggta | ctgagacacg | gaccaaactc | ctacgggagg | cagcagtgag |
| 361 | gaatattggt | caatggccga | gaggctgaac | cagccaagtc | gcgtgaagga | agaaggatct |
| 421 | atggtttgta | aacttctttt | ataggggaat | aaagtggagg | acgtgtccctt | ttttgtatgt |
| 481 | accctatgaa | taagcatcgg | ctaactccgt | gccagcagcc | gcggtaatac | ggaggatgcg |
| 541 | agcgttatcc | ggatttattg | ggtttaaagg | gtgcgtaggc | ggtgatttaa | gtcagcggtg |
| 601 | aaagtttgtg | gctcaaccat | aaaattgccg | ttgaaactgg | gttacttgag | tgtgtttgag |
| 661 | gtaggcggaa | tgcgtggtgt | agcggtgaaa | tgcatagata | tcacgcagaa | ctccgattgc |
| 721 | gaaggcagct | tactaaacca | taactgacac | tgaagcacga | aagcgtgggg | atcaaacagg |
| 781 | attagatacc | ctggtagtcc | acgcagtaaa | cgatgattac | taggagtttg | cgatacaatg |
| 841 | taagctctac | agcgaaagcg | ttaagtaatc | cacctgggga | gtacgccggc | aacggtgaaa |
| 901 | ctcaaaggaa | ttgacggggg | cccgcacaag | cggaggaaca | tgtggtttaa | ttcgatgata |
| 961 | cgcgaggaac | cttacccggg | tttgaacgta | gtctgaccgg | agtggaaaca | ctccttctag |
| 1021 | caatagcaga | ttacgaggtg | ctgcatggtt | gtcgtcagct | cgtgccgtga | ggtgtcggct |
| 1081 | taagtgccat | aacgagcgca | acccttatca | ctagttacta | acaggtgaag | ctgaggactc |
| 1141 | tggtgagact | gccagcgtaa | gctgtgagga | aggtggggat | gacgtcaaat | cagcacggcc |
| 1201 | cttacatccg | gggcgacaca | cgtgttacaa | tggcatggac | aaagggcagc | tacctggcga |
| 1261 | caggatgcta | atctccaaac | catgtctcag | ttcggatcgg | agtctgcaac | tcgactccgt |
| 1321 | gaagctggat | tcgctagtaa | tcgcgcatca | gccatggcgc | ggtgaatacg | ttcccgggcc |
| 1381 | ttgtacacac | cgcccgtcaa | gccatgggag | ccggggtac | ctgaagtccg | taaccgcaag |
| 1441 | gatcggccta | gggtaaaact | ggtgactggg | gctaagtcgt | aacaaggtaa | cc |

SEQ ID NO: 9 (consensus 16S rRNA gene sequence for *Parabacteroides distasonis* strain 755/NCIMB 42382)
AMCCGGGTGGCGACCGGCGCACGGGTGAGTAACGCGTATGCAACTTGCCTATCAGAGGGGGATAACCCGGCGAAAGT
CGGACTAATACCGCATGAAGCAGGGATCCCGCATGGGAATATTTGCTAAAGATTCATCGCTGATAGATAGGCATGCG
TTCCATTAGGCAGTTGGCGGGGTAACGGCCCACCAAACCGACGATGGATAGGGGTTCTGAGAGGAAGGTCCCCCACA
TTGGTACTGAGACACGGACCAAACTCCTACGGGAGGCAGCAGTGAGGAATATTGGTCAATGGCGTGAGCCTGAACC
AGCCAAGTCGCGTGAGGGATGAAGGTTCTATGGATCGTAAACCTCTTTTATAAGGGAATAAAGTGCGGGACGTGTCC
CGTTTTGTATGTACCTTATGAATAAGGATCGGCTAACTCCGTGCCAGCAGCCGCGGTAATACGGAGGATCCGAGCGT
TATCCGGATTTATTGGGTTTAAAGGGTGCGTAGGCGGCCTTTTAAGTCAGCGGTGAAAGTCTGTGGCTCAACCATAG
AATTGCCGTTGAAACTGGGAGGCTTGAGTATGTTTGAGGCAGGCGGAATGCGTGGTGTAGCGGTGAAATGCATAGAT
ATCACGCAGAACCCCGATTGCGAAGGCAGCCTGCCAAGCCATTACTGACGCTGATGCACGAAAGCGTGGGGATCAAA
CAGGATTAGATACCCTGGTAGTCCACGCAGTAAACGATGATCACTAGCTGTTTGCGATACACTGTAAGCGGCACAGC
GAAAGCGTTAAGTGATCCACCTGGGGAGTACGCCGGCAACGGTGAAACTCAAAGGAATTGACGGGGGCCCGCACAAG
CGGAGGAACATGTGGTTTAATTCGATGATACGCGAGGAACCTTACCCGGGTTTGAACGMGAKGTGGAA
ACACATTTTCTAGCAATAGCCATTTGCGAGGTGCTGCATGGTTGTCGTCAGCTCGTGCCGTGAGGTGTCGGCTTAAG
TGCCATAACGAGCGCAACCCTTGCCACTAGTTACTAACAGGTAAAGCTGAGGACTCTGGTGGGACTGCCAGCGTAAG
CTGCGAGGAAGGCGGGGATGACGTCAAATCAGCACGGCCCTTACATCCGGGGCGACACACGTGTTACAATGGCGTGG
ACAAAGGGAAGCCACCTGGCGACAGGGAGCGAATCCCCAAACCACGTCTCAGTTCGGATCGGAGTCTGCAACCCGAC
TCCGTGAAGCTGGATTCGCTAGTAATCGCGCATCAGCCATGGCGCGGTGAATACGTTCCCGGGCCTTGTACACACCG
CCCGTCAAGCCATGGGAGCCGGGGTACCTGAAGTCCGTAACCGCGAGGATCGGCCTAGGGTAAAACTGGTGACTGG
GGCTAAGTCGTACGGGG SEQ ID NO: 10 (*Parabacteroides goldsteinii* strain WAL 12034 16S ribosomal RNA gene, partial sequence - GenBank: AY974070.1)

|   |   |   |   |   |   |
|---|---|---|---|---|---|
| 1 | gtcgagggc | agcacggatg | tagcaataca | ttggtggcga | ccggcgcacg | ggtgagtaac |
| 61 | gcgtatgcaa | cctgcctatc | agaggggaat | aacccgcga | aagtcggact | aataccgcat |
| 121 | aaaacagggg | ttccacatgg | aaatatttgt | taaagaatta | tcgctgatag | atgggcatgc |
| 181 | gttccattag | atagttggtg | aggtaacggc | tcaccaagtc | cacgatggat | aggggttctg |
| 241 | agaggaaggt | cccccacact | ggtactgaga | cacggaccag | actcctacgg | gaggcagcag |
| 301 | tgaggaatat | tggtcaatgg | gcgagagcct | gaaccagcca | agtcgcgtga | aggatgaagg |
| 361 | atctatggtt | tgtaaacttc | ttttatatgg | gaataaagtg | aggaacgtgt | tccttttgt |
| 421 | atgtaccata | tgaataagca | tcggctaact | ccgtgccagc | agccgcggta | atacggagga |
| 481 | tgcgagcgtt | atccggattt | attgggttta | aagggtgcgt | aggtggttaa | ttaagtcagc |
| 541 | ggtgaaagtt | tgtggctcaa | ccataaaatt | gccgttgaaa | ctggttgact | tgagtatatt |
| 601 | tgaggtaggc | ggaatgcgtg | gtgtagcggt | gaaatgcata | gatatcacgc | agaactccga |
| 661 | ttgcgaaggc | agcttactaa | actataactg | acactgaagc | acgaaagcgt | ggggatcaaa |
| 721 | caggattaga | taccctggta | gtccacgcag | taaacgatg | ttactacgtg | tttgcgatac |
| 781 | acagtaagcg | gcacagcgaa | agcgttaagt | aatccacctg | gggagtacgc | cggcaacggt |
| 841 | gaaactcaaa | ggaattgacg | gggcccgca | caagcggagg | aacatgtggt | ttaattcgat |
| 901 | gatacgcgag | gaaccttacc | cgggtttgaa | cgcattatga | cagctctgga | aacacattct |
| 961 | ctagtaatag | caatttgcga | ggtgctgcat | ggttgtcgtc | agctcgtgcc | gtgaggtgtc |
| 1021 | ggcttaagtg | ccataacgag | cgcaaccctt | atcactagtt | actaacaggt | caagctgagg |

```
1081 actctagtga gactgccagc gtaagctgtg aggaaggtgg ggatgacgtc aaatcagcac
1141 ggcccttaca tccggggcga cacacgtgtt acaatggtgg ggacaaaggg cagctacctg
1201 gcgacaggat gctaatctcc aaaccccatc tcagttcgga tcgaagtctg caacccgact
1261 tcgtgaagct ggattcgcta gtaatcgcgc atcagccatg gcgcggtgaa tacgttcccg
1321 ggccttgtac acaccgcccg tcaagccatg ggagttgggg gtacctaaag tccgtaaccg
1381 caaggatcgg cctagg
```

Primers used for qPCR

| Name | Forward sequence | Reverse sequence |
|---|---|---|
| GAPDH | ggtatcgtggaaggac tcatg (SEQ ID NO: 11) | atgccagtgagcttcc cgttc (SEQ ID NO: 12) |
| MAP2 | ctcagcaccgctaaca gagg (SEQ ID NO: 13) | cattggcgcttctctc ctc (SEQ ID NO: 14) |
| GPR109a | atgttggctatgaacc gccag (SEQ ID NO: 15) | gctgctgtccgattgg aga (SEQ ID NO: 16) |

SEQ ID NO: 17 (*Parabacteroides goldsteinii* strain DSMZ 19448/JCM13446, 16S ribosomal RNA gene, partial sequence - GenBank: EU136697.1):

```
   1 gtttgatcct ggctcaggat gaacgctagc gacaggctta acacatgcaa gtcgagggc
  61 agcacgatgt agcaatacat tggtggcgac cggcgcacgg gtgagtaacg cgtatgcaac
 121 ctacctatca gagggaata acccggcgaa agtcggacta ataccgcata aaacaggggt
 181 tccacatgga aatatttgtt aaagaattat cgctgataga tgggcatgcg ttccattaga
 241 tagttggtga ggtaacggct caccaagtcc acgatggata ggggttctga gaggaaggtc
 301 ccccacactg gtactgagac acggaccaga ctcctacggg aggcagcagt gaggaatatt
 361 ggtcaatggg cgagagcctg aaccagccaa gtcgcgtgaa ggatgaagga tctatggttt
 421 gtaaacttct tttatatggg aataaagtga ggaacgtgtt ccttttttgta tgtaccatat
 481 gaataagcat cggctaactc cgtgccagca gccgcggtaa tacggaggat gcgagcgtta
 541 tccggattta ttgggtttaa agggtgcgta ggtggttaat taagtcagcg gtgaaagttt
 601 gtggctcaac cataaaattg ccgttgaaac tggttgactt gagtatattt gaggtaggcg
 661 gaatgcgtgg tgtagcggtg aaatgcatag atatcacgca gaactccgat tgcgaaggca
 721 gcttactaaa ctataactga cactgaagca cgaaagcgtg gggatcaaac aggattagat
 781 accctggtag tccacgcagt aaacgatgat tactagctgt ttgcgataca cagtaagcgg
 841 cacagcgaaa gcgttaagta atccacctgg ggagacgccg gcaacggtga aactcaaagg
 901 aattgacggg ggcccgcaca agcggaggaa catgtggttt aattcgatga tacgcgagga
 961 accttacccg ggtttgaacg catattgaca gctctggaaa cagagtctct agtaatagca
1021 atttgcgagg tgctgcatgg ttgtcgtcag ctcgtgccgt gaggtgtcgg cttaagtgcc
1081 ataacgagcg caaccttat cactagttac taacaggtca tgctgaggac tctagtgaga
1141 ctgccagcgt aagctgtgag gaaggtgggg atgacgtcaa atcagcacgg cccttacatc
1201 cggggcgaca cacgtgttac aatggtgggg acaaagggca gctaccgtgt gagcggatgc
1261 gaatctccaa accccatctc agttcggatc gaagtctgca acccgacttc gtgaagctgg
1321 attcgctagt aatcgcgcat cagccatggc gcggtgaata cgttcccggg ccttgtacac
```

```
1381 accacccgtc aagccatggg agttgggggt acctaaagtc cgtaaccgca aggatcggcc 1441 tagggtaaaa ccgatgactg gggctaagtc gtaacaaggt agccgtaccg gaaggtgcgg 1501 ctggaacacc tcctttctgg agcgcagagt tcgttatcaa gttgactcag aggtattagt 1561 taacttgtac tacggttgaa tatgtataaa atatagatct accggcaata aagtgtcggc 1621 aagagagaaa aatgatgctg agggaaacca aggcaaagtt gacagtccta tagctcagtt 1681 ggttagagcg ctacactgat aatgtagagg tcggcagttc aactctgcct gggactacag 1741 aatctctaag agagaatttt gggggattag ctcagctggc tagagcatct gccttgcacg 1801 cagagggtca acggttcgaa tccgttattc tccacaaaaa gttaccgaga catcagaaac 1861 gtaaagtaac gacaagatct ttgacatgat ggacaacgta aaataaagta acaagagcaa 1921 gctgaagata tatcaatccg atttaccccct gtggtaaccg gaaataagaa agtaagcaag 1981 ggcagacggt ggatgccttg gc
```

SEQ ID NO: 18 (*Parabacteroides goldsteinii* strain DSMZ29187/BS-C3-2 16S, ribosomal RNA gene, partial sequence - Genbank GQ456205.2):

```
   1 ctggctcagg atgaacgcta gcgacaggct taacacatgc aagtcgaggg gcagcacgat 61 gtagcaatac attggtggcg accggcgcac gggtgagtaa cgcgtatgca acctacctat 121 cagagggaa taacccggcg aaagtcggac taataccgca taaaacaggg gttccacatg 181 gaaatatttg ttaaagaatt atcgctgata gatgggcatg cgttccatta gatagttggt 241 gaggtaacgc tcaccaagt ccacgatgga taggggttct gagaggaagg tcccccacac 301 tggtactgag acacggacca gactcctacg ggaggcagca gtgaggaata ttggtcaatg 361 ggcgagagc tgaaccagcc aagtcgcgtg aaggatgaag gatctatggt ttgtaaactt 421 cttttatatg ggaataaagt gaggaaacgt gttcctttt gtatgtacca tatgaataag 481 catcggctaa cttccgtgcc agcagccgcg gtaatacgga ggatgcgagc gttatccgga 541 tttattgggt ttaaagggtg cgtaggtggt taattaagtc agcggtgaaa gtttgtggct 601 caaccataaa attgccgttg aaactggttg acttgagtat atttgaggta ggcggaatgc 661 gtggtgtagc ggtgaaatgc atagatatca cgcagaactc cgattgcgaa ggcagcttac 721 taaactataa ctgacactga agcacgaaag cgtggggatc aaacaggatt agataccctg 781 gtagtccacg cagtaaacga tgattactag ctgtttgcga tacacagtaa gcggcacagc 841 gaaagcgtta agtaatccac ctggggagta cgccggcaac ggtgaaactc aaaggaattg 901 acggggggccc gcacaagcgg aggaacatgt ggtttaattc gatgatacgc gaggaaccctt 961 acccgggttt gaacgcattc ggaccggagt ggaaacactt cttctagtaa tagccgtttg 1021 cgaggtgctg catggttgtc gtcagctcgt gccgtgaggt gtcggcttaa gtgccataac 1081 gagcgcaacc cttatcacta gttactaaca ggtcaagctg aggactctag tgagactgcc 1141 agcgtaagct gtgaggaagg tggggatgac gtcaaatcag cacggccctt acatccgggg 1201 cgacacacgt gttacaatgg tggggacaaa gggcagctac ctggcgacag gatgctaatc 1261 tccaaacctc atctcagttc ggatcgaagt ctgcaacccg acttcgtgaa gctggattcg 1321 ctagtaatcg cgcatcagcc atggcgcggt gaatacgttc ccgggccttg tacacaccgc 1381 ccgtcaagcc atgggagttg ggggtaccta agtccgtaa ccgcaagg
```

SEQ ID NO: 19: Strain ref. 1 (*P. distasonis*) 16S ribosomal RNA gene, assembled using Geneious:

```
AAGGCCGATCCTTGTCGGTTACGGACTTCAGGTACCCCCGGCTCCCATGGCTTGACGGGCGGTGTGTACAAGGCCCG

GGAACGTATTCACCGCGCCATGGCTGATGCGCGATTACTAGCGAATCCAGCTTCACGGAGTCGGGTTGCAGACTCCG

ATCCGAACTGAGACGTGGTTTGGGGATTCGCTCCCTGTCACCAGGTGGCCTCCCTTTGTCCACGCCATTGTAACACG

TGTGTCGCCCCGGATGTAAGGGCCGTGCTGATTTGACGTCATCCCCGCCTTCCTCGCAGCTTACGCTGGCAGTCCCA
```

CCAGAGTCCTCAGCTTTACCTGTTAGTAACTAGTGGCAAGGGTTGCGCTCGTTATGGCACTTAAGCCGACACCTCAC

GGCACGAGCTGACGACAACCATGCAGCACCTCGCAAACGGCTATTGCTAGAAAAGGTGTTTCCACCTCGGTCCGAAT

GCGTTCAAACCCGGGTAAGGTTCCTCGCGTATCATCGAATTAAACCACATGTTCCTCCGCTTGTGCGGGCCCCCGTC

AATTCCTTTGAGTTTCACCGTTGCCGGCGTACTCCCCAGGTGGATCACTTAACGCTTTCGCTGTGCCGCTTACAGTG

TATCGCAAACAGCTAGTGATCATCGTTTACTGCGTGGACTACCAGGGTATCTAATCCTGTTTGATCCCCACGCTTTC

GTGCATCAGCGTCAGTCATGGCTTGGCAGGCTGCCTTCGCAATCGGGGTTCTGCGTGATATCTATGCATTTCACCGC

TACACCACGCATTCCGCCTGCCTCAAACATACTCAAGCCCCCAGTTTCAACGGCAATTCTATGGTTGAGCCACAGA

CTTTCACCGCTGACTTAAAAGGCCGCCTACGCACCCTTTAAACCCAATAAATCCGGATAACGCTCGGATCCTCCGTA

TTACCGCGGCTGCTGGCACGGAGTTAGCCGATCCTTATTCATAAGGTACATACAAAACGGGACACGTCCCGCACTTT

ATTCCCTTATAAAGAGGTTTACGATCCATAGAACCTTCATCCCTCACGCGACTTGGCTGGTTCAGCCTCTCGGCCA

TTGACCAATATTCCTCACTGCTGCCTCCCGTAGGAGTTTGGTCCGTGTCTCAGTACCAATGTGGGGACCTTCCTCT

CAGAACCCCTATCCATCGTCGGTTTGGTGGGCCGTTACCCCGCCAACTGCCTAATGGAACGCATGCCTATCTATCAG

CGATGAATCTTTAGCAAATATCCCCATGCGGGCCCCTGCTTCATGCGGTATTAGTCCGACTTTCGCCGGGTTATCC

CCCTCTGATAGGTAAGTTGCATACGCGTTACTCACCCGTGCGCCGGTCGCCACCCGGTATTGCTACCTGTGCTGCCG

CCTCGACTGCA

SEQ ID NO: 20: Strain ref. 2 (*P. distasonis*) 16S ribosomal RNA gene,
assembled using Geneious:
AGGCCGATCCTTGTCGGTTACGGACTTCAGGTACCCCCGGCTCCCATGGCTTGACGGGCGGTGTGTACAAGGCCCGG

GAACGTATTCACCGCGCCATGGCTGATGCGCGATTACTAGCGAATCCAGCTTCACGGAGTCGGGTTGCAGACTCCGA

TCCGAACTGAGACGTGGTTTGGGGATTCGCTCCCTGTCGCCAGGTGGCATCCCTTTGTCCACGCCATTGTAACACGT

GTGTCGCCCCGGATGTAAGGGCCGTGCTGATTTGACGTCATCCCCGCCTTCCTCGCAGCTTACGCTGGCAGTCCCAC

CAGAGTCCTCAGCTTTACCTGTTAGTAACTAGTGGCAAGGGTTGCGCTCGTTATGGCACTTAAGCCGACACCTCACG

GCACGAGCTGACGACAACCATGCAGCACCTCGCAAATCGCTATTGCTAGAGGCTGTGTTTCCACAGCGGTCCAAATG

CGTTCAAACCCGGGTAAGGTTCCTCGCGTATCATCGAATTAAACCACATGTTCCTCCGCTTGTGCGGGCCCCCGTCA

ATTCCTTTGAGTTTCACCGTTGCCGGCGTACTCCCCAGGTGGATCACTTAACGCTTTCGCTGTGCCGCTTACCGTGT

ATCGCAAACAGCTAGTGATCATCGTTTACTGCGTGGACTACCAGGGTATCTAATCCTGTTTGATCCCCACGCTTTCG

TGCATCAGCGTCAGTCATGGCTTGGCAGGCTGCCTTCGCAATCGGGGTTSTGCGTGATATCTAAGCATTTCACCGCT

ACACCACGCATTCCGCCTGCCTCAAACATACTCAAGCCCCCAGTTTCAACGGCAATTCTATGGTTGAGCCACAGAC

TTTCACCGCTGACTTAAAAGGCCGCCTACGCACCCTTTAAACCCAATAAATCCGGATAACGCTCGGATCCTCCGTAT

TACCGCGGCTGCTGGCACGGAGTTAGCCGATCCTTATTCATAAGGTACATACAAAACGGGACACGTCCCGCACTTTA

TTCCCTTATAAAGAGGTTTACGATCCATAGAACCTTCATCCCTCACGCGACTTGGCTGGTTCAGGCTTACGCCCAT

TGACCAATATTCCTCACTGCTGCCTCCCGTAGGAGTTTGGTCCGTGTCTCAGTACCAATGTGGGGACCTTCCTCTC

AGAACCCCTATCCATCGTCGGTTTGGTGGGCCGTTACCCCGCCAACTGCCTAATGGAACGCATGCCTATCTATCAGC

GATGAATCTTTAGCAAATATCCCCATGCGGGACCCCTGCTTCATGCGGTATTAGTCCGACTTTCGCCGGGTTATCCC

CCTCTGATAGGTAAGTTGCATACGCGTTACTCACCCGTGCGCCGGTCGCCACCCGGTATTGCTACCTGTGCTGCCCC

TCGACTTGCATGTGTAA

SEQ ID NO: 21: Strain ref. 3 (*Parabacteroides* sp.) 16S ribosomal RNA gene,
assembled using Geneious:
GGGCCCAATTTAACTAGGCCGATCCTTGCGGTTACGGACTTCAGGTACCCCCGGCTCCCATGGCTTGACGGGCGGTG

TGTACAAGGCCCGGGAACGTATTCACCGCGCCATGGCTGATGCGCGATTACTAGCGAATCCAGCTTCACGGAGTCGA

GTTGCAGACTCCGATCCGAACTGAGACATGGTTTGGAGATTTGCATCACATCGCTGTGTAGCTGCCCTTTGTCCATG

CCATTGTAACACGTGTGTCGCCCCGGATGTAAGGGCCGTGCTGATTTGACGTCATCCCCACCTTCCTCACAGCTTAC

GCTGGCAGTCTCACCAGAGTCCTCAGCTTGACCTGTTAGTAACTAGTGATAAGGGTTGCGCTCGTTATGGCACTTAA

GCCGACACCTCACGGCACGAGCTGACGACAACCATGCAGCACYTCGCAAACGGTCATTGCTGAAAGGAGCGTTTCCA

CTCCGGTCCGAATGCGTTCAAACCCGGGTAAGGTTCCTCGCGTATCATCGAATTAAACCACATGTTCCTCCGCTTGT

GCGGGCCCCCGTCAATTCCTTTGAGTTTCACCGTTGCCGGCGTACTCCCCAGGTGGATTACTTAACGCTTTCGCTGT

AGAGCTTACTGTCTATCGCAAACTCCTAGTAATCATCGTTTACTGCGTGGACTACCAGGGTATCTAATCCTGTTTGA

TCCCCACGCTTTCGTGCTTCAGTGTCAGTTATAGTTTAGTAAGCTGCCTTCGCAATCGGAGTTCTGCGTGATATCTA

TGCATTTCACCGCTACACCACGCATTCCGCCTACCTCAAATATACTCAAGTCATCCAGTTTCAACGGCAATTTTATG

GTTGAGCCACAAACTTTCACCGCTGACTTAAACAACCACCTACGCACCCTTTAAACCCAATAAATCCGGATAACGCT

CGCATCCTCCGTATTACCGCGGCTGCTGGCACGGAGTTAGCCGATGCTTATTCATACGGTACATACAAAATGGGACA

CGTCCCACACTTTATTCCCSKATAAAAGAAGTTTACAAACCATAGATCCTTCATCCTTCACGCGACTTGGCTGGTTC

AGCCTCCCGGCCATTGACCAATATTCCTCACTGCTGCCTCCCGTAGGARTTTGGACCGTGTCTCAGTTCCAATGTGG

GGGACCTTCCTCTCAGAACCCCTATCCATCGTCGGTTTGGTGGGCCGTTACCCCGCCAACTGCCTAATGGAACGCAT

GCCTATCTATCAGCGATGAATCTTTAACAAATATTCCCATGCGGGACCCCTGTTTTATGGAGCATTAATCCGACTTT

CGCCGGGCTATTCCCCTCTGATAGGCAAGTTGCATACGCGTTACTCACCCGTGCGCCGGTCGCCGGCAGGCATTGCT

GCCCCCGCTGCCCCTCGACTTGCATGGTTAGCCTCCAATTCCCC

SEQ ID NO: 22: Strain ref. 4 (*P. distasonis*) 16S ribosomal RNA gene,
assembled using Geneious:
TAGGCCGATCCTTGCGGTTACGGACTTCAGGTACCCCCGGCTCCCATGGCTTGACGGGCGGTGTGTACAAGGCCCGG

GAACGTATTCACCGCGCCATGGCTGATGCGCGATTACTAGCGAATCCAGCTTCACGGAGTCGAGTTGCAGACTCCGA

TCCGAACTGAGACATGGTTTGGAGATTTGCATCACATCGCTGTGTAGCTGCCCTTTGTCCATGCCATTGTAACACGT

GTGTCGCCCCGGATGTAAGGGCCGTGCTGATTTGACGTCATCCCCACCTTCCTCACAGCTTACGCTGGCAGTCTCAC

CAGAGTCCTCAGCTTGACCTGTTAGTAACTAGTGATAAGGGTTGCGCTCGTTATGGCACTTAAGCCGACACCTCACG

GCACGAGCTGACGACAACCATGCAGCACCTCGCAAACGGTCATTGCTGAAAGGAGCGTTTCCACTCCGGTCCGAATG

CGTTCAAACCCGGGTAAGGTTCCTCGCGTATCATCGAATTAAACCACATGTTCCTCCGCTTGTGCGGGCCCCYGTCA

ATTCCTTTGAGTTTCACCGTTGCCGGCGTACTCCCCAGGTGGATTACTTAACGCTTTCGCTGTAGAGCTTACTGTCT

ATCGCAMACTCCTAGTAATCATCGTTTACTGCGTGGACTACCAGGGTATCTAATCCTGTTTGATCCCCACGCTTTCG

TGCTTCAGTGTCAGTTATAGTTTAGTAAGCTGCCTTCGCAATCGGAGTTCTGCGTGATATCTATGCATTTCACCGCT

ACACCACGCATTCCGCCTACCTCAAATATACTCAAGTCATCCAGTTTCAACGGCAATTTTATGGTTGAGCCACAAAC

TTTCACCGCTGACTTAAACAACCACCTACGCACCCTTTAAACCCAATAAATCCGGATAACGCTCGCATCCTCCGTAT

TACCGCGGCTGCTGGCACGGAGTTAGCCGATGCTTATTCATACGGTACATACAAAATGGGACACGTCCCACACTTTA

TTCCCGTATAAAAGAAGTTTACAAACCATAGATCCTTCATCCTTCACGCGACTTGGCTGGTTCAGCCTCCCGGCCAT

TGACCAATATTCCTCACTGCTGCCTCCCGTAGGAGTTTGGACCGTGTCTCAGTTCCAATGTGGGGGACCTTCCTCTC

AGAACCCCTATCCATCGTCGGTTTGGTGGGCCGTTACCCCGCCAACTGCCTAATGGAACGCATGCCTATCTATCAGC

GATGAATCTTTAACAAATATTCCCATGCGGGACCCCTGTTTTATGGAGCATTAATCCGACTTTCGCCGGGCTATTCC

CCTCTGATAGGCAAGTTGCATACGCGTTACTCACCCGTGCGCCGGTCGCCGGCAGGCATTGCTGCCCCCGCTGCCCC

TCGACTTGCATGTGTT

SEQ ID NO: 23: Strain ref. 5 (*P. distasonis*) 16S ribosomal RNA gene,
assembled using Geneious:
GTAGGCCGATCCTCGCGGTTACGGACTTCAGGTACCCCCGGCTCCCATGGCTTGACGGGCGGTGTGTACAAGGCCCG

GGAACGTATTCACCGCGCCATGGCTGATGCGCGATTACTAGCGAATCCAGCTTCACGGAGTCGGGTTGCAGACTCCG

ATCCGAACTGAGACGTGGTTTGGGGATTCGCTCCCTGTCGCCAGGTGGCTTCCCTTTGTCCACGCCATTGTAACACG

TGTGTCGCCCCGGATGTAAGGGCCGTGCTGATTTGACGTCATCCCCGCCTTCCTCGCAGCTTACGCTGGCAGTCCCA

CCAGAGTCCTCAGCYTWACCTGTTAGTAACTAGTGGCAAGGGTTGCGCTCGTTATGGCACTTAAGCCGACACCTCAC

-continued

GGCACGAGCTGACGACAACCATGCAGCACCTCGCAAACGGCTATTGCTAGAAAAGGTGTTTCCACCTCGGTCCGAAT

GCGTTCAAACCCGGGTAAGGTTCCTCGCGTATCATCGAATTAAACCACATGTTCCTCCGCTTGTGCGGGCCCCCGTC

AATTCCTTTGAGTTTCACCGTTGCCGGCGTACTCCCCAGGTGGATCACTTAACGCTTTCGCTGTGCCGCTTACACTG

TATCGCAAACAGCTAGTGATCATCGTTTACTGCGTGGACTACCAGGGTATCTAATCCTGTTTGATCCCCACGCTTTC

GTGCATCAGCGTCAGTCATGGCTTGGCAGGCTGCCTTCGCAATCGGGGTTCTGCGTGATATCTATGCATTTCACCGC

TACACCACGCATTCCGCCTGCCTCAAACATACTCAAGCCCCCCAGTTTCAACGGCAATTCTATGGTTGAGCCACAGA

CTTTCACCGCTGACTTAAAAGGCCGCCTACGCACCCTTTAAACCCAATAAATCCGGATAACGCTCGGATCCTCCGTA

TTACCGCGGCTGCTGGCACGGAGTTAGCCGATCCTTATTCATAAGGTACATACAAAACGGGACACGTCCTACACTTT

ATTCCCTTATAAAGAGGTTTACGATCCATAGAACCTTCATCCCTCACGCGACTTGGCTGGTTCAGGCTTACGCCCA

TTGACCAATATTCCTCACTGCTGCCTCCCGTAGGAGTTTGGTCCGTGTCTCAGTACCAATGTGGGGGACCTTCCTCT

CAGAACCCCTATCCATCGTCGGTTTGGTGGGCCGTTACCCCGCCAACTGCCTAATGGAACGCATGCMTATMTATCAG

CGATGWATCTTKMGCAAATATCCCCRTGCGGGGCCCGTGCTTCRTGCGGTATTAGTCMGACTTTCGCCGGGTTATCC

CCCTCTGATAGGYAAGTTGCATACGCGTTACTCACCCGTGCGCCGGTCGCCRGCCGCGGTATCTGCTACCCCGCGCT

GCCCCTCGACTTGCATGGT

SEQ ID NO: 24: Strain ref. 6 (P. distasonis) 16S ribosomal RNA gene,
assembled using Geneious:
GATCCTCGCGGTTACGGACTTCAGGTACCCCCGGCTCCCATGGCTTGACGGGCGGTGTGTACAAGGCCCGGGAACGT

ATTCACCGCGCCATGGCTGATGCGCGATTACTAGCGAATCCAGCTTCACGGAGTCGGGTTGCAGACTCCGATCCGAA

CTGAGACGTGGTTTGGGGATTCGCTCCCTGTCGCCAGGTGGCCTCCCTTTGTCCACGCCATTGTAACACGTGTGTCG

CCCCGGATGTAAGGGCCGTGCTGATTTGACGTCATCCCCGCCTTCCTCGCAGCTTACGCTGGCAGTCCCACCAGAGT

CCTCAGCATCACCTGTTAGTAACTAGTGGCAAGGGTTGCGCTCGTTATGGCACTTAAGCCGACACCTCACGGCACGA

GCTGACGACAACCATGCAGCACCTCGCAAACGGCTATTGCTAGAAAAGGTGTTTCCACCTCGGTCCGAATGCGTTCA

AACCCGGGTAAGGTTCCTCGCGTATCATCGAATTAAACCACATGTTCCTCCGCTTGTGCGGGCCCCCGTCAATTCCT

TTGAGTTTCACCGTTGCCGGCGTACTCCCCAGGTGGATCACTTAACGCTTTCGCTGTGCCGCTTACAGTGTATCGCA

AACAGCTAGTGATCATCGTTTACTGCGTGGACTACCAGGGTATCTAATCCTGTTTGATCCCCACGCTTTCGTGCATC

AGCGTCAGTCATGGCTTGGCAGGCTGCCTTCGCAATCGGGGTTCTGCGTGATATCTATGCATTTCACCGCTACACCA

CGCATTCCGCCTGCCTCAAACATACTCAAGCCCCCCAGTTTCAACGGCAATTCTATGGTTGAGCCACAGACTTTCAC

CGCTGACTTAAAAGGCCGCCTACGCACCCTTTAAACCCAATAAATCCGGATAACGCTCGGATCCTCCGTATTACCGC

GGCTGCTGGCACGGAGTTAGCCGATCCTTATTCATAAGGTACATACAAAACGGGACACGTCCCGCACTTTATTCCCT

TATAAAGAGGTTTACGATCCATAGAACCTTCATCCCTCACGCGACTTGGCTGGTTCAGCCTTTCGGCCATTGACCA

ATATTCCTCACTGCTGCCTCCCGTAGGAGTTTGGTCCGTGTCTCAGTACCAATGTGGGGACCTTCCTCTCAGAACC

CCTATCCATCGTCGGTTTGGTGGGCCGTTACCCCGCCAACTGCCTAATGGAACGCATGCCTATCTATCAGCGATGAA

TCTTTAGCAAATATCCCCATGCGGGCCCCTGCTTCATGCGGTATTAGTCCGACTTTCGCCGGGTTATCCCCCTCTG

ATAGGTAAGTTGCATACGCGTTACTCACCCGTGCGCCGGTCGCCACCCGGTATTGC

SEQ ID NO: 25: Strain ref. 7 (P. merdae) 16S ribosomal RNA gene, assembled using Geneious:
TTAAATAGGCCGATCCTTGCGGTTACGGACTTCAGGTACCCCCGGCTCCCATGGCTTGACGGGCGGTGTGTACAAGG

CCCGGGAACGTATTCACCGCGCCATGGCTGATGCGCGATTACTAGCGAATCCAGCTTCACGGAGTCGAGTTGCAGAC

TCCGATCCGAACTGAGACATGGTTTGGAGATTAGCATCCTGTCACCAGGTAGCTGCCCTTTGTCCATGCCATTGTAA

CACGTGTGTCGCCCCGGATGTAAGGGCCGTGCTGATTTGACGTCATCCCCACCTTCCTCACAGCTTACGCTGGCAGT

CTCACCAGAGTCCTCAGCTTCACCTGTTAGTAACTAGTGATAAGGGTTGCGCTCGTTATGGCACTTAAGCCGACACC

TCACGGCACGAGCTGACGACAACCATGCAGCACCTCGTAATCTGCTATTGCTAGAAAGAGTGTTTCCACTCCGGTCA

GACTACGTTCAAACCCGGGTAAGGTTCCTCGCGTATCATCGAATTAAACCACATGTTCCTCCGCTTGTGCGGGCCCC

-continued

CGTCAATTCCTTTGAGTTTCACCGTTGCCGGCGTACTCCCCAGGTGGATTACTTAACGCTTTCGCTGTAGAGCTTAC

ATTGTATCGCAAACTCCTAGTAATCATCGTTTACTGCGTGGACTACCAGGGTATCTAATCCTGTTTGATCCCCACGC

TTTCGTGCTTCAGTGTCAGTTATGGTTTAGTAAGCTGCCTTCGCAATCGGAGTTCTGCGTGATATCTATGCATTTCA

CCGCTACACCACGCATTCCGCCTACCTCAAACACACTCAAGTAACCCAGTTTCAACGGCAATTTTATGGTTGAGCCA

CAAACTTTCACCGCTGACTTAAATCACCACCTACGCACCCTTTAAACCCAATAAATCCGGATAACGCTCGCATCCTC

CGTATTACCGCGGCTGCTGGCACGGAGTTAGCCGATGCTTATTCATAGGGTACATACAAAAAAGGACACGTCCTCCA

CTTTATTCCCCTATAAAAGAAGTTTACAAACCATAGATCCTTCTTCCTTCACGCGACTTGGCTGGTTCAGCCTCTCG

GCCATTGACCAATATTCCTCACTGCTGCCTCCCGTAGGAGTTTGGTCCGTGTCTCAGTACCAATGTGGGGGACCTTC

CTCTCAGAACCCCTATCCATCGTCGGTTTGGTGGGCCGTTACCCCGCCAACTGCCTAATGGAACGCATGCCTATCTA

TCAGCGATGAATCTTTAACAAATATTCCCATGCGGGACCCCTGTTTTATGGGGTATTAATCCGACTTTCGCCGGGCT

ATCCCCCTCTGATAGGTAAGTTGCATACGCGTTACTCACCCGTGCGCCGGTCGCCATCAATCTGTATTGCTACAAAT

CATGCTGCCCCTCGACTTGCATGGTTAAG

SEQ ID NO: 26 Strain ref. 8 (*P. distasonis*) 16S ribosomal RNA gene,
assembled using Geneious:
WTCGGTTACGGACTTCAGGTACCCCCGGCTCCCATGGCTTGACGGGCGGTGTGTACAAGGCCCGGGAACGTATTCAC

CGCGCCATGGCTGATGCGCGATTACTAGCGAATCCAGCTTCACGGAGTCGGGTTGCAGACTCCGATCCGAACTGAGA

CGTGGTTTGGGGATTCGCTCCCTGTCGCCAGGTGGCCTCCCTTTGTCCACGCCATTGTAACACGTGTGTCGCCCCGG

ATGTAAGGGCCGTGCTGATTTGACGTCATCCCCGCCTTCCTCGCAGCTTACGCTGGCAGTCCCACCAGAGTCCTCAG

CTTTACCTGTTAGTAACTAGTGGCAAGGGTTGCGCTCGTTATGGCACTTAAGCCGACACCTCACGGCACGAGCTGAC

GACAACCATGCAGCACCTCGCAAACGGCTATTGCTAGAAAAGGTGTTTCCACCTCGGTCCGAATGCGTTCAAACCCG

GGTAAGGTTCCTCGCGTATCATCGAATTAAACCACATGTTCCTCCGCTTGTGCGGGCCCCCGTCAATTCCTTTGAGT

TTCACCGTTGCCGGCGTACTCCCCAGGTGGATCACTTAACGCTTTCGCTGTGCCGCTTACAGTGTATCGCAAACAGC

TAGTGATCATCGTTTACTGCGTGGACTACCAGGGTATCTAATCCTGTTTGATCCCCACGCTTTCGTGCATCAGCGTC

AGTAATGGCTTGGCAGGCTGCCTTCGCAATCGGGGTTCTGCGTGATATCTATGCATTTCACCGCTACACCACGCATT

CCGCCTGCCTCAAACATACTCAAGCCCCCCAGTTTCAACGGCAATTCTATGGTTGAGCCACAGACTTTCACCGCTGA

CTTAAAAGGCCGCCTACGCACCCTTTAAACCCAATAAATCCGGATAACGCTCGGATCCTCCGTATTACCGCGGCTGC

TGGCACGGAGTTAGCCGATCCTTATTCATAAGGTACATACAAAACGGGACACGTCCCGCACTTTATTCCCTTATAAA

AGAGGTTTACGATCCATAGAACCTTCATCCCTCACGCGACTTGGCTGGTTCAGCCTCTCGGCCATTGACCAATATTC

CTCACTGCTGCCTCCCGTWGGAGTTTGGTCCGTGTCTCAGTACCAATGTGGGGGACCTTCCTCTCAGAACCCCTATC

CATCGTCGGTTTGGTGGGCCGTTACCCCGCCAACTGCCTAATGGAACGCATGCCTATCTATCAGCGATGAATCTTTA

GCAAATATYCCCATGCGGGRYCCCTGCTTCATGCGGTATTAGTCCGACTTTCGCCGGGTTATCCCCCTCTGATAGGC

AAGTTGCATACGCGTTACTCACCCGTGCGCCGGTCGCCACCCGGTATTGCTACCTGTGCTGCCCCW

SEQ ID NO: 27 Strain ref. 9 (*P. distasonis*) 16S ribosomal RNA gene,
assembled using Geneious:
GATCTCGCGGTTTACGGACTTCAGGTACCCCCGGCTCCCATGGCTTGACGGGCGGTGTGTACAAGGCCCGGGAACGT

ATTCACCGCGCCATGGCTGATGCGCGATTACTAGCGAATCCAGCTTCACGGAGTCGGGTTGCAGACTCCGATCCGAA

CTGAGACGTGGTTTGGGGATTCGCTCCCTGTCGCCAGGTGGCCTCCCTTTGTCCACGCCATTGTAACACGTGTGTCG

CCCCGGATGTAAGGGCCGTGCTGATTTGACGTCATCCCCGCCTTCCTCGCAGCTTACGCTGGCAGTCCCACCAGAGT

CCTCAGCATCACCTGTTAGTAACTAGTGGCAAGGGTTGCGCTCGTTATGGCACTTAAGCCGACACCTCACGGCACGA

GCTGACGACAACCATGCAGCACCTCGCAAACGGCTATTGCTAGAAAAGGTGTTTCCACCTCGGTCCGAATGCGTTCA

AACCCGGGTAAGGTTCCTCGCGTATCATCGAATTAAACCACATGTTCCTCCGCTTGTGCGGGCCCCCGTCAATTCCT

TTGAGTTTCACCGTTGCCGGCGTACTCCCCAGGTGGATCACTTAACGCTTTCGCTGTGCCGCTTACAGTGTATCGCA

```
AACAGCTAGTGATCATCGTTTACTGCGTGGACTACCAGGGTATCTAATCCTGTTTGATCCCCACGCTTTCGTGCATC
AGCGTCAGTCATGGCTTGGCAGGCTGCCTTCGCAATCGGGGTTCTGCGTGATATCTATGCATTTCACCGCTACACCA
CGCATTCCGCCTGCCTCAAACATACTCAAGCCCCCCAGTTTCAACGGCAATTCTATGGTTGAGCCACAGACTTTCAC
CGCTGACTTAAAAGGCCGCCTACGCACCCTTTAAACCCAATAAATCCGGATAACGCTCGGATCCTCCGTATTACCGC
GGCTGCTGGCACGGAGTTAGCCGATCCTTATTCATAAGGTACATACAAAACGGGACACGTCCCGCACTTTATTCCCT
TATAAAGAGGTTTACGATCCATAGAACCTTCATCCCTCACGCGACTTGGCTGGTTCAGCCTTTCGGCCATTGACCA
ATATTCCTCACTGCTGCCTCCCGTAGGAGTTTGGTCCGTGTCTCAGTACCAATGTGGGGGACCTTCCTCTCAGAACC
CCTATCCATCGTCGGTTTGGTGGGCCGTTACCCCGCCAACTGCCTAATGGAACGCATGCCTATCTATCAGCGATGAA
TCTTTAGCAAATATCCCCATGCGGGGCCCCTGCTTCATGCGGTATTAGTCCGACTTTCGCCGGGTTATCCCCCTCTG
ATAGGTAAGTTGCATACGCGTTACTCACCCGTGCGCCGGTCGCCACCCGGTATTGCTACCTGGTGCTGCCCCCTCGA
CTGC
```

SEQ ID NO: 28 Strain ref. 10 (*Parabacteroides johnsonii*) 16S ribosomal RNA gene, assembled using Geneious:
```
TTTTANCTAGGCCGATCCTTGCGGTTACGGACTTCAGGTACCCCCGGCTCCCATGGCTTGACGGGCGGTGTGTACAA
GGCCCGGGAACGTATTCACCGCGCCATGGCTGATGCGCGATTACTAGCGAATCCAGCTTCACGGAGTCGAGTTGCAG
ACTCCGATCCGAACTGAGACATGGTTTAGAGATTAGCATCCTGTCGCCAGGTAGCTGCCCTTTGTCCATGCCATTGT
AACACGTGTGTCGCCCCGGATGTAAGGGCCGTGCTGATTTGACGTCATCCCCACCTTCCTCACAGCTTACGCTGGCA
GTCTCACCAGAGTCCTCAGCTTAACCTGTTAGTAACTAGTGATAAGGGTTGCGCTCGTTATGGCACTTAAGCCGACA
CCTCACGGCACGAGCTGACGACAACCATGCAGCACCTCGTAATCAGCTATTGCTAGAAGACCTCTTTCAAGGTCGGT
CTGACTACGTTCAAACCCGGGTAAGGTTCCTCGCGTATCATCGAATTAAACCACATGTTCCTCCGCTTGTGCGGGCC
CCCGTCAATTCCTTTGAGTTTCACCGTTGCCGGCGTACTCCCCAGGTGGATTACTTAACGCTTTCGCTGTAGAGCTT
ACTGTCTATCGCAAACTCCTAGTAATCATCGTTTACTGCGTGGACTACCAGGGTATCTAATCCTGTTTGATACCCAC
GCTTTCGTGCTTCAGTGTCAGTTATGGTTTAGTAAGCTGCCTTCGCAATTGGAGTTCTGCGTGATATCTATGCATTT
CACCGCTACACCACGCATTCCGCCTACCTCAAACACACTCAAGTAACCCAGTTTCAACGGCAATTTTATGGTTGAGC
CACAAACTTTCACCGCTGACTTAAATTACCACCTACGCACCCTTTAAACCCAATAAATCCGGATAACGCTCGCATCC
TCCGTATTACCGCGGCTGCTGGCACGGAGTTAGCCGATGCTTATTCATAGGGTACATACAAAATGGGACACGTCCCA
CACTTTATTCCCCTATAAAGAAGTTTACAAACCATAGATCCTTCATCCTTCACGCGACTTGGCTGGTTCAGCCTCT
CGGCCATTGACCAATATTCCTCACTGCTGCCTCCCGTAGGAGTTTGGTCCGTGTCTCAGTACCAATGTGGGGGACCT
TCCTCTCAGAACCCCTATCCATCGTCGGTTTGGTGGGCCGTTACCCCGCCAACTGCCTAATGGAACGCATGCCTATC
TATCAGCGATGAATCTTTAACAAATAKTCCCATGCGGGAYCCCTGTTTTATGGAGTATTAATCCGACTTTCGCCGGG
CTATCCTCCTCTGATAGGTAAGTTGCATACGCGTTACTCACCCGTGCGCCGGTCGCCATCAATAAGTATTGCTACCT
ACCATGCTGCCCCTCGACTTGCATGTGTAAGCCKC
```

SEQ ID NO: 29 Strain ref. 11 (*Parabacteroides* sp.) 16S ribosomal RNA gene, assembled using Geneious:
```
CCGATCCTTTCGGTTACGGACTTCAGGTACCCCCGGCTCCCATGGCTTGACGGGCGGTGTGTACAAGGCCCGGGAAC
GTATTCACCGCGCCATGGCTGATGCGCGATTACTAGCGAATCCAGCTTCACGGAGTCGGGTTGCAGACTCCGATCCG
AACTGAGACGTGGTTTGGGATTCGCTCCCTGTCGCCAGGTGGCCTCCCTTTGTCCACGCCATTGTAACACGTGTGT
CGCCCCGGATGTAAGGGCCGTGCTGATTTGACGTCATCCCCGCCTTCCTCGCAGCTTACGCTGGCAGTCCCACCAGA
GTCCTCAGCATCACCTGTTAGTAACTAGTGGCAAGGGTTGCGCTCGTTATGGCACTTAAGCCGACACCTCACGGCAC
GAGCTGACGACAACCATGCAGCACCTCGCAAATCGCTATCGCTAGAGACTCTGTTTCCAGAGCTGTCGAAATGCGTT
CAAACCCGGGTAAGGTTCCTCGCGTATCATCGAATTAAACCACATGTTCCTCCGCTTGTGCGGGCCCCCGTCAATTC
CTTTGAGTTTCACCGTTGCCGGCGTACTCCCCAGGTGGATCACTTAACGCTTTCGCTGTGCCGCTTACAGTGTATCG
CAAACAGCTAGTGATCATCGTTTACTGCGTGGACTACCAGGGTATCTAATCCTGTTTGATCCCCACGCTTTCGTGCA
```

TCAGCGTCAGTAATGGCTTGGCAGGCTGCCTTCGCAATCGGGGTTCTGCGTGATATCTATGCATTTCACCGCTACAC

CACGCATTCYGCCTGCCTCAAACATACTCAAGCCCCCCAGTTTCAACGGCAATTCTATGGTTGAGCCACAGACTTTC

ACCGCTGACTTAAAAGGCCGCCTACGCACCCTTTAAACCCAATAAATCCGGATAACGCTCGGATCCTCCGTATTACC

GCGGCTGCTGGCACGGAGTTAGCCGATCCTTATTCATAAGGTACATACMAAACGGGACACGTCCCGCACTTTATTCC

CTTATAAAAGAGGTTTACGATCCATAGAACCTTCATCCCTCACGCGACTTGGCTGGTTCAGSCTCTCGCCCATTGAC

CAATATTCCTCACTGCTGCCTCCCGTAGGAGTTTGGTCCGTGTCTCAGTACCAATGTGGGGACCTTCCTCTCAGAA

CCCCTATCCATCGTCGGTTTGGTGGGCCGTTACCCCGCCAACTGCCTAATGGAACGCMWGCCKATYTATCAGCGAWG

AATCTTTAGCAAATATCCCCATGCGGGGCCCCTGCTTCMTGCGGTATTAGTCCGACTTTCGCCGGGTTATCCCCCTC

TGATAGGCAAGTWGCATACGCGTTACTCACCCGTGCGCCGGTCGCCACCCGGTATTGCTACCCTGYGCTGCCCCTCG

ACTTGCATGKTAA

SEQ ID NO: 30 Strain ref. 12 (*Parabacteroides* sp.) 16S ribosomal RNA gene, assembled using Geneious:
GCGCGGTTTAACTAGGCCGATCCTTTCGGTTACGGACTTCAGGTACCCCCGGCTCCCATGGCTTGACGGGCGGTGTG

TACAAGGCCCGGGAACGTATTCACCGCGCCATGGCTGATGCGCGATTACTAGCGAATCCAGCTTCACGGAGTCGGGT

TGCAGACTCCGATCCGAACTGAGACGTGGTTTGGGGATTCGCTCCCTGTCGCCAGGTGGCCTCCCTTTGTCCACGCC

ATTGTAACACGTGTGTCGCCCCGGATGTAAGGGCCGTGCTGATTTGACGTCATCCCCGCCTTCCTCGCAGCTTACGC

TGGCAGTCCCACCAGAGTCCTCAGCATCACCTGTTAGTAACTAGTGGCAAGGGTTGCGCTCGTTATGGCACTTAAGC

CGACACCTCACGGCACGAGCTGACGACAACCATGCAGCACCTCGCAAATCGCTATCGCTAGAGACTCTGTTTCCAGA

GCTGTCGAAATGCGTTCAAACCCGGGTAAGGTTCCTCGCGTATCATCGAATTAAACCACATGTTCCTCCGCTTGTGN

CGGGCCCCCGTCAATTCCTTTGAGTTTCACCGTTGCCGGCGTAYTCCCCAGGTGGATCACTTAACGCTTTCGCTGTG

CCGCTTACAGTGTATCGCAAACAGCTAGTGATCATCGTTTACTGCGTGGACTACCAGGGTATCTAATCCTGTTTGAT

CCCCACGCTTTCGTGCATCAGCGTCAGTAATGGCTTGGCAGGCTGCCTTCGCAATCGGGGTTCTGCGTGATATCTAT

GCATTTCACCGCTACACCACGCATTCCGCCTGCCTCAAACATACTCAAGCCCCCCANTTTCAACGGCAATTCTATGG

TTGAGCCACAGACTTTCACCGCTGACTTAAAAGGCCGCCTACGCACCCTTTAAACCCAATAAATCCGGATAACGCTC

GGATCCTCCGTATTACCGCGGCTGCTGGCACGGAGTTAGCCGATCCTTATTCATAAGGTACATACAAAACGGGACAC

GTCCCGCACTTTATTCCCTTATAAAAGAGGTTTACGATCCATAGAACCTTCATCCCTCACGCGACTTGGCTGGTTCA

GCCTTTCGGCCATTGACCAATATTCCTCACTGCTGCCTCCCGTAGGAGTTTGGTCCGTGTCTCAGTACCAATGTGGG

GGACCTTCCTCTCAGAACCCCTATCCATTGTCGGTTTGGTGGGCCGTTACCCCGCCAACTGCCTAATGGAACGCATG

CCTATCTATCAGCGATGAATCTTTAGCAAATATCCCCATGCGGGCCCCTGCTTCATGCGGTATTAGTCCGACTTTC

GCCGGGTTATCCCCCTCTGATAGGCAAGTTGCATACGCGTTACTCACCCGTGCGCCGGTCGCCGAGCCGCGGTATTG

CTACCCTCGTGCTGCCCCTCGACTTGCATGGTTAGCCTCCATCCC

SEQ ID NO: 31 Strain ref. 14 (*Parabacteroides* sp.) 16S ribosomal RNA gene, assembled using Geneious:
CTTAGGCCGATCCCTCGCGGTTCGGACTTCAGGTACCCCCGGCTCCCATGGCTTGACGGGCGGTGTGTACAAGGCCC

GGGAACGTATTCACCGCGCCATGGCTGATGCGCGATTACTAGCGAATCCAGCTTCACGGAGTCGGGTTGCAGACTCC

GATCCGAACTGAGACGTGGTTTGGGGATTCGCTCCCTGTCGCCAGGTGGCCTCCCTTTGTCCACGCCATTGTAACAC

GTGTGTCGCCCCGGATGTAAGGGCCGTGCTGATTTGACGTCATCCCCGCCTTCCTCGCAGCTTACGCTGGCAGTCCC

ACCAGAGTCCTCAGCATCACCTGTTAGTAACTAGTGGCAAGGGTTGCGCTCGTTATGGCACTTAAGCCGACACCTCA

CGGCACGAGCTGACGACAACCATGCAGCACCTCGCAAACGGCTATTGCTAGAAAAGGTGTTTCCACCTCGGTCCGAA

TGCGTTCAAACCCGGGTAAGGTTCCTCGCGTATCATCGAATTAAACCACATGTTCCTCCGCTTGTGCGGGCCCCCGT

CAATTCCTTTGAGTTTCACCGTTGCCGGCGTACTCCCCAGGTGGATCACTTAACGCTTTCGCTGTGCCGCTTACAGT

GTATCGCAAACAGCTAGTGATCATCGTTTACTGCGTGGACTACCAGGGTATCTAATCCTGTTTGATCCCCACGCTTT

-continued

CGTGCATCAGCGTCAGTCATGGCTTGGCAGGCTGCCTTCGCAATCGGGGTTCTGCGTGATATCTATGCATTTCACCG

CTACACCACGCATTCCGCCTGCCTCAAACATACTCAAGCCCCCCAGTTTCAACGGCAATTCTATGGTTGAGCCACAG

ACTTTCACCGCTGACTTAAAAGGCCGCCTACGCACCCTTTAAACCCAATAAATCCGGATAACGCTCGGATCCTCCGT

ATTACCGCGGCTGCTGGCACGGAGTTAGCCGATCCTTATTCATAAGGTACATACAAAACGGGACACGTCCCGCACTT

TATTCCCTTATAAAGAGGTTTACGATCCATAGAACCTTCATCCCTCACGCGACTTGGCTGGTTCAGCCTTTCGGCC

ATTGACCAATATTCCTCACTGCTGCCTCCCGTAGGAGTTTGGTCCGTGTCTCAGTACCAATGTGGGGACCTTCCTC

TCAGAACCCCTATCCATCGTCGGTTTGGTGGGCCGTTACCCCGCCAACTGCCTAATGGAACGCATGCCTATCTATCA

GCGATGAATCTTTAGCAAATATCCCCATGCGGGGCCCCTGCTTCATGCGGTATTAGTCCGACTTTCGCCGGGTTATC

CCCCTCTGATAGGTAAGTTGCATACGCGTTACTCACCCGTGCGCCGGTCGCCACCCGGTATTGCTACCTGGTGCTGC

CCCTCGACTGCAT

SEQ ID NO: 32 Strain ref. 15 (Parabacteroides sp.) 16S ribosomal RNA gene, assembled using Geneious:
GCGAGGTATCGAGACTACTAGGTACCCCCGGCTCCCATGGCTTGACGGGCGGTGTGTACAAGGCCCGGGAACGTATT

CACCGCGCCATGGCTGATGCGCGATTACTAGCGAATCCAGCTTCACGGAGTCGGTTGCAGACTCCGATCCGAACTG

AGACGTGGTTTGGGGATTCGCTCCCTGTCGCCAGGTGGCATCCCTTTGTCCACGCCATTGTAACACGTGTGTCGCCC

CGGATGTAAGGGCCGTGCTGATTTGACGTCATCCCCGCCTTCCTCGCAGCTTACGCTGGCAGTCCCACCAGAGTCCT

CAGCTTTACCTGTTAGTAACTAGTGGCAAGGGTTGCGCTCGTTATGGCACTTAAGCCGACACCTCACGGCACGAGCT

GACGACAACCATGCAGCACCTCGCAAATCGCTATTGCTAGAGGCTCTGTTTCCACATCGGTCCAAATGCGTTCAAAC

CCGGGTAAGGTTCCTCGCGTATCATCGAATTAAACCACATGTTCCTCCGCTTGTGCGGGCCCCCGTCAATTCCTTTG

AGTTTCACCGTTGCCGGCGTACTCCCCAGGTGGATCACTTAACGCTTTCGCTGTGCCGCTTACCGTGTATCGCAAAC

AGCTAGTGATCATCGTTTACTGCGTGGACTACCAGGGTATCTAATCCTGTTTGATCCCCACGCTTTCGTGCATCAGC

GTCAGTCATGGCTTGGCAGGCTGCCTTCGCAATCGAGGTTCTGCGTGATATCTAAGCATTTCACCGCTACACCACGC

ATTCCGCCTGCCTCAAACATACTCAAGCCCCCAGTTTCAACGGCAATTCTATGGTTGAGCCACAGACTTTCACCGC

TGACTTAAAAGGCCGCCTACGCACCCTTTAAACCCAATAAATCCGGATAACGCTCGGATCCTCCGTATTACCGCGGC

TGCTGGCACGGAGTTAGCCGATCCTTATTCATAAGGTACATACAAAACRGGACACGTCCCGCACTTTATTCCCTTAT

AAAGAGGTTTACGATCCATAGAACCTTCATCCCTCACGCGACTTGGCTGGTTCAGGCTTACGCCCATTGACCAATA

TTCCTCACTGCTGCCTCCCGTTGGAGTTTGGTCCGTGTCTCAGTACCAATGTGGGGACCTTCCTCTCAGAACCCCT

ATCCATCGTCGGTTTGGTGGGCCGTTACCCCGCCAACTGCATAATGGAACGCATGCCTATCTATCAGCGATGAATCT

TTAGCAAATATCCCCATGCGGGACCCCTGCTTCATGCGGTATTAGTCCGACTTTCGCCGGGTTATCCCCCTCTGATA

GGTAAGTTGCATACGCGTTACTCACCCGTGCGCCGGTCGCCACCCGGTATTGCTACGGGTGA

SEQ ID NO: 33 Parabacteroides gordonii gene for 16S ribosomal RNA, partial sequence, strain: JCM15724:
  1 agagtttgat cctggctcag gatgaacgct agcgacaggc ttaacacatg caagtcgagg 61 ggcagcagga agtagcaata ctttgctggc gaccggcgca cgggtgagta acgcgtatgc 121 aacctaccta tcagaggggg ataacccggc gaaagtcgga ctaataccgc ataaaacagg 181 ggtcccgcat gggaatattt gttaaagatt aattgctgat agatgggcat gcgttccatt 241 agatagttgg taaggtaacg gcttaccaag tctgcgatgg ataggggttc tgagaggaag 301 gtcccccaca ctggtactga gacacggacc agactcctac gggaggcagc agtgaggaat 361 attggtcaat gggcgagagc ctgaaccagc caagtcgcgt gaaggatgaa ggatctatgg 421 ttcgtaaact tcttttataa gggaataaag tgcggacgtg tcctgttttg tatgtacctt 481 atgaataagg atcggctaac tccgtgccag cagccgcggt aatacggagg atccgagcgt 541 tatccggatt tattgggttt aaagggtgcg taggtggttt attaagtcag cggtgaaagt 601 ttgtggctca accataaaat tgccgttgaa actggttaac ttgagtatat ttgaggtagg

```
 661 cggaatgcgt ggtgtagcgg tgaaatgcat agatatcacg cagaactcca attgcgaagg 721 cagcttacta aactataact gacactgaag cacgaaagcg tggggatcaa acaggattag 781 atacccggt agtccacgca gtaaacgatg attactagga gtttgcgata cacagtaagc 841 tctacagcga aagcgttaag taatccacct ggggagtacg ccggcaacgg tgaaactcaa 901 aggaattgac gggggcccgc acaagcgag gaacatgtgg tttaattcga tgatacgcga 961 ggaaccttac ccgggtttga acgcattgga cagtccttga aagaggatct ctagcaatag 1021 ccatttgcga ggtgctgcat ggttgtcgtc agctcgtgcc gtgaggtgtc ggcttaagtg 1081 ccataacgag cgcaacccttt atctttagtt actaacaggt ctgctgagga ctctaaagag 1141 actgccagcg taagctgtga ggaaggtggg gatgacgtca aatcagcacg gcccttacat 1201 ccggggcgac acacgtgtta caatggtggg gacaaagggc agctacacag cgatgtgatg 1261 ctaatctcca aacccatct cagttcggat cgaagtctgc aacccgactt cgtgaagctg 1321 gattcgctag taatcgcgca tcagccatgg cgcggtgaat acgttcccgg gccttgtaca 1381 caccgcccgt caagccatgg gagttggggg tacctaaagt ccgtaaccgc aaggatcggc 1441 ctaggtaaaa ccgatgactg gggctaagtc gtaaccaagg taacc
```

REFERENCES

[1] Spor et al. (2011) *Nat Rev Microbiol.* 9(4):279-90.
[2] Eckburg et al. (2005) *Science.* 10; 308(5728):1635-8.
[3] Macpherson et al. (2001) *Microbes Infect.* 3(12):1021-35
[4] Macpherson et al. (2002) *Cell Mol Life Sci.* 59(12):2088-96.
[5] Mazmanian et al. (2005) *Cell* 15; 122(1):107-18.
[6] Frank et al. (2007) *PNAS* 104(34):13780-5.
[7] Scanlan et al. (2006) *J Clin Microbiol.* 44(11):3980-8.
[8] Kang et al. (2010) *Inflamm Bowel Dis.* 16(12):2034-42.
[9] Machiels et al. (2013) *Gut.* 63(8):1275-83.
[10] WO 2013/050792
[11] WO 03/046580
[12] WO 2013/008039
[13] WO 2014/167338
[14] Goldin and Gorbach (2008) *Clin Infect Dis.* 46 Suppl 2:S96-100.
[15] Azad et al. (2013) *BMJ.* 347:f6471.
[16] WO 2016/203220
[17] Koh et al., *International Journal of Cancer*, volume 143, issue 7, pages 1797-1805
[18] WO 2016/149449
[19] Wu et al., Gut, doi: 10.1136/gutjnl-2017-315458
[20] WO 2018/112365
[21] WO 2018/112363
[22] WO2018/094190
[23] Sakamoto and Benno (2006) *Int J Syst Evol Microbiol.* 56 (Pt 7):1599-605.
[24] Masco et al. (2003) *Systematic and Applied Microbiology,* 26:557-563.
[25] Srůtková et al. (2011) *J. Microbiol. Methods,* 87(1):10-6.
[26] Liu et al., (2018) Acta Pharmaceutica Sinica B; 8, 4; 552-562
[27] Kubica & Brewer (2012), Mayo Clin Proc 87(1): 991-1003
[28] Viguer et al. (2004), J Immunol 173: 1444-1453
[29] McCarter et al. (2007). Ann Surg Oncol. 14(10): 2854-60
[30] Dankner et al., (2018) Oncogene 37:3183-3199
[31] Jones et al. (2017). J Clin Oncol. 2017 Aug. 10; 35(23): 2624-2630
[32] Ascierto et al. (2012) Journal of Translational Medicine. 10, 85
[33] https://www.uniprot.org/uniprot/P15056
[34] Soltani M H et al, (2005) *Am J Pathol;* 166:1841-50
[35] Xie (2016); *Med Res Rev;* 36, 2: 300-312
[36] https://www.medicines.org.uk/emc/product/3948/smpc
[37] https://www.medicines.org.uk/emc/product/6468/smpc
[38] https://www.medicines.org.uk/emc/product/6362/smpc
[39] Shi et al. (2014); Cancer Discov, 4, 80-93.
[40] Miyamoto-Shinohara et al. (2008) *J. Gen. Appl. Microbiol.,* 54, 9-24.
[41] Cryopreservation and Freeze-Drying Protocols, ed. by Day and McLellan, Humana Press.
[42] Leslie et al. (1995) *Appl. Environ. Microbiol.* 61, 3592-3597.
[43] Mitropoulou et al. (2013) *J Nutr Metab.* (2013) 716861.
[44] Kailasapathy et al. (2002) *Curr Issues Intest Microbiol.* 3(2):39-48.
[45] Handbook of Pharmaceutical Excipients, 2nd Edition, (1994), Edited by A Wade and PJ Weller
[46] Remington's Pharmaceutical Sciences, Mack Publishing Co. (A. R. Gennaro edit. 1985)
[47] *Handbook of Microbiological Media*, Fourth Edition (2010) Ronald Atlas, CRC Press.
[48] *Maintaining Cultures for Biotechnology and Industry* (1996) Jennie C. Hunter-Cevera, Academic Press
[49] Strobel (2009) *Methods Mol Biol.* 581:247-61.
[50] Gennaro (2000) *Remington: The Science and Practice of Pharmacy.* 20th edition, ISBN: 0683306472.
[51] *Molecular Biology Techniques: An Intensive Laboratory Course*, (Ream et al., eds., 1998, Academic Press).
[52] *Methods In Enzymology* (S. Colowick and N. Kaplan, eds., Academic Press, Inc.)
[53] *Handbook of Experimental Immunology*, Vols. I-IV (D. M. Weir and C. C. Blackwell, eds, 1986, Blackwell Scientific Publications)
[54] Sambrook et al. (2001) *Molecular Cloning: A Laboratory Manual,* 3rd edition (Cold Spring Harbor Laboratory Press).

[55] Handbook of Surface and Colloidal Chemistry (Birdi, K. S. ed., CRC Press, 1997)
[56] Ausubel et al. (eds) (2002) *Short protocols in molecular biology*, 5th edition (Current Protocols).
[57] *PCR (Introduction to Biotechniques Series)*, 2nd ed. (Newton & Graham eds., 1997, Springer Verlag)
[58] *Current Protocols in Molecular Biology* (F. M. Ausubel et al., eds., 1987) Supplement 30
[59] Smith & Waterman (1981) *Adv. Appl. Math.* 2: 482-489.
[60] Livak & Schmittgen (2001). *Methods.* 25, 4:402-8.
[61] Thangaraju et al. (2009). *Cancer Res.* 67, 9: 2826-2832
[62] Qin et al. (2011). *Oncol Res.* 19, 12: 573-582
[63] Bronte et al. (2013) *Immunity.* 2013 14; 39(5): 806-818
[64] Berraondo (2019) British Journal of Cancer 120:6-15
[65] Yan et al (2017) *Immunotherapy* 9(4), 347-360
[66] Ni & Lu (2018) *Cancer Med.* 7(9): 4509-4516
[67] Fabbi et al (2017) *Mediators of Inflammation; Article ID* 3958069, 1-14
[68] Abel et al (2018) *Front. Immunol.* 9:1869
[69] Morvan and Lanier (2016) *Nature Reviews Cancer* 16:7-19

The invention claimed is:

1. A method of treating cancer in a subject in need thereof, comprising administering to the subject a pharmaceutical composition comprising a therapeutically effective amount of a bacterial strain of the species *Parabacteroides distasonis*, wherein the bacterial strain comprises a 16s rRNA gene sequence having at least 98% sequence identity to the polynucleotide sequence of SEQ ID NO: 9, and wherein the cancer comprises oncogenic ERK signaling, and comprises an oncogenic mutation in, or overexpression of, BRAF, NRAS, ARAF, CRAF, EGFR, GRB2, SOS, HRAS, KRAS, MEK1, MEK2, ERK1 or ERK2.

2. The method of claim 1, wherein the cancer comprises an oncogenic mutation in BRAF.

3. The method of claim 2, wherein the oncogenic mutation is at amino acid position 600 in BRAF.

4. The method of claim 2, wherein the oncogenic mutation is selected from the group consisting of V600E, V600K, V600R, V600D, K601E, G469A, G469V, L597R, K601N, G464V, N581S, L597Q, A598V, G464R, G466A, G469E, and any combinations thereof.

5. The method of claim 1, wherein the cancer comprises V600E mutation in BRAF.

6. The method of claim 2, wherein the cancer further comprises overexpression of BRAF.

7. The method of claim 1, wherein the cancer comprises an oncogenic mutation in NRAS, wherein the oncogenic mutation is Q61R.

8. The method of claim 7, wherein the cancer further comprises overexpression of NRAS.

9. The method of claim 1, wherein the cancer comprises an oncogenic mutation in KRAS, wherein the oncogenic mutation is G13D.

10. The method of claim 1, wherein the cancer comprises colorectal cancer or melanoma.

11. The method of claim 1, wherein the pharmaceutical composition is formulated for delivery to a gastrointestinal tract of the subject.

12. The method of claim 1, wherein the therapeutically effective amount comprises from about $1\times10^3$ to about $1\times10^{11}$ colony forming units (CFU).

13. The method of claim 1, wherein the bacterial strain is the *Parabacteroides distasonis* strain deposited under accession number NCIMB 42382.

14. The method of claim 1, wherein the bacterial strain comprises a 16s rRNA gene sequence having at least 99% sequence identity to the polynucleotide sequence of SEQ ID NO: 9.

15. The method of claim 1, wherein the bacterial strain comprises a 16s rRNA gene sequence of the polynucleotide sequence of SEQ ID NO: 9.

16. The method of claim 1, wherein the subject is immunocompromised or immunosuppressed.

17. A method of treating cancer in a subject in need thereof, comprising administering to the subject a pharmaceutical composition comprising a therapeutically effective amount of a bacterial strain of the species *Parabacteroides distasonis*, wherein the bacterial strain comprises a 16s rRNA gene sequence having at least 98% sequence identity to the polynucleotide sequence of SEQ ID NO: 9, and wherein the cancer comprises oncogenic ERK signaling.

18. The method of claim 17, wherein the cancer is colorectal cancer or melanoma.

19. The method of claim 17, wherein the bacterial strain comprises a 16s rRNA gene sequence having at least 99% sequence identity to the polynucleotide sequence of SEQ ID NO: 9.

20. The method of claim 17, wherein the therapeutically effective amount comprises from about $1\times10^3$ to about $1\times10^{11}$ colony forming units (CFU).

* * * * *

SEQUENCE LISTING

<160> NUMBER OF SEQ ID NOS: 33

<210> SEQ ID NO 1
<211> LENGTH: 1488
<212> TYPE: DNA
<213> ORGANISM: Parabacteroides distasonis

<400> SEQUENCE: 1

```
agagtttgat cctggctcag gatgaacgct agcgacaggc ttaacacatg caagtcgagg      60
ggcagcgggg tgtagcaata caccgccggc gaccggcgca cgggtgagta acgcgtatgc     120
aacttgccta tcagaggggg ataacccggc gaaagtcgga ctaataccgc atgaagcagg     180
gatcccgcat gggaatattt gctaaagatt catcgctgat agataggcat gcgttccatt     240
aggcagttgg cggggtaacg gcccaccaaa ccgacgatgg ataggggttc tgagaggaag     300
gtcccccaca ttggtactga gacacggacc aaactcctac gggaggcagc agtgaggaat     360
attggtcaat gggcgtaagc ctgaaccagc caagtcgcgt gagggatgaa ggttctatgg     420
atcgtaaacc tcttttataa gggaataaag tgcgggacgt gtcccgtttt gtatgtacct     480
tatgaataag gatcggctaa ctccgtgcca gcagccgcgg taatacggag gatccgagcg     540
ttatccggat ttattgggtt taaagggtgc gtaggcggcc ttttaagtca gcggtgaaag     600
tctgtggctc aaccatagaa ttgccgttga aactgggggg cttgagtatg tttgaggcag     660
gcggaatgcg tggtgtagcg gtgaaatgca tagatatcac gcagaacccc gattgcgaag     720
gcagcctgcc aagccattac tgacgctgat gcacgaaagc gtggggatca aacaggatta     780
gataccctgg tagtccacgc agtaaacgat gatcactagc tgtttgcgat acactgtaag     840
cggcacagcg aaagcgttaa gtgatccacc tggggagtac gccggcaacg tgaaactca     900 aaggaattga cggggcccg cacaagcgga ggaacatgtg gtttaattcg atgatacgcg     960
aggaacctta cccgggtttg aacgcattcg gaccgaggtg gaaacacctt ttctagcaat    1020
agccgtttgc gaggtgctgc atggttgtcg tcagctcgtg ccgtgaggtg tcggcttaag    1080
tgccataacg agcgcaaccc ttgccactag ttactaacag gttaggctga ggactctggt    1140
gggactgcca gcgtaagctg cgaggaaggc ggggatgacg tcaaatcagc acggccctta    1200
catccggggc gacacacgtg ttacaatggc gtggacaaag ggaggccacc tggcgacagg    1260
gagcgaatcc ccaaaccacg tctcagttcg gatcggagtc tgcaacccga ctccgtgaag    1320
ctggattcgc tagtaatcgc gcatcagcca tggcgcggtg aatacgttcc cgggccttgt    1380
acacaccgcc cgtcaagcca tgggagccgg gggtacctga agtccgtaac cgaaaggatc    1440
ggcctagggt aaaactggtg actggggcta agtcgtaaca aggtaacc                 1488
```

<210> SEQ ID NO 2
<211> LENGTH: 1486
<212> TYPE: DNA
<213> ORGANISM: Parabacteroides distasonis -continued

```
<400> SEQUENCE: 2
agagtttgat cctggctcag gatgaacgct agcgacaggc ttaacacatg caagtcgagg      60
ggcagcacag gtagcaatac cgggtggcga ccggcgcacg ggtgagtaac gcgtatgcaa     120
cttacctatc agagggggat aacccggcga agtcggact aataccgcat gaagcagggg     180
ccccgcatgg ggatatttgc taaagattca tcgctgatag ataggcatgc gttccattag     240
gcagttggcg gggtaacggc ccaccaaacc gacgatggat aggggttctg agaggaaggt     300
cccccacatt ggtactgaga cacggaccaa actcctacgg gaggcagcag tgaggaatat     360
tggtcaatgg gcgtaagcct gaaccagcca gtcgcgtga gggatgaagg ttctatggat      420
cgtaaacctc ttttataagg gaataaagtg cgggacgtgt cctgttttgt atgtaccta     480 tgaataagga tcggctaact ccgtgccagc agccgcggta atacggagga tccgagcgtt     540
atccggattt attgggttta aagggtgcgt aggcggcctt ttaagtcagc ggtgaaagtc     600
tgtggctcaa ccatagaatt gccgttgaaa ctgggggct tgagtatgtt tgaggcaggc     660
ggaatgcgtg gtgtagcggt gaaatgctta gatatcacgc agaaccccga ttgcgaaggc     720
agcctgccaa gccatgactg acgctgatgc acgaaagcgt ggggatcaaa caggattaga     780 tacccctggta gtccacgcag taaacgatga tcactagctg tttgcgatac agtgtaagcg     840
gcacagcgaa agcgttaagt gatccacctg gggagtacgc cggcaacggt gaaactcaaa     900
ggaattgacg ggggcccgca caagcggagg aacatgtggt ttaattcgat gatacgcgag     960
gaaccttacc cggtttgaa cgcattcgga ccgaggtgga acaccttttt ctagcaatag    1020
ccgtttgcga ggtgctgcat ggttgtcgtc agctcgtgcc gtgaggtgtc ggcttaagtg    1080
ccataacgag cgcaacccct tgccactagtt actaacaggt aaagctgagg actctggtgg    1140
gactgccagc gtaagctgcg aggaaggcgg ggatgacgtc aaatcagcac ggcccttaca    1200
tccggggcga cacacgtgtt acaatggcgt ggacaaaggg aagccacctg gcgacaggga    1260
gcgaatcccc aaaccacgtc tcagttcgga tcggagtctg caacccgact ccgtgaagct    1320
ggattcgcta gtaatcgcgc atcagccatg gcgcggtgaa tacgttcccg ggccttgtac    1380
acaccgcccg tcaagccatg ggagccgggg gtacctgaag tccgtaaccg aaaggatcgg    1440
cctagggtaa aactggtgac tggggctaag tcgtaacaag gtaacc                  1486

<210> SEQ ID NO 3
<211> LENGTH: 1486
<212> TYPE: DNA
<213> ORGANISM: Parabacteroides distasonis

<400> SEQUENCE: 3
agagtttgat cctggctcag gatgaacgct agcgacaggc ttaacacatg caagtcgagg      60
ggcagcacag gtagcaatac cgccggcga ccggcgcacg ggtgagtaac gcgtatgcaa     120
cttgcctatc agagggggat aacccggcga agtcggact aataccgcat gaagcagggg     180
ccccgcatgg ggatatttgc taaagattca tcgctgatag ataggcatgc gttccattag     240
gcagttggcg gggtaacggc ccaccaaacc gacgatggat aggggttctg agaggaaggt     300
cccccacatt ggtactgaga cacggaccaa actcctacgg gaggcagcag tgaggaatat     360
tggtcaatgg gcgtaagcct gaaccagcca gtcgcgtga gggatgaagg ttctatggat      420
cgtaaacctc ttttataagg gaataaagtg tgggacgtgt cctgttttgt atgtaccta     480 tgaataagga tcggctaact ccgtgccagc agccgcggta atacggagga tccgagcgtt     540
```

```
atccggattt attgggttta aagggtgcgt aggcggcctt ttaagtcagc ggtgaaagtc      600
tgtggctcaa ccatagaatt gccgttgaaa ctgggaggct tgagtatgtt tgaggcaggc      660
ggaatgcgtg gtgtagcggt gaaatgctta gatatcacgc agaaccccga ttgcgaaggc      720
agcctgccaa gccatgactg acgctgatgc acgaaagcgt ggggatcaaa caggattaga      780
taccctggta gtccacgcag taaacgatga tcactagctg tttgcgatac actgtaagcg      840
gcacagcgaa agcgttaagt gatccacctg gggagtacgc cggcaacggt gaaactcaaa      900
ggaattgacg ggggcccgca caagcggagg aacatgtggt ttaattcgat gatacgcgag      960
gaaccttacc cggktttgaa cgcattcgga ccgaggtgga acacctttt ctagcaatag     1020 ccgtttgcga ggtgctgcat ggttgtcgtc agctcgtgcc gtgaggtgtc ggcttaagtg     1080
ccataacgag cgcaaccctt gccactagtt actaacaggt gatgctgagg actctggtgg     1140
gactgccagc gtaagctgcg aggaaggcgg ggatgacgtc aaatcagcac ggcccttaca     1200
tccggggcga cacacgtgtt acaatggcgt ggacaaaggg atgccacctg gcgacaggga     1260
gcgaatcccc aaaccacgtc tcagttcgga tcggagtctg caacccgact ccgtgaagct     1320
ggattcgcta gtaatcgcgc atcagccatg gcgcggtgaa tacgttcccg ggccttgtac     1380
acaccgcccg tcaagccatg ggagccgggg gtacctgaag tccgtaaccg aaaggatcgg     1440
cctagggtaa aactggtgac tggggctaag tcgtaacaag gtaacc                    1486
```

<210> SEQ ID NO 4
<211> LENGTH: 1486
<212> TYPE: DNA
<213> ORGANISM: Parabacteroides distasonis

<400> SEQUENCE: 4

```
agagtttgat cctggctcag gatgaacgct agcgacaggc ttaacacatg caagtcgagg       60
ggcagcacag gtagcaatac cgggtggcga ccggcgcacg ggtgagtaac gcgtatgcaa      120
cttacctatc agagggggat aacccggcga agtcggact aataccgcat gaagcagggg      180
ccccgcatgg ggatatttgc taaagattca tcgctgatag ataggcatgc gttccattag      240
gcagttggcg gggtaacggc ccaccaaacc gacgatggat aggggttctg agaggaaggt      300
cccccacatt ggtactgaga cacggaccaa actcctacgg gaggcagcag tgaggaatat      360
tggtcaatgg gcgtaagcct gaaccagcca agtcgcgtga gggatgaagg ttctatggat      420
cgtaaacctc ttttataagg gaataaagtg cgggacgtgt cccgttttgt atgtaccttta     480 tgaataagga tcggctaact ccgtgccagc agccgcggta atacgaggga tccgagcgtt     540
atccggattt attgggttta aagggtgcgt aggcggcctt ttaagtcagc ggtgaaagtc     600
tgtggctcaa ccatagaatt gccgttgaaa ctgggaggct tgagtatgtt tgaggcaggc     660
ggaatgcgtg gtgtagcggt gaaatgctta gatatcacgc agaaccccga ttgcgaaggc     720
agcctgccaa gccatgactg acgctgatgc acgaaagcgt ggggatcaaa caggattaga     780
taccctggta gtccacgcag taaacgatga tcactagctg tttgcgatac actgtaagcg     840
gcacagcgaa agcgttaagt gatccacctg gggagtacgc cggcaacggt gaaactcaaa     900
ggaattgacg ggggcccgca caagcggagg aacatgtggt ttaattcgat gatacgcgag     960
gaaccttacc cggktttgaa cgcattcgga ccgaggtgga acacctttt ctagcaatag    1020 ccgtttgcga ggtgctgcat ggttgtcgtc agctcgtgcc gtgaggtgtc ggcttaagtg    1080
ccataacgag cgcaaccctt gccactagtt actaacaggt aaagctgagg actctggtgg    1140
gactgccagc gtaagctgcg aggaaggcgg ggatgacgtc aaatcagcac ggcccttaca    1200
```

| | |
|---|---|
| tccggggcga cacacgtgtt acaatggcgt ggacaaaggg aggccacctg gcgacaggga | 1260 |
| gcgaatcccc aaaccacgtc tcagttcgga tcggagtctg caacccgact ccgtgaagct | 1320 |
| ggattcgcta gtaatcgcgc atcagccatg gcgcggtgaa tacgttcccg ggccttgtac | 1380 |
| acaccgcccg tcaagccatg ggagccgggg gtacctgaag tccgtaaccg aaaggatcgg | 1440 |
| cctagggtaa aactggtgac tggggctaag tcgtaacaag gtaacc | 1486 |

<210> SEQ ID NO 5
<211> LENGTH: 1486
<212> TYPE: DNA
<213> ORGANISM: Parabacteroides distasonis

<400> SEQUENCE: 5

| | |
|---|---|
| agagtttgat cctggctcag gatgaacgct agcgacaggc ttaacacatg caagtcgagg | 60 |
| ggcagcacag gtagcaatac cgggtggcga ccggcgcacg ggtgagtaac gcgtatgcaa | 120 |
| cttacctatc agaggggat aacccggcga agtcggact aataccgcat gaagcagggg | 180 |
| ccccgcatgg ggatatttgc taaagattca tcgctgatag ataggcatgc gttccattag | 240 |
| gcagttggcg gggtaacggc ccaccaaacc gacgatggat aggggttctg agaggaaggt | 300 |
| cccccacatt ggtactgaga cacggaccaa actcctacgg gaggcagcag tgaggaatat | 360 |
| tggtcaatgg gcgtaagcct gaaccagcca agtcgcgtga gggatgaagg ttctatggat | 420 |
| cgtaaacctc tttataagg gaataaagtg tgggacgtgt cccgttttgt atgtaccta | 480 |
| tgaataagga tcggctaact ccgtgccagc agccgcggta atacggagga tccgagcgtt | 540 |
| atccggattt attgggttta aagggtgcgt aggcggcctt ttaagtcagc ggtgaaagtc | 600 |
| tgtggctcaa ccatagaatt gccgttgaaa ctgggaggct tgagtatgtt tgaggcaggc | 660 |
| ggaatgcgtg gtgtagcggt gaaatgctta gatatcacgc agaaccccga ttgcgaaggc | 720 |
| agcctgccaa gccatgactg acgctgatgc acgaaagcgt ggggatcaaa caggattaga | 780 |
| taccctggta gtccacgcag taaacgatga tcactagctg tttgcgatac attgtaagcg | 840 |
| gcacagcgaa agcgttaagt gatccacctg gggagtacgc cggcaacggt gaaactcaaa | 900 |
| ggaattgacg ggggcccgca caagcggagg aacatgtggt ttaattcgat gatacgcgag | 960 |
| gaaccttacc cgggtttgaa cgcattcgga ccgaggtgga aacacctttt ctagcaatag | 1020 |
| ccgtttgcga ggtgctgcat ggttgtcgtc agctcgtgcc gtgaggtgtc ggcttaagtg | 1080 |
| ccataacgag cgcaaccctt gccactagtt actaacaggt aaagctgagg actctggtgg | 1140 |
| gactgccagc gtaagctgcg aggaaggcgg ggatgacgtc aaatcagcac ggcccttaca | 1200 |
| tccggggcga cacacgtgtt acaatggcgt ggacaaaggg aggccacctg gcgacaggga | 1260 |
| gcgaatcccc aaaccacgtc tcagttcgga tcggagtctg caacccgact ccgtgaagct | 1320 |
| ggattcgcta gtaatcgcgc atcagccatg gcgcggtgaa tacgttcccg ggccttgtac | 1380 |
| acaccgcccg tcaagccatg ggagccgggg gtacctgaag tccgtaaccg aaaggatcgg | 1440 |
| cctagggtaa aactggtgac tggggctaag tcgtaacaag gtaacc | 1486 |

<210> SEQ ID NO 6
<211> LENGTH: 1486
<212> TYPE: DNA
<213> ORGANISM: Parabacteroides distasonis

<400> SEQUENCE: 6

| | |
|---|---|
| agagtttgat cctggctcag gatgaacgct agcgacaggc ttaacacatg caagtcgagg | 60 |

| | |
|---|---|
| ggcagcacag gtagcaatac cgggtggcga ccggcgcacg ggtgagtaac gcgtatgcaa | 120 |
| cttacctatc agaggggat aacccggcga aagtcggact aataccgcat gaagcagggg | 180 |
| ccccgcatgg ggatatttgc taaagattca tcgctgatag ataggcatgc gttccattag | 240 |
| gcagttggcg gggtaacggc ccaccaaacc gacgatggat aggggttctg agaggaaggt | 300 |
| cccccacatt ggtactgaga cacggaccaa actcctacgg gaggcagcag tgaggaatat | 360 |
| tggtcaatgg gcgtaagcct gaaccagcca agtcgcgtga gggatgaagg ttctatggat | 420 |
| cgtaaacctc ttttataagg gaataaagtg tgggacgtgt cccgttttgt atgtacctta | 480 |
| tgaataagga tcggctaact ccgtgccagc agccgcggta atacggagga tccgagcgtt | 540 |
| atccggattt attgggttta aagggtgcgt aggcggcctt ttaagtcagc ggtgaaagtc | 600 |
| tgtggctcaa ccatagaatt gccgttgaaa ctgggaggct tgagtatgtt tgaggcaggc | 660 |
| ggaatgcgtg gtgtagcggt gaaatgctta gatatcacgc agaaccccga ttgcgaaggc | 720 |
| agcctgccaa gccatgactg acgctgatgc acgaaagcgt ggggatcaaa caggattaga | 780 |
| taccctggta gtccacgcag taaacgatga tcactagctg tttgcgatac attgtaagcg | 840 |
| gcacagcgaa agcgttaagt gatccacctg gggagtacgc cggcaacggt gaaactcaaa | 900 |
| ggaattgacg ggggcccgca caagcggagg aacatgtggt ttaattcgat gatacgcgag | 960 |
| gaaccttacc cgggtttgaa cgcattcgga ccgaggtgga acacctttt ctagcaatag | 1020 |
| ccgtttgcga ggtgctgcat ggttgtcgtc agctcgtgcc gtgaggtgtc ggcttaagtg | 1080 |
| ccataacgag cgcaacccct tgccactagtt actaacaggt aaagctgagg actctggtgg | 1140 |
| gactgccagc gtaagctgcg aggaaggcgg ggatgacgtc aaatcagcac ggcccttaca | 1200 |
| tccggggcga cacacgtgtt acaatggcgt ggacaaaggg aggccacctg cgacaggga | 1260 |
| gcgaatcccc aaaccacgtc tcagttcgga tcggagtctg caacccgact ccgtgaagct | 1320 |
| ggattcgcta gtaatcgcgc atcagccatg gcgcggtgaa tacgttcccg ggccttgtac | 1380 |
| acaccgcccg tcaagccatg ggagccgggg gtacctgaag tccgtaaccg aaaggatcgg | 1440 |
| cctagggtaa aactggtgac tggggctaag tcgtaacaag gtaacc | 1486 |

<210> SEQ ID NO 7
<211> LENGTH: 1492
<212> TYPE: DNA
<213> ORGANISM: Parabacteroides merdae

<400> SEQUENCE: 7

| | |
|---|---|
| agagtttgat cctggctcag gatgaacgct agcgacaggc ttaacacatg caagtcgagg | 60 |
| ggcagcatga tttgtagcaa tacagattga tggcgaccgg cgcacgggtg agtaacgcgt | 120 |
| atgcaactta cctatcagag ggggatagcc cggcgaaagt cggattaata ccccataaaa | 180 |
| cagggtccc gcatgggaat atttgttaaa gattcatcgc tgatagatag gcatgcgttc | 240 |
| cattaggcag ttggcggggt aacggccac caaccgacg atggataggg gttctgagag | 300 |
| gaaggtcccc cacattggta ctgagacacg gaccaaactc ctacgggagg cagcagtgag | 360 |
| gaatattggt caatggccga gaggctgaac cagccaagtc gcgtgaagga agaaggatct | 420 |
| atggtttgta aacttctttt ataggggaat aaagtggagg acgtgtcctt ttttgtatgt | 480 |
| accctatgaa taagcatcgg ctaactccgt gccagcagcc gcggtaatac ggaggatgcg | 540 |
| agcgttatcc ggatttattg ggtttaaagg gtgcgtaggt ggtgatttaa gtcagcggtg | 600 |
| aaagtttgtg gctcaaccat aaaattgccg ttgaaactgg gttacttgag tgtgtttgag | 660 |
| gtaggcggaa tgcgtggtgt agcggtgaaa tgcatagata tcacgcagaa ctccgattgc | 720 |

| | |
|---|---|
| gaaggcagct tactaaacca taactgacac tgaagcacga aagcgtgggg atcaaacagg | 780 |
| attagatacc ctggtagtcc acgcagtaaa cgatgattac taggagtttg cgatacaatg | 840 |
| taagctctac agcgaaagcg ttaagtaatc cacctgggga gtacgccggc aacggtgaaa | 900 |
| ctcaaaggaa ttgacggggg cccgcacaag cggaggaaca tgtggtttaa ttcgatgata | 960 |
| cgcgaggaac cttacccggg tttgaacgta gtctgaccgg agtggaaaca ctccttctag | 1020 |
| caatagcaga ttacgaggtg ctgcatggtt gtcgtcagct cgtgccgtga ggtgtcggct | 1080 |
| taagtgccat aacgagcgca acccttatca ctagttacta acaggtgaag ctgaggactc | 1140 |
| tggtgagact gccagcgtaa gctgtgagga aggtggggat gacgtcaaat cagcacggcc | 1200 |
| cttacatccg gggcgacaca cgtgttacaa tggcatggac aaagggcagc tacctggcga | 1260 |
| caggatgcta atctccaaac catgtctcag ttcggatcgg agtctgcaac tcgactccgt | 1320 |
| gaagctggat tcgctagtaa tcgcgcatca gccatggcgc ggtgaatacg ttcccgggcc | 1380 |
| ttgtacacac cgcccgtcaa gccatgggag ccggggggtac ctgaagtccg taaccgcaag | 1440 |
| gatcggccta gggtaaaact ggtgactggg gctaagtcgt aacaaggtaa cc | 1492 |

<210> SEQ ID NO 8
<211> LENGTH: 1492
<212> TYPE: DNA
<213> ORGANISM: Parabacteroides merdae

<400> SEQUENCE: 8

| | |
|---|---|
| agagtttgat cctggctcag gatgaacgct agcgacaggc ttaacacatg caagtcgagg | 60 |
| ggcagcatga tttgtagcaa tacagattga tggcgaccgg cgcacgggtg agtaacgcgt | 120 |
| atgcaactta cctatcagag ggggatagcc cggcgaaagt cggattaata cccataaaa | 180 |
| caggggttcc gcatgggaat atttgttaaa gattcatcgc tgatagatag gcatgcgttc | 240 |
| cattaggcag ttggcggggt aacggcccac caaaccgacg atggataggg ttctgagag | 300 |
| gaaggtcccc cacattggta ctgagacacg gaccaaactc ctacgggagg cagcagtgag | 360 |
| gaatattggt caatggccga gaggctgaac cagccaagtc gcgtgaagga agaaggatct | 420 |
| atggtttgta aacttctttt ataggggaat aaagtggagg acgtgtcctt ttttgtatgt | 480 |
| accctatgaa taagcatcgg ctaactccgt gccagcagcc gcggtaatac ggaggatgcg | 540 |
| agcgttatcc ggatttattg ggtttaaagg gtgcgtaggt ggtgatttaa gtcagcggtg | 600 |
| aaagtttgtg gctcaaccat aaaattgccg ttgaaactgg gttacttgag tgtgtttgag | 660 |
| gtaggcggaa tgcgtggtgt agcggtgaaa tgcatagata tcacgcagaa ctccgattgc | 720 |
| gaaggcagct tactaaacca taactgacac tgaagcacga aagcgtgggg atcaaacagg | 780 |
| attagatacc ctggtagtcc acgcagtaaa cgatgattac taggagtttg cgatacaatg | 840 |
| taagctctac agcgaaagcg ttaagtaatc cacctgggga gtacgccggc aacggtgaaa | 900 |
| ctcaaaggaa ttgacggggg cccgcacaag cggaggaaca tgtggtttaa ttcgatgata | 960 |
| cgcgaggaac cttacccggg tttgaacgta gtctgaccgg agtggaaaca ctccttctag | 1020 |
| caatagcaga ttacgaggtg ctgcatggtt gtcgtcagct cgtgccgtga ggtgtcggct | 1080 |
| taagtgccat aacgagcgca acccttatca ctagttacta acaggtgaag ctgaggactc | 1140 |
| tggtgagact gccagcgtaa gctgtgagga aggtggggat gacgtcaaat cagcacggcc | 1200 |
| cttacatccg gggcgacaca cgtgttacaa tggcatggac aaagggcagc tacctggcga | 1260 |
| caggatgcta atctccaaac catgtctcag ttcggatcgg agtctgcaac tcgactccgt | 1320 |

```
gaagctggat tcgctagtaa tcgcgcatca gccatggcgc ggtgaatacg ttcccgggcc     1380
ttgtacacac cgcccgtcaa gccatgggag ccggggtac  ctgaagtccg taaccgcaag     1440
gatcggccta gggtaaaact ggtgactggg gctaagtcgt aacaaggtaa cc            1492

<210> SEQ ID NO 9
<211> LENGTH: 1403
<212> TYPE: DNA
<213> ORGANISM: Parabacteroides distasonis

<400> SEQUENCE: 9
amccgggtgg cgaccggcgc acgggtgagt aacgcgtatg caacttgcct atcagagggg      60
gataacccgg cgaaagtcgg actaataccg catgaagcag ggatcccgca tgggaatatt    120
tgctaaagat tcatcgctga tagataggca tgcgttccat taggcagttg gcggggtaac    180
ggcccaccaa accgacgatg gatagggggtt ctgagaggaa ggtcccccac attggtactg    240
agacacggac caaactccta cgggaggcag cagtgaggaa tattggtcaa tgggcgtgag    300
cctgaaccag ccaagtcgcg tgagggatga aggtttctatg gatcgtaaac ctcttttata    360
agggaataaa gtgcgggacg tgtcccgttt tgtatgtacc ttatgaataa ggatcggcta    420
actccgtgcc agcagccgcg gtaatacgga ggatccgagc gttatccgga tttattgggt    480
ttaaagggtg cgtaggcggc cttttaagtc agcggtgaaa gtctgtggct caaccataga    540
attgccgttg aaactgggag gcttgagtat gtttgaggca ggcggaatgc gtggtgtagc    600
ggtgaaatgc atagatatca cgcagaaccc cgattgcgaa ggcagcctgc caagccatta    660
ctgacgctga tgcacgaaag cgtggggatc aaacaggatt agataccctg gtagtccacg    720
cagtaaacga tgatcactag ctgtttgcga tacactgtaa gcggcacagc gaaagcgtta    780
agtgatccac ctggggagta cgccggcaac ggtgaaactc aaaggaattg acgggggccc    840
gcacaagcgg aggaacatgt ggtttaattc gatgatacgc gaggaaccct acccgggttt    900
gaacgcattc ggacmgakgt ggaaacacat tttctagcaa tagccatttg cgaggtgctg    960
catggttgtc gtcagctcgt gccgtgaggt gtcggcttaa gtgccataac gagcgcaacc    1020
cttgccacta gttactaaca ggtaaagctg aggactctgg tgggactgcc agcgtaagct    1080
gcgaggaagg cggggatgac gtcaaatcag cacggcccttt acatccgggg cgacacacgt    1140
gttacaatgg cgtggacaaa gggaagccac ctggcgacag ggagcgaatc cccaaaccac    1200
gtctcagttc ggatcggagt ctgcaacccg actccgtgaa gctggattcg ctagtaatcg    1260
cgcatcagcc atggcgcggt gaatacgttc ccgggccttg tacacaccgc ccgtcaagcc    1320
atgggagccg ggggtacctg aagtccgtaa ccgcgaggat cggcctaggg taaaactggt    1380
gactggggct aagtcgtacg ggg                                            1403

<210> SEQ ID NO 10
<211> LENGTH: 1396
<212> TYPE: DNA
<213> ORGANISM: Parabacteroides goldsteinii

<400> SEQUENCE: 10
gtcgaggggc agcacggatg tagcaataca ttggtggcga ccggcgcacg ggtgagtaac      60
gcgtatgcaa cctgcctatc agaggggaat aacccggcga aagtcggact aataccgcat    120
aaaacagggg ttccacatgg aaatatttgt taaagaatta tcgctgatag atgggcatgc    180
gttccattag atagttggtg aggtaacggc tcaccaagtc cacgatggat aggggttctg    240
agaggaaggt cccccacact ggtactgaga cacggaccag actcctacgg gaggcagcag    300
```

```
tgaggaatat tggtcaatgg gcgagagcct gaaccagcca agtcgcgtga aggatgaagg    360
atctatggtt tgtaaacttc ttttatatgg gaataaagtg aggaacgtgt tccttttgt     420 atgtaccata tgaataagca tcggctaact ccgtgccagc agccgcggta atacggagga    480
tgcgagcgtt atccggattt attgggttta aagggtgcgt aggtggttaa ttaagtcagc    540
ggtgaaagtt tgtggctcaa ccataaaatt gccgttgaaa ctggttgact tgagtatatt    600
tgaggtaggc ggaatgcgtg gtgtagcggt gaaatgcata gatatcacgc agaactccga    660
ttgcgaaggc agcttactaa actataactg acactgaagc acgaaagcgt ggggatcaaa    720
caggattaga tacctggta gtccacgcag taaacgatga ttactagctg tttgcgatac      780
acagtaagcg gcacagcgaa agcgttaagt aatccacctg gggagtacgc cggcaacggt    840
gaaactcaaa ggaattgacg ggggcccgca caagcggagg aacatgtggt ttaattcgat    900
gatacgcgag gaaccttacc cgggtttgaa cgcattatga cagctctgga aacacattct    960
ctagtaatag caatttgcga ggtgctgcat ggttgtcgtc agctcgtgcc gtgaggtgtc   1020
ggcttaagtg ccataacgag cgcaaccctt atcactagtt actaacaggt caagctgagg   1080
actctagtga gactgccagc gtaagctgtg aggaaggtgg ggatgacgtc aaatcagcac   1140
ggcccttaca tccggggcga cacacgtgtt acaatggtgg ggacaaaggg cagctacctg   1200
gcgacaggat gctaatctcc aaacccatc tcagttcgga tcgaagtctg caacccgact    1260
tcgtgaagct ggattcgcta gtaatcgcgc atcagccatg gcgcggtgaa tacgttcccg   1320
ggccttgtac acaccgcccg tcaagccatg ggagttgggg gtacctaaag tccgtaaccg   1380
caaggatcgg cctagg                                                    1396

<210> SEQ ID NO 11
<211> LENGTH: 21
<212> TYPE: DNA
<213> ORGANISM: Artificial sequence
<220> FEATURE:
<223> OTHER INFORMATION: Description of Artificial Sequence: Synthetic
      primer

<400> SEQUENCE: 11
ggtatcgtgg aaggactcat g                                              21

<210> SEQ ID NO 12
<211> LENGTH: 21
<212> TYPE: DNA
<213> ORGANISM: Artificial sequence
<220> FEATURE:
<223> OTHER INFORMATION: Description of Artificial Sequence: Synthetic
      primer

<400> SEQUENCE: 12
atgccagtga gcttcccgtt c                                              21

<210> SEQ ID NO 13
<211> LENGTH: 20
<212> TYPE: DNA
<213> ORGANISM: Artificial sequence
<220> FEATURE:
<223> OTHER INFORMATION: Description of Artificial Sequence: Synthetic
      primer

<400> SEQUENCE: 13
ctcagcaccg ctaacagagg                                                20
```

```
<210> SEQ ID NO 14
<211> LENGTH: 19
<212> TYPE: DNA
<213> ORGANISM: Artificial sequence
<220> FEATURE:
<223> OTHER INFORMATION: Description of Artificial Sequence: Synthetic
      primer

<400> SEQUENCE: 14
cattggcgct tctctcctc                                                    19

<210> SEQ ID NO 15
<211> LENGTH: 21
<212> TYPE: DNA
<213> ORGANISM: Artificial sequence
<220> FEATURE:
<223> OTHER INFORMATION: Description of Artificial Sequence: Synthetic
      primer

<400> SEQUENCE: 15
atgttggcta tgaaccgcca g                                                 21

<210> SEQ ID NO 16
<211> LENGTH: 19
<212> TYPE: DNA
<213> ORGANISM: Artificial sequence
<220> FEATURE:
<223> OTHER INFORMATION: Description of Artificial Sequence: Synthetic
      primer

<400> SEQUENCE: 16
gctgctgtcc gattggaga                                                    19

<210> SEQ ID NO 17
<211> LENGTH: 2002
<212> TYPE: DNA
<213> ORGANISM: Parabacteroides goldsteinii
<220> FEATURE:
<223> OTHER INFORMATION: Parabacteroides goldsteinii strain DSMZ 19448
      or JCM13446

<400> SEQUENCE: 17
gtttgatcct ggctcaggat gaacgctagc gacaggctta acacatgcaa gtcgaggggc        60
agcacgatgt agcaatacat tggtggcgac cggcgcacgg gtgagtaacg cgtatgcaac       120
ctacctatca gagggaata acccggcgaa agtcggacta ataccgcata aaacaggggt        180
tccacatgga aatatttgtt aaagaattat cgctgataga tgggcatgcg ttccattaga       240
tagttggtga ggtaacggct caccaagtcc acgatggata ggggttctga gaggaaggtc       300
ccccacactg gtactgagac acggaccaga ctcctacggg aggcagcagt gaggaatatt       360
ggtcaatggg cgagagcctg aaccagccaa gtcgcgtgaa ggatgaagga tctatggttt      420
gtaaacttct tttatatggg aataaagtga ggaacgtgtt ccttttgta tgtaccatat        480 gaataagcat cggctaactc cgtgccagca gccgcggtaa tacggaggat gcgagcgtta       540
tccggattta ttgggtttaa agggtgcgta ggtggttaat taagtcagcg gtgaaagttt      600
gtggctcaac cataaaattg ccgttgaaac tggttgactt gagtatattt gaggtaggcg       660
gaatgcgtgg tgtagcggtg aaatgcatag atatcacgca gaactccgat tgcgaaggca     720
gcttactaaa ctataactga cactgaagca cgaaagcgtg gggatcaaac aggattagat     780
accctggtag tccacgcagt aaacgatgat tactagctgt ttgcgataca cagtaagcgg     840
cacagcgaaa gcgttaagta atccacctgg ggagacgccg gcaacggtga aactcaaagg     900
```

```
aattgacggg ggcccgcaca agcggaggaa catgtggttt aattcgatga tacgcgagga    960
accttacccg ggtttgaacg catattgaca gctctggaaa cagagtctct agtaatagca   1020
atttgcgagg tgctgcatgg ttgtcgtcag ctcgtgccgt gaggtgtcgg cttaagtgcc   1080
ataacgagcg caaccttat cactagttac taacaggtca tgctgaggac tctagtgaga    1140
ctgccagcgt aagctgtgag gaaggtgggg atgacgtcaa atcagcacgg cccttacatc   1200
cggggcgaca cacgtgttac aatggtgggg acaaagggca gctaccgtgt gagcggatgc   1260
gaatctccaa accccatctc agttcggatc gaagtctgca acccgacttc gtgaagctgg   1320
attcgctagt aatcgcgcat cagccatggc gcggtgaata cgttcccggg ccttgtacac   1380
accacccgtc aagccatggg agttggggt acctaaagtc cgtaaccgca aggatcggcc   1440
tagggtaaaa ccgatgactg gggctaagtc gtaacaaggt agccgtaccg gaaggtgcgg   1500
ctggaacacc tcctttctgg agcgcagagt tcgttatcaa gttgactcag aggtattagt   1560
taacttgtac tacggttgaa tatgtataaa atatagatct accggcaata agtgtcggc    1620
aagagagaaa aatgatgctg agggaaacca aggcaaagtt gacagtccta tagctcagtt   1680
ggttagagcg ctacactgat aatgtagagg tcggcagttc aactctgcct gggactacag   1740
aatctctaag agagaatttt gggggattag ctcagctggc tagagcatct gccttgcacg   1800
cagagggtca acggttcgaa tccgttattc tccacaaaaa gttaccgaga catcagaaac   1860
gtaaagtaac gacaagatct ttgacatgat ggacaacgta aaataaagta acaagagcaa   1920
gctgaagata tatcaatccg atttaccect gtggtaaccg gaaataagaa agtaagcaag   1980
ggcagacggt ggatgccttg gc                                             2002

<210> SEQ ID NO 18
<211> LENGTH: 1428
<212> TYPE: DNA
<213> ORGANISM: Parabacteroides goldsteinii
<220> FEATURE:
<223> OTHER INFORMATION: Parabacteroides goldsteinii strain DSMZ29187 or
      BS-C3-2

<400> SEQUENCE: 18
ctggctcagg atgaacgcta gcgacaggct taacacatgc aagtcgaggg gcagcacgat     60
gtagcaatac attggtggcg accggcgcac gggtgagtaa cgcgtatgca acctacctat    120
cagagggaa taacccggcg aaagtcggac taataccgca taaaacaggg gttccacatg     180
gaaatatttg ttaaagaatt atcgctgata gatgggcatg cgttccatta gatagttggt    240
gaggtaacgg ctcaccaagt ccacgatgga tagggttct gagaggaagg tcccccacac     300
tggtactgag acacggacca gactcctacg ggaggcagca gtgaggaata ttggtcaatg    360
ggcgagagcc tgaaccagcc aagtcgcgtg aaggatgaag gatctatggt ttgtaaactt    420
cttttatatg ggaataaagt gaggaaacgt gttccttttt gtatgtacca tatgaataag    480
catcggctaa cttccgtgcc agcagccgcg gtaatacgga ggatgcgagc gttatccgga    540
tttattgggt ttaaagggtg cgtaggtggt taattaagtc agcggtgaaa gtttgtggct    600
caaccataaa attgccgttg aaactggttg acttgagtat atttgaggta ggcggaatgc    660
gtggtgtagc ggtgaaatgc atagatatca cgcagaactc cgattgcgaa ggcagcttac    720
taaactataa ctgacactga agcacgaaag cgtgggatc aaacaggatt agatacctg     780
gtagtccacg cagtaaacga tgattactag ctgtttgcga tacacagtaa gcggcacagc    840
gaaagcgtta agtaatccac ctggggagta cgccggcaac ggtgaaactc aaaggaattg    900
```

| | |
|---|---|
| acgggggccc gcacaagcgg aggaacatgt ggtttaattc gatgatacgc gaggaacctt | 960 |
| acccgggttt gaacgcattc ggaccggagt ggaaacactt cttctagtaa tagccgtttg | 1020 |
| cgaggtgctg catggttgtc gtcagctcgt gccgtgaggt gtcggcttaa gtgccataac | 1080 |
| gagcgcaacc cttatcacta gttactaaca ggtcaagctg aggactctag tgagactgcc | 1140 |
| agcgtaagct gtgaggaagg tggggatgac gtcaaatcag cacggcccTT acatccgggg | 1200 |
| cgacacacgt gttacaatgg tggggacaaa gggcagctac ctggcgacag gatgctaatc | 1260 |
| tccaaacctc atctcagttc ggatcgaagt ctgcaacccg acttcgtgaa gctggattcg | 1320 |
| ctagtaatcg cgcatcagcc atggcgcggt gaatacgttc ccgggccttg tacacaccgc | 1380 |
| ccgtcaagcc atgggagttg ggggtaccta aagtccgtaa ccgcaagg | 1428 |

```
<210> SEQ ID NO 19
<211> LENGTH: 1397
<212> TYPE: DNA
<213> ORGANISM: Parabacteroides distasonis

<400> SEQUENCE: 19
```

| | |
|---|---|
| aaggccgatc cttgtcggtt acggacttca ggtaccccg gctcccatgg cttgacgggc | 60 |
| ggtgtgtaca aggcccggga acgtattcac cgcgccatgg ctgatgcgcg attactagcg | 120 |
| aatccagctt cacggagtcg ggttgcagac tccgatccga actgagacgt ggtttgggga | 180 |
| ttcgctccct gtcaccaggt ggcctccctt tgtccacgcc attgtaacac gtgtgtcgcc | 240 |
| ccggatgtaa gggccgtgct gatttgacgt catccccgcc ttcctcgcag cttacgctgg | 300 |
| cagtcccacc agagtcctca gctttacctg ttagtaacta gtggcaaggg ttgcgctcgt | 360 |
| tatggcactt aagccgacac ctcacggcac gagctgacga caaccatgca gcacctcgca | 420 |
| aacggctatt gctagaaaag gtgttccac ctcggtccga atgcgttcaa acccgggtaa | 480 |
| ggttcctcgc gtatcatcga attaaaccac atgttcctcc gcttgtgcgg gccccgtca | 540 |
| attcctttga gtttcaccgt tgccggcgta ctccccaggt ggatcactta acgctttcgc | 600 |
| tgtgccgctt acagtgtatc gcaaacagct agtgatcatc gtttactgcg tggactacca | 660 |
| gggtatctaa tcctgtttga tccccacgct ttcgtgcatc agcgtcagtc atggcttggc | 720 |
| aggctgcctt cgcaatcggg gttctgcgtg atatctatgc atttcaccgc tacaccacgc | 780 |
| attccgcctg cctcaaacat actcaagccc ccagtttca acggcaattc tatggttgag | 840 |
| ccacagactt tcaccgctga cttaaaaggc cgcctacgca cccttttaaac ccaataaatc | 900 |
| cggataacgc tcggatcctc cgtattaccg cggctgctgg cacggagtta gccgatcctt | 960 |
| attcataagg tacatacaaa acgggacacg tcccgcactt tattcccTTa taaaagaggt | 1020 |
| ttacgatcca tagaaccttc atccctcacg cgacttggct ggttcagcct ctcggccatt | 1080 |
| gaccaatatt cctcactgct gcctcccgta ggagtttggt ccgtgtctca gtaccaatgt | 1140 |
| ggggggacctt cctctcagaa cccctatcca tcgtcggttt ggtgggccgt taccccgcca | 1200 |
| actgccTaat ggaacgcatg cctatctatc agcgatgaat ctttagcaaa tatccccatg | 1260 |
| cggggcccct gcttcatgcg gtattagtcc gactttcgcc gggttatccc cctctgatag | 1320 |
| gtaagttgca tacgcgttac tcacccgtgc gccggtcgcc acccggtatt gctacctgtg | 1380 |
| ctgccgcctc gactgca | 1397 |

```
<210> SEQ ID NO 20
<211> LENGTH: 1403
<212> TYPE: DNA
<213> ORGANISM: Parabacteroides distasonis
```

<400> SEQUENCE: 20

```
aggccgatcc ttgtcggtta cggacttcag gtaccccgg ctcccatggc ttgacgggcg        60
gtgtgtacaa ggcccgggaa cgtattcacc gcgccatggc tgatgcgcga ttactagcga       120
atccagcttc acggagtcgg gttgcagact ccgatccgaa ctgagacgtg gtttggggat       180
tcgctccctg tcgccaggtg gcatcccttt gtccacgcca ttgtaacacg tgtgtcgccc       240
cggatgtaag ggccgtgctg atttgacgtc atccccgcct tcctcgcagc ttacgctggc       300
agtcccacca gagtcctcag ctttacctgt tagtaactag tggcaagggt tgcgctcgtt       360
atggcactta agccgacacc tcacggcacg agctgacgac aaccatgcag cacctcgcaa       420
atcgctattg ctagaggctg tgtttccaca gcggtccaaa tgcgttcaaa cccgggtaag       480
gttcctcgcg tatcatcgaa ttaaaccaca tgttcctccg cttgtgcggg ccccgtcaa       540
ttcctttgag tttcaccgtt gccggcgtac tccccaggtg gatcacttaa cgctttcgct       600
gtgccgctta ccgtgtatcg caaacagcta gtgatcatcg tttactgcgt ggactaccag       660
ggtatctaat cctgtttgat ccccacgctt tcgtgcatca gcgtcagtca tggcttggca       720
ggctgccttc gcaatcgggg ttstgcgtga tatctaagca tttcaccgct acaccacgca       780
ttccgcctgc ctcaaacata ctcaagcccc ccagtttcaa cggcaattct atggttgagc       840
cacagacttt caccgctgac ttaaaaggcc gcctacgcac cctttaaacc caataaatcc       900
ggataacgct cggatcctcc gtattaccgc ggctgctggc acggagttag ccgatcctta       960
ttcataaggt acatcaaaa cgggacacgt cccgcacttt attcccttat aaaagaggtt      1020
tacgatccat agaaccttca tccctcacgc gacttggctg gttcaggctt acgcccattg      1080
accaatattc ctcactgctg cctcccgtag gagtttggtc cgtgtctcag taccaatgtg      1140
ggggaccttc ctctcagaac ccctatccat cgtcggtttg gtgggccgtt accccgccaa      1200
ctgcctaatg gaacgcatgc ctatctatca gcgatgaatc tttagcaaat atccccatgc      1260
gggaccctg cttcatgcgg tattagtccg actttcgccg ggttatcccc ctctgatagg      1320
taagttgcat acgcgttact cacccgtgcg ccggtcgcca cccggtattg ctacctgtgc      1380
tgcccctcga cttgcatgtg taa                                              1403
```

<210> SEQ ID NO 21
<211> LENGTH: 1430
<212> TYPE: DNA
<213> ORGANISM: Parabacteroides sp.

<400> SEQUENCE: 21

```
gggcccaatt taactaggcc gatccttgcg gttacggact tcaggtaccc ccggctccca        60
tggcttgacg gcggtgtgt acaaggcccg ggaacgtatt caccgcgcca tggctgatgc       120
gcgattacta gcgaatccag cttcacggag tcgagttgca gactccgatc cgaactgaga       180
catggtttgg agatttgcat cacatcgctg tgtagctgcc ctttgtccat gccattgtaa       240
cacgtgtgtc gccccggatg taagggccgt gctgatttga cgtcatcccc accttcctca       300
cagcttacgc tggcagtctc accagagtcc tcagcttgac ctgttagtaa ctagtgataa       360
gggttgcgct cgttatggca cttaagccga cacctcacgg cacgagctga cgacaaccat       420
gcagcacytc gcaaacggtc attgctgaaa ggagcgtttc cactccggtc gaatgcgtt       480
caaacccggg taaggttcct cgcgtatcat cgaattaaac cacatgttcc tccgcttgtg       540
cgggcccccg tcaattcctt tgagtttcac cgttgccggc gtactcccca ggtggattac       600
```

| | |
|---|---|
| ttaacgcttt cgctgtagag cttactgtct atcgcaaact cctagtaatc atcgtttact | 660 |
| gcgtggacta ccagggtatc taatcctgtt tgatccccac gctttcgtgc ttcagtgtca | 720 |
| gttatagttt agtaagctgc cttcgcaatc ggagttctgc gtgatatcta tgcatttcac | 780 |
| cgctacacca cgcattccgc ctacctcaaa tatactcaag tcatccagtt tcaacggcaa | 840 |
| ttttatggtt gagccacaaa cttttcaccgc tgacttaaac aaccacctac gcacccttta | 900 |
| aacccaataa atccggataa cgctcgcatc ctccgtatta ccgcggctgc tggcacggag | 960 |
| ttagccgatg cttattcata cggtacatac aaaatgggac acgtcccaca ctttattccc | 1020 |
| skataaaaga agtttacaaa ccatagatcc ttcatccttc acgcgacttg gctggttcag | 1080 |
| cctcccggcc attgaccaat attcctcact gctgcctccc gtaggartttt ggaccgtgtc | 1140 |
| tcagttccaa tgtgggggac cttcctctca gaacccctat ccatcgtcgg tttggtgggc | 1200 |
| cgttaccccg ccaactgcct aatggaacgc atgcctatct atcagcgatg aatctttaac | 1260 |
| aaatattccc atgcgggacc cctgttttat ggagcattaa tccgactttc gccgggctat | 1320 |
| tccctctga taggcaagtt gcatacgcgt tactcacccg tgcgccggtc gccggcaggc | 1380 |
| attgctgccc ccgctgcccc tcgacttgca tggttagcct ccaattcccc | 1430 |

<210> SEQ ID NO 22
<211> LENGTH: 1402
<212> TYPE: DNA
<213> ORGANISM: Parabacteroides distasonis

<400> SEQUENCE: 22

| | |
|---|---|
| taggccgatc cttgcggtta cggacttcag gtaccccccgg ctcccatggc ttgacgggcg | 60 |
| gtgtgtacaa ggcccgggaa cgtattcacc gcgccatggc tgatgcgcga ttactagcga | 120 |
| atccagcttc acggagtcga gttgcagact ccgatccgaa ctgagacatg gtttggagat | 180 |
| ttgcatcaca tcgctgtgta gctgcccttt gtccatgcca ttgtaacacg tgtgtcgccc | 240 |
| cggatgtaag ggccgtgctg atttgacgtc atccccacct tcctcacagc ttacgctggc | 300 |
| agtctcacca gagtcctcag cttgacctgt tagtaactag tgataagggt tgcgctcgtt | 360 |
| atggcactta agccgacacc tcacggcacg agctgacgac aaccatgcag cacctcgcaa | 420 |
| acggtcattg ctgaaaggag cgtttccact ccggtccgaa tgcgttcaaa cccgggtaag | 480 |
| gttcctcgcg tatcatcgaa ttaaaccaca tgttcctccg cttgtgcggg ccccgtcaa | 540 |
| ttcctttgag tttcaccgtt gccggcgtac tccccaggtg gattacttaa cgctttcgct | 600 |
| gtagagctta ctgtctatcg camactccta gtaatcatcg tttactgcgt ggactaccag | 660 |
| ggtatctaat cctgtttgat ccccacgctt tcgtgcttca gtgtcagtta gtttagta | 720 |
| agctgccttc gcaatcggag ttctgcgtga tatctatgca tttcaccgct acaccacgca | 780 |
| ttccgcctac ctcaaatata ctcaagtcat ccagtttcaa cggcaatttt atggttgagc | 840 |
| cacaaacttt caccgctgac ttaaacaacc cctacgcac cctttaaacc caataaatcc | 900 |
| ggataacgct cgcatcctcc gtattaccgc ggctgctggc acggagttag ccgatgctta | 960 |
| ttcatacggt acatacaaaa tgggacacgt cccacacttt attcccgtat aaaagaagtt | 1020 |
| tacaaaccat agatccttca tccttcacgc gacttggctg gttcagcctc ccggccattg | 1080 |
| accaatattc ctcactgctg cctcccgtag gagtttggac cgtgtctcag ttccaatgtg | 1140 |
| ggggaccttc ctctcagaac ccctatccat cgtcggtttg gtgggccgtt acccgccaa | 1200 |
| ctgcctaatg gaacgcatgc ctatctatca gcgatgaatc tttaacaaat attcccatgc | 1260 |
| gggacccctg ttttatggag cattaatccg actttcgccg ggctattccc ctctgatagg | 1320 |

<210> SEQ ID NO 23
<211> LENGTH: 1405
<212> TYPE: DNA
<213> ORGANISM: Parabacteroides distasonis

<400> SEQUENCE: 23

| | | | | | |
|---|---|---|---|---|---|
| gtaggccgat | cctcgcggtt | acggacttca | ggtaccccg | gctcccatgg | cttgacgggc | 60 |
| ggtgtgtaca | aggcccggga | acgtattcac | cgcgccatgg | ctgatgcgcg | attactagcg | 120 |
| aatccagctt | cacggagtcg | ggttgcagac | tccgatccga | actgagacgt | ggtttgggga | 180 |
| ttcgctccct | gtcgccaggt | ggcttcccct | tgtccacgcc | attgtaacac | gtgtgtcgcc | 240 |
| ccggatgtaa | gggccgtgct | gatttgacgt | catccccgcc | ttcctcgcag | cttacgctgg | 300 |
| cagtcccacc | agagtcctca | gcytwacctg | ttagtaacta | gtggcaaggg | ttgcgctcgt | 360 |
| tatggcactt | aagccgacac | ctcacggcac | gagctgacga | caaccatgca | gcacctcgca | 420 |
| aacggctatt | gctagaaaag | gtgttttccac | ctcggtccga | atgcgttcaa | acccgggtaa | 480 |
| ggttcctcgc | gtatcatcga | attaaaccac | atgttcctcc | gcttgtgcgg | gccccccgtca | 540 |
| attcctttga | gtttcaccgt | tgccggcgta | ctccccaggt | ggatcactta | acgctttcgc | 600 |
| tgtgccgctt | acactgtatc | gcaaacagct | agtgatcatc | gtttactgcg | tggactacca | 660 |
| gggtatctaa | tcctgtttga | tccccacgct | ttcgtgcatc | agcgtcagtc | atggcttggc | 720 |
| aggctgcctt | cgcaatcggg | gttctgcgtg | atatctatgc | atttcaccgc | tacaccacgc | 780 |
| attccgcctg | cctcaaacat | actcaagccc | ccagtttca | acggcaattc | tatggttgag | 840 |
| ccacagactt | tcaccgctga | cttaaaaggc | cgcctacgca | ccctttaaac | ccaataaatc | 900 |
| cggataacgc | tcggatcctc | cgtattaccg | cggctgctgg | cacggagtta | gccgatcctt | 960 |
| attcataagg | tacatacaaa | acgggacacg | tcctacactt | tattcccctta | taaaagaggt | 1020 |
| ttacgatcca | tagaaccttc | atccctcacg | cgacttggct | ggttcaggct | tacgcccatt | 1080 |
| gaccaatatt | cctcactgct | gcctcccgta | ggagtttggt | ccgtgtctca | gtaccaatgt | 1140 |
| gggggacctt | cctctcagaa | cccctatcca | tcgtcggttt | ggtgggccgt | taccccgcca | 1200 |
| actgcctaat | ggaacgcatg | cmtatmtatc | agcgatgwat | cttkmgcaaa | tatccccrtg | 1260 |
| cggggcccgt | gcttcrtgcg | gtattagtcm | gactttcgcc | gggttatccc | cctctgatag | 1320 |
| gyaagttgca | tacgcgttac | tcacccgtgc | gccggtcgcc | rgccgcggta | tctgctaccc | 1380 |
| cgcgctgccc | ctcgacttgc | atggt | | | | 1405 |

<210> SEQ ID NO 24
<211> LENGTH: 1365
<212> TYPE: DNA
<213> ORGANISM: Parabacteroides distasonis

<400> SEQUENCE: 24

| | | | | | |
|---|---|---|---|---|---|
| gatcctcgcg | gttacggact | tcaggtaccc | ccggctccca | tggcttgacg | ggcggtgtgt | 60 |
| acaaggcccg | ggaacgtatt | caccgcgcca | tggctgatgc | gcgattacta | gcgaatccag | 120 |
| cttcacggag | tcgggttgca | gactccgatc | cgaactgaga | cgtggtttgg | ggattcgctc | 180 |
| cctgtcgcca | ggtggcctcc | ctttgtccac | gccattgtaa | cacgtgtgtc | gcccggatg | 240 |
| taagggccgt | gctgatttga | cgtcatcccc | gccttcctcg | cagcttacgc | tggcagtccc | 300 |

```
accagagtcc tcagcatcac ctgttagtaa ctagtggcaa gggttgcgct cgttatggca      360
cttaagccga cacctcacgg cacgagctga cgacaaccat gcagcacctc gcaaacggct      420
attgctagaa aaggtgtttc cacctcggtc cgaatgcgtt caaacccggg taaggttcct      480
cgcgtatcat cgaattaaac cacatgttcc tccgcttgtg cgggcccccg tcaattcctt      540
tgagtttcac cgttgccggc gtactcccca ggtggatcac ttaacgcttt cgctgtgccg      600
cttacagtgt atcgcaaaca gctagtgatc atcgtttact gcgtggacta ccagggtatc      660
taatcctgtt tgatccccac gctttcgtgc atcagcgtca gtcatggctt ggcaggctgc      720
cttcgcaatc ggggttctgc gtgatatcta tgcatttcac cgctacacca cgcattccgc      780
ctgcctcaaa catactcaag ccccccagtt tcaacggcaa ttctatggtt gagccacaga      840
ctttcaccgc tgacttaaaa ggccgcctac gcacccttta aacccaataa atccggataa      900
cgctcggatc ctccgtatta ccgcggctgc tggcacggag ttagccgatc cttattcata      960
aggtacatac aaaacgggac acgtcccgca ctttattccc ttataaaaga ggtttacgat     1020
ccatagaacc ttcatccctc acgcgacttg gctggttcag cctttcggcc attgaccaat     1080
attcctcact gctgcctccc gtaggagttt ggtccgtgtc tcagtaccaa tgtggggggac    1140
cttcctctca gaaccccctat ccatcgtcgg tttggtgggc cgttacccg ccaactgcct     1200
aatggaacgc atgcctatct atcagcgatg aatctttagc aaatatcccc atgcggggcc     1260
cctgcttcat gcgtattag tccgacttc gccgggttat cccctctga taggtaagtt        1320
gcatacgcgt tactcacccg tgcgccggtc gccacccggt attgc                     1365
```

<210> SEQ ID NO 25
<211> LENGTH: 1415
<212> TYPE: DNA
<213> ORGANISM: Parabacteroides merdae

<400> SEQUENCE: 25

```
ttaaataggc cgatccttgc ggttacggac ttcaggtacc cccggctccc atggcttgac       60
gggcggtgtg tacaaggccc gggaacgtat tcaccgcgcc atggctgatg cgcgattact      120
agcgaatcca gcttcacgga gtcgagttgc agactccgat ccgaactgag acatggtttg      180
gagattagca tcctgtcacc aggtagctgc cctttgtcca tgccattgta acacgtgtgt      240
cgccccggat gtaagggccg tgctgatttg acgtcatccc caccttcctc acagcttacg      300
ctggcagtct caccagagtc ctcagcttca cctgttagta actagtgata agggttgcgc      360
tcgttatggc acttaagccg cacctcacgg cacgagctg acgacaacca tgcagcacct      420
cgtaatctgc tattgctaga aagagtgttt ccactccggt cagactacgt tcaaacccgg      480
gtaaggttcc tcgcgtatca tcgaattaaa ccacatgttc ctccgcttgt gcgggccccc      540
gtcaattcct ttgagtttca ccgttgccgg cgtactcccc aggtggatta cttaacgctt      600
tcgctgtaga gcttacattg tatcgcaaac tcctagtaat catcgtttac tgcgtggact      660
accagggtat ctaatcctgt tgatcccca cgctttcgtg cttcagtgtc agttatggtt      720
tagtaagctg ccttcgcaat cggagttctg cgtgatatct atgcatttca ccgctacacc      780
acgcattccg cctacctcaa acacactcaa gtaacccagt ttcaacggca attttatggt      840
tgagccacaa actttcaccg ctgacttaaa tcaccaccta cgcaccctt aaacccaata      900
aatccggata acgctcgcat cctccgtatt accgcggctg ctggcacgga gttagccgat      960
gcttattcat agggtacata caaaaaagga cacgtcctcc actttattcc cctataaaag     1020
aagtttacaa accatagatc cttcttcctt cacgcgactt ggctggttca gcctctcggc     1080
```

| | |
|---|---|
| cattgaccaa tattcctcac tgctgcctcc cgtaggagtt tggtccgtgt ctcagtacca | 1140 |
| atgtggggga ccttcctctc agaacccta tccatcgtcg gtttggtggg ccgttacccc | 1200 |
| gccaactgcc taatggaacg catgccatc tatcagcgat gaatctttaa caaatattcc | 1260 |
| catgcgggac cctgttttta tggggtatta atccgacttt cgccgggcta tccccctctg | 1320 |
| ataggtaagt tgcatacgcg ttactcaccc gtgcgccggt cgccatcaat ctgtattgct | 1380 |
| acaaatcatg ctgcccctcg acttgcatgg ttaag | 1415 |

<210> SEQ ID NO 26
<211> LENGTH: 1375
<212> TYPE: DNA
<213> ORGANISM: Parabacteroides distasonis

<400> SEQUENCE: 26

| | |
|---|---|
| wtcggttacg gacttcaggt accccggct cccatggctt gacgggcggt gtgtacaagg | 60 |
| cccgggaacg tattcaccgc gccatggctg atgcgcgatt actagcgaat ccagcttcac | 120 |
| ggagtcgggt tgcagactcc gatccgaact gagacgtggt ttggggattc gctccctgtc | 180 |
| gccaggtggc ctccctttgt ccacgccatt gtaacgtg tgtcgccccg gatgtaaggg | 240 |
| ccgtgctgat ttgacgtcat ccccgccttc ctcgcagctt acgctggcag tccaccaga | 300 |
| gtcctcagct ttacctgtta gtaactagtg gcaagggttg cgctcgttat ggcacttaag | 360 |
| ccgacacctc acggcacgag ctgacgacaa ccatgcagca cctcgcaaac ggctattgct | 420 |
| agaaaaggtg tttccacctc ggtccgaatg cgttcaaacc cgggtaaggt tcctcgcgta | 480 |
| tcatcgaatt aaaccacatg ttcctccgct tgtgcgggcc ccgtcaatt cctttgagtt | 540 |
| tcaccgttgc cggcgtactc cccaggtgga tcacttaacg ctttcgctgt gccgcttaca | 600 |
| gtgtatcgca aacagctagt gatcatcgtt tactgcgtgg actaccaggg tatctaatcc | 660 |
| tgtttgatcc ccacgctttc gtgcatcagc gtcagtaatg gcttggcagg ctgccttcgc | 720 |
| aatcggggtt ctgcgtgata tctatgcatt tcaccgctac accacgcatt ccgcctgcct | 780 |
| caaacatact caagccccc agtttcaacg gcaattctat ggttgagcca cagactttca | 840 |
| ccgctgactt aaaaggccgc ctacgcaccc tttaaaccca ataaatccgg ataacgctcg | 900 |
| gatcctccgt attaccgcgg ctgctggcac ggagttagcc gatccttatt cataaggtac | 960 |
| atacaaaacg ggacacgtcc cgcactttat tcccttataa aagagttta cgatccatag | 1020 |
| aaccttcatc cctcacgcga cttggctggt tcagcctctc ggccattgac caatattcct | 1080 |
| cactgctgcc tcccgtwgga gtttggtccg tgtctcagta ccaatgtggg ggaccttcct | 1140 |
| ctcagaaccc ctatccatcg tcggtttggt gggccgttac cccgccaact gcctaatgga | 1200 |
| acgcatgcct atctatcagc gatgaatctt tagcaaatat yccatgcgg grycctgct | 1260 |
| tcatgcggta ttagtccgac tttcgccggg ttatcccct ctgataggca agttgcatac | 1320 |
| gcgttactca cccgtgcgcc ggtcgccacc cggtattgct acctgtgctg ccccw | 1375 |

<210> SEQ ID NO 27
<211> LENGTH: 1390
<212> TYPE: DNA
<213> ORGANISM: Parabacteroides distasonis

<400> SEQUENCE: 27

| | |
|---|---|
| gatctcgcgg tttacggact tcaggtaccc ccggctccca tggcttgacg ggcggtgtgt | 60 |
| acaaggcccg ggaacgtatt caccgcgcca tggctgatgc gcgattacta gcgaatccag | 120 |

```
cttcacggag tcgggttgca gactccgatc cgaactgaga cgtggtttgg ggattcgctc        180
cctgtcgcca ggtggcctcc ctttgtccac gccattgtaa cacgtgtgtc gccccggatg        240
taagggccgt gctgatttga cgtcatcccc gccttcctcg cagcttacgc tggcagtccc        300
accagagtcc tcagcatcac ctgttagtaa ctagtggcaa gggttgcgct cgttatggca        360
cttaagccga cacctcacgg cacgagctga cgacaaccat gcagcacctc gcaaacggct        420
attgctagaa aaggtgtttc cacctcggtc cgaatgcgtt caaacccggg taaggttcct        480
cgcgtatcat cgaattaaac cacatgttcc tccgcttgtg cgggccccg tcaattcctt         540 tgagtttcac cgttgccggc gtactcccca ggtggatcac ttaacgcttt cgctgtgccg        600
cttacagtgt atcgcaaaca gctagtgatc atcgtttact gcgtggacta ccagggtatc        660
taatcctgtt tgatccccac gctttcgtgc atcagcgtca gtcatggctt ggcaggctgc        720
cttcgcaatc ggggttctgc gtgatatcta tgcatttcac cgctacacca cgcattccgc        780
ctgcctcaaa catactcaag ccccccagtt caacggcaa ttctatggtt gagccacaga         840 cttttcaccgc tgacttaaaa ggccgcctac gcacccttta aacccaataa atccggataa       900
cgctcggatc ctccgtatta ccgcggctgc tggcacggag ttagccgatc cttattcata       960
aggtacatac aaaacgggac acgtcccgca ctttattccc ttataaaaga ggtttacgat      1020
ccatagaacc ttcatccctc acgcgacttg gctggttcag cctttcggcc attgaccaat      1080
attcctcact gctgcctccc gtaggagttt ggtccgtgtc tcagtaccaa tgtggggac       1140 cttcctctca gaacccctat ccatcgtcgg tttggtgggc cgttacccg ccaactgcct       1200 aatgaacgc atgcctatct atcagcgatg aatcttagc aaatatcccc atgcggggcc       1260
cctgcttcat gcggtattag tccgactttc gccgggttat ccccctctga taggtaagtt      1320
gcatacgcgt tactcacccg tgcgccggtc gccaccggt attgctacct ggtgctgccc       1380
cctcgactgc                                                              1390
```

<210> SEQ ID NO 28
<211> LENGTH: 1421
<212> TYPE: DNA
<213> ORGANISM: Parabacteroides johnsonii

<400> SEQUENCE: 28

```
ttttamctag gccgatcctt gcggttacgg acttcaggta ccccggctc ccatggcttg         60 acgggcggtg tgtacaaggc ccgggaacgt attcaccgcg ccatggctga tgcgcgatta       120
ctagcgaatc cagcttcacg gagtcgagtt gcagactccg atccgaactg agacatggtt      180
tagagattag catcctgtcg ccaggtagct gcccttgtc catgccattg taacacgtgt       240
gtcgccccgg atgtaagggc cgtgctgatt tgacgtcatc cccaccttcc tcacagctta      300
cgctggcagt ctcaccagag tcctcagctt aacctgttag taactagtga taagggttgc       360
gctcgttatg gcacttaagc cgacacctca cggcacgagc tgacgacaac catgcagcac       420
ctcgtaatca gctattgcta aagacctct ttcaaggtcg gtctgactac gttcaaaccc        480
gggtaaggtt cctcgcgtat catcgaatta aaccacatgt tcctccgctt gtgcgggccc       540
ccgtcaattc ctttgagttt caccgttgcc ggcgtactcc ccaggtggat acttaacgc        600 tttcgctgta gagcttactg tctatcgcaa actcctagta atcatcgttt actgcgtgga       660
ctaccagggt atctaatcct gtttgatacc cacgctttcg tgcttcagtg tcagttatgg       720
tttagtaagc tgccttcgca attggagttc tgcgtgatat ctatgcattt caccgctaca       780
ccacgcattc cgcctaccctc aaacacactc aagtaaccca gtttcaacgg caatttatg      840
```

```
gttgagccac aaactttcac cgctgactta aattaccacc tacgcaccct ttaaacccaa    900
taaatccgga taacgctcgc atcctccgta ttaccgcggc tgctggcacg gagttagccg    960
atgcttattc atagggtaca tacaaaatgg gacacgtccc acactttatt ccctataaa    1020 agaagtttac aaaccataga tccttcatcc ttcacgcgac ttggctggtt cagcctctcg   1080
gccattgacc aatattcctc actgctgcct cccgtaggag tttggtccgt gtctcagtac   1140
caatgtgggg gaccttcctc tcagaacccc tatccatcgt cggtttggtg ggccgttacc   1200
ccgccaactg cctaatggaa cgcatgccta tctatcagcg atgaatcttt aacaaatakt   1260
cccatgcggg ayccctgttt tatggagtat taatccgact ttcgccgggc tatcctcctc   1320
tgataggtaa gttgcatacg cgttactcac ccgtgcgccg gtcgccatca ataagtattg   1380
ctacctacca tgctgcccct cgacttgcat gtgtaagcck c                       1421

<210> SEQ ID NO 29
<211> LENGTH: 1399
<212> TYPE: DNA
<213> ORGANISM: Parabacteroides sp.

<400> SEQUENCE: 29
ccgatccttt cggttacgga cttcaggtac ccccggctcc catggcttga cgggcggtgt     60
gtacaaggcc cgggaacgta ttcaccgcgc catggctgat gcgcgattac tagcgaatcc    120
agcttcacgg agtcgggttg cagactccga tccgaactga gacgtggttt ggggattcgc    180
tccctgtcgc caggtggcct ccctttgtcc acgccattgt aacacgtgtg tcgcccggga    240
tgtaagggcc gtgctgattt gacgtcatcc ccgccttcct cgcagcttac gctggcagtc    300
ccaccagagt cctcagcatc acctgttagt aactagtggc aagggttgcg ctcgttatgg    360
cacttaagcc gacacctcac ggcacgagct gacgacaacc atgcagcacc tgcaaatcg    420 ctatcgctag agactctgtt ccagagctg tcgaaatgcg ttcaaacccg ggtaaggttc    480
ctcgcgtatc atcgaattaa accacatgtt cctccgcttg tgcgggcccc cgtcaattcc    540
tttgagtttc accgttgccg gcgtactccc caggtggatc acttaacgct ttcgctgtgc    600
cgcttacagt gtatcgcaaa cagctagtga tcatcgttta ctgcgtggac taccagggta    660
tctaatcctg tttgatcccc acgctttcgt gcatcagcgt cagtaatggc ttggcaggct    720
gccttcgcaa tcggggttct gcgtgatatc tatgcatttc accgctacac cacgcattcy    780
gcctgcctca aacatactca agccccccag tttcaacggc aattctatgg ttgagccaca    840
gactttcacc gctgacttaa aaggccgcct acgcacccctt taaacccaat aaatccggat    900
aacgctcgga tcctccgtat taccgcggct gctggcacgg agttagccga tccttattca    960
taaggtacat acmaaacggg acacgtcccg cactttattc ccttataaaa gaggtttacg   1020
atccatagaa ccttcatccc tcacgcgact tggctggttc agsctctcgc ccattgacca   1080
atattcctca ctgctgcctc ccgtaggagt ttggtccgtg tctcagtacc aatgtggggg   1140
accttcctct cagaacccct atccatcgtc ggtttggtgg gccgttaccc cgccaactgc   1200
ctaatggaac gcmwgcckat ytatcagcga wgaatcttta gcaaatatcc ccatgcgggg   1260
cccctgcttc mtgcggtatt agtccgactt tcgccgggt atcccctct dataggcaag    1320 twgcatacgc gttactcacc cgtgcgccgg tcgccacccg gtattgctac cctgygctgc   1380
ccctcgactt gcatgktaa                                                1399

<210> SEQ ID NO 30
```

<211> LENGTH: 1431
<212> TYPE: DNA
<213> ORGANISM: Parabacteroides sp.
<220> FEATURE:
<221> NAME/KEY: n
<222> LOCATION: 539
<223> OTHER INFORMATION: c, g, t or a
<220> FEATURE:
<221> NAME/KEY: n
<222> LOCATION: 827
<223> OTHER INFORMATION: c, g, t or a

<400> SEQUENCE: 30

| | | | | | |
|---|---|---|---|---|---|
| gcgcggttta | actaggccga | tcctttcggt | tacggacttc | aggtaccccc | ggctcccatg | 60 |
| gcttgacggg | cggtgtgtac | aaggcccggg | aacgtattca | ccgcgccatg | gctgatgcgc | 120 |
| gattactagc | gaatccagct | tcacggagtc | gggttgcaga | ctccgatccg | aactgagacg | 180 |
| tggtttgggg | attcgctccc | tgtcgccagg | tggcctccct | tgtccacgc | cattgtaaca | 240 |
| cgtgtgtcgc | cccggatgta | agggccgtgc | tgatttgacg | tcatcccgc | cttcctcgca | 300 |
| gcttacgctg | gcagtcccac | cagagtcctc | agcatcacct | gttagtaact | agtggcaagg | 360 |
| gttgcgctcg | ttatggcact | taagccgaca | cctcacggca | cgagctgacg | acaaccatgc | 420 |
| agcacctcgc | aaatcgctat | cgctagagac | tctgtttcca | gagctgtcga | aatgcgttca | 480 |
| aacccgggta | aggttcctcg | cgtatcatcg | aattaaacca | catgttcctc | cgcttgtgnc | 540 |
| gggcccccgt | caattccttt | gagtttcacc | gttgccggcg | taytcccag | gtggatcact | 600 |
| taacgctttc | gctgtgccgc | ttacagtgta | tcgcaaacag | ctagtgatca | tcgtttactg | 660 |
| cgtggactac | cagggtatct | aatcctgttt | gatcccacg | ctttcgtgca | tcagcgtcag | 720 |
| taatggcttg | gcaggctgcc | ttcgcaatcg | gggttctgcg | tgatatctat | gcatttcacc | 780 |
| gctacaccac | gcattccgcc | tgcctcaaac | atactcaagc | ccccanttt | caacggcaat | 840 |
| tctatggttg | agccacagac | tttcaccgct | gacttaaaag | gccgcctacg | cacccttaaa | 900 |
| acccaataaa | tccggataac | gctcggatcc | tccgtattac | gcggctgct | ggcacggagt | 960 |
| tagccgatcc | ttattcataa | ggtacataca | aaacgggaca | cgtcccgcac | tttattccct | 1020 |
| tataaaagag | gtttacgatc | catagaacct | tcatccctca | cgcgacttgg | ctggttcagc | 1080 |
| ctttcggcca | ttgaccaata | ttcctcactg | ctgcctcccg | taggagtttg | gtccgtgtct | 1140 |
| cagtaccaat | gtgggggacc | ttcctctcag | aaccccatc | cattgtcggt | ttggtgggcc | 1200 |
| gttaccccgc | caactgccta | atggaacgca | tgcctatcta | tcagcgatga | atctttagca | 1260 |
| aatatcccca | tgcggggccc | ctgcttcatg | cggtattagt | ccgactttcg | ccgggttatc | 1320 |
| cccctctgat | aggcaagttg | catacgcgtt | actcacccgt | gcgccggtcg | ccgagccgcg | 1380 |
| gtattgctac | cctcgtgctg | cccctcgact | tgcatggtta | gcctccatcc | c | 1431 |

<210> SEQ ID NO 31
<211> LENGTH: 1399
<212> TYPE: DNA
<213> ORGANISM: Parabacteroides sp.

<400> SEQUENCE: 31

| | | | | | |
|---|---|---|---|---|---|
| cttaggccga | tccctcgcgg | ttcggacttc | aggtaccccc | ggctcccatg | gcttgacggg | 60 |
| cggtgtgtac | aaggcccggg | aacgtattca | ccgcgccatg | gctgatgcgc | gattactagc | 120 |
| gaatccagct | tcacggagtc | gggttgcaga | ctccgatccg | aactgagacg | tggtttgggg | 180 |
| attcgctccc | tgtcgccagg | tggcctccct | tgtccacgc | cattgtaaca | cgtgtgtcgc | 240 |
| cccggatgta | agggccgtgc | tgatttgacg | tcatcccgc | cttcctcgca | gcttacgctg | 300 |

```
gcagtcccac cagagtcctc agcatcacct gttagtaact agtggcaagg gttgcgctcg    360
ttatggcact taagccgaca cctcacggca cgagctgacg acaaccatgc agcacctcgc    420
aaacggctat tgctagaaaa ggtgtttcca cctcggtccg aatgcgttca aacccgggta    480
aggttcctcg cgtatcatcg aattaaacca catgttcctc cgcttgtgcg ggccccgtc     540
aattcctttg agtttcaccg ttgccggcgt actccccagg tggatcactt aacgctttcg    600
ctgtgccgct tacagtgtat cgcaaacagc tagtgatcat cgtttactgc gtggactacc    660
agggtatcta atcctgtttg atccccacgc tttcgtgcat cagcgtcagt catggcttgg    720
caggctgcct tcgcaatcgg ggttctgcgt gatatctatg catttcaccg ctacaccacg    780
cattccgcct gcctcaaaca tactcaagcc ccccagtttc aacggcaatt ctatggttga    840
gccacagact ttcaccgctg acttaaaagg ccgcctacgc acccttttaaa cccaataaat   900
ccggataacg ctcggatcct ccgtattacc gcggctgctg gcacggagtt agccgatcct    960
tattcataag gtacatacaa aacgggacac gtcccgcact ttattcccctt ataaaagagg   1020
tttacgatcc atagaacctt catccctcac gcgacttggc tggttcagcc tttcggccat    1080
tgaccaatat tcctcactgc tgcctcccgt aggagtttgg tccgtgtctc agtaccaatg    1140
tgggggacct tcctctcaga accccctatcc atcgtcggtt tggtgggccg ttaccccgcc   1200
aactgcctaa tggaacgcat gcctatctat cagcgatgaa tctttagcaa atatccccat    1260
gcggggcccc tgcttcatgc ggtattagtc cgactttcgc cgggttatcc ccctctgata    1320
ggtaagttgc atacgcgtta ctcacccgtg cgccggtcgc cacccggtat tgctacctgg    1380
tgctgcccct cgactgcat                                                 1399
```

<210> SEQ ID NO 32
<211> LENGTH: 1371
<212> TYPE: DNA
<213> ORGANISM: Parabacteroides sp.

<400> SEQUENCE: 32

```
gcgaggtatc gagactacta ggtaccccg gctcccatgg cttgacgggc ggtgtgtaca     60
aggcccggga acgtattcac cgcgccatgg ctgatgcgcg attactagcg aatccagctt    120
cacggagtcg ggttgcagac tccgatccga actgagacgt ggtttgggga ttcgctccct    180
gtcgccaggt ggcatccctt tgtccacgcc attgtaacac gtgtgtcgcc ccggatgtaa    240
gggccgtgct gatttgacgt catccccgcc ttcctcgcag cttacgctgg cagtcccacc    300
agagtcctca gctttacctg ttagtaacta gtggcaaggg ttgcgctcgt tatggcactt    360
aagccgacac ctcacggcac gagctgacga caaccatgca gcacctcgca aatcgctatt    420
gctagaggct ctgtttccac atcggtccaa atgcgttcaa acccgggtaa ggttcctcgc    480
gtatcatcga attaaaccac atgttcctcc gcttgtgcgg gccccgtca attcctttga    540
gtttcaccgt tgccggcgta ctccccaggt ggatcactta acgctttcgc tgtgccgctt    600
accgtgtatc gcaaacagct agtgatcatc gtttactgcg tggactacca gggtatctaa    660
tcctgtttga tccccacgct ttcgtgcatc agcgtcagtc atggcttggc aggctgcctt    720
cgcaatcgag gttctgcgtg atatctaagc atttcaccgc tacaccacgc attccgcctg    780
cctcaaacat actcaagccc ccagtttca acggcaattc tatggttgag ccacagactt    840
tcaccgctga cttaaaaggc cgcctacgca ccctttaaac ccaataaatc cggataacgc    900
tcggatcctc cgtattaccg cggctgctgg cacggagtta gccgatcctt attcataagg    960
```

```
tacatacaaa acrggacacg tcccgcactt tattcccttta taaaagaggt ttacgatcca    1020
tagaaccttc atccctcacg cgacttggct ggttcaggct tacgcccatt gaccaatatt    1080
cctcactgct gcctcccgtt ggagtttggt ccgtgtctca gtaccaatgt gggggacctt    1140
cctctcagaa cccctatcca tcgtcggttt ggtgggccgt taccccgcca actgcataat    1200
ggaacgcatg cctatctatc agcgatgaat ctttagcaaa tatccccatg cgggacccct    1260
gcttcatgcg gtattagtcc gactttcgcc gggttatccc cctctgatag gtaagttgca    1320
tacgcgttac tcaccgtgc gccggtcgcc acccggtatt gctacgggtg a              1371

<210> SEQ ID NO 33
<211> LENGTH: 1485
<212> TYPE: DNA
<213> ORGANISM: Parabacteroides gordonii

<400> SEQUENCE: 33
agagtttgat cctggctcag gatgaacgct agcgacaggc ttaacacatg caagtcgagg      60
ggcagcagga agtagcaata ctttgctggc gaccggcgca cgggtgagta acgcgtatgc    120
aacctaccta tcagaggggg ataacccggc gaaagtcgga ctaataccgc ataaaacagg    180
ggtcccgcat gggaatattt gttaaagatt aattgctgat agatgggcat gcgttccatt    240
agatagttgg taaggtaacg gcttaccaag tctgcgatgg ataggggttc tgagaggaag    300
gtcccccaca ctggtactga gacacggacc agactcctac gggaggcagc agtgaggaat    360
attggtcaat gggcgagagc ctgaaccagc caagtcgcgt gaaggatgaa ggatctatgg    420
ttcgtaaact tcttttataa gggaataaag tgcggacgtg tcctgtttttg tatgtacctt    480 atgaataagg atcggctaac tccgtgccag cagccgcggt aatacggagg atccgagcgt    540
tatccggatt tattgggttt aaagggtgcg taggtggttt attaagtcag cggtgaaagt    600
ttgtggctca accataaaat tgccgttgaa actggttaac ttgagtatat ttgaggtagg    660
cggaatgcgt ggtgtagcgg tgaaatgcat agatatcacg cagaactcca attgcgaagg    720
cagcttacta aactataact gacactgaag cacgaaagcg tggggatcaa acaggattag    780
ataccctggt agtccacgca gtaaacgatg attactagga gtttgcgata cacagtaagc    840
tctacagcga aagcgttaag taatccacct ggggagtacg ccggcaacgg tgaaactcaa    900
aggaattgac gggggcccgc acaagcggag gaacatgtgg tttaattcga tgatacgcga    960
ggaaccttac ccgggtttga acgcattgga cagtccttga aagaggatct ctagcaatag   1020
ccatttgcga ggtgctgcat ggttgtcgtc agctcgtgcc gtgaggtgtc ggcttaagtg   1080
ccataacgag cgcaaccctt atctttagtt actaacaggt ctgctgagga ctctaaagag   1140
actgccagcg taagctgtga ggaaggtggg gatgacgtca aatcagcacg gcccttacat   1200
ccggggcgac acacgtgtta caatggtggg gacaaagggc agctacacag cgatgtgatg   1260
ctaatctcca aacccatct cagttcggat cgaagtctgc aacccgactt cgtgaagctg    1320
gattcgctag taatcgcgca tcagccatgg cgcggtgaat acgttcccgg gccttgtaca   1380
caccgcccgt caagccatgg gagttggggg tacctaaagt ccgtaaccgc aaggatcggc   1440
ctaggtaaaa ccgatgactg gggctaagtc gtaaccaagg taacc                    1485
```